US012577201B2

(12) United States Patent
Li et al.

(10) Patent No.: US 12,577,201 B2
(45) Date of Patent: Mar. 17, 2026

(54) GLUTAMINE ANALOGS

(71) Applicant: Jacobio Pharmaceuticals Co., Ltd., Beijing (CN)

(72) Inventors: Runze Li, Beijing (CN); Cunbo Ma, Beijing (CN); Zhenchang Lian, Beijing (CN); Jing Xiong, Beijing (CN); Yanping Wang, Beijing (CN); Wei Long, Beijing (CN)

(73) Assignee: JACOBIO PHARMACEUTICALS CO., LTD., Beijing (CN)

( * ) Notice: Subject to any disclaimer, the term of this patent is extended or adjusted under 35 U.S.C. 154(b) by 406 days.

(21) Appl. No.: 18/031,893

(22) PCT Filed: Oct. 14, 2021

(86) PCT No.: PCT/CN2021/123674
§ 371 (c)(1),
(2) Date: Apr. 14, 2023

(87) PCT Pub. No.: WO2022/078416
PCT Pub. Date: Apr. 21, 2022

(65) Prior Publication Data

US 2023/0399297 A1 Dec. 14, 2023

(30) Foreign Application Priority Data

Oct. 15, 2020 (WO) ................ PCT/CN2020/121114
Jan. 15, 2021 (WO) ................ PCT/CN2021/072111
Feb. 10, 2021 (WO) ................ PCT/CN2021/076491

(51) Int. Cl.

| | |
|---|---|
| *C07D 209/20* | (2006.01) |
| *A61P 35/00* | (2006.01) |
| *C07C 245/18* | (2006.01) |
| *C07D 207/09* | (2006.01) |
| *C07D 207/337* | (2006.01) |
| *C07D 211/66* | (2006.01) |
| *C07D 213/30* | (2006.01) |
| *C07D 213/74* | (2006.01) |
| *C07D 233/64* | (2006.01) |
| *C07D 239/20* | (2006.01) |
| *C07D 263/32* | (2006.01) |
| *C07D 265/30* | (2006.01) |
| *C07D 277/30* | (2006.01) |
| *C07D 305/08* | (2006.01) |
| *C07D 307/16* | (2006.01) |
| *C07D 307/93* | (2006.01) |
| *C07D 309/06* | (2006.01) |
| *C07D 309/08* | (2006.01) |
| *C07D 313/04* | (2006.01) |
| *C07D 331/04* | (2006.01) |
| *C07D 333/24* | (2006.01) |
| *C07D 493/04* | (2006.01) |

(52) U.S. Cl.
CPC ............ *C07D 209/20* (2013.01); *A61P 35/00* (2018.01); *C07C 245/18* (2013.01); *C07D 207/09* (2013.01); *C07D 207/337* (2013.01); *C07D 211/66* (2013.01); *C07D 213/30* (2013.01); *C07D 213/74* (2013.01); *C07D 233/64* (2013.01); *C07D 239/20* (2013.01); *C07D 263/32* (2013.01); *C07D 265/30* (2013.01); *C07D 277/30* (2013.01); *C07D 305/08* (2013.01); *C07D 307/16* (2013.01); *C07D 307/93* (2013.01); *C07D 309/06* (2013.01); *C07D 309/08* (2013.01); *C07D 313/04* (2013.01); *C07D 331/04* (2013.01); *C07D 333/24* (2013.01); *C07D 493/04* (2013.01); *C07C 2601/02* (2017.05); *C07C 2601/04* (2017.05); *C07C 2601/08* (2017.05); *C07C 2601/14* (2017.05); *C07C 2601/16* (2017.05); *C07C 2601/18* (2017.05)

(58) Field of Classification Search
CPC .................................................. C07D 209/20
See application file for complete search history.

(56) References Cited

U.S. PATENT DOCUMENTS

| | | | |
|---|---|---|---|
| 2002/0132776 | A1 | 9/2002 | Fuchsbauer et al. |
| 2018/0221337 | A1 | 8/2018 | Slusher et al. |

FOREIGN PATENT DOCUMENTS

| | | | |
|---|---|---|---|
| CN | 108290827 A | | 7/2018 |
| CN | 108348492 A | | 7/2018 |
| JP | 2018528261 A | | 9/2018 |
| WO | 2017/023774 A1 | | 2/2017 |
| WO | 2019/071110 A1 | | 4/2019 |
| WO | 2020150639 A1 | | 7/2020 |

OTHER PUBLICATIONS

Hausch, F. et al. "Design, Synthesis, and Evaluation of Gluten Peptide Analogs as Selective Inhibitors of Human Tissue Transglutaminase." Chemistry & Biology, vol. 10, 225-231, Mar. 2003, cited in Japanese Office Action dated Aug. 5, 2025.
Extended European Search Report (EESR) for corresponding European Patent App. No. 21879459.2; issued Sep. 19, 2024; 8 pages.
"RN 2241788-97-4", STN REG,Aug. 29, 2018 (Aug. 29, 2018), pp. 1-10.
"RN 2241788-96-3", STN REG,Aug. 29, 2018 (Aug. 29, 2018), pp. 1-10.
"RN 2232131-70-1", STN REG,Jul. 29, 2018 (Jul. 29, 2018), pp. 1-10.
"RN 2232131-59-6", STN REG,Jul. 29, 2018 (Jul. 29, 2018), pp. 1-10.

(Continued)

*Primary Examiner* — Golam M Shameem
(74) *Attorney, Agent, or Firm* — Jason A. Smith; Shumaker, Loop & Kendrick, LLP

(57) ABSTRACT

The invention relates to novel glutamine analogs, a composition containing the glutamine analogs and the use thereof.

4 Claims, 4 Drawing Sheets

(56) References Cited

OTHER PUBLICATIONS

"RN 2230818-45-7", STN REG,Jul. 16, 2018 (Jul. 16, 2018), pp. 1-10.

"RN 2204460-16-0", STN REG,Apr. 3, 2018 (Apr. 3, 2018), pp. 1-10.

"RN 2079939-28-7", STN REG,Mar. 2, 2017 (Mar. 2, 2017), pp. 1-10.

"RN 2079939-26-5", STN REG,Mar. 2, 2017 (Mar. 2, 2017), pp. 1-10.

"RN 2079939-24-3", STN REG,Mar. 2, 2017 (Mar. 2, 2017), pp. 1-10.

"RN 2079939-22-1", STN REG,Mar. 2, 2017 (Mar. 2, 2017), pp. 1-10.

"RN 2079939-21-0", STN REG,Mar. 2, 2017 (Mar. 2, 2017), pp. 1-10.

"RN 2079939-20-9", STN REG,Mar. 2, 2017 (Mar. 2, 2017), pp. 1-10.

"RN 2079939-19-6", STN REG,Mar. 2, 2017 (Mar. 2, 2017), pp. 1-10.

"RN 2079939-15-2", STN REG,Mar. 2, 2017 (Mar. 2, 2017), pp. 1-10.

"RN 115-02-6", STN REG,Nov. 16, 1984 (Nov. 16, 1984), pp. 1-10.

GLUTAMINE ANALOGS

CROSS-REFERENCE TO RELATED APPLICATIONS

The application is a U.S. Nat'l Phase of Int'l Appl. No. PCT/CN2021/123674, filed Oct. 14, 2021, which claims the benefit of PCT application Ser. No. PCT/CN2020/121114 filed on Oct. 15, 2020; PCT application Ser. No. PCT/CN2021/072111 filed on Jan. 15, 2021; and PCT application Ser. No. PCT/CN2021/076491 filed on Feb. 10, 2021. The entire contents of these applications are incorporated herein by reference in their entirety.

TECHNICAL FIELD

The invention relates to a novel glutamine analogs, a composition containing the glutamine analogs and the use thereof.

BACKGROUND ART

Glutamine analogs, such as 6-diazo-5-oxo-L-norleucine (DON) have been shown to exhibit anti-cancer activities. However, the occurrence of severe toxicity (e.g., dose limiting GI toxicities, such as oral mucositis, gastric bleeding, nausea and vomiting, and abdominal pain) has hampered their clinical development when administering such glutamine antagonists at therapeutic dose levels.

Prior attempts to mitigate the severe toxicity associated with glutamine antagonists such as DON, have been unsuccessful. Therefore, it's needed to develop novel glutamine antagonists to meet the clinical needs.

SUMMARY OF INVENTION

In one aspect, provided here is a compound of formula I, a pharmaceutically acceptable salt thereof, a stereoisomer thereof, a tautomer thereof, and an isotopic substitution thereof:

Formula I

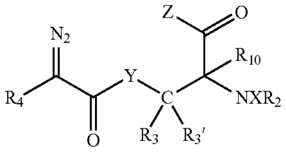

Wherein,

Z is $OR_1$ or $SR_1$; $R_1$ is selected from the group consisting of hydrogen, deuterium, halogen, $C_{1-6}$ alkyl, $C_{1-6}$alkoxy, —$C_{3-8}$cycloalkyl, —$C_{0-6}$alkylene-$C_{3-8}$heterocyclyl, —$C_{0-6}$alkylene-NH—$C_{0-6}$alkylene $C_{6-10}$aryl, —$C_{0-6}$alkylene-NH—$C_{0-6}$alkylene-5-12 membered heteroaryl, —$C_{0-6}$alkylene-$C_{6-10}$aryl and —$C_{0-6}$alkylene-5-12 membered heteroaryl; and each of which can be optional substituted with one or more substituents independently selected from the group consisting of deuterium, halogen, —OH, oxo, —CN, —$C_{1-6}$ alkyl, —$C_{1-6}$ alkoxy, —$C_{3-8}$cycloalkyl, —$NH_2$, —NH($C_{1-6}$alkyl), —N($C_{1-6}$alkyl)$_2$, —NH—$C_{3-8}$cycloalkyl, carboxyl, —CO—$C_{1-6}$alkyl; each of the heteroaryl and heterocyclyl contains 1, 2 or 3 heteroatoms selected from N, O or S;

X is selected from the group consisting of hydrogen, deuterium, $C_{1-6}$alkyl, —C(═O)-G, —C(═O)—W—$(CR_{X1}R_{X2})_m$—O—$R_{X3}$, —C(═O)—W—$(CR_{X1}R_{X2})_m$—S—$R_{X3}$, C(═O)—W—$(CR_{X1}R_{X2})_m$—SO—$R_{X3}$, C(═O)—W—$(CR_{X1}R_{X2})_m$—$SO_2$—$R_{X3}$, —C(═O)—W—$(CR_{X1}R_{X2})_m$-G, —C(═O)—W—$(CR_{X1}R_{X2})_m$—$NR_5R_5'$, —P(═O)$(OR_6)_p(NHR_7)_q$, —C(═O)—W—$(CR_{X1}R_{X2})_m$-G-O—C(═O)—$R_8$, —C(═O)—W—$(CR_{X1}R_{X2})_m$-G-O—$R_8$, —C(═O)—O—$(CR_{X1}R_{X2})_m$—O—C(═O)—$R_9$, —C(═O)—O—$R_7$, —C(═O)—W—$(CR_{X1}R_{X2})_m$-G-O—C(═O)-G, and —C(═O)—W—$(CR_{X1}R_{X2})_m$-G-$NR_5R_5'$;

W is oxygen, CO or a bond;

m is selected from 1, 2, 3, 4, 5, 6, 7 or 8;

p and q are each independently selected from 0, 1 or 2 provided that the sum of p and q is 2;

$R_{X1}$ and $R_{X2}$ are each independently selected from the group consisting of hydrogen, deuterium, halogen, CN, OH, $NH_2$, $C_{1-6}$ alkyl, $C_{1-6}$alkoxy, $C_{4-10}$ cycloalkyl, —C(═O)—$C_{1-6}$alkyl, $C_{5-12}$aryl, —$C_{1-6}$ alkylene-$C_{5-12}$aryl, -5-12 membered heteroaryl, and —$C_{1-6}$ alkylene-5-12 membered heteroaryl, and wherein said $C_{1-6}$ alkyl, said $C_{1-6}$alkoxy, said $C_{4-10}$ cycloalkyl, said $C_{5-12}$aryl, said-$C_{1-6}$ alkylene-$C_{5-12}$aryl, said -5-12 membered heteroaryl, and said-$C_{1-6}$ alkylene-5-12 membered heteroaryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$cycloalkyl, —$NH_2$, —NH($C_{1-6}$ alkyl), —N($C_{1-6}$alkyl)$_2$, —S—$C_{1-6}$alkyl, carboxyl; and each of the heteroaryl independently optionally contains 1, 2 or 3 heteroatoms selected from N, O or S;

or $R_{X1}$ and $R_{X2}$ together with the carbon atom to which they are attached form $C_{3-10}$carbocyclic ring, $C_{3-10}$ membered heterocyclyl, and each of the heterocyclyl independently optionally contains 1, 2 or 3 heteroatoms selected from N, O or S; each of which can be optional substituted with one or more substituents, which are independently selected from the group consisting of deuterium, halogen, —$NH_2$, —CN, —OH, —$NO_2$, carbonyl, ═O, oxo, carboxyl, $C_{1-6}$alkoxy, $C_{1-6}$alkyl;

$R_{X3}$ is independently selected from the group consisting of hydrogen, deuterium, $C_{1-6}$ alkyl, $C_{1-6}$ alkoxy, $C_{3-8}$ cycloalkyl, —C(═O)—$C_{1-6}$ alkyl, and —$C_{1-6}$alkylenen-$C_{5-12}$ aryl, wherein said $C_{1-6}$ alkyl, said $C_{1-6}$ alkoxy, said $C_{3-8}$ cycloalkyl, said —C(═O)—$C_{1-6}$ alkyl, and said —$C_{1-6}$alkylenen-$C_{5-12}$ aryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl, 4-8 membered heterocyclyl,

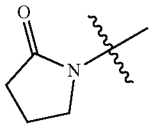

,

—$C_{6-12}$aryl, —C(=O)—$C_{1-6}$alkyl, —NH—C(=O)—$C_{1-6}$alkyl, —C(=O)—$NH_2$, —C(=O)—NH—$C_{1-6}$alkyl, and —C(=O)—N($C_{1-6}$ alkyl)$_2$;

or $R_{X1}$ and $R_{X3}$ together with the carbon atom and the oxygen atom to which they are attached respectively form a 5-12 membered heterocyclyl, wherein said 5-12 membered heterocyclyl can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl; and each of the heterocyclyl independently optionally contains 1, 2 or 3 heteroatoms selected from N, O or S;

$R_5$ and $R_5$' are each independently selected from the group consisting of hydrogen, deuterium, —$C_{1-6}$ alkyl, —$C_{1-6}$ alkoxy, —$C_{3-8}$ cycloalkyl, $C_{5-12}$ aryl, 5-12 membered heteroaryl, 5-12 membered heterocyclyl, and wherein said —$C_{1-6}$ alkyl, said —$C_{1-6}$ alkoxy, said —$C_{3-8}$ cycloalkyl, said $C_{5-12}$ aryl, said 5-12 membered heteroaryl, said 5-12 membered heterocyclyl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

each of $R_6$ is independently selected from the group consisting of hydrogen, deuterium, —$C_{1-6}$ alkyl, —$C_{3-8}$ cycloalkyl, 5-12 membered heterocyclyl ring, —$C_{1-6}$ alkenyl, and —$C_{3-8}$ cycloalkenyl, and wherein said —$C_{1-6}$ alkyl, said —$C_{3-8}$ cycloalkyl, said 5-12 membered heterocyclyl ring, said —$C_{1-6}$ alkenyl, and said —$C_{3-8}$ cycloalkenyl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

or $R_6$ together with the oxygen atom to which it is attached forms a purine or pyrimidine nucleoside;

each of $R_7$ is independent selected from the group consisting of hydrogen, deuterium, halogen, $C_{1-6}$ alkyl, $C_{3-8}$ cycloalkyl, 5-12 membered heterocyclyl ring, $C_{1-6}$ alkenyl, $C_{3-8}$ cycloalkenyl, $C_{5-12}$ aryl, and 5-12 membered heteroaryl, and wherein said $C_{1-6}$ alkyl, said $C_{3-8}$ cycloalkyl, said 5-12 membered heterocyclyl ring, said $C_{1-6}$ alkenyl, said $C_{3-8}$ cycloalkenyl, said $C_{5-12}$ aryl, and said 5-12 membered heteroaryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

$R_8$ and $R_9$ are each independently selected from the group consisting of $C_{1-6}$ alkyl, $C_{3-8}$ cycloalkyl, monosaccharide, acylated monosaccharide, $C_{5-12}$ aryl, and 5-12 membered heteroaryl, and wherein said $C_{1-6}$ alkyl, said $C_{3-8}$ cycloalkyl, said monosaccharide, said acylated monosaccharide, said $C_{5-12}$ aryl, and said 5-12 membered heteroaryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

G is $C_{5-12}$ aryl, or 5-12 membered heteroaryl, wherein $C_{5-12}$ aryl, and 5-12 membered heteroaryl can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

$R_2$ is selected from the group consisting of hydrogen, deuterium, halogen, $C_{1-6}$ alkyl, and $C_{1-6}$ alkoxy, and wherein said $C_{1-6}$ alkyl, and said $C_{1-6}$ alkoxy can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

$R_3$ and $R_3$' are each independently selected from the group consisting of hydrogen, deuterium, halogen, $C_{1-6}$ alkyl, and $C_{1-6}$ alkoxy, and wherein said $C_{1-6}$ alkyl, and said $C_{1-6}$ alkoxy can be optional substituted with one or more substituents, which are independently from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

Y is a bond, oxygen, or —($CR_{Y1}R_{Y2}$)$_n$—;

n is selected from 1, 2, 3, 4, 5, 6, 7 or 8;

$R_{Y1}$ and $R_{Y2}$ are each independently selected from the group consisting of hydrogen, deuterium, halogen, $C_{1-6}$ alkyl, and $C_{1-6}$ alkoxy, and wherein said $C_{1-6}$ alkyl, and said $C_{1-6}$ alkoxy can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

$R_4$ is selected from the group consisting of hydrogen, deuterium, halogen, $C_{1-6}$ alkyl, and $C_{1-6}$ alkoxy, and wherein said $C_{1-6}$ alkyl, and said $C_{1-6}$ alkoxy can be optional substituted with one or more substituents, which are independently selected from the group consisting of deuterium, halogen, —OH, oxo, —CN, —$C_{1-6}$alkyl, —$C_{1-6}$alkoxy, —$C_{3-8}$cycloalkyl, —$NH_2$, —NH($C_{1-6}$ alkyl), —N($C_{1-6}$alkyl)$_2$, carboxyl;

$R_{10}$ is selected from the group consisting of hydrogen, deuterium, halogen, $C_{1-6}$ alkyl, and $C_{1-6}$ alkoxy, and wherein said $C_{1-6}$ alkyl, and said $C_{1-6}$ alkoxy can be optional substituted with one or more substituents, which are independently selected from the group consisting of deuterium, halogen, —OH, oxo, —CN, —$C_{1-6}$alkyl, —$C_{1-6}$alkoxy, —$C_{3-8}$cycloalkyl, —$NH_2$, —NH($C_{1-6}$ alkyl), —N($C_{1-6}$alkyl)$_2$, carboxyl.

In some embodiments of the compound of Formula I, the pharmaceutically acceptable salt thereof, the stereoisomer thereof, the tautomer thereof, and the isotopic substitution thereof of the present invention, wherein the compound is of formula I-A:

Formula I-A

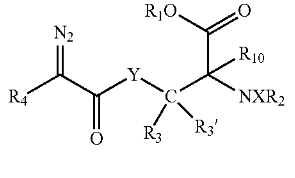

In some embodiments of the compound of Formula I, the pharmaceutically acceptable salt thereof, the stereoisomer thereof, the tautomer thereof, and the isotopic substitution thereof of the present invention, wherein the compound is of formula I-B:

Formula I-B

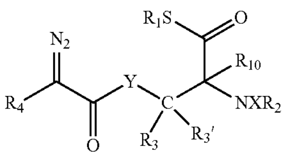

In some embodiments of the compound of Formula I, I-A, I-B, the pharmaceutically acceptable salt thereof, the stereoisomer thereof, the tautomer thereof, and the isotopic substitution thereof of the present invention, wherein $R_1$ is selected from the group consisting of hydrogen, deuterium, halogen, $C_{1-3}$ alkyl, $C_{1-3}$ alkoxy, —$C_{3-8}$cycloalkyl, —$C_{0-3}$ alkylene-$C_{3-8}$heterocyclyl, —$C_{0-3}$alkylene-NH—$C_{0-3}$alkylene $C_{6-10}$aryl, —$C_{0-3}$alkylene-NH—$C_{0-3}$alkylene-5-12membered heteroaryl, —$C_{0-3}$alkylene-$C_{6-10}$aryl and —$C_{0-3}$alkylene-5-12 membered heteroaryl; and each of which can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —NH—$C_{3-8}$ cycloalkyl, —N($C_{1-6}$alkyl)$_2$, carboxyl, —CO—$C_{1-6}$ alkyl; each of the heteroaryl and heterocyclyl contains 1 or 2 heteroatoms selected from N, O or S.

In some embodiments of the compound of Formula I, I-A, I-B, the pharmaceutically acceptable salt thereof, the stereoisomer thereof, the tautomer thereof, and the isotopic substitution thereof of the present invention, wherein $R_1$ is selected from the group consisting of hydrogen, deuterium, halogen, $C_{1-3}$ alkyl, $C_{1-3}$ alkoxy, —$C_{3-8}$cycloalkyl, —$C_{0-3}$alkylene-$C_{3-8}$heterocyclyl, —$C_{0-3}$alkylene-NH—$C_{0-3}$alkylene $C_{6-10}$aryl, —$C_{0-3}$alkylene-NH—$C_{0-3}$alkylene-5-12 membered heteroaryl, —$C_{0-3}$alkylene-$C_{6-10}$aryl and —$C_{0-3}$alkylene-5-12 membered heteroaryl; each of the heteroaryl and heterocyclyl contains 1 or 2 heteroatoms selected from N or O; and wherein each of which can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-6}$ alkyl), —NH—$C_{3-6}$ cycloalkyl, —N($C_{1-3}$alkyl)$_2$, carboxyl, —CO—$C_{1-3}$alkyl; each of the heteroaryl and heterocyclyl contains 1 or 2 heteroatoms selected from N or O.

In some embodiments of the compound of Formula I, I-A, I-B, the pharmaceutically acceptable salt thereof, the stereoisomer thereof, the tautomer thereof, and the isotopic substitution thereof of the present invention, wherein $R_1$ is selected from the group consisting of hydrogen, deuterium, F, Cl, Br, I, methyl, ethyl, propyl, isopropyl, methoxy, ethoxy, propoxy, isopropoxy,

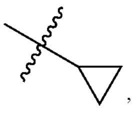, 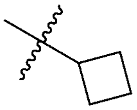, 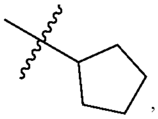,

-continued

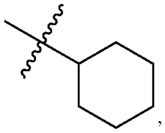, 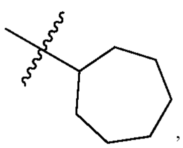, 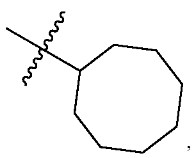,

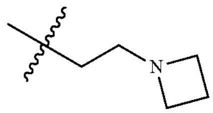, 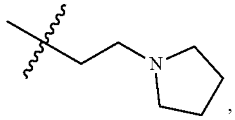,

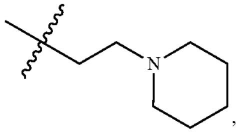, 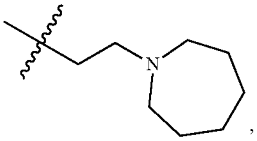,

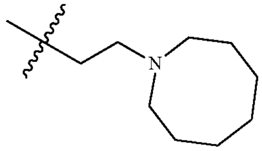, 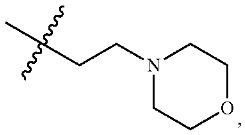,

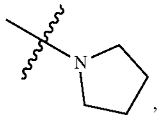, 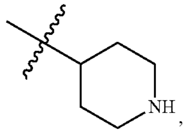, 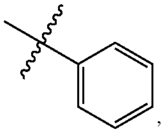,

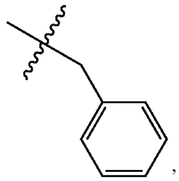, 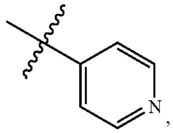, 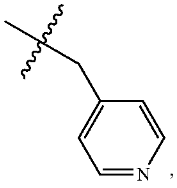,

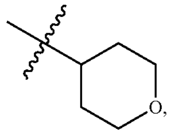, 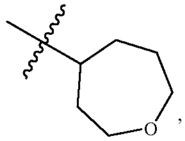, 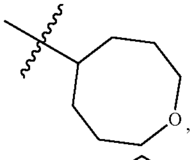,

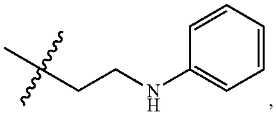, 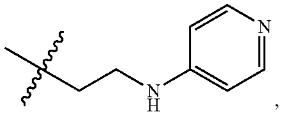,

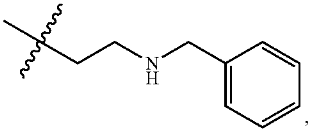,

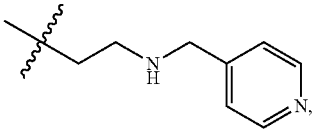, 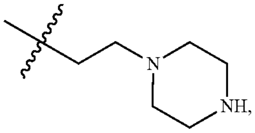, and each of which can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-6}$ alkyl), —NH—$C_{3-6}$ cycloalkyl, —N($C_{1-3}$ alkyl)$_2$, carboxyl, —CO—$C_{1-3}$alkyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_1$ is selected from the group consisting of hydrogen, deuterium, F, Cl, Br, I, methyl, ethyl, propyl, isopropyl, methoxy, ethoxy, propoxy, isopropoxy,

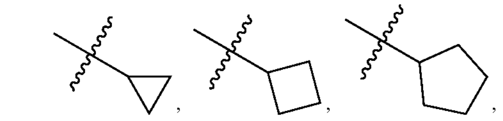
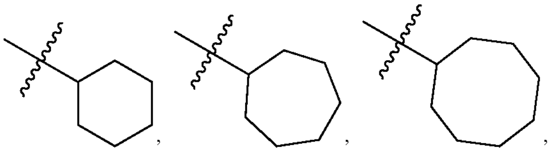
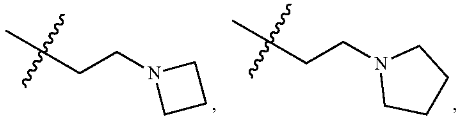
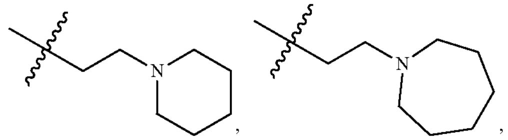
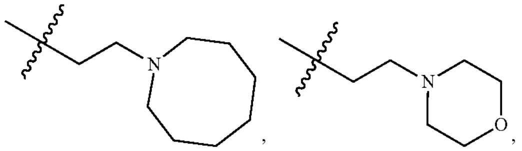
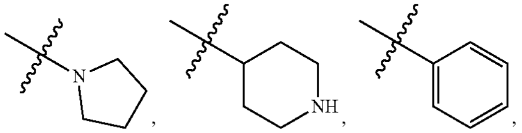
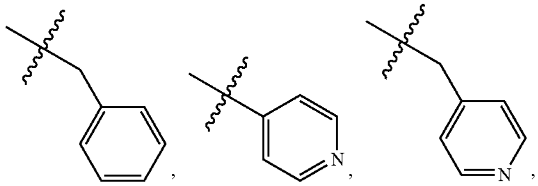
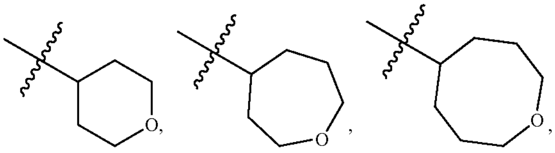
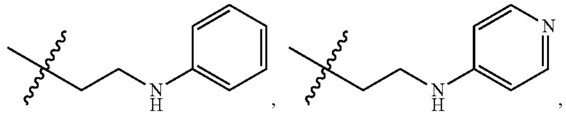
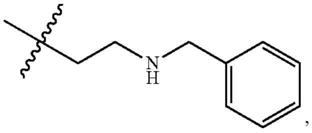
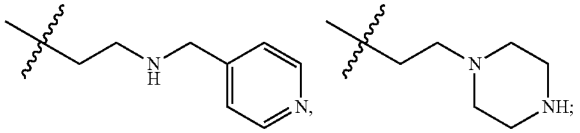 [SMILES: *CCNCc1ccncc1 ; *CCN1CCNCC1]

and each of which can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, —NH-cyclopropyl, —NH-cyclobutyl, —NH-cyclopentyl, —NH-cyclohexyl, carboxyl and —CO-tert-butyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_1$ is selected from hydrogen, deuterium, isopropyl, methyl, ethyl, -tert-butyl, —$CF_3$, —$CH_2CF_3$, —$CH(CH_3)CF_3$, —$CH(CH_3)CH_2CF_3$, —$(CH_2)_2CF_3$, —$(CH_2)_2$—$CH(CH_3)_2$, —$C(CH_3)_2CF_3$, —$C(CH_3)_2CH_2CF_3$, —CN, —$CH_2CN$, —$CH(CH_3)CN$, —$CH_2CH_2CN$, —$CH(CH_3)CH_2CN$, —$C(CH_3)_2CN$, —$C(CH_3)_2CH_2CN$, —$CH_2OH$, —$CH_2$—O—$CH_3$, —$CH_2$—O—$CH_2CH_3$, —$CH_2$—O—$CH(CH_3)_2$,

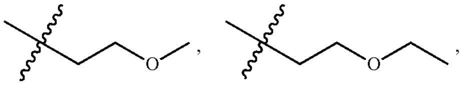
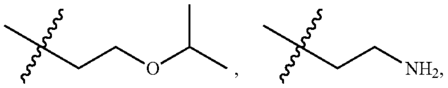
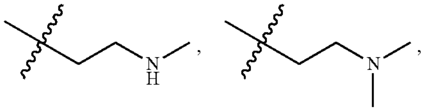
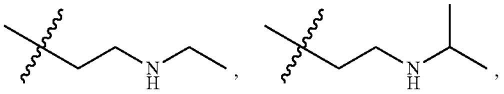
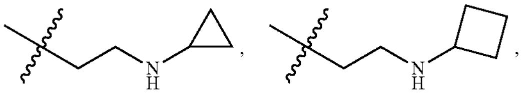
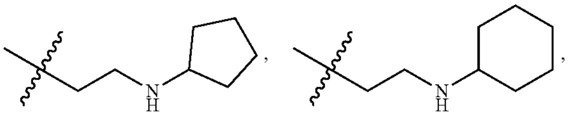
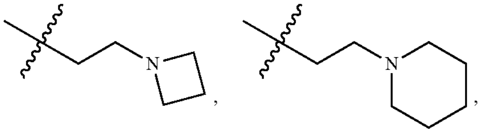
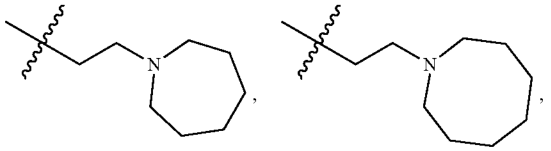
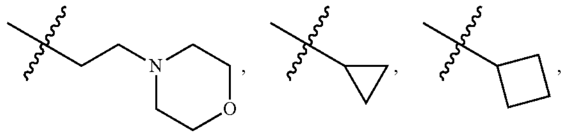
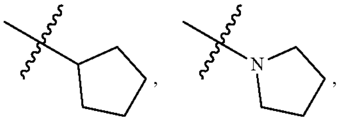
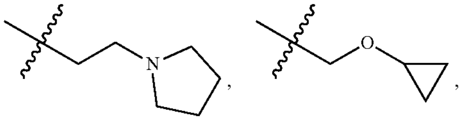

-continued

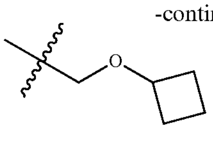, 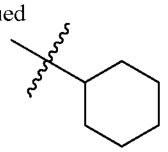, 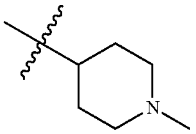, 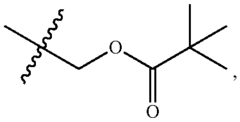, 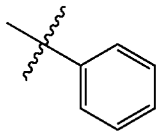, 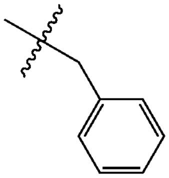, 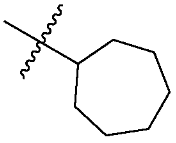, 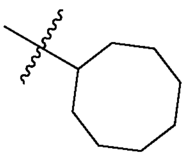, 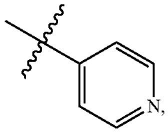 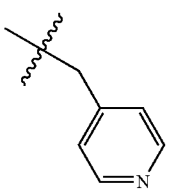, 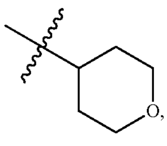 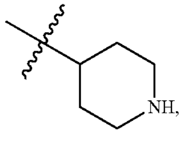 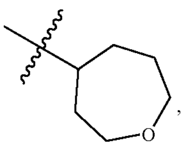, 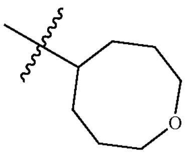, 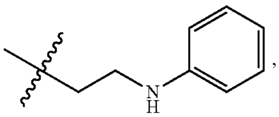, 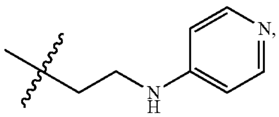 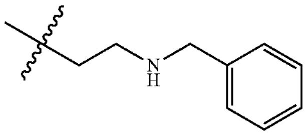, 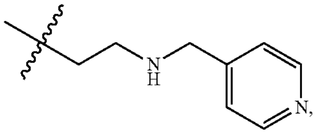 or 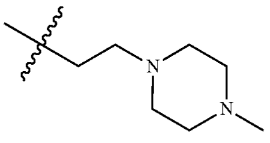.

In some embodiments of the compound of Formula I, I-A, I-B, the pharmaceutically acceptable salt thereof, the stereoisomer thereof, the tautomer thereof, and the isotopic substitution thereof of the present invention, wherein X is selected from the group consisting of hydrogen, deuterium, $C_{1-6}$ alkyl, —C(=O)-G, —C(=O)—W—$(CR_{X1}R_{X2})_m$—O—$R_{X3}$, —C(=O)—W—$(CR_{X1}R_{X2})_m$—S—$R_{X3}$, C(=O)—W—$(CR_{X1}R_{X2})_m$—SO—$R_{X3}$, C(=O)—W—$(CR_{X1}R_{X2})_m$—$SO_2$—$R_{X3}$, —C(=O)—W—$(CR_{X1}R_{X2})_m$-G, —C(=O)—W—$(CR_{X1}R_{X2})_m$—$NR_5R_5'$, —P(=O)$(OR_6)_p(NHR_7)_q$, —C(=O)—W—$(CR_{X1}R_{X2})_m$-G-O—C(=O)—$R_8$, —C(=O)—W—$(CR_{X1}R_{X2})_m$-G-O—$R_8$, —C(=O)—O—$(CR_{X1}R_{X2})_m$—O—C(=O)—$R_9$, —C(=O)—O—$R_7$, —C(=O)—W—$(CR_{X1}R_{X2})_m$-G-O—C(=O)-G, and —C(=O)—W—$(CR_{X1}R_{X2})_m$-G-$NR_5R_5'$;

W is oxygen, CO or a bond;

m is selected from 1, 2 or 3;

p and q are each independently selected from 0, 1 or 2 provided that the sum of p and q is 2;

$R_{X1}$ and $R_{X2}$ are each independently selected from the group consisting of hydrogen, deuterium, halogen, CN, OH, $C_{1-4}$alkyl, $C_{1-3}$alkoxy, $C_{4-8}$ cycloalkyl, —C(=O)—$C_{1-3}$alkyl, $C_{5-10}$aryl, —$C_{1-3}$ alkylene-$C_{5-10}$aryl, 5-10 membered heteroaryl, and —$C_{1-3}$ alkylene-5-10 membered heteroaryl, and wherein said $C_{1-3}$ alkyl, said $C_{1-3}$alkoxy, said $C_{4-8}$ cycloalkyl, said $C_{5-10}$aryl, said —$C_{1-3}$ alkylene-$C_{5-10}$aryl, said 5-10 membered heteroaryl, and said —$C_{1-3}$ alkylene-5-10 membered heteroaryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$cycloalkyl, —$NH_2$, —NH($C_{1-6}$ alkyl), —N($C_{1-6}$alkyl)$_2$, —S—$C_{1-6}$alkyl or carboxyl; and each of the heteroaryl independently optionally contains 1, 2 or 3 heteroatoms selected from N, O or S;

or $R_{X1}$ and $R_{X2}$ together with the carbon atom to which they are attached form $C_{4-8}$carbocyclic ring, $C_{4-8}$ membered heterocyclyl, and each of the heterocyclyl independently optionally contains 1, 2 or 3 heteroatoms selected from N, O or S; each of which can be optional substituted with one or more substituents, which are independently selected from the group consisting of deuterium, halogen, —$NH_2$, —CN, —OH, —$NO_2$, carbonyl, =O, oxo, carboxyl, $C_{1-6}$alkoxy, $C_{1-6}$alkyl;

$R_{X3}$ is independently selected from the group consisting of hydrogen, deuterium, $C_{1-3}$ alkyl, $C_{1-3}$ alkoxy, $C_{3-6}$ cycloalkyl, —C(=O)—$C_{1-3}$ alkyl, and —$C_{1-3}$alkylenen-$C_{5-10}$ aryl, wherein said $C_{1-3}$ alkyl, said $C_{1-3}$ alkoxy, said $C_{3-6}$ cycloalkyl, said —C(=O)—$C_{1-3}$ alkyl, and said —$C_{1-3}$alkylenen-$C_{5-10}$ aryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl, 4-8 membered heterocyclyl,

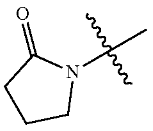,

—$C_{6-12}$aryl, —C(=O)—$C_{1-6}$alkyl, —NH—C(=O)—$C_{1-6}$alkyl, —C(=O)—$NH_2$, —C(=O)—NH—$C_{1-6}$alkyl, and —C(=O)—N($C_{1-6}$ alkyl)$_2$;

or $R_{X1}$ and $R_{X3}$ together with the carbon atom and the oxygen atom to which they are attached respectively form a 5-10 membered heterocyclyl, wherein said 5-10 membered heterocyclyl can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl; and each of the heterocyclyl independently optionally contains 1, 2 or 3 heteroatoms selected from N, O or S;

$R_5$ and $R_5$' are each independently selected from the group consisting of hydrogen, deuterium, —$C_{1-3}$ alkyl, —$C_{1-3}$ alkoxy, —$C_{3-6}$ cycloalkyl, $C_{5-10}$ aryl, 5-10 membered heteroaryl, 5-10 membered heterocyclyl, and wherein said —$C_{1-3}$ alkyl, —$C_{1-3}$ alkoxy, said —$C_{3-6}$cycloalkyl, said $C_{5-10}$ aryl, said 5-10 membered heteroaryl, said 5-10 membered heterocyclyl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

each of $R_6$ is independently selected from the group consisting of hydrogen, deuterium, —$C_{1-3}$ alkyl, —$C_{3-6}$ cycloalkyl, 5-10 membered heterocyclyl ring, —$C_{1-3}$alkenyl, and —$C_{3-6}$ cycloalkenyl, and wherein said —$C_{1-3}$ alkyl, said —$C_{3-6}$ cycloalkyl, said 5-10 membered heterocyclyl ring, said —$C_{1-3}$ alkenyl, and said —$C_{3-6}$ cycloalkenyl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

or $R_6$ together with the oxygen atom to which it is attached forms a purine or pyrimidine nucleoside;

each of $R_7$ is independent selected from the group consisting of hydrogen, deuterium, halogen, $C_{1-3}$ alkyl, $C_{3-6}$ cycloalkyl, 5-10 membered heterocyclyl ring, $C_{1-3}$ alkenyl, $C_{3-6}$ cycloalkenyl, $C_{5-10}$ aryl, and 5-10 membered heteroaryl, and wherein said $C_{1-3}$ alkyl, said $C_{3-6}$ cycloalkyl, said 5-10 membered heterocyclyl ring, said $C_{1-3}$ alkenyl, said $C_{3-6}$ cycloalkenyl, said $C_{5-10}$ aryl, and said 5-10 membered heteroaryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl;

$R_8$ and $R_9$ are each independently selected from the group consisting of $C_{1-3}$ alkyl, $C_{3-6}$ cycloalkyl, monosaccharide, acylated monosaccharide, $C_{5-10}$ aryl, and 5-10 membered heteroaryl, and wherein said $C_{1-3}$ alkyl, said $C_{3-6}$ cycloalkyl, said monosaccharide, said acylated monosaccharide, said $C_{5-10}$ aryl, and said 5-10 membered heteroaryl, can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl; or G is $C_{5-10}$ aryl, or 5-10 membered heteroaryl, wherein $C_{5-10}$ aryl, and 5-10 membered heteroaryl can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein X is selected from the group consisting of hydrogen, deuterium, $C_{1-3}$ alkyl, —C(═O)-G, —C(═O)—W—($CR_{X1}R_{X2}$)$_m$—O—$R_{X3}$, —C(═O)—W—($CR_{X1}R_{X2}$)$_m$—S—$R_{X3}$, C(═O)—W—($CR_{X1}R_{X2}$)$_m$—SO—$R_{X3}$, C(═O)—W—($CR_{X1}R_{X2}$)$_m$—$SO_2$—$R_{X3}$, —C(═O)—W—($CR_{X1}R_{X2}$)$_m$-G, —C(═O)—W—($CR_{X1}R_{X2}$)$_m$—$NR_5R_5$', —P(═O)($OR_6$)$_p$($NHR_7$)$_q$, —C(═O)—W—($CR_{X1}R_{X2}$)$_m$-G-O—C(═O)—$R_8$, —C(═O)—W—($CR_{X1}R_{X2}$)$_m$-G-O—$R_8$, —C(═O)—O—($CR_{X1}R_{X2}$)$_m$—O—C(═O)—$R_9$, —C(═O)—O—$R_7$, —C(═O)—W—($CR_{X1}R_{X2}$)$_m$-G-O—C(═O)-G, and —C(═O)—W—($CR_{X1}R_{X2}$)$_m$-G-$NR_5R_5$';

W is oxygen or a bond;

m is selected from 1, 2 or 3;

p and q are each independently selected from 0, 1 or 2 provided that the sum of p and q is 2;

$R_{X1}$ and $R_{X2}$ are each independently selected from the group consisting of hydrogen, deuterium, halogen, CN, OH, $C_{1-4}$ alkyl, $C_{1-3}$alkoxy, $C_{4-8}$ cycloalkyl, —C(═O)—$C_{1-3}$alkyl, $C_{5-10}$aryl, —$C_{1-3}$ alkylene-$C_{5-10}$aryl, 5-10 membered heteroaryl, and —$C_{1-3}$ alkylene-5-10 membered heteroaryl, and wherein said $C_{1-3}$ alkyl, said $C_{1-3}$alkoxy, said $C_{4-8}$cycloalkyl, said $C_{5-10}$aryl, said-$C_{1-3}$ alkylene-$C_{5-10}$aryl, said 5-10 membered heteroaryl, and said —$C_{1-3}$ alkylene-5-10 membered heteroaryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-6}$ alkyl), —N($C_{1-3}$alkyl)$_2$, —S—$C_{1-3}$alkyl carboxyl; and each of the heteroaryl independently optionally contains 1, 2 or 3 heteroatoms selected from N, O or S;

or $R_{X1}$ and $R_{X2}$ together with the carbon atom to which they are attached form $C_{4-6}$carbocyclic ring, $C_4$-6 membered heterocyclyl, and each of the heterocyclyl independently optionally contains 1, 2 or 3 heteroatoms selected from N, O or S; each of which can be optional substituted with one or more substituents, which are independently selected from the group consisting of deuterium, halogen, —$NH_2$, —CN, —OH, —$NO_2$, oxo, carboxyl, $C_{1-3}$alkoxy, $C_{1-3}$alkyl;

$R_{X3}$ is independently selected from the group consisting of hydrogen, deuterium, $C_{1-3}$ alkyl, $C_{1-3}$ alkoxy, $C_{3-6}$ cycloalkyl, —C(═O)—$C_{1-3}$ alkyl, and —$C_{1-3}$alkylenen-$C_{5-10}$aryl, wherein said $C_{1-3}$ alkyl, said $C_{1-3}$ alkoxy, said $C_{3-6}$ cycloalkyl, said —C(═O)—$C_{1-3}$ alkyl, and said —$C_{1-3}$alkylenen-$C_{5-10}$ aryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, —S—$C_{1-3}$alkyl carboxyl, 4-6 membered heterocyclyl,

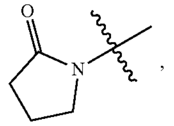 [SMILES: *N1CCCC1=O]

—$C_{6-10}$aryl, —C(=O)—$C_{1-3}$alkyl, —NH—C(=O)—$C_{1-3}$alkyl, —C(=O)—$NH_2$, —C(=O)—NH—$C_{1-3}$alkyl, —C(=O)—N($C_{1-3}$alkyl)$_2$;

or $R_{X1}$ and $R_{X3}$ together with the carbon atom and the oxygen atom to which they are attached respectively form a 5-10 membered heterocyclyl, wherein said 5-10 membered heterocyclyl can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl; and each of the heterocyclyl independently optionally contains 1, 2 or 3 heteroatoms selected from N, O or S;

$R_5$ and $R_5$' are each independently selected from the group consisting of hydrogen, deuterium, —$C_{1-3}$ alkyl, —$C_{1-3}$ alkoxy, —$C_{3-6}$ cycloalkyl, $C_{5-10}$ aryl, 5-10 membered heteroaryl, 5-10 membered heterocyclyl, and wherein said —$C_{1-3}$ alkyl, —$C_{1-3}$ alkoxy, said —$C_{3-6}$cycloalkyl, said $C_{5-10}$ aryl, said 5-10 membered heteroaryl, said 5-10 membered heterocyclyl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl;

each of $R_6$ is independently selected from the group consisting of hydrogen, deuterium, —$C_{1-3}$ alkyl, —$C_{3-6}$ cycloalkyl, 5-10 membered heterocyclyl ring, —$C_{1-3}$alkenyl, and —$C_{3-6}$ cycloalkenyl, and wherein said —$C_{1-3}$ alkyl, said —$C_{3-6}$ cycloalkyl, said 5-10 membered heterocyclyl ring, said —$C_{1-3}$alkenyl, and said —$C_{3-6}$ cycloalkenyl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl;

or $R_6$ together with the oxygen atom to which it is attached forms a purine or pyrimidine nucleoside;

each of $R_7$ is independent selected from the group consisting of hydrogen, deuterium, halogen, $C_{1-3}$ alkyl, $C_{3-6}$ cycloalkyl, 5-10 membered heterocyclyl ring, $C_{1-3}$ alkenyl, $C_{3-6}$ cycloalkenyl, $C_{5-10}$ aryl, and 5-10 membered heteroaryl, and wherein said $C_{1-3}$ alkyl, said $C_{3-6}$ cycloalkyl, said 5-10 membered heterocyclyl ring, said $C_{1-3}$ alkenyl, said $C_{3-6}$ cycloalkenyl, said $C_{5-10}$ aryl, and said 5-10 membered heteroaryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl;

$R_8$ and $R_9$ are each independently selected from the group consisting of $C_{1-3}$ alkyl, $C_{3-6}$ cycloalkyl, monosaccharide, acylated monosaccharide, $C_{5-10}$ aryl, and 5-10 membered heteroaryl, and wherein said $C_{1-3}$ alkyl, said $C_{3-6}$ cycloalkyl, said monosaccharide, said acylated monosaccharide, said $C_{5-10}$ aryl, and said 5-10 membered heteroaryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl; or G is $C_{5-10}$ aryl, or 5-10 membered heteroaryl, wherein $C_{5-10}$ aryl, and 5-10 membered heteroaryl can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein X is selected from the group consisting of hydrogen, deuterium, methyl, ethyl, propyl, isopropyl, —C(=O)-G, —C(=O)—W—$(CR_{X1}R_{X2})_m$—O—$R_{X3}$, —C(=O)—W—$(CR_{X1}R_{X2})_m$—S—$R_{X3}$, C(=O)—W—$(CR_{X1}R_{X2})_m$—SO—$R_{X3}$, C(=O)—W—$(CR_{X1}R_{X2})_m$—$SO_2$—$R_{X3}$, —C(=O)—W—$(CR_{X1}R_{X2})_m$-G, —C(=O)—W—$(CR_{X1}R_{X2})_m$—$NR_5R_5$', —P(=O)$(OR_6)_p(NHR_7)_q$, —C(=O)—W—$(CR_{X1}R_{X2})_m$-G-O—C(=O)—$R_8$, —C(=O)—W—$(CR_{X1}R_{X2})_m$-G-O—$R_8$, —C(=O)—O—$(CR_{X1}R_{X2})_m$—O—C(=O)—$R_9$, —C(=O)—O—$R_7$, —C(=O)—W—$(CR_{X1}R_{X2})_m$-G-O—C(=O)-G, and —C(=O)—W—$(CR_{X1}R_{X2})_m$-G-$NR_5R_5$';

W is oxygen or a bond;

m is selected from 1, 2 or 3;

p and q are each independently selected from 0, 1 or 2 provided that the sum of p and q is 2;

$R_{X1}$ and $R_{X2}$ are each independently selected from the group consisting of hydrogen, deuterium, halogen, CN, OH, methyl, ethyl, propyl, isopropyl, methoxy, ethoxy, propoxy, isopropoxy, butyl, sec-butyl, isobutyl, tert-butyl, $C_4$ cycloalkyl, $C_5$ cycloalkyl, $C_6$ cycloalkyl, —C(=O)—$CH_3$, —C(=O)—$CH_2CH_3$, —C(=O)—$CH_2CH_2CH_3$, —C(=O)—$CH(CH_3)_2$, $C_5$ aryl, $C_6$aryl, $C_7$ aryl, $C_8$ aryl, $C_9$ aryl, $C_{10}$ aryl, —$CH_2$—$C_5$ aryl, —$CH_2$—$C_6$aryl, —$CH_2$—$C_7$ aryl, —$CH_2$—$C_8$ aryl, —$CH_2$—$C_9$ aryl, —$CH_2$—$C_{10}$ aryl, —$(CH_2)_2$—$C_5$ aryl, —$(CH_2)_2$-$C_6$aryl, —$(CH_2)_2$ —$C_7$ aryl, —$(CH_2)_2$—$C_5$ aryl, —$(CH_2)_2$ —$C_9$ aryl, —$(CH_2)_2$—$C_{10}$ aryl, —$(CH_2)_3$—$C_5$ aryl, —$(CH_2)_3$-$C_6$aryl, —$(CH_2)_3$—$C_7$ aryl, —$(CH_2)_3$—$C_5$ aryl, —$(CH_2)_3$—$C_9$ aryl, —$(CH_2)_3$—$C_{10}$ aryl, 5 membered heteroaryl, 6 membered heteroaryl, 7 membered heteroaryl, 8 membered heteroaryl, 9 membered heteroaryl, 10 membered heteroaryl, —$CH_2$-5 membered heteroaryl, —$CH_2$-6 membered heteroaryl, —$CH_2$-7 membered heteroaryl, —$CH_2$-8 membered heteroaryl, —$CH_2$-9 membered heteroaryl, —$CH_2$-10 membered heteroaryl, —$(CH_2)_2$-5 membered heteroaryl, —$(CH_2)_2$-6 membered heteroaryl, —$(CH_2)_2$-7 membered heteroaryl, —$(CH_2)_2$-8 membered heteroaryl, —$(CH_2)_2$-9 membered heteroaryl, —$(CH_2)_2$-10 membered heteroaryl, —$(CH_2)_3$-5 membered heteroaryl, —$(CH_2)_3$-6 membered heteroaryl, —$(CH_2)_3$-7 membered heteroaryl, —$(CH_2)_3$-8 membered heteroaryl, —$(CH_2)_3$-9 membered heteroaryl, and —$(CH_2)_3$-10 membered heteroaryl, and wherein said methyl, said ethyl, said propyl, said isopropyl, said methoxy, said ethoxy, said propoxy, said isopropoxy, said $C_5$ aryl, said $C_6$aryl, said $C_7$ aryl, said $C_8$ aryl, said $C_9$ aryl, said $C_{10}$ aryl, said —$CH_2$—$C_5$ aryl, said —$CH_2$—$C_6$aryl, said —$CH_2$—$C_7$ aryl, said —$CH_2$—$C_8$ aryl, said —$CH_2$—$C_9$ aryl, said —$CH_2$—$C_{10}$ aryl, said —$(CH_2)_2$—$C_8$ aryl, said —$(CH_2)_2$-$C_6$aryl, said —$(CH_2)_2$—$C_7$ aryl, said —$(CH_2)_2$—$C_5$ aryl, said —$(CH_2)_2$—$C_9$ aryl, said —$(CH_2)_2$—$C_{10}$ aryl, said —$(CH_2)_3$—$C_5$ aryl, said —$(CH_2)_3$-$C_6$aryl, said —$(CH_2)_3$—$C_7$ aryl, said —$(CH_2)_3$—$C_5$ aryl, said —$(CH_2)_3$—$C_9$ aryl, said —$(CH_2)_3$—$C_{10}$ aryl, said 5 membered heteroaryl, said 6 membered heteroaryl, said 7 membered heteroaryl, said 8 membered heteroaryl, said 9 membered heteroaryl, said 10 membered heteroaryl, said —$CH_2$-5 membered heteroaryl, said —$CH_2$-6 membered heteroaryl, said —$CH_2$-7 membered heteroaryl, said —$CH_2$-8 membered heteroaryl, said —$CH_2$-9 membered heteroaryl, said —$CH_2$-10 membered heteroaryl, said —$(CH_2)_2$-5 membered heteroaryl, said —$(CH_2)_2$-6 membered heteroaryl, said —$(CH_2)_2$-7 membered heteroaryl, said —$(CH_2)_2$-8 membered heteroaryl, said —$(CH_2)_2$-9 membered heteroaryl, said —$(CH_2)_2$-10 membered heteroaryl, said —$(CH_2)_3$-5 membered heteroaryl, said —$(CH_2)_3$-6 membered heteroaryl, said —$(CH_2)_3$-7 membered heteroaryl, said —$(CH_2)_3$-8 membered heteroaryl, said —$(CH_2)_3$-9 membered heteroaryl, and said —$(CH_2)_3$-10 membered heteroaryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —$NH(C_{1-6}$ alkyl), —$N(C_{1-3}alkyl)_2$, —S—$C_{1-3}$alkyl, carboxyl; and each of the heteroaryl independently optionally contains 1 or 2 heteroatoms selected from N, O or S;

or $R_{X1}$ and $R_{X2}$ together with the carbon atom to which they are attached form 3-membered carbocyclic ring, 4-membered carbocyclic ring, 5-membered carbocyclic ring, or 6-membered carbocyclic ring, 4 membered heterocyclyl, 5 membered heterocyclyl, 6 membered heterocyclyl, and each of the heterocyclyl independently optionally contains 1 or 2 heteroatoms selected from N or O;

each of which can be optional substituted with one or more substituents, which are independently selected from the group consisting of deuterium, —F, —Cl, —Br, —I, —$NH_2$, —CN, —OH, —$NO_2$, oxo, carboxyl, $C_{1-3}$alkoxy, $C_{1-3}$alkyl;

$R_{X3}$ is independently selected from the group consisting of hydrogen, deuterium, methyl, ethyl, propyl, isopropyl, tert-butyl, methoxy, ethoxy, propoxy, isopropoxy, $C_3$ cycloalkyl, $C_4$ cycloalkyl, $C_5$ cycloalkyl, $C_6$ cycloalkyl, —C(═O)—$CH_3$, —C(═O)—$CH_2CH_3$, —C(═O)—$CH_2CH_2CH_3$, —C(═O)—$CH(CH_3)_2$, —$CH_2$—$C_5$ aryl, —$(CH_2)_2$—$C_5$ aryl, —$(CH_2)_3$—$C_5$ aryl, —$CH_2$—$C_6$ aryl, —$(CH_2)_2$—$C_6$ aryl, —$(CH_2)_3$—$C_6$ aryl, —$CH_2$—$C_7$ aryl, —$(CH_2)_2$—$C_7$ aryl, —$(CH_2)_3$—$C_7$ aryl, —$CH_2$—$C_8$ aryl, —$(CH_2)_2$—$C_8$ aryl, —$(CH_2)_3$—$C_8$ aryl, —$CH_2$—$C_9$ aryl, —$(CH_2)_2$—$C_9$ aryl, —$(CH_2)_3$—$C_9$ aryl, —$CH_2$—$C_{10}$ aryl, —$(CH_2)_2$—$C_{10}$ aryl, —$(CH_2)_3$—$C_{10}$ aryl, wherein said methyl, said ethyl, said propyl, said isopropyl, said methoxy, said ethoxy, said propoxy, said isopropoxy, said $C_3$ cycloalkyl, said $C_4$ cycloalkyl, said $C_5$ cycloalkyl, said $C_6$ cycloalkyl, said —C(═O)—$CH_3$, said —C(═O)—$CH_2CH_3$, said —C(═O)—$CH_2CH_2CH_3$, said —C(═O)—$CH(CH_3)_2$, said —$CH_2$—$C_5$ aryl, said —$(CH_2)_2$—$C_5$ aryl, said —$(CH_2)_3$-$C_5$ aryl, said —$CH_2$-$C_6$ aryl, said —$(CH_2)_2$-$C_6$ aryl, said —$(CH_2)_3$-$C_6$ aryl, said —$CH_2$-$C_7$ aryl, said —$(CH_2)_2$-$C_7$ aryl, said —$(CH_2)_3$-$C_7$ aryl, said —$CH_2$-$C_8$ aryl, said —$(CH_2)_2$-$C_8$ aryl, said —$(CH_2)_3$-$C_8$ aryl, said —$CH_2$-$C_9$ aryl, said —$(CH_2)_2$-$C_9$ aryl, said —$(CH_2)_3$-$C_9$ aryl, said —$CH_2$-$C_{10}$ aryl, said —$(CH_2)_2$-$C_{10}$ aryl, and said —$(CH_2)_3$-$C_{10}$ aryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —$NH(C_{1-3}$ alkyl), —$N(C_{1-3}alkyl)_2$, carboxyl, 4-6 membered heterocyclyl,

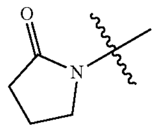

, $C_{6-10}$aryl, —C(═O)—$C_{1-3}$alkyl, —NH—C(═O)—$C_{1-3}$alkyl, —C(═O)—$NH_2$, —C(═O)—NH—$C_{1-3}$ alkyl, and —C(═O)—$N(C_{1-3}alkyl)_2$;

or $R_{X1}$ and $R_{X3}$ together with the carbon atom and the oxygen atom to which they are attached respectively form 4 membered heterocyclyl, 5 membered heterocyclyl, 6 membered heterocyclyl, 7 membered heterocyclyl, 8 membered heterocyclyl, 9 membered heterocyclyl, 10 membered heterocyclyl, wherein said 4 membered heterocyclyl, said 5 membered heterocyclyl, said 6 membered heterocyclyl, said 7 membered heterocyclyl, said 8 membered heterocyclyl, said 9 membered heterocyclyl, said 10 membered heterocyclyl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —$NH(C_{1-3}$ alkyl), —$N(C_{1-3}alkyl)_2$, carboxyl; and each of the heterocyclyl independently optionally contains 1 or 2 heteroatoms selected from N, O or S;

$R_5$ and $R_5$' are each independently selected from the group consisting of hydrogen, deuterium, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, $C_5$ aryl, $C_6$ aryl, $C_7$ aryl, $C_8$ aryl, $C_9$ aryl, $C_{10}$ aryl, 5 membered heteroaryl, 6 membered heteroaryl, 7 membered heteroaryl, 8 membered heteroaryl, 9 membered heteroaryl, 10 membered heteroaryl, 5 membered heterocyclyl, 6 membered heterocyclyl, 7 membered heterocyclyl, 8 membered heterocyclyl, 9 membered heterocyclyl, 10 membered heterocyclyl, and wherein said methyl, said ethyl, said propyl, said isopropyl, said methoxy, said ethoxy, said propoxy, said isopropoxy, said —$C_3$ cycloalkyl, said —$C_4$ cycloalkyl, said —$C_5$ cycloalkyl, said —$C_6$ cycloalkyl, said $C_5$ aryl, said $C_6$ aryl, said $C_7$ aryl, said $C_8$ aryl, said $C_9$ aryl, said $C_{10}$ aryl, said 5 membered heteroaryl, said 6 membered heteroaryl, said 7 membered heteroaryl, said 8 membered heteroaryl, said 9 membered heteroaryl, said 10 membered heteroaryl, said 5 membered heterocyclyl, said 6 membered heterocyclyl, said 7 membered heterocyclyl, said 8 membered heterocyclyl, said 9 membered heterocyclyl, said 10 membered heterocyclyl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl;

each of $R_6$ is independently selected from the group consisting of hydrogen, deuterium, methyl, ethyl, propyl, isopropyl, —$C_3$ cycloalkyl, —$C_4$ cycloalkyl, —$C_5$ cycloalkyl, —$C_6$ cycloalkyl, 5 membered heterocyclyl ring, 6 membered heterocyclyl ring, 7 membered heterocyclyl ring, 8 membered heterocyclyl ring, 9 membered heterocyclyl ring, 10 membered heterocyclyl ring, vinyl, allyl, —$C_3$ cycloalkenyl, —$C_4$ cycloalkenyl, —$C_5$ cycloalkenyl, —$C_6$ cycloalkenyl, and wherein said methyl, said ethyl, said propyl, said isopropyl, said —$C_3$ cycloalkyl, said —$C_4$ cycloalkyl, said —$C_5$ cycloalkyl, said —$C_6$ cycloalkyl, said 5 membered heterocyclyl ring, said 6 membered heterocyclyl ring, said 7 membered heterocyclyl ring, said 8 membered heterocyclyl ring, said 9 membered heterocyclyl ring, said 10 membered heterocyclyl ring, said vinyl, said allyl, said —$C_3$ cycloalkenyl, said —$C_4$ cycloalkenyl, said —$C_5$ cycloalkenyl, said —$C_6$ cycloalkenyl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl;

or $R_6$ together with the oxygen atom to which it is attached forms a purine or pyrimidine nucleoside;

each of $R_7$ is independent selected from the group consisting of hydrogen, deuterium, halogen, methyl, ethyl, propyl, isopropyl, $C_3$ cycloalkyl, $C_4$ cycloalkyl, $C_5$ cycloalkyl, $C_6$ cycloalkyl, 5-10 membered heterocyclyl ring, 5 membered heterocyclyl ring, 6 membered heterocyclyl ring, 7 membered heterocyclyl ring, 8 membered heterocyclyl ring, 9 membered heterocyclyl ring, 10 membered heterocyclyl ring, vinyl, allyl, $C_3$ cycloalkenyl, $C_4$ cycloalkenyl, $C_5$ cycloalkenyl, $C_6$ cycloalkenyl, $C_5$ aryl, $C_6$ aryl, $C_7$ aryl, $C_8$ aryl, $C_9$ aryl, $C_{10}$ aryl, 5 membered heteroaryl, 6 membered heteroaryl, 7 membered heteroaryl, 8 membered heteroaryl, 9 membered heteroaryl, 10 membered heteroaryl, and wherein said methyl, said ethyl, said propyl, said isopropyl, said $C_3$ cycloalkyl, said $C_4$ cycloalkyl, said $C_5$ cycloalkyl, said $C_6$ cycloalkyl, said 5-10 membered heterocyclyl ring, said 5 membered heterocyclyl ring, said 6 membered heterocyclyl ring, said 7 membered heterocyclyl ring, said 8 membered heterocyclyl ring, said 9 membered heterocyclyl ring, said 10 membered heterocyclyl ring, said vinyl, said allyl, said $C_3$ cycloalkenyl, said $C_4$ cycloalkenyl, said $C_5$ cycloalkenyl, said $C_6$ cycloalkenyl, said $C_5$ aryl, said $C_6$ aryl, said $C_7$ aryl, said $C_8$ aryl, said $C_9$ aryl, said $C_{10}$ aryl, said 5 membered heteroaryl, said 6 membered heteroaryl, said 7 membered heteroaryl, said 8 membered heteroaryl, said 9 membered heteroaryl, said 10 membered heteroaryl, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxyl;

$R_8$ and $R_9$ are each independently selected from the group consisting of $C_{1-3}$ alkyl, $C_{3-6}$ cycloalkyl, monosaccharide, acylated monosaccharide, $C_{5-10}$ aryl, and 5-10 membered heteroaryl, and wherein said $C_{1-3}$ alkyl, said $C_{3-6}$ cycloalkyl, said monosaccharide, said acylated monosaccharide, said $C_{5-10}$ aryl, and said 5-10 membered heteroaryl, can be optional substituted with one or more substituents, which are independently selected from the group consisting of deuterium, F, Cl, Br, I, —OH, oxo, —CN, —$C_{1-3}$alkyl, —$C_{1-3}$alkoxy, —$C_{3-6}$cycloalkyl, —$NH_2$, —NH($C_{1-3}$alkyl), —N($C_{1-3}$alkyl)$_2$, or carboxyl; or G is $C_5$ aryl, $C_6$ aryl, $C_7$ aryl, $C_8$ aryl, $C_9$ aryl, $C_{10}$ aryl, 5 membered heteroaryl, 6 membered heteroaryl, 7 membered heteroaryl, 8 membered heteroaryl, 9 membered heteroaryl, or 10 membered heteroaryl, wherein said $C_5$ aryl, said $C_6$ aryl, said $C_7$ aryl, said $C_8$ aryl, said $C_9$ aryl, said $C_{10}$ aryl, said 5 membered heteroaryl, said 6 membered heteroaryl, said 7 membered heteroaryl, said 8 membered heteroaryl, said 9 membered heteroaryl, or said 10 membered heteroaryl, can be optional substituted with one or more substituents, which are independently selected from the group consisting of deuterium, F, Cl, Br, I, —OH, oxo, —CN, —$C_{1-3}$alkyl, —$C_{1-3}$alkoxy, —$C_{3-6}$cycloalkyl, —$NH_2$, —NH($C_{1-3}$alkyl), —N($C_{1-3}$alkyl)$_2$, carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein X is selected from the group consisting of hydrogen, deuterium, methyl, ethyl, propyl, isopropyl, —C(═O)-G, —C(═O)—W—($CR_{X1}R_{X2}$)$_m$—O—$R_{X3}$, —C(═O)—W—($CR_{X1}R_{X2}$)$_m$—S—$R_{X3}$, C(═O)—W—($CR_{X1}R_{X2}$)$_m$—SO—$R_{X3}$, C(═O)—W—($CR_{X1}R_{X2}$)$_m$—$SO_2$—$R_{X3}$, —C(═O)—W—($CR_{X1}R_{X2}$)$_m$-G, —C(═O)—W—($CR_{X1}R_{X2}$)$_m$—$NR_5R_5$', —P(═O)($OR_6$)$_p$($NHR_7$)$_q$, —C(═O)—W—($CR_{X1}R_{X2}$)$_m$-G-O—C(═O)—$R_8$, —C(═O)—W—($CR_{X1}R_{X2}$)$_m$-G-O—$R_8$, —C(═O)—O—($CR_{X1}R_{X2}$)$_m$—O—C(═O)—$R_9$, —C(═O)—O—$R_7$, —C(═O)—W—($CR_{X1}R_{X2}$)$_m$-G-O—C(═O)-G, and —C(═O)—W—($CR_{X1}R_{X2}$)$_m$-G-$NR_5R_5$';

W is oxygen or a bond;

m is selected from 1, 2 or 3;

p and q are each independently selected from 0, 1 or 2 provided that the sum of p and q is 2;

$R_{X1}$ and $R_{X2}$ are each independently selected from the group consisting of hydrogen, deuterium, halogen, CN, OH, methyl, ethyl, propyl, isopropyl, methoxy, ethoxy, propoxy, isopropoxy, butyl, sec-butyl, isobutyl, tert-butyl, $C_4$ cycloalkyl, $C_5$ cycloalkyl, $C_6$ cycloalkyl, —C(═O)—$CH_3$, —C(═O)—$CH_2CH_3$, —C(═O)—$CH_2CH_2CH_3$, —C(═O)—CH($CH_3$)$_2$, $C_5$ aryl, $C_6$ aryl, $C_7$ aryl, $C_8$ aryl, $C_9$ aryl, $C_{10}$ aryl, —$CH_2$—$C_5$ aryl, —$CH_2$—$C_6$aryl, —$CH_2$—$C_7$ aryl, —$CH_2$—$C_5$ aryl, —$CH_2$—$C_9$ aryl, —$CH_2$—$C_{10}$ aryl, $-(CH_2)_2-C_5$ aryl, $-(CH_2)_2-C_6$aryl, $-(CH_2)_2-C_7$ aryl, $-(CH_2)_2-C_5$ aryl, $-(CH_2)_2-C_9$ aryl, $-(CH_2)_2-C_{10}$ aryl, $-(CH_2)_3-C_5$ aryl, $-(CH_2)_3-C_6$aryl, $-(CH_2)_3-C_7$ aryl, $-(CH_2)_3-C_8$ aryl, $-(CH_2)_3-C_9$ aryl, $-(CH_2)_3-C_{10}$ aryl, 5 membered heteroaryl, 6 membered heteroaryl, 7 membered heteroaryl, 8 membered heteroaryl, 9 membered heteroaryl, 10 membered heteroaryl, $-CH_2$-5 membered heteroaryl, $-CH_2$-6 membered heteroaryl, $-CH_2$-7 membered heteroaryl, $-CH_2$-8 membered heteroaryl, $-CH_2$-9 membered heteroaryl, $-CH_2$-10 membered heteroaryl, $-(CH_2)_2$-5 membered heteroaryl, $-(CH_2)_2$-6 membered heteroaryl, $-(CH_2)_2$-7 membered heteroaryl, $-(CH_2)_2$-8 membered heteroaryl, $-(CH_2)_2$-9 membered heteroaryl, $-(CH_2)_2$-10 membered heteroaryl, $-(CH_2)_3$-5 membered heteroaryl, $-(CH_2)_3$-6 membered heteroaryl, $-(CH_2)_3$-7 membered heteroaryl, $-(CH_2)_3$-8 membered heteroaryl, $-(CH_2)_3$-9 membered heteroaryl, and $-(CH_2)_3$-10 membered heteroaryl, and wherein said methyl, said ethyl, said propyl, said isopropyl, said methoxy, said ethoxy, said propoxy, said isopropoxy, said $C_5$ aryl, said $C_6$aryl, said $C_7$ aryl, said $C_8$ aryl, said $C_9$ aryl, said $C_{10}$ aryl, said $-CH_2-C_5$ aryl, said $-CH_2-C_6$aryl, said $-CH_2-C_7$ aryl, said $-CH_2-C_8$ aryl, said $-CH_2-C_9$ aryl, said $-CH_2-C_{10}$ aryl, said $-(CH_2)_2-C_5$ aryl, said $-(CH_2)_2-C_6$aryl, said $-(CH_2)_2-C_7$ aryl, said $-(CH_2)_2-C_8$ aryl, said $-(CH_2)_2-C_9$ aryl, said $-(CH_2)_2-C_{10}$ aryl, said $-(CH_2)_3-C_5$ aryl, said $-(CH_2)_3-C_6$aryl, said $-(CH_2)_3-C_7$ aryl, said $-(CH_2)_3-C_8$ aryl, said $-(CH_2)_3-C_9$ aryl, said $-(CH_2)_3-C_{10}$ aryl, said 5 membered heteroaryl, said 6 membered heteroaryl, said 7 membered heteroaryl, said 8 membered heteroaryl, said 9 membered heteroaryl, said 10 membered heteroaryl, said $-CH_2$-5 membered heteroaryl, said $-CH_2$-6 membered heteroaryl, said $-CH_2$-7 membered heteroaryl, said $-CH_2$-8 membered heteroaryl, said $-CH_2$-9 membered heteroaryl, said $-CH_2$-10 membered heteroaryl, said $-(CH_2)_2$-5 membered heteroaryl, said $-(CH_2)_2$-6 membered heteroaryl, said $-(CH_2)_2$-7 membered heteroaryl, said $-(CH_2)_2$-8 membered heteroaryl, said $-(CH_2)_2$-9 membered heteroaryl, said $-(CH_2)_2$-10 membered heteroaryl, said $-(CH_2)_3$-5 membered heteroaryl, said $-(CH_2)_3$-6 membered heteroaryl, said $-(CH_2)_3$-7 membered heteroaryl, said $-(CH_2)_3$-8 membered heteroaryl, said $-(CH_2)_3$-9 membered heteroaryl, and said $-(CH_2)_3$-10 membered heteroaryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, $-C_3$ cycloalkyl, $-C_4$ cycloalkyl, $-C_5$ cycloalkyl, $-C_6$ cycloalkyl, $-NH_2$, $-NHCH_3$, $-NHCH_2CH_3$, $-NHCH_2CH_2CH_3$, $-NHCH(CH_3)_2$, $-N(CH_3)_2$, $-N(CH_2CH_3)_2$, $-N(CH_2CH_2CH_3)_2$, $-N(CH(CH_3)_2)_2$, —NH-cyclopropyl, —NH-cyclobutyl, —NH-cyclopentyl, —NH-cyclohexyl, —S-methyl and carboxyl; and each of the heteroaryl independently optionally contains 1 or 2 heteroatoms selected from N, O or S;

or $R_{X1}$ and $R_{X2}$ together with the carbon atom to which they are attached form 3-membered carbocyclic ring, 4-membered carbocyclic ring, 5-membered carbocyclic ring, 4 membered heterocyclyl, 5 membered heterocyclyl, 6 membered heterocyclyl, and each of the heterocyclyl independently optionally contains 1 or 2 heteroatoms selected from N or O; each of which can be optional substituted with one or more substituents, which are independently selected from the group consisting of deuterium, —F, —Cl, —Br, —I, $-NH_2$, —CN, —OH, $-NO_2$, oxo, carboxyl, methyl, ethyl, propyl, isopropyl, methoxy, ethoxy, propoxy, isopropoxy;

$R_{X3}$ is independently selected from the group consisting of hydrogen, deuterium, methyl, ethyl, propyl, isopropyl, tert-butyl, methoxy, ethoxy, propoxy, isopropoxy, $C_3$ cycloalkyl, $C_4$ cycloalkyl, $C_5$ cycloalkyl, $C_6$ cycloalkyl, $-C(=O)-CH_3$, $-C(=O)-CH_2CH_3$, $-C(=O)-CH_2CH_2CH_3$, $-C(=O)-CH(CH_3)_2$, $-CH_2-C_5$ aryl, $-(CH_2)_2-C_6$ aryl, $-(CH_2)_3-C_5$ aryl, $-CH_2-C_6$ aryl, $-(CH_2)_2-C_6$ aryl, $-(CH_2)_3-C_6$ aryl, $-CH_2-C_7$ aryl, $-(CH_2)_2-C_7$ aryl, $-(CH_2)_3-C_7$ aryl, $-CH_2-C_5$ aryl, $-(CH_2)_2-C_6$ aryl, $-(CH_2)_3-C_8$ aryl, $-CH_2-C_9$ aryl, $-(CH_2)_2-C_9$ aryl, $-(CH_2)_3-C_9$ aryl, $-CH_2-C_{10}$ aryl, $-(CH_2)_2-C_{10}$ aryl, $-(CH_2)_3-C_{10}$ aryl, wherein said methyl, said ethyl, said propyl, said isopropyl, said methoxy, said ethoxy, said propoxy, said isopropoxy, said $C_3$ cycloalkyl, said $C_4$ cycloalkyl, said $C_5$ cycloalkyl, said $C_6$ cycloalkyl, said $-C(=O)-CH_3$, said $-C(=O)-CH_2CH_3$, said $-C(=O)-CH_2CH_2CH_3$, said $-C(=O)-CH(CH_3)_2$, said $-CH_2-C_5$ aryl, said $-(CH_2)_2-C_5$ aryl, said $-(CH_2)_3-C_5$ aryl, said $-CH_2-C_6$ aryl, said $-(CH_2)_2-C_6$ aryl, said $-(CH_2)_3-C_6$ aryl, said $-CH_2-C_7$ aryl, said $-(CH_2)_2-C_7$ aryl, said $-(CH_2)_3-C_7$ aryl, said $-CH_2-C_5$ aryl, said $-(CH_2)_2-C_5$ aryl, said $-(CH_2)_3-C_8$ aryl, said $-CH_2-C_9$ aryl, said $-(CH_2)_2-C_9$ aryl, said $-(CH_2)_3-C_9$ aryl, said $-CH_2-C_{10}$ aryl, said $-(CH_2)_2-C_{10}$ aryl, and said $-(CH_2)_3-C_{10}$ aryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, $-C_3$ cycloalkyl, $-C_4$ cycloalkyl, $-C_5$ cycloalkyl, $-C_6$ cycloalkyl, 4 membered heterocyclyl, 5 membered heterocyclyl, 6 membered heterocyclyl,

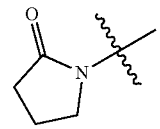
, $-C_6$aryl, $-C(=O)-CH_3$, $-NH-C(=O)-CH_3$, $-C(=O)-NH_2$, $-C(=O)-NH-CH_3$, $-C(=O)-N(CH_3)_2$, $-NH_2$, $-NHCH_3$, $-NHCH_2CH_3$, $-NHCH_2CH_2CH_3$, $-NHCH(CH_3)_2$, $-N(CH_3)_2$, $-N(CH_2CH_3)_2$, $-N(CH_2CH_2CH_3)_2$, $-N(CH(CH_3)_2)_2$, and carboxyl;

or $R_{X1}$ and $R_{X3}$ together with the carbon atom and the oxygen atom to which they are attached respectively form 4 membered heterocyclyl, 5 membered heterocyclyl, 6 membered heterocyclyl, 7 membered heterocyclyl, 8 membered heterocyclyl, 9 membered heterocyclyl, 10 membered heterocyclyl, wherein said 4 membered heterocyclyl, said 5 membered heterocyclyl, said 6 membered heterocyclyl, said 7 membered heterocyclyl, said 8 membered heterocyclyl, said 9 membered heterocyclyl, said 10 membered heterocyclyl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl; and each of the heterocyclyl independently optionally contains 1 or 2 heteroatoms selected from N, O or S;

$R_5$ and $R_5$' are each independently selected from the group consisting of hydrogen, deuterium, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, $C_5$ aryl, $C_6$ aryl, $C_7$ aryl, $C_8$ aryl, $C_9$ aryl, $C_{10}$ aryl, 5 membered heteroaryl, 6 membered heteroaryl, 7 membered heteroaryl, 8 membered heteroaryl, 9 membered heteroaryl, 10 membered heteroaryl, 5 membered heterocyclyl, 6 membered heterocyclyl, 7 membered heterocyclyl, 8 membered heterocyclyl, 9 membered heterocyclyl, 10 membered heterocyclyl, and wherein said methyl, said ethyl, said propyl, said isopropyl, said methoxy, said ethoxy, said propoxy, said isopropoxy, said —$C_3$ cycloalkyl, said —$C_4$ cycloalkyl, said —$C_5$ cycloalkyl, said —$C_6$ cycloalkyl, said $C_5$ aryl, said $C_6$ aryl, said $C_7$ aryl, said $C_8$ aryl, said $C_9$ aryl, said $C_{10}$ aryl, said 5 membered heteroaryl, said 6 membered heteroaryl, said 7 membered heteroaryl, said 8 membered heteroaryl, said 9 membered heteroaryl, said 10 membered heteroaryl, said 5 membered heterocyclyl, said 6 membered heterocyclyl, said 7 membered heterocyclyl, said 8 membered heterocyclyl, said 9 membered heterocyclyl, said 10 membered heterocyclyl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl;

each of $R_6$ is independently selected from the group consisting of hydrogen, deuterium, methyl, ethyl, propyl, isopropyl, —$C_3$ cycloalkyl, —$C_4$ cycloalkyl, —$C_5$ cycloalkyl, —$C_6$ cycloalkyl, 5 membered heterocyclyl ring, 6 membered heterocyclyl ring, 7 membered heterocyclyl ring, 8 membered heterocyclyl ring, 9 membered heterocyclyl ring, 10 membered heterocyclyl ring, vinyl, allyl, —$C_3$ cycloalkenyl, —$C_4$ cycloalkenyl, —$C_5$ cycloalkenyl, —$C_6$ cycloalkenyl, and wherein said methyl, said ethyl, said propyl, said isopropyl, said —$C_3$ cycloalkyl, said —$C_4$ cycloalkyl, said —$C_5$ cycloalkyl, said —$C_6$ cycloalkyl, said 5 membered heterocyclyl ring, said 6 membered heterocyclyl ring, said 7 membered heterocyclyl ring, said 8 membered heterocyclyl ring, said 9 membered heterocyclyl ring, said 10 membered heterocyclyl ring, said vinyl, said allyl, said —$C_3$ cycloalkenyl, said —$C_4$ cycloalkenyl, said —$C_5$ cycloalkenyl, said —$C_6$ cycloalkenyl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl;

or $R_6$ together with the oxygen atom to which it is attached forms a purine or pyrimidine nucleoside;

each of $R_7$ is independent selected from the group consisting of hydrogen, deuterium, halogen, methyl, ethyl, propyl, isopropyl, $C_3$ cycloalkyl, $C_4$ cycloalkyl, $C_5$ cycloalkyl, $C_6$ cycloalkyl, 5-10 membered heterocyclyl ring, 5 membered heterocyclyl ring, 6 membered heterocyclyl ring, 7 membered heterocyclyl ring, 8 membered heterocyclyl ring, 9 membered heterocyclyl ring, 10 membered heterocyclyl ring, vinyl, allyl, $C_3$ cycloalkenyl, $C_4$ cycloalkenyl, $C_5$ cycloalkenyl, $C_6$ cycloalkenyl, $C_5$ aryl, $C_6$ aryl, $C_7$ aryl, $C_8$ aryl, $C_9$ aryl, $C_{10}$ aryl, 5 membered heteroaryl, 6 membered heteroaryl, 7 membered heteroaryl, 8 membered heteroaryl, 9 membered heteroaryl, 10 membered heteroaryl, and wherein said methyl, said ethyl, said propyl, said isopropyl, said $C_3$ cycloalkyl, said $C_4$ cycloalkyl, said $C_5$ cycloalkyl, said $C_6$ cycloalkyl, said 5-10 membered heterocyclyl ring, said 5 membered heterocyclyl ring, said 6 membered heterocyclyl ring, said 7 membered heterocyclyl ring, said 8 membered heterocyclyl ring, said 9 membered heterocyclyl ring, said 10 membered heterocyclyl ring, said vinyl, said allyl, said $C_3$ cycloalkenyl, said $C_4$ cycloalkenyl, said $C_5$ cycloalkenyl, said $C_6$ cycloalkenyl, said $C_5$ aryl, said $C_6$ aryl, said $C_7$ aryl, said $C_8$ aryl, said $C_9$ aryl, said $C_{10}$ aryl, said 5 membered heteroaryl, said 6 membered heteroaryl, said 7 membered heteroaryl, said 8 membered heteroaryl, said 9 membered heteroaryl, said 10 membered heteroaryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl;

$R_8$ and $R_9$ are each independently selected from the group consisting of $C_{1-3}$ alkyl, $C_{3-6}$ cycloalkyl, monosaccharide, acylated monosaccharide, $C_{5-10}$ aryl, and 5-10 membered heteroaryl, and wherein said $C_{1-3}$ alkyl, said $C_{3-6}$ cycloalkyl, said monosaccharide, said acylated monosaccharide, said $C_{5-10}$ aryl, and said 5-10 membered heteroaryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl; or G is $C_5$ aryl, $C_6$ aryl, $C_7$ aryl, $C_8$ aryl, $C_9$ aryl, $C_{10}$ aryl, 5 membered heteroaryl, 6 membered heteroaryl, 7 membered heteroaryl, 8 membered heteroaryl, 9 membered heteroaryl, or 10 membered heteroaryl, wherein said $C_5$ aryl, said $C_6$ aryl, said $C_7$ aryl, said $C_8$ aryl, said $C_9$ aryl, said $C_{10}$ aryl, said 5 membered heteroaryl, said 6 membered heteroaryl, said 7 membered heteroaryl, said 8 membered heteroaryl, said 9 membered heteroaryl, or said 10 membered heteroaryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein X is —C(═O)—W—$(CR_{X1}R_{X2})_m$—O—$R_{X3}$;

W is a bond;

m is 1 or 2;

$R_{X1}$ and $R_{X2}$ are each independently selected from the group consisting of hydrogen, deuterium, halogen, CN, OH, methyl, ethyl, propyl, isopropyl, methoxy, ethoxy, propoxy, isopropoxy, butyl, sec-butyl, isobutyl, tert-butyl, $C_4$ cycloalkyl, $C_5$ cycloalkyl, $C_6$ cycloalkyl, —C(═O)—$CH_3$, —C(═O)—$CH_2CH_3$, —C(═O)—$CH_2CH_2CH_3$, —C(═O)—$CH(CH_3)_2$, $C_5$ aryl, $C_6$aryl, $C_7$ aryl, $C_8$ aryl, $C_9$ aryl, $C_{10}$ aryl, —$CH_2$—$C_5$ aryl, —$CH_2$—$C_6$aryl, —$CH_2$—$C_7$ aryl, —$CH_2$—$C_8$ aryl, —$CH_2$—$C_9$ aryl, —$CH_2$—$C_{10}$ aryl, —$(CH_2)_2$—$C_5$ aryl, —$(CH_2)_2$-$C_6$aryl, —$(CH_2)_2$ —$C_7$ aryl, —$(CH_2)_2$—$C_8$ aryl, —$(CH_2)_2$ —$C_9$ aryl, —$(CH_2)_2$—$C_{10}$ aryl, —$(CH_2)_3$—$C_5$ aryl, —$(CH_2)_3$-$C_6$aryl, —$(CH_2)_3$—$C_7$ aryl, —$(CH_2)_3$—$C_8$ aryl, —$(CH_2)_3$—$C_9$ aryl, —$(CH_2)_3$—$C_{10}$ aryl, 5 membered heteroaryl, 6 membered heteroaryl, 7 membered heteroaryl, 8 membered heteroaryl, 9 membered heteroaryl, 10 membered heteroaryl, —$CH_2$-5 membered heteroaryl, —$CH_2$-6 membered heteroaryl, —$CH_2$-7 membered heteroaryl, —$CH_2$-8 membered heteroaryl, —$CH_2$-9 membered heteroaryl, —$CH_2$-10 membered heteroaryl, —$(CH_2)_2$-5 membered heteroaryl, —$(CH_2)_2$-6 membered heteroaryl, —$(CH_2)_2$-7 membered heteroaryl, —$(CH_2)_2$-8 membered heteroaryl, —$(CH_2)_2$-9 membered heteroaryl, —$(CH_2)_2$-10 membered heteroaryl, —$(CH_2)_3$-5 membered heteroaryl, —$(CH_2)_3$-6 membered heteroaryl, —$(CH_2)_3$-7 membered heteroaryl, —$(CH_2)_3$-8 membered heteroaryl, —$(CH_2)_3$-9 membered heteroaryl, and —$(CH_2)_3$-10 membered heteroaryl, and wherein said methyl, said ethyl, said propyl, said isopropyl, said methoxy, said ethoxy, said propoxy, said isopropoxy, said $C_5$ aryl, said $C_6$aryl, said $C_7$ aryl, said $C_8$ aryl, said $C_9$ aryl, said $C_{10}$ aryl, said —$CH_2$—$C_5$ aryl, said —$CH_2$—$C_6$aryl, said —$CH_2$—$C_7$ aryl, said —$CH_2$—$C_8$ aryl, said —$CH_2$—$C_9$ aryl, said —$CH_2$—$C_{10}$ aryl, said —$(CH_2)_2$—$C_5$ aryl, said —$(CH_2)_2$-$C_6$aryl, said —$(CH_2)_2$—$C_7$ aryl, said —$(CH_2)_2$—$C_8$ aryl, said —$(CH_2)_2$—$C_9$ aryl, said —$(CH_2)_2$—$C_{10}$ aryl, said —$(CH_2)_3$—$C_5$ aryl, said —$(CH_2)_3$-$C_6$aryl, said —$(CH_2)_3$—$C_7$ aryl, said —$(CH_2)_3$—$C_8$ aryl, said —$(CH_2)_3$—$C_9$ aryl, said —$(CH_2)_3$—$C_{10}$ aryl, said 5 membered heteroaryl, said 6 membered heteroaryl, said 7 membered heteroaryl, said 8 membered heteroaryl, said 9 membered heteroaryl, said 10 membered heteroaryl, said —$CH_2$-5 membered heteroaryl, said —$CH_2$-6 membered heteroaryl, said —$CH_2$-7 membered heteroaryl, said —$CH_2$-8 membered heteroaryl, said —$CH_2$-9 membered heteroaryl, said —$CH_2$-10 membered heteroaryl, said —$(CH_2)_2$-5 membered heteroaryl, said —$(CH_2)_2$-6 membered heteroaryl, said —$(CH_2)_2$-7 membered heteroaryl, said —$(CH_2)_2$-8 membered heteroaryl, said —$(CH_2)_2$-9 membered heteroaryl, said —$(CH_2)_2$-10 membered heteroaryl, said —$(CH_2)_3$-5 membered heteroaryl, said —$(CH_2)_3$-6 membered heteroaryl, said —$(CH_2)_3$-7 membered heteroaryl, said —$(CH_2)_3$-8 membered heteroaryl, said —$(CH_2)_3$-9 membered heteroaryl, and said —$(CH_2)_3$-10 membered heteroaryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, —NH—cyclopropyl, —NH-cyclobutyl, —NH-cyclopentyl, —NH-cyclohexyl, —S-methyl and carboxyl; and each of the heteroaryl independently optionally contains 1 or 2 heteroatoms selected from N, O or S;

or $R_{X1}$ and $R_{X2}$ together with the carbon atom to which they are attached form 3-membered carbocyclic ring, 4-membered carbocyclic ring, 5-membered carbocyclic ring, 4 membered heterocyclyl, 5 membered heterocyclyl, 6 membered heterocyclyl, and each of the heterocyclyl independently optionally contains 1 or 2 heteroatoms selected from N or O; each of which can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy; or $R_{X3}$ is independently selected from the group consisting of hydrogen, deuterium, methyl, ethyl, propyl, isopropyl, tert-butyl, methoxy, ethoxy, propoxy, isopropoxy, $C_3$ cycloalkyl, $C_4$ cycloalkyl, $C_5$ cycloalkyl, $C_6$ cycloalkyl, —C(═O)—$CH_3$, —C(═O)—$CH_2CH_3$, —C(═O)—$CH_2CH_2CH_3$, —C(═O)—$CH(CH_3)_2$, —$CH_2$-$C_5$ aryl, —$(CH_2)_2$-$C_5$ aryl, —$(CH_2)_3$-$C_5$ aryl, —$CH_2$-$C_6$ aryl, —$(CH_2)_2$-$C_6$ aryl, —$(CH_2)_3$—$C_6$ aryl, —$CH_2$-$C_7$ aryl, —$(CH_2)_2$-$C_7$ aryl, —$(CH_2)_3$-$C_7$ aryl, —$CH_2$-$C_8$ aryl, —$(CH_2)_2$-$C_8$ aryl, —$(CH_2)_3$—$C_8$ aryl, —$CH_2$-$C_9$ aryl, —$(CH_2)_2$-$C_9$ aryl, —$(CH_2)_3$-$C_9$ aryl, —$CH_2$-$C_{10}$ aryl, —$(CH_2)_2$-$C_{10}$ aryl, —$(CH_2)_3$—$C_{10}$ aryl, wherein said methyl, said ethyl, said propyl, said isopropyl, said methoxy, said ethoxy, said propoxy, said isopropoxy, said $C_3$ cycloalkyl, said $C_4$ cycloalkyl, said $C_5$ cycloalkyl, said $C_6$ cycloalkyl, said —C(═O)—$CH_3$, said —C(═O)—$CH_2CH_3$, said —C(═O)—$CH_2CH_2CH_3$, said —C(═O)—$CH(CH_3)_2$, said —$CH_2$-$C_5$ aryl, said —$(CH_2)_2$-$C_5$ aryl, said —$(CH_2)_3$-$C_5$ aryl, said —$CH_2$-$C_6$ aryl, said —$(CH_2)_2$-$C_6$ aryl, said —$(CH_2)_3$-$C_6$ aryl, said —$CH_2$-$C_7$ aryl, said —$(CH_2)_2$-$C_7$ aryl, said —$(CH_2)_3$-$C_7$ aryl, said —$CH_2$-$C_8$ aryl, said —$(CH_2)_2$-$C_8$ aryl, said —$(CH_2)_3$-$C_8$ aryl, said —$CH_2$-$C_9$ aryl, said —$(CH_2)_2$-$C_9$ aryl, said —$(CH_2)_3$-$C_9$ aryl, said —$CH_2$-$C_{10}$ aryl, said —$(CH_2)_2$-$C_{10}$ aryl, and said —$(CH_2)_3$-$C_{10}$ aryl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, 4 membered heterocyclyl, 5 membered heterocyclyl, 6 membered heterocyclyl,

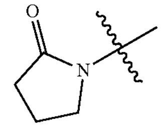,

—$C_6$aryl, —C(═O)—$CH_3$, —NH—C(═O)—$CH_3$, —C(═O)—$NH_2$, —C(═O)—NH—$CH_3$, —C(═O)—$N(CH_3)_2$, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl;

or $R_{X1}$ and $R_{X3}$ together with the carbon atom and the oxygen atom to which they are attached respectively form 4 membered heterocyclyl, 5 membered heterocyclyl, 6 membered heterocyclyl, 7 membered heterocyclyl, 8 membered heterocyclyl, 9 membered heterocyclyl, 10 membered heterocyclyl, wherein said 4 membered heterocyclyl, said 5 membered heterocyclyl, said 6 membered heterocyclyl, said 7 membered heterocyclyl, said 8 membered heterocyclyl, said 9 membered heterocyclyl, said 10 membered heterocyclyl, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl; and each of the heterocyclyl independently optionally contains 1 or 2 heteroatoms selected from N, O or S.

In some embodiments of the compound of Formula I, I-A, I-B, the pharmaceutically acceptable salt thereof, the stereoisomer thereof, the tautomer thereof, and the isotopic substitution thereof of the present invention, wherein X is —C(═O)—W—$(CR_{X1}R_{X2})_m$—O—$R_{X3}$;

W is a bond;

m is 1 or 2;

$R_{X1}$ and $R_{X2}$ are each independently selected from the group consisting of hydrogen, deuterium, CN, $CF_3$, methyl, ethyl, propyl, isopropyl, methoxy, ethoxy, propoxy, isopropoxy, butyl, sec-butyl, iso-butyl, tert-butyl, cyclobutyl, cyclopentyl, —C(O)—$CH_3$,

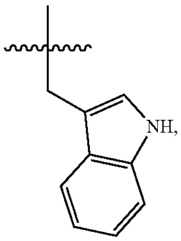 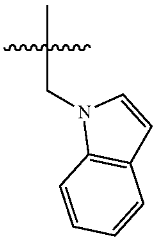, 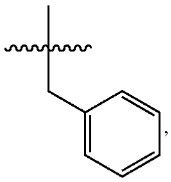,

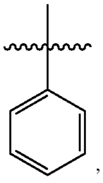, 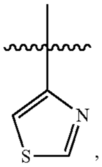, 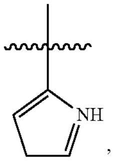, 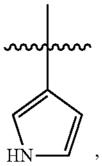, 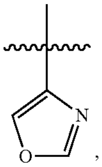,

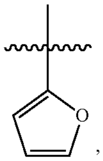, 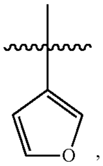, 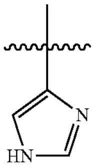, 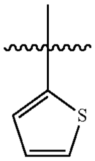, 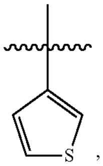,

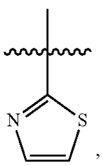, 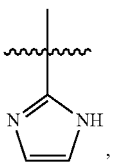, 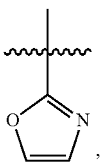, 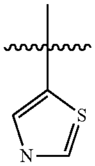, 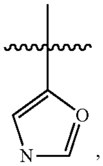,

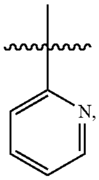 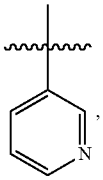, 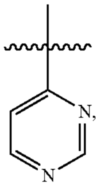 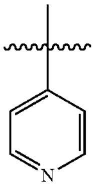, 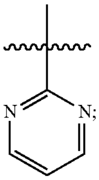;

and each of which is independently optionally substituted with deuterium, —F, —Cl, —Br, —I, —$NH_2$, —CN, —OH, oxo, carboxyl, methyl, ethyl, propyl, isopropyl, methoxy, ethoxy, propoxy, isopropoxy, cyclopropyl, cyclobutyl, cyclopentyl, cyclohexyl, —NHmethyl, —NHethyl, —NHpropyl, —NHcyclopropyl, —NHisopropyl, —$N(CH_3)_2$, —NH-cyclobutyl, —NH— cyclopentyl, —NH-cyclohexyl, or —S-methyl;

or $R_{X1}$ and $R_{X2}$ together with the carbon atom to which they are attached form

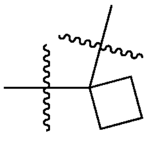, 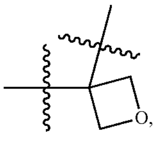 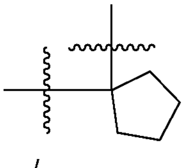,

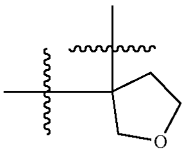, 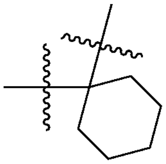, or

-continued

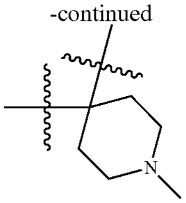

;

$R_{X3}$ is independently selected from the group consisting of hydrogen, methyl, ethyl, isopropyl, tert-butyl, $—CD_3$, $—C(═O)—CH_2—CN$, $—C(═O)—C(CH_3)_3$, $—C(═O)—CH_3$, $—C(═O)—CH_2CH_3$, $—C(═O)—NH—CH_3$, $—C(═O)—CH_2—N(CH_3)_2$, $—CH_2—C(═O)—CH_3$, $—CH_2—C(═O)—NHCH_3$, $—CH_2—C(═O)—N(CH_3)_2$, $—CH_2—NH_2$, $—CH_2—NH—CH_3$, $—CH_2CH_2—OH$, $—CH_2CH_2—CN$, $—CH_2—CN$, $—CH_2CH_2—C(═O)—NH_2$, $—CH_2CH_2—C(═O)—NH—CH_3$, $—CH_2CH_2—NH—C(═O)—CH_3$,

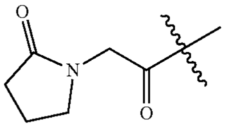
,
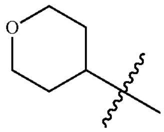
,
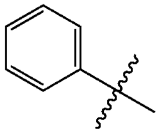
,
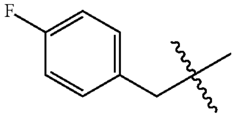
and
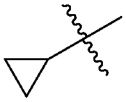
;

or $R_{X1}$ and $R_{X3}$ together with the carbon atom and the oxygen atom to which they are attached respectively form

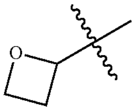
,
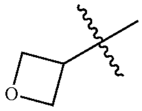
,
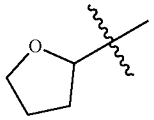
,
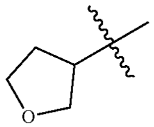
,
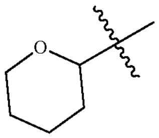
,
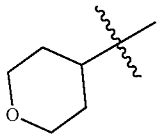
,
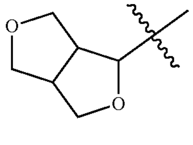
,
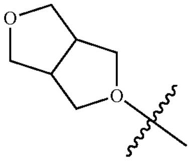
or
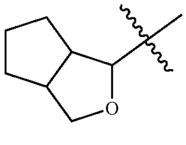
.

In some embodiments of the compound of Formula I, I-A, I-B, the pharmaceutically acceptable salt thereof, the stereoisomer thereof, the tautomer thereof, and the isotopic substitution thereof of the present invention, wherein X is $—C(═O)—CR_{X1}R_{X2}—O—R_{X3}$;

$R_{X1}$ and $R_{X2}$ are each independently selected from the group consisting of hydrogen, deuterium, CN, $CF_3$, methyl, ethyl, propyl, isopropyl, methoxy, ethoxy, propoxy, isopropoxy, butyl, sec-butyl, iso-butyl, tert-butyl, cyclobutyl, cyclopentyl, $—C(═O)—CH_3$, $—CH_2—$ cyclopropyl, $—CH_2—$ cyclobutyl, $—CH_2$-cyclopentyl, $—CH_2$-cyclohexyl,

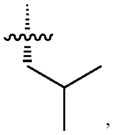
,
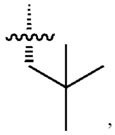
,
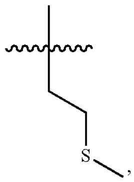
,
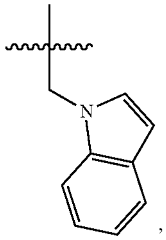
,
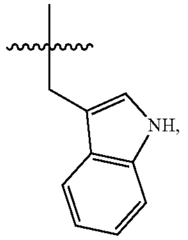
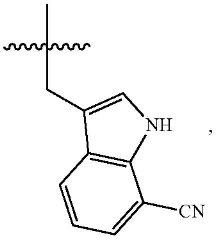
,
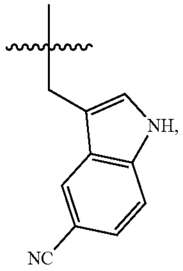
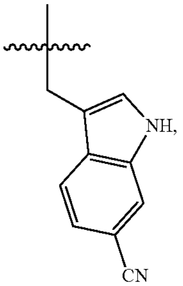
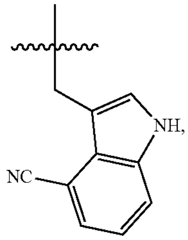
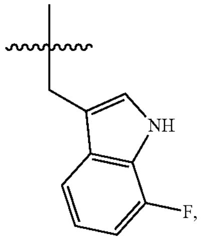
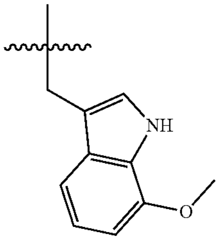
,
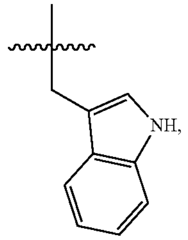
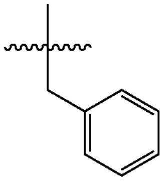
,
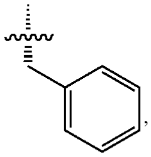
, -continued

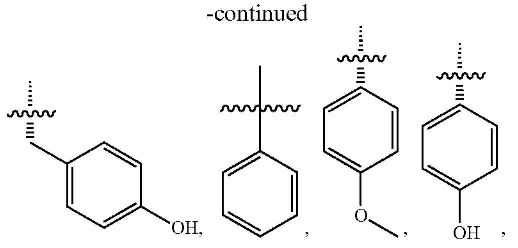

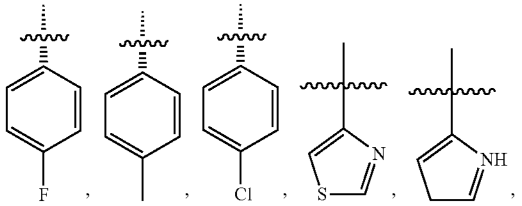

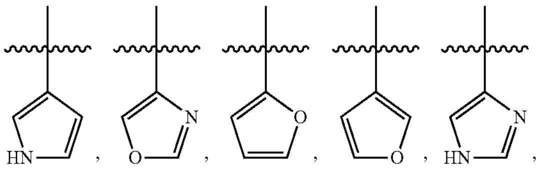

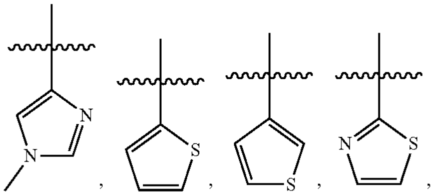

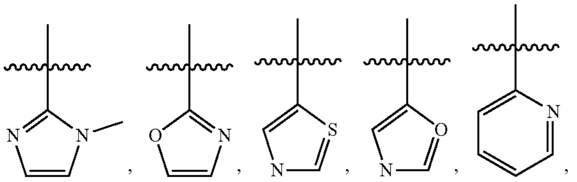

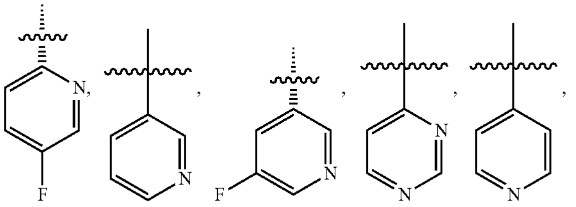

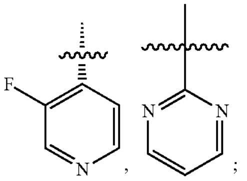

$R_{X3}$ is independently selected from the group consisting of hydrogen, methyl, ethyl, isopropyl, tert-butyl, $-CD_3$, $-C(=O)-CH_2-CN$, $-C(=O)-C(CH_3)_3$, $-C(=O)-CH_3$, $-C(=O)-CH_2CH_3$,

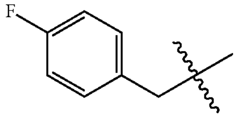

,

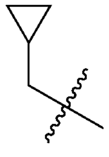

or

-continued

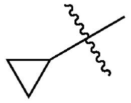

.

In some embodiments of the compound of Formula I, I-A, I-B, the pharmaceutically acceptable salt thereof, the stereoisomer thereof, the tautomer thereof, and the isotopic substitution thereof of the present invention, wherein $R_2$ is selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, halogen, —OH, oxo, —CN, $-C_{1-6}$ alkyl, $-C_{1-6}$ alkoxy, $-C_{3-8}$ cycloalkyl, $-NH_2$, $-NH(C_{1-6}$ alkyl), $-N(C_{1-6}alkyl)_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_2$ is selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, F, Cl, Br, I, —OH, oxo, —CN, $-C_{1-3}$ alkyl, $-C_{1-3}$ alkoxy, $-C_{3-6}$ cycloalkyl, $-NH_2$, $-NH(C_{1-3}$ alkyl), $-N(C_{1-3}alkyl)_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_2$ is selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, $-C_{1-3}$ alkyl, $-C_{1-3}$ alkoxy, $-C_{3-6}$ cycloalkyl, $-NH_2$, $-NH(C_{1-3}$ alkyl), $-N(C_{1-3}alkyl)_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_2$ is selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, $-C_3$ cycloalkyl, $-C_4$ cycloalkyl, $-C_5$ cycloalkyl, $-C_6$ cycloalkyl, $-NH_2$, $-NHCH_3$, $-NHCH_2CH_3$, $-NHCH_2CH_2CH_3$, $-NHCH(CH_3)_2$, $-N(CH_3)_2$, $-N(CH_2CH_3)_2$, $-N(CH_2CH_2CH_3)_2$, $-N(CH(CH_3)_2)_2$, and carboxyl. Preferably, $R_2$ is selected from hydrogen or deuterium.

In some embodiments of the compound of Formula I, I-A, I-B, the pharmaceutically acceptable salt thereof, the stereoisomer thereof, the tautomer thereof, and the isotopic substitution thereof of the present invention, wherein $R_3$ and $R_3'$ are each independently selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_3$ and $R_3$' are each independently selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_3$ and $R_3$' are each independently selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_3$ and $R_3$' are each independently selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, —$N(CH(CH_3)_2)_2$, and carboxyl. Preferably, $R_3$ and $R_3$' are each independently selected from hydrogen or deuterium.

In some embodiments of the compound of Formula I, I-A, I-B, the pharmaceutically acceptable salt thereof, the stereoisomer thereof, the tautomer thereof, and the isotopic substitution thereof of the present invention, wherein Y is a bond, or —$(CR_{Y1}R_{Y2})_n$—;

n is selected from 1, 2, or 3;

$R_{Y1}$ and $R_{Y2}$ are each independently selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$alkyl), —N($C_{1-6}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein Y is a bond, or —$(CR_{Y1}R_{Y2})_n$—;

n is selected from 1, 2, or 3;

$R_{Y1}$ and $R_{Y2}$ are each independently selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$ alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein Y is a bond, or —$(CR_{Y1}R_{Y2})_n$—;

n is selected from 1, 2, or 3;

$R_{Y1}$ and $R_{Y2}$ are each independently selected from the group consisting of F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein Y is a bond, or —$(CR_{Y1}R_{Y2})_n$—;

n is selected from 1, 2, or 3;

$R_{Y1}$ and $R_{Y2}$ are each independently selected from the group consisting of F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, and —$N(CH(CH_3)_2)_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein Y is —$CH_2$—.

In some embodiments of the compound of Formula I, I-A, I-B, the pharmaceutically acceptable salt thereof, the stereoisomer thereof, the tautomer thereof, and the isotopic substitution thereof of the present invention, wherein $R_4$ is selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_4$ is selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, F, Cl, Br, I, —OH, oxo, —CN, —$C_{1-3}$ alkyl, —$C_{1-3}$alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_4$ is selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_4$ is selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, and —$N(CH(CH_3)_2)_2$, and carboxyl. Preferably, $R_4$ is selected from hydrogen or deuterium.

In some embodiments of the compound of Formula I, I-A, I-B, the pharmaceutically acceptable salt thereof, the stereoisomer thereof, the tautomer thereof, and the isotopic substitution thereof of the present invention, wherein $R_{10}$ is selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, halogen, —OH, oxo, —CN, —$C_{1-6}$ alkyl, —$C_{1-6}$ alkoxy, —$C_{3-8}$ cycloalkyl, —$NH_2$, —NH($C_{1-6}$ alkyl), —N($C_{1-6}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_{10}$ is selected from the group consisting of hydrogen, deuterium, halogen, $C_{1-3}$ alkyl, and $C_{1-3}$ alkoxy, and wherein said $C_{1-3}$ alkyl, and said $C_{1-3}$ alkoxy can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_{10}$ is selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, and carboxyl.

In some embodiments of the compound of Formula I, I-A, I-B, the pharmaceutically acceptable salt thereof, the stereoisomer thereof, the tautomer thereof, and the isotopic substitution thereof of the present invention, wherein $R_{10}$ is selected from the group consisting of hydrogen, deuterium, F, Cl, Br, I, methyl, ethyl, propyl, isopropyl, methoxy, ethoxy, propoxy, and isopropoxy, and wherein said methyl, said ethyl, said propyl, said isopropyl, said methoxy, said ethoxy, said propoxy, and said isopropoxy, can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy, —$C_3$ cycloalkyl, —$C_4$ cycloalkyl, —$C_5$ cycloalkyl, —$C_6$ cycloalkyl, —$NH_2$, —$NHCH_3$, —$NHCH_2CH_3$, —$NHCH_2CH_2CH_3$, —$NHCH(CH_3)_2$, —$N(CH_3)_2$, —$N(CH_2CH_3)_2$, —$N(CH_2CH_2CH_3)_2$, and —$N(CH(CH_3)_2)_2$, and carboxyl. Preferably, $R_{10}$ is hydrogen or deuterium.

A compound of Formula I-C, a pharmaceutically acceptable salt thereof, a stereoisomer thereof, a tautomer thereof, and an isotopic substitution thereof:

Formula I-C

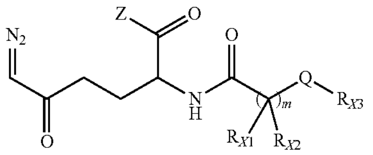

wherein Q is O, S, SO, or $SO_2$; Z, $R_{X1}$, $R_{X2}$, $R_{X3}$, and m are the same as defined herein.

A compound of Formula II, a pharmaceutically acceptable salt thereof, a stereoisomer thereof, a tautomer thereof, and an isotopic substitution thereof:

Formula II

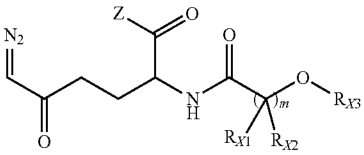

wherein Z, $R_{X1}$, $R_{X2}$, $R_{X3}$, and m are the same as defined herein.

In some embodiments of the compound of Formula I, I-A, I-B, I-C, or II, the pharmaceutically acceptable salt thereof, the stereoisomer thereof, the tautomer thereof, and the isotopic substitution thereof of the present invention, the compound is of Formula III:

Formula III

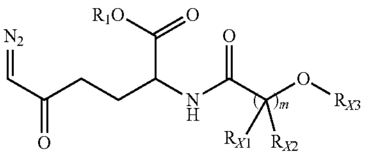

wherein $R_1$, $R_{X1}$, $R_{X2}$, $R_{X3}$, and m are the same as defined herein.

In some embodiments of the compound of Formula I, I-A, I-B, I-C, II, or III, the pharmaceutically acceptable salt thereof, the stereoisomer thereof, the tautomer thereof, and the isotopic substitution thereof of the present invention, the compound is of Formula IV:

Formula IV

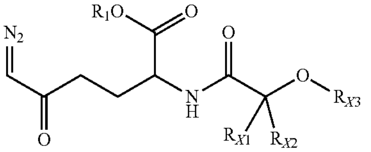

In some embodiments of the compound of Formula I, I-A, I-B, I-C, II, III, or IV, the pharmaceutically acceptable salt thereof, the stereoisomer thereof, the tautomer thereof, and the isotopic substitution thereof of the present invention, the compound is of Formula V:

Formula V

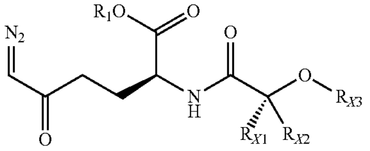

In some embodiments of the compound of Formula I, I-A, I-B, I-C, II, III, or IV, the pharmaceutically acceptable salt thereof, the stereoisomer thereof, the tautomer thereof, and the isotopic substitution thereof of the present invention, the compound is of Formula VI:

Formula VI

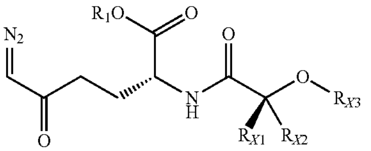

In some embodiments of the compound of Formula I, I-A, I-B, I-C, II, III, or IV, the pharmaceutically acceptable salt thereof, the stereoisomer thereof, the tautomer thereof, and the isotopic substitution thereof of the present invention, the compound is of Formula VII:

Formula VII

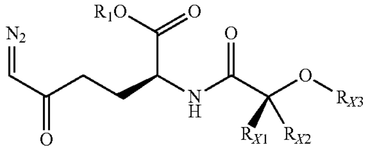

In some embodiments of the compound of Formula I, I-A, I-B, I-C, II, III, or IV, the pharmaceutically acceptable salt thereof, the stereoisomer thereof, the tautomer thereof, and the isotopic substitution thereof of the present invention, the compound is of Formula VIII and a pharmaceutically acceptable salt thereof, a stereoisomer thereof, a tautomer thereof, an isotopic substitution thereof:

Formula VIII

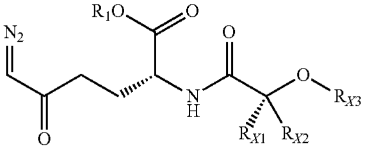

wherein $R_1$, $R_{X1}$, $R_{X2}$, $R_{X3}$, and m are the same as defined herein In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein one or more hydrogen is optionally substituted with deuterium.

In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein one or more hydrogen in R1 or RX3 is substituted with deuterium, preferably, all hydrogens on one or more methyl groups, methylene groups, or methane groups are substituted with deuterium.

In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein $R_1$ is selected from the group consisting of hydrogen, deuterium, hydrogen, deuterium, $C_{1-3}$ alkyl, $C_{1-3}$ alkoxy, and each of which can be optional substituted with one or more substituents, which are independently selected from the group consisting of deuterium, F, Cl, Br, I, —OH, oxo, —CN, —$C_{1-3}$ alkyl, —$C_{1-3}$ alkoxy;

$R_{X1}$ and $R_{X2}$ are each independently selected from the group consisting of hydrogen, deuterium, CN, OH, $C_{1-4}$alkyl, $C_{1-3}$alkoxy, each of which can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-6}$ alkyl), —N($C_{1-3}$alkyl)$_2$, —S—$C_{1-3}$alkyl; or $R_{X3}$ is independently selected from the group consisting of hydrogen, deuterium, $C_{1-3}$ alkyl, $C_{1-3}$ alkoxy, each of which can be optional substituted with one or more substituents, which are independently selected from the group consisting of deuterium, F, Cl, Br, I, —OH, oxo, —CN, —$C_{1-3}$ alkyl, —$C_{1-3}$ alkoxy, —$C_{3-6}$ cycloalkyl, —$NH_2$, —NH($C_{1-3}$ alkyl), —N($C_{1-3}$alkyl)$_2$, carboxy, —S—$C_{1-3}$alkyl.

In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein $R_1$ is selected from the group consisting of hydrogen, deuterium, methyl, ethyl, propyl, isopropyl, methoxy, ethoxy, propoxy, isopropoxy; and each of which can be optional substituted with one or more substituents, which are independently selected from the group consisting of deuterium, F, Cl, Br, I, —OH, oxo, —CN, methyl, ethyl, propyl, isopropyl, methoxy, ethoxy, propoxy, isopropoxy;

$R_{X1}$ and $R_{X2}$ are each independently selected from the group consisting of hydrogen, deuterium, CN, $CF_3$, methyl, ethyl, propyl, isopropyl, methoxy, ethoxy, propoxy, isopropoxy, butyl, sec-butyl, iso-butyl, tert-butyl, and each of which is independently optionally substituted with deuterium, —F, —Cl, —Br, —I, —$NH_2$, —CN, —OH, oxo, carboxyl, methyl, ethyl, propyl, isopropyl, methoxy, ethoxy, propoxy, isopropoxy; or $R_{X3}$ is independently selected from the group consisting of hydrogen, methyl, ethyl, isopropyl, tert-butyl, each of which can be substituted with deuterium.

In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein $R_1$ is selected from hydrogen, deuterium, isopropyl, methyl, ethyl, -tert-butyl, isopentyl, —$CD_3$, —$CH_2CD_3$, —$CD_2CD_3$, —$CD(CD_3)_2$, —$CH(CD_3)_2$,

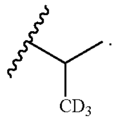 [SMILES: *C(C)C([2H])([2H])[2H]]

.

$R_{X1}$ and $R_{X2}$ are each independently selected from the group consisting of hydrogen, deuterium, halogen, CN, OH, methyl, ethyl, propyl, isopropyl, methoxy, ethoxy, propoxy, isopropoxy, butyl, sec-butyl, iso-butyl, tert-butyl,

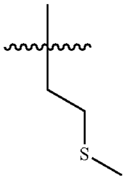

;

or $R_{X3}$ is independently selected from the group consisting of hydrogen, methyl, ethyl, isopropyl, tert-butyl, —$CD_3$, —$CH_2CD_3$, —$CD_2CD_3$.

In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein $R_1$ is selected from —$CD_3$, —$CH_2CD_3$, —$CD_2CD_3$, —$CD(CD_3)_2$, —$CH(CD_3)_2$,

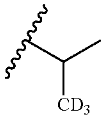

, the deuterated $R_{X3}$ is selected from —$CD_3$, —$CH_2CD_3$, —$CD_2CD_3$

In some embodiments of the compound of Formula I, I-A, I-B, I-C, II, III, IV, V, VI, VII, or VIII, the pharmaceutically acceptable salt thereof, the stereoisomer thereof, the tautomer thereof, and the isotopic substitution thereof of the present invention, wherein the compound is selected from:

| | |
|---|---|
| 1 | isopropyl (S)-6-diazo-2-((S)-3-(7-fluoro-1H-indol-3-yl)-2-hydroxypropanamido)-5-oxohexanoate |
| 2 | isopropyl (S)-6-diazo-2-((S)-2-methoxypropanamido)-5-oxohexanoate |
| 3 | isopropyl (S)-6-diazo-2-((S)-2-hydroxy-3-(7-methoxy-1H-indol-3-yl)propanamido)-5-oxohexanoate |
| 4 | isopropyl (S)-6-diazo-2-((S)-2-hydroxy-3-(1H-indol-3-yl)propanamido)-5-oxohexanoate |
| 5 | isopropyl (S)-6-diazo-2-(2-methoxyacetamido)-5-oxohexanoate |
| 6 | isopropyl (S)-6-diazo-2-(2-ethoxyacetamido)-5-oxohexanoate |
| 7 | isopropyl (S)-6-diazo-2-((S)-2-hydroxypropanamido)-5-oxohexanoate |
| 8 | isopropyl (S)-6-diazo-2-((S)-2-hydroxy-3-phenylpropanamido)-5-oxohexanoate |
| 9 | isopropyl (S)-6-diazo-2-((S)-2-methoxy-3-phenylpropanamido)-5-oxohexanoate |
| 10 | isopropyl (S)-6-diazo-2-((S)-2-hydroxy-4-methylpentanamido)-5-oxohexanoate |
| 11 | isopropyl (S)-6-diazo-2-((S)-2-hydroxy-2-phenylacetamido)-5-oxohexanoate |
| 12 | isopropyl (S)-6-diazo-2-((S)-2-methoxy-2-phenylacetamido)-5-oxohexanoate |
| 13 | isopropyl (S)-2-((S)-2-(2-cyanoacetoxy)-3-(1H-indol-3-yl)propanamido)-6-diazo-5-oxohexanoate |
| 14 | isopropyl (S)-2-((S)-3-(1H-indol-3-yl)-2-(pivaloyloxy)propanamido)-6-diazo-5-oxohexanoate |
| 15 | isopropyl (S)-6-diazo-2-((S)-2-hydroxy-3-(1H-indol-1-yl)propanamido)-5-oxohexanoate |
| 16 | isopropyl (S)-6-diazo-2-((S)-2-(4-fluorophenyl)-2-hydroxyacetamido)-5-oxohexanoate |
| 17 | isopropyl (S)-6-diazo-2-(2-((4-fluorobenzyl)oxy)acetamido)-5-oxohexanoate |
| 18 | isopropyl (S)-2-((S)-3-(7-cyano-1H-indol-3-yl)-2-hydroxypropanamido)-6-diazo-5-oxohexanoate |
| 19 | isopropyl (S)-2-((S)-3-(6-cyano-1H-indol-3-yl)-2-hydroxypropanamido)-6-diazo-5-oxohexanoate |
| 20 | isopropyl (S)-2-((S)-3-(5-cyano-1H-indol-3-yl)-2-hydroxypropanamido)-6-diazo-5-oxohexanoate |
| 21 | isopropyl (S)-2-((S)-3-(4-cyano-1H-indol-3-yl)-2-hydroxypropanamido)-6-diazo-5-oxohexanoate |
| 22 | isopropyl (S)-2-((S)-3-(7-cyano-1H-indol-3-yl)-2-methoxypropanamido)-6-diazo-5-oxohexanoate |
| 23 | isopropyl (S)-2-((S)-3-(6-cyano-1H-indol-3-yl)-2-methoxypropanamido)-6-diazo-5-oxohexanoate |
| 24 | isopropyl (S)-2-((S)-3-(5-cyano-1H-indol-3-yl)-2-methoxypropanamido)-6-diazo-5-oxohexanoate |
| 25 | isopropyl (S)-2-((S)-3-(4-cyano-1H-indol-3-yl)-2-methoxypropanamido)-6-diazo-5-oxohexanoate |
| 26 | isopropyl (S)-6-diazo-2-((S)-2-hydroxy-3-(6-methoxy-1H-indol-3-yl)propanamido)-5-oxohexanoate |
| 27 | isopropyl (S)-6-diazo-2-((S)-2-hydroxy-3-(5-methoxy-1H-indol-3-yl)propanamido)-5-oxohexanoate |
| 28 | isopropyl (S)-6-diazo-2-((S)-2-hydroxy-3-(4-methoxy-1H-indol-3-yl)propanamido)-5-oxohexanoate |

-continued

| | |
|---|---|
| 29 | isopropyl (S)-6-diazo-2-((S)-2-methoxy-3-(6-methoxy-1H-indol-3-yl)propanamido)-5-oxohexanoate |
| 30 | isopropyl (S)-6-diazo-2-((S)-2-methoxy-3-(5-methoxy-1H-indol-3-yl)propanamido)-5-oxohexanoate |
| 31 | isopropyl (S)-6-diazo-2-((S)-2-methoxy-3-(4-methoxy-1H-indol-3-yl)propanamido)-5-oxohexanoate |
| 32 | isopropyl (S)-6-diazo-2-((S)-2-methoxy-3-(7-methoxy-1H-indol-3-yl)propanamido)-5-oxohexanoate |
| 33 | isopropyl (S)-6-diazo-2-((S)-2-methoxy-3-(1-methyl-1H-imidazol-4-yl)propanamido)-5-oxohexanoate |
| 34 | isopropyl (2S)-6-diazo-2-(2-hydroxy-3-(1H-indol-3-yl)-2-methylpropanamido)-5-oxohexanoate |
| 35 | isopropyl (S)-6-diazo-2-((S)-3-(6-fluoro-1H-indol-3-yl)-2-hydroxypropanamido)-5-oxohexanoate |
| 36 | isopropyl (S)-6-diazo-2-((S)-3-(5-fluoro-1H-indol-3-yl)-2-hydroxypropanamido)-5-oxohexanoate |
| 37 | isopropyl (S)-6-diazo-2-((S)-3-(4-fluoro-1H-indol-3-yl)-2-hydroxypropanamido)-5-oxohexanoate |
| 38 | isopropyl (S)-6-diazo-2-((S)-3-(7-fluoro-1H-indol-3-yl)-2-methoxypropanamido)-5-oxohexanoate |
| 39 | isopropyl (S)-6-diazo-2-((S)-3-(6-fluoro-1H-indol-3-yl)-2-methoxypropanamido)-5-oxohexanoate |
| 40 | isopropyl (S)-6-diazo-2-((S)-3-(5-fluoro-1H-indol-3-yl)-2-methoxypropanamido)-5-oxohexanoate |
| 41 | isopropyl (S)-6-diazo-2-((S)-3-(4-fluoro-1H-indol-3-yl)-2-methoxypropanamido)-5-oxohexanoate |
| 42 | isopropyl (S)-2-((S)-3-(7-chloro-1H-indol-3-yl)-2-hydroxypropanamido)-6-diazo-5-oxohexanoate |
| 43 | isopropyl (S)-2-((S)-3-(6-chloro-1H-indol-3-yl)-2-hydroxypropanamido)-6-diazo-5-oxohexanoate |
| 44 | isopropyl (S)-2-((S)-3-(5-chloro-1H-indol-3-yl)-2-hydroxypropanamido)-6-diazo-5-oxohexanoate |
| 45 | isopropyl (S)-2-((S)-3-(4-chloro-1H-indol-3-yl)-2-hydroxypropanamido)-6-diazo-5-oxohexanoate |
| 46 | isopropyl (S)-2-((S)-3-(7-chloro-1H-indol-3-yl)-2-methoxypropanamido)-6-diazo-5-oxohexanoate |
| 47 | isopropyl (S)-2-((S)-3-(6-chloro-1H-indol-3-yl)-2-methoxypropanamido)-6-diazo-5-oxohexanoate |
| 48 | isopropyl (S)-2-((S)-3-(5-chloro-1H-indol-3-yl)-2-methoxypropanamido)-6-diazo-5-oxohexanoate |
| 49 | isopropyl (S)-2-((S)-3-(4-chloro-1H-indol-3-yl)-2-methoxypropanamido)-6-diazo-5-oxohexanoate |
| 50 | isopropyl (S)-6-diazo-2-((S)-2-hydroxy-3-(7-methyl-1H-indol-3-yl)propanamido)-5-oxohexanoate |
| 51 | isopropyl (S)-6-diazo-2-((S)-2-hydroxy-3-(6-methyl-1H-indol-3-yl)propanamido)-5-oxohexanoate |
| 52 | isopropyl (S)-6-diazo-2-((S)-2-hydroxy-3-(5-methyl-1H-indol-3-yl)propanamido)-5-oxohexanoate |
| 53 | isopropyl (S)-6-diazo-2-((S)-2-hydroxy-3-(4-methyl-1H-indol-3-yl)propanamido)-5-oxohexanoate |
| 54 | isopropyl (S)-6-diazo-2-((S)-2-methoxy-3-(7-methyl-1H-indol-3-yl)propanamido)-5-oxohexanoate |
| 55 | isopropyl (S)-6-diazo-2-((S)-2-methoxy-3-(6-methyl-1H-indol-3-yl)propanamido)-5-oxohexanoate |
| 56 | isopropyl (S)-6-diazo-2-((S)-2-methoxy-3-(5-methyl-1H-indol-3-yl)propanamido)-5-oxohexanoate |
| 57 | isopropyl (S)-6-diazo-2-((S)-2-methoxy-3-(4-methyl-1H-indol-3-yl)propanamido)-5-oxohexanoate |
| 58 | isopropyl (S)-6-diazo-2-((S)-3-(7-(dimethylamino)-1H-indol-3-yl)-2-hydroxypropanamido)-5-oxohexanoate |
| 59 | isopropyl (S)-6-diazo-2-((S)-3-(6-(dimethylamino)-1H-indol-3-yl)-2-hydroxypropanamido)-5-oxohexanoate |
| 60 | isopropyl (S)-6-diazo-2-((S)-3-(5-(dimethylamino)-1H-indol-3-yl)-2-hydroxypropanamido)-5-oxohexanoate |
| 61 | isopropyl (S)-6-diazo-2-((S)-3-(4-(dimethylamino)-1H-indol-3-yl)-2-hydroxypropanamido)-5-oxohexanoate |
| 62 | isopropyl (S)-6-diazo-2-((S)-3-(7-(dimethylamino)-1H-indol-3-yl)-2-methoxypropanamido)-5-oxohexanoate |
| 63 | isopropyl (S)-6-diazo-2-((S)-3-(6-(dimethylamino)-1H-indol-3-yl)-2-methoxypropanamido)-5-oxohexanoate |
| 64 | isopropyl (S)-6-diazo-2-((S)-3-(5-(dimethylamino)-1H-indol-3-yl)-2-methoxypropanamido)-5-oxohexanoate |
| 65 | isopropyl (S)-6-diazo-2-((S)-3-(4-(dimethylamino)-1H-indol-3-yl)-2-methoxypropanamido)-5-oxohexanoate |
| 66 | S-isopropyl (S)-6-diazo-2-((S)-2-hydroxy-3-(1H-indol-3-yl)propanamido)-5-oxohexanethioate |
| 67 | isopropyl (S)-6-diazo-2-((S)-2-ethoxypropanamido)-5-oxohexanoate |
| 68 | isopropyl (S)-6-diazo-2-((S)-2-isopropoxypropanamido)-5-oxohexanoate |
| 69 | isopropyl (S)-2-((S)-2-cyclopropoxypropanamido)-6-diazo-5-oxohexanoate |
| 70 | isopropyl (S)-6-diazo-2-(2-hydroxyacetamido)-5-oxohexanoate |
| 71 | isopropyl (S)-2-(2-cyclopropoxyacetamido)-6-diazo-5-oxohexanoate |
| 72 | isopropyl (S)-6-diazo-2-((S)-2-hydroxybutanamido)-5-oxohexanoate |
| 73 | isopropyl (S)-6-diazo-2-((S)-2-methoxybutanamido)-5-oxohexanoate |
| 74 | isopropyl (S)-6-diazo-2-((S)-2-ethoxybutanamido)-5-oxohexanoate |
| 75 | isopropyl (S)-6-diazo-2-((S)-2-isopropoxybutanamido)-5-oxohexanoate |
| 76 | isopropyl (S)-2-((S)-2-cyclopropoxybutanamido)-6-diazo-5-oxohexanoate |
| 77 | isopropyl (S)-6-diazo-2-((S)-2-hydroxy-3-methylbutanamido)-5-oxohexanoate |
| 78 | isopropyl (S)-6-diazo-2-((S)-2-methoxy-3-methylbutanamido)-5-oxohexanoate |
| 79 | isopropyl (S)-6-diazo-2-((S)-2-ethoxy-3-methylbutanamido)-5-oxohexanoate |
| 80 | isopropyl (S)-6-diazo-2-((S)-2-isopropoxy-3-methylbutanamido)-5-oxohexanoate |
| 81 | isopropyl (S)-2-((S)-2-cyclopropoxy-3-methylbutanamido)-6-diazo-5-oxohexanoate |
| 82 | isopropyl (S)-6-diazo-2-((2S,3R)-2-hydroxy-3-methylpentanamido)-5-oxohexanoate |
| 83 | isopropyl (S)-6-diazo-2-((2S,3R)-2-methoxy-3-methylpentanamido)-5-oxohexanoate |
| 84 | isopropyl (S)-6-diazo-2-((2S,3R)-2-ethoxy-3-methylpentanamido)-5-oxohexanoate |
| 85 | isopropyl (S)-6-diazo-2-((2S,3R)-2-isopropoxy-3-methylpentanamido)-5-oxohexanoate |
| 86 | isopropyl (S)-2-((2S,3R)-2-cyclopropoxy-3-methylpentanamido)-6-diazo-5-oxohexanoate |
| 87 | isopropyl (S)-6-diazo-2-((S)-2-hydroxypentanamido)-5-oxohexanoate |
| 88 | isopropyl (S)-6-diazo-2-((S)-2-methoxypentanamido)-5-oxohexanoate |
| 89 | isopropyl (S)-6-diazo-2-((S)-2-ethoxypentanamido)-5-oxohexanoate |
| 90 | isopropyl (S)-6-diazo-2-((S)-2-isopropoxypentanamido)-5-oxohexanoate |
| 91 | isopropyl (S)-2-((S)-2-cyclopropoxypentanamido)-6-diazo-5-oxohexanoate |
| 92 | isopropyl (S)-6-diazo-2-((S)-2-methoxy-4-methylpentanamido)-5-oxohexanoate |
| 93 | isopropyl (S)-6-diazo-2-((S)-2-ethoxy-4-methylpentanamido)-5-oxohexanoate |
| 94 | isopropyl (S)-6-diazo-2-((S)-2-isopropoxy-4-methylpentanamido)-5-oxohexanoate |
| 95 | isopropyl (S)-2-((S)-2-cyclopropoxy-4-methylpentanamido)-6-diazo-5-oxohexanoate |
| 96 | isopropyl (S)-6-diazo-2-((S)-2-hydroxy-3,3-dimethylbutanamido)-5-oxohexanoate |
| 97 | isopropyl (S)-6-diazo-2-((S)-2-methoxy-3,3-dimethylbutanamido)-5-oxohexanoate |
| 98 | isopropyl (S)-6-diazo-2-((S)-2-ethoxy-3,3-dimethylbutanamido)-5-oxohexanoate |
| 99 | isopropyl (S)-6-diazo-2-((S)-2-isopropoxy-3,3-dimethylbutanamido)-5-oxohexanoate |
| 100 | isopropyl (S)-2-((S)-2-cyclopropoxy-3,3-dimethylbutanamido)-6-diazo-5-oxohexanoate |
| 101 | isopropyl (S)-6-diazo-2-((S)-2-hydroxyhexanamido)-5-oxohexanoate |
| 102 | isopropyl (S)-6-diazo-2-((S)-2-methoxyhexanamido)-5-oxohexanoate |
| 103 | isopropyl (S)-6-diazo-2-((S)-2-ethoxyhexanamido)-5-oxohexanoate |
| 104 | isopropyl (S)-6-diazo-2-((S)-2-isopropoxyhexanamido)-5-oxohexanoate |
| 105 | isopropyl (S)-2-((S)-2-cyclopropoxyhexanamido)-6-diazo-5-oxohexanoate |
| 106 | isopropyl (S)-2-((S)-2-cyclopentyl-2-hydroxyacetamido)-6-diazo-5-oxohexanoate |
| 107 | isopropyl (S)-2-((S)-2-cyclopentyl-2-methoxyacetamido)-6-diazo-5-oxohexanoate |

-continued

| | |
|---|---|
| 108 | isopropyl (S)-2-((S)-2-cyclopentyl-2-ethoxyacetamido)-6-diazo-5-oxohexanoate |
| 109 | isopropyl (S)-2-((S)-2-cyclopentyl-2-isopropoxyacetamido)-6-diazo-5-oxohexanoate |
| 110 | isopropyl (S)-2-((S)-2-cyclopentyl-2-cyclopropoxyacetamido)-6-diazo-5-oxohexanoate |
| 111 | isopropyl (S)-2-((S)-3-cyclopentyl-2-hydroxypropanamido)-6-diazo-5-oxohexanoate |
| 112 | isopropyl (S)-2-((S)-3-cyclopentyl-2-methoxypropanamido)-6-diazo-5-oxohexanoate |
| 113 | isopropyl (S)-2-((S)-3-cyclopentyl-2-ethoxypropanamido)-6-diazo-5-oxohexanoate |
| 114 | isopropyl (S)-2-((S)-3-cyclopentyl-2-isopropoxypropanamido)-6-diazo-5-oxohexanoate |
| 115 | isopropyl (S)-2-((S)-3-cyclopentyl-2-cyclopropoxypropanamido)-6-diazo-5-oxohexanoate |
| 116 | isopropyl (S)-2-((S)-2-cyclohexyl-2-hydroxyacetamido)-6-diazo-5-oxohexanoate |
| 117 | isopropyl (S)-2-((S)-2-cyclohexyl-2-methoxyacetamido)-6-diazo-5-oxohexanoate |
| 118 | isopropyl (S)-2-((S)-2-cyclohexyl-2-ethoxyacetamido)-6-diazo-5-oxohexanoate |
| 119 | isopropyl (S)-2-((S)-2-cyclohexyl-2-isopropoxyacetamido)-6-diazo-5-oxohexanoate |
| 120 | isopropyl (S)-2-((S)-2-cyclohexyl-2-cyclopropoxyacetamido)-6-diazo-5-oxohexanoate |
| 121 | isopropyl (S)-6-diazo-2-((S)-2-ethoxy-2-phenylacetamido)-5-oxohexanoate |
| 122 | isopropyl (S)-6-diazo-2-((S)-2-isopropoxy-2-phenylacetamido)-5-oxohexanoate |
| 123 | isopropyl (S)-2-((S)-2-cyclopropoxy-2-phenylacetamido)-6-diazo-5-oxohexanoate |
| 124 | isopropyl (S)-6-diazo-2-((S)-2-(4-fluorophenyl)-2-methoxyacetamido)-5-oxohexanoate |
| 125 | isopropyl (S)-2-((S)-2-(4-chlorophenyl)-2-methoxyacetamido)-6-diazo-5-oxohexanoate |
| 126 | isopropyl (S)-2-((S)-2-(4-chlorophenyl)-2-hydroxyacetamido)-6-diazo-5-oxohexanoate |
| 127 | isopropyl (S)-6-diazo-2-((S)-2-hydroxy-2-(4-methoxyphenyl)acetamido)-5-oxohexanoate |
| 128 | isopropyl (S)-6-diazo-2-((S)-2-methoxy-2-(4-methoxyphenyl)acetamido)-5-oxohexanoate |
| 129 | isopropyl (S)-6-diazo-2-((S)-2-hydroxy-2-(4-hydroxyphenyl)acetamido)-5-oxohexanoate |
| 130 | isopropyl (S)-6-diazo-2-((S)-2-(4-hydroxyphenyl)-2-methoxyacetamido)-5-oxohexanoate |
| 131 | isopropyl (S)-6-diazo-2-((S)-2-hydroxy-2-(p-tolyl)acetamido)-5-oxohexanoate |
| 132 | isopropyl (S)-6-diazo-2-((S)-2-methoxy-2-(p-tolyl)acetamido)-5-oxohexanoate |
| 133 | isopropyl (S)-6-diazo-2-((S)-2-ethoxy-3-phenylpropanamido)-5-oxohexanoate |
| 134 | isopropyl (S)-6-diazo-2-((S)-2-isopropoxy-3-phenylpropanamido)-5-oxohexanoate |
| 135 | isopropyl (S)-2-((S)-2-cyclopropoxy-3-phenylpropanamido)-6-diazo-5-oxohexanoate |
| 136 | isopropyl (S)-6-diazo-2-((S)-3-(4-fluorophenyl)-2-hydroxypropanamido)-5-oxohexanoate |
| 137 | isopropyl (S)-6-diazo-2-((S)-3-(4-fluorophenyl)-2-methoxypropanamido)-5-oxohexanoate |
| 138 | isopropyl (S)-6-diazo-2-((S)-2-ethoxy-3-(4-fluorophenyl)propanamido)-5-oxohexanoate |
| 139 | isopropyl (S)-6-diazo-2-((S)-3-(4-fluorophenyl)-2-isopropoxypropanamido)-5-oxohexanoate |
| 140 | isopropyl (S)-2-((S)-2-cyclopropoxy-3-(4-fluorophenyl)propanamido)-6-diazo-5-oxohexanoate |
| 141 | isopropyl (S)-6-diazo-2-((S)-2-hydroxy-3-(4-hydroxyphenyl)propanamido)-5-oxohexanoate |
| 142 | isopropyl (S)-6-diazo-2-((S)-3-(4-hydroxyphenyl)-2-methoxypropanamido)-5-oxohexanoate |
| 143 | isopropyl (S)-6-diazo-2-((S)-2-ethoxy-3-(4-hydroxyphenyl)propanamido)-5-oxohexanoate |
| 144 | isopropyl (S)-6-diazo-2-((S)-3-(4-hydroxyphenyl)-2-isopropoxypropanamido)-5-oxohexanoate |
| 145 | isopropyl (S)-2-((S)-2-cyclopropoxy-3-(4-hydroxyphenyl)propanamido)-6-diazo-5-oxohexanoate |
| 146 | isopropyl (S)-6-diazo-2-(1-hydroxycyclobutane-1-carboxamido)-5-oxohexanoate |
| 147 | isopropyl (S)-6-diazo-2-(1-methoxycyclobutane-1-carboxamido)-5-oxohexanoate |
| 148 | isopropyl (S)-6-diazo-2-(3-hydroxyoxetane-3-carboxamido)-5-oxohexanoate |
| 149 | isopropyl (S)-6-diazo-2-(3-methoxyoxetane-3-carboxamido)-5-oxohexanoate |
| 150 | isopropyl (S)-6-diazo-2-(1-hydroxycyclopentane-1-carboxamido)-5-oxohexanoate |
| 151 | isopropyl (S)-6-diazo-2-(1-methoxycyclopentane-1-carboxamido)-5-oxohexanoate |
| 152 | isopropyl (2S)-6-diazo-2-(3-hydroxytetrahydrofuran-3-carboxamido)-5-oxohexanoate |
| 153 | isopropyl (2S)-6-diazo-2-(3-methoxytetrahydrofuran-3-carboxamido)-5-oxohexanoate |
| 154 | isopropyl (S)-6-diazo-2-(1-hydroxycyclohexane-1-carboxamido)-5-oxohexanoate |
| 155 | isopropyl (S)-6-diazo-2-(1-methoxycyclohexane-1-carboxamido)-5-oxohexanoate |
| 156 | isopropyl (S)-6-diazo-2-(4-hydroxy-1-methylpiperidine-4-carboxamido)-5-oxohexanoate |
| 157 | isopropyl (S)-6-diazo-2-(4-methoxy-1-methylpiperidine-4-carboxamido)-5-oxohexanoate |
| 158 | isopropyl (2S)-6-diazo-5-oxo-2-(tetrahydrofuran-2-carboxamido)hexanoate |
| 159 | isopropyl (2S)-6-diazo-5-oxo-2-(tetrahydro-2H-pyran-2-carboxamido)hexanoate or |
| 160 | isopropyl (2S)-6-diazo-2-(hexahydro-1H-cyclopenta[c]furan-1-carboxamido)-5-oxohexanoate. |
| 161 | isopropyl (S)-2-(2-(cyclopropylmethoxy)acetamido)-6-diazo-5-oxohexanoate |
| 162 | isopropyl (S)-6-diazo-2-((R)-2-hydroxy-2-phenylpropanamido)-5-oxohexanoate |
| 163 | isopropyl (S)-6-diazo-2-((S)-2-hydroxy-2-phenylpropanamido)-5-oxohexanoate |
| 164 | isopropyl (S)-2-((S)-2-(2-cyanoacetoxy)-3-(7-fluoro-1H-indol-3-yl)propanamido)-6-diazo-5-oxohexanoate |
| 165 | isopropyl (S)-2-((S)-2-acetoxy-3-(7-fluoro-1H-indol-3-yl)propanamido)-6-diazo-5-oxohexanoate |
| 166 | isopropyl (S)-6-diazo-2-((S)-3-(7-fluoro-1H-indol-3-yl)-2-(isobutyryloxy)propanamido)-5-oxohexanoate |
| 167 | (S)-6-diazo-2-((S)-2-methoxypropanamido)-5-oxohexanoic acid |
| 168 | methyl (S)-6-diazo-2-((S)-2-methoxypropanamido)-5-oxohexanoate |
| 169 | 1-methylpiperidin-4-yl (S)-6-diazo-2-((S)-2-methoxypropanamido)-5-oxohexanoate |
| 170 | isopropyl (S)-6-diazo-5-oxo-2-((S)-tetrahydrofuran-2-carboxamido)hexanoate |
| 171 | isopropyl (S)-6-diazo-5-oxo-2-((S)-tetrahydro-2H-pyran-2-carboxamido)hexanoate |
| 172 | isopropyl (S)-6-diazo-5-oxo-2-((S)-tetrahydrofuran-3-carboxamido)hexanoate |
| 173 | isopropyl (S)-6-diazo-5-oxo-2-((S)-tetrahydro-2H-pyran-3-carboxamido)hexanoate |
| 174 | isopropyl (S)-6-diazo-2-(3-methoxy-2-oxopropanamido)-5-oxohexanoate |
| 175 | isopropyl (S)-6-diazo-2-(3-hydroxy-2-oxopropanamido)-5-oxohexanoate |
| 176 | ethyl (S)-6-diazo-2-((S)-2-methoxypropanamido)-5-oxohexanoate |
| 177 | cyclopropyl (S)-6-diazo-2-((S)-2-methoxypropanamido)-5-oxohexanoate |
| 178 | cyclobutyl (S)-6-diazo-2-((S)-2-methoxypropanamido)-5-oxohexanoate |
| 179 | cyclopentyl (S)-6-diazo-2-((S)-2-methoxypropanamido)-5-oxohexanoate |
| 180 | 2-(pyrrolidin-1-yl)ethyl (S)-6-diazo-2-((S)-2-methoxypropanamido)-5-oxohexanoate |
| 181 | (pivaloyloxy)methyl (S)-6-diazo-2-((S)-2-methoxypropanamido)-5-oxohexanoate |
| 182 | isopentyl (S)-6-diazo-2-((S)-2-methoxypropanamido)-5-oxohexanoate |
| 183 | isopropyl (S)-6-diazo-2-(3-hydroxypropanamido)-5-oxohexanoate |
| 184 | isopropyl (S)-6-diazo-2-((S)-3-hydroxybutanamido)-5-oxohexanoate |
| 185 | isopropyl (S)-6-diazo-2-(3-methoxypropanamido)-5-oxohexanoate |
| 186 | isopropyl (S)-6-diazo-2-((S)-3-methoxybutanamido)-5-oxohexanoate |

-continued

| | |
|---|---|
| 187 | isopropyl (S)-6-diazo-2-((S)-3-hydroxy-2-methylpropanamido)-5-oxohexanoate |
| 188 | isopropyl (S)-6-diazo-2-((S)-3-methoxy-2-methylpropanamido)-5-oxohexanoate |
| 189 | isopropyl (S)-6-diazo-2-((S)-oxetane-2-carboxamido)-5-oxohexanoate |
| 190 | isopropyl (S)-6-diazo-2-((2S,3R)-3-hydroxy-2-methylbutanamido)-5-oxohexanoate |
| 191 | isopropyl (S)-6-diazo-2-((2S,3R)-3-methoxy-2-methylbutanamido)-5-oxohexanoate |
| 192 | isopropyl (S)-6-diazo-2-((2R,3R)-3-hydroxy-2-methylbutanamido)-5-oxohexanoate |
| 193 | isopropyl (S)-6-diazo-2-((2R,3R)-3-methoxy-2-methylbutanamido)-5-oxohexanoate |
| 194 | isopropyl (S)-6-diazo-2-((2R,3S)-3-hydroxy-2-methylbutanamido)-5-oxohexanoate |
| 195 | isopropyl (S)-6-diazo-2-((2R,3S)-3-methoxy-2-methylbutanamido)-5-oxohexanoate |
| 196 | isopropyl (S)-6-diazo-2-((R)-3-hydroxybutanamido)-5-oxohexanoate |
| 197 | isopropyl (S)-6-diazo-2-((2S,3S)-3-hydroxy-2-methylbutanamido)-5-oxohexanoate |
| 198 | isopropyl (S)-6-diazo-2-((2S,3S)-3-methoxy-2-methylbutanamido)-5-oxohexanoate |
| 199 | isopropyl (S)-6-diazo-5-oxo-2-((R)-tetrahydrofuran-2-carboxamido)hexanoate |
| 200 | isopropyl (S)-6-diazo-5-oxo-2-((R)-tetrahydro-2H-pyran-2-carboxamido)hexanoate |
| 201 | isopropyl (S)-6-diazo-5-oxo-2-((R)-tetrahydrofuran-3-carboxamido)hexanoate |
| 202 | isopropyl (S)-6-diazo-5-oxo-2-((R)-tetrahydro-2H-pyran-3-carboxamido)hexanoate |
| 203 | isopropyl (S)-6-diazo-2-((R)-3-methoxybutanamido)-5-oxohexanoate |
| 204 | isopropyl (S)-6-diazo-5-oxo-2-((R)-3,3,3-trifluoro-2-methoxypropanamido)hexanoate |
| 205 | isopropyl (S)-6-diazo-5-oxo-2-((R)-3,3,3-trifluoro-2-hydroxypropanamido)hexanoate |
| 206 | isopropyl (S)-6-diazo-5-oxo-2-((S)-3,3,3-trifluoro-2-methoxypropanamido)hexanoate |
| 207 | isopropyl (S)-6-diazo-5-oxo-2-((S)-3,3,3-trifluoro-2-hydroxypropanamido)hexanoate |
| 208 | isopropyl (S)-6-diazo-2-((R)-oxetane-2-carboxamido)-5-oxohexanoate |
| 209 | isopropyl (S)-6-diazo-2-(oxetane-3-carboxamido)-5-oxohexanoate |
| 210 | isopropyl (S)-6-diazo-2-((R)-3-hydroxy-2-methylpropanamido)-5-oxohexanoate |
| 211 | isopropyl (S)-6-diazo-5-oxo-2-(tetrahydro-2H-pyran-4-carboxamido)hexanoate |
| 212 | isopropyl (2S)-6-diazo-5-oxo-2-((1S)-tetrahydro-1H,3H-furo[3,4-c]furan-1-carboxamido)hexanoate |
| 213 | isopropyl (2S)-6-diazo-5-oxo-2-((1R)-tetrahydro-1H,3H-furo[3,4-c]furan-1-carboxamido)hexanoate |
| 214 | isopropyl (S)-2-((S)-2-cyano-2-hydroxyacetamido)-6-diazo-5-oxohexanoate |
| 215 | isopropyl (S)-2-((S)-2-cyano-2-methoxyacetamido)-6-diazo-5-oxohexanoate |
| 216 | isopropyl (S)-6-diazo-2-((S)-2-methoxy-3-oxobutanamido)-5-oxohexanoate |
| 217 | isopropyl (S)-6-diazo-2-((S)-2-hydroxy-3-oxobutanamido)-5-oxohexanoate |
| 218 | isopropyl (S)-6-diazo-2-((R)-3-methoxy-2-methylpropanamido)-5-oxohexanoate |
| 219 | isopropyl (S)-6-diazo-2-((S)-2-methoxy-2-(thiazol-4-yl)acetamido)-5-oxohexanoate |
| 220 | isopropyl (S)-6-diazo-2-((S)-2-hydroxy-2-(thiazol-4-yl)acetamido)-5-oxohexanoate |
| 221 | isopropyl (S)-2-((R)-2-cyano-2-hydroxyacetamido)-6-diazo-5-oxohexanoate |
| 222 | isopropyl (S)-2-((R)-2-cyano-2-methoxyacetamido)-6-diazo-5-oxohexanoate |
| 223 | isopropyl (S)-6-diazo-2-((R)-2-methoxy-3-oxobutanamido)-5-oxohexanoate |
| 224 | isopropyl (S)-6-diazo-2-((R)-2-hydroxy-3-oxobutanamido)-5-oxohexanoate |
| 225 | isopropyl (S)-6-diazo-2-((R)-2-methoxy-2-(thiazol-4-yl)acetamido)-5-oxohexanoate |
| 226 | isopropyl (S)-6-diazo-2-((R)-2-hydroxy-2-(thiazol-4-yl)acetamido)-5-oxohexanoate |
| 227 | isopropyl (S)-6-diazo-2-((S)-2-methoxy-2-(1H-pyrrol-2-yl)acetamido)-5-oxohexanoate |
| 228 | isopropyl (S)-6-diazo-2-((S)-2-methoxy-2-(1H-pyrrol-3-yl)acetamido)-5-oxohexanoate |
| 229 | isopropyl (S)-6-diazo-2-((S)-2-hydroxy-2-(1H-pyrrol-2-yl)acetamido)-5-oxohexanoate |
| 230 | isopropyl (S)-6-diazo-2-((S)-2-hydroxy-2-(1H-pyrrol-3-yl)acetamido)-5-oxohexanoate |
| 231 | isopropyl (S)-6-diazo-2-((S)-2-methoxy-2-(oxazol-4-yl)acetamido)-5-oxohexanoate |
| 232 | isopropyl (S)-6-diazo-2-((S)-2-hydroxy-2-(oxazol-4-yl)acetamido)-5-oxohexanoate |
| 233 | isopropyl (S)-6-diazo-2-((S)-2-(furan-2-yl)-2-methoxyacetamido)-5-oxohexanoate |
| 234 | isopropyl (S)-6-diazo-2-((S)-2-(furan-3-yl)-2-methoxyacetamido)-5-oxohexanoate |
| 235 | isopropyl (S)-6-diazo-2-((S)-2-(furan-2-yl)-2-hydroxyacetamido)-5-oxohexanoate |
| 236 | isopropyl (S)-6-diazo-2-((S)-2-(furan-3-yl)-2-hydroxyacetamido)-5-oxohexanoate |
| 237 | isopropyl (S)-2-((S)-2-(1H-imidazol-4-yl)-2-methoxyacetamido)-6-diazo-5-oxohexanoate |
| 238 | isopropyl (S)-6-diazo-2-((S)-2-hydroxy-2-(1H-imidazol-4-yl)acetamido)-5-oxohexanoate |
| 239 | isopropyl (S)-6-diazo-2-((R)-2-methoxy-2-(1H-pyrrol-2-yl)acetamido)-5-oxohexanoate |
| 240 | isopropyl (S)-6-diazo-2-((R)-2-methoxy-2-(1H-pyrrol-3-yl)acetamido)-5-oxohexanoate |
| 241 | isopropyl (S)-6-diazo-2-((R)-2-hydroxy-2-(1H-pyrrol-2-yl)acetamido)-5-oxohexanoate |
| 242 | isopropyl (S)-6-diazo-2-((R)-2-hydroxy-2-(1H-pyrrol-3-yl)acetamido)-5-oxohexanoate |
| 243 | isopropyl (S)-6-diazo-2-((R)-2-methoxy-2-(oxazol-4-yl)acetamido)-5-oxohexanoate |
| 244 | isopropyl (S)-6-diazo-2-((R)-2-hydroxy-2-(oxazol-4-yl)acetamido)-5-oxohexanoate |
| 245 | isopropyl (S)-6-diazo-2-((R)-2-(furan-2-yl)-2-methoxyacetamido)-5-oxohexanoate |
| 246 | isopropyl (S)-6-diazo-2-((R)-2-(furan-3-yl)-2-methoxyacetamido)-5-oxohexanoate |
| 247 | isopropyl (S)-6-diazo-2-((R)-2-(furan-2-yl)-2-hydroxyacetamido)-5-oxohexanoate |
| 248 | isopropyl (S)-6-diazo-2-((R)-2-(furan-3-yl)-2-hydroxyacetamido)-5-oxohexanoate |
| 249 | isopropyl (S)-2-((R)-2-(1H-imidazol-4-yl)-2-methoxyacetamido)-6-diazo-5-oxohexanoate |
| 250 | isopropyl (S)-6-diazo-2-((R)-2-hydroxy-2-(1H-imidazol-4-yl)acetamido)-5-oxohexanoate |
| 251 | isopropyl (S)-6-diazo-2-((R)-2-methoxy-2-(thiophen-2-yl)acetamido)-5-oxohexanoate |
| 252 | isopropyl (S)-6-diazo-2-((S)-2-methoxy-2-(thiophen-3-yl)acetamido)-5-oxohexanoate |
| 253 | isopropyl (S)-6-diazo-2-((R)-2-hydroxy-2-(thiophen-2-yl)acetamido)-5-oxohexanoate |
| 254 | isopropyl (S)-6-diazo-2-((S)-2-hydroxy-2-(thiophen-3-yl)acetamido)-5-oxohexanoate |
| 255 | isopropyl (S)-6-diazo-2-((R)-2-methoxy-2-(thiazol-2-yl)acetamido)-5-oxohexanoate |
| 256 | isopropyl (S)-6-diazo-2-((R)-2-hydroxy-2-(thiazol-2-yl)acetamido)-5-oxohexanoate |
| 257 | isopropyl (S)-6-diazo-2-((S)-2-methoxy-2-(1-methyl-1H-imidazol-2-yl)acetamido)-5-oxohexanoate |
| 258 | isopropyl (S)-6-diazo-2-((S)-2-hydroxy-2-(1-methyl-1H-imidazol-2-yl)acetamido)-5-oxohexanoate |
| 259 | isopropyl (S)-6-diazo-2-((S)-2-methoxy-2-(1-methyl-1H-imidazol-4-yl)acetamido)-5-oxohexanoate |
| 260 | isopropyl (S)-6-diazo-2-((S)-2-hydroxy-2-(1-methyl-1H-imidazol-4-yl)acetamido)-5-oxohexanoate |
| 261 | isopropyl (S)-6-diazo-2-((S)-2-methoxy-2-(oxazol-2-yl)acetamido)-5-oxohexanoate |
| 262 | isopropyl (S)-6-diazo-2-((S)-2-hydroxy-2-(oxazol-2-yl)acetamido)-5-oxohexanoate |
| 263 | isopropyl (S)-6-diazo-2-((R)-2-methoxy-2-(1-methyl-1H-imidazol-4-yl)acetamido)-5-oxohexanoate |
| 264 | isopropyl (S)-6-diazo-2-((R)-2-hydroxy-2-(1-methyl-1H-imidazol-4-yl)acetamido)-5-oxohexanoate |
| 265 | isopropyl (S)-6-diazo-2-((R)-2-methoxy-2-(oxazol-2-yl)acetamido)-5-oxohexanoate |

-continued

| | |
|---|---|
| 266 | isopropyl (S)-6-diazo-2-((R)-2-hydroxy-2-(oxazol-2-yl)acetamido)-5-oxohexanoate |
| 267 | isopropyl (S)-6-diazo-2-((S)-2-methoxy-2-(thiophen-2-yl)acetamido)-5-oxohexanoate |
| 268 | isopropyl (S)-6-diazo-2-((R)-2-methoxy-2-(thiophen-3-yl)acetamido)-5-oxohexanoate |
| 269 | isopropyl (S)-6-diazo-2-((S)-2-hydroxy-2-(thiophen-2-yl)acetamido)-5-oxohexanoate |
| 270 | isopropyl (S)-6-diazo-2-((R)-2-hydroxy-2-(thiophen-3-yl)acetamido)-5-oxohexanoate |
| 271 | isopropyl (S)-6-diazo-2-((S)-2-methoxy-2-(thiazol-2-yl)acetamido)-5-oxohexanoate |
| 272 | isopropyl (S)-6-diazo-2-((S)-2-hydroxy-2-(thiazol-2-yl)acetamido)-5-oxohexanoate |
| 273 | isopropyl (S)-6-diazo-2-((R)-2-methoxy-2-(1-methyl-1H-imidazol-2-yl)acetamido)-5-oxohexanoate |
| 274 | isopropyl (S)-6-diazo-2-((R)-2-hydroxy-2-(1-methyl-1H-imidazol-2-yl)acetamido)-5-oxohexanoate |
| 275 | isopropyl (S)-6-diazo-2-((R)-2-methoxy-2-(thiazol-5-yl)acetamido)-5-oxohexanoate |
| 276 | isopropyl (S)-6-diazo-2-((R)-2-hydroxy-2-(thiazol-5-yl)acetamido)-5-oxohexanoate |
| 277 | isopropyl (S)-6-diazo-2-((R)-2-methoxy-2-(1-methyl-1H-imidazol-5-yl)acetamido)-5-oxohexanoate |
| 278 | isopropyl (S)-6-diazo-2-((R)-2-hydroxy-2-(1-methyl-1H-imidazol-5-yl)acetamido)-5-oxohexanoate |
| 279 | isopropyl (S)-2-((R)-2-(1H-imidazol-2-yl)-2-methoxyacetamido)-6-diazo-5-oxohexanoate |
| 280 | isopropyl (S)-6-diazo-2-((R)-2-hydroxy-2-(1H-imidazol-2-yl)acetamido)-5-oxohexanoate |
| 281 | isopropyl (S)-6-diazo-2-((R)-2-methoxy-2-(oxazol-5-yl)acetamido)-5-oxohexanoate |
| 282 | isopropyl (S)-6-diazo-2-((R)-2-hydroxy-2-(oxazol-5-yl)acetamido)-5-oxohexanoate |
| 283 | isopropyl (S)-2-((S)-2-(1H-imidazol-5-yl)-2-methoxyacetamido)-6-diazo-5-oxohexanoate |
| 284 | isopropyl (S)-6-diazo-2-((S)-2-hydroxy-2-(1H-imidazol-5-yl)acetamido)-5-oxohexanoate |
| 285 | isopropyl (S)-6-diazo-2-((S)-2-methoxy-2-(pyridin-2-yl)acetamido)-5-oxohexanoate |
| 286 | isopropyl (S)-6-diazo-2-((S)-2-hydroxy-2-(pyridin-2-yl)acetamido)-5-oxohexanoate |
| 287 | isopropyl (S)-6-diazo-2-((S)-2-methoxy-2-(pyrimidin-4-yl)acetamido)-5-oxohexanoate |
| 288 | isopropyl (S)-6-diazo-2-((S)-2-hydroxy-2-(pyrimidin-4-yl)acetamido)-5-oxohexanoate |
| 289 | isopropyl (S)-6-diazo-2-((S)-2-methoxy-2-(pyrimidin-2-yl)acetamido)-5-oxohexanoate |
| 290 | isopropyl (S)-6-diazo-2-((S)-2-hydroxy-2-(pyrimidin-2-yl)acetamido)-5-oxohexanoate |
| 291 | isopropyl (S)-6-diazo-2-((S)-2-(3-fluoropyridin-4-yl)-2-methoxyacetamido)-5-oxohexanoate |
| 292 | isopropyl (S)-6-diazo-2-((S)-2-(3-fluoropyridin-4-yl)-2-hydroxyacetamido)-5-oxohexanoate |
| 293 | isopropyl (S)-6-diazo-2-((S)-2-(5-fluoropyridin-2-yl)-2-methoxyacetamido)-5-oxohexanoate |
| 294 | isopropyl (S)-6-diazo-2-((S)-2-(5-fluoropyridin-2-yl)-2-hydroxyacetamido)-5-oxohexanoate |
| 295 | isopropyl (S)-6-diazo-2-((S)-2-(5-fluoropyridin-3-yl)-2-methoxyacetamido)-5-oxohexanoate |
| 296 | isopropyl (S)-6-diazo-2-((S)-2-(5-fluoropyridin-3-yl)-2-hydroxyacetamido)-5-oxohexanoate |
| 297 | isopropyl (S)-6-diazo-2-((S)-2-methoxy-2-(3-methoxypyridin-4-yl)acetamido)-5-oxohexanoate |
| 298 | isopropyl (S)-6-diazo-2-((S)-2-hydroxy-2-(3-methoxypyridin-4-yl)acetamido)-5-oxohexanoate |
| 299 | isopropyl (S)-6-diazo-2-((S)-2-methoxy-2-(5-methoxypyridin-2-yl)acetamido)-5-oxohexanoate |
| 300 | isopropyl (S)-6-diazo-2-((S)-2-hydroxy-2-(5-methoxypyridin-2-yl)acetamido)-5-oxohexanoate |
| 301 | isopropyl (S)-6-diazo-2-((S)-2-methoxy-2-(5-methoxypyridin-3-yl)acetamido)-5-oxohexanoate |
| 302 | isopropyl (S)-6-diazo-2-((S)-2-hydroxy-2-(5-methoxypyridin-3-yl)acetamido)-5-oxohexanoate |
| 303 | isopropyl (S)-6-diazo-2-((R)-2-methoxy-2-(5-methoxypyridin-2-yl)acetamido)-5-oxohexanoate |
| 304 | isopropyl (S)-6-diazo-2-((R)-2-hydroxy-2-(5-methoxypyridin-2-yl)acetamido)-5-oxohexanoate |
| 305 | isopropyl (S)-6-diazo-2-((R)-2-methoxy-2-(5-methoxypyridin-3-yl)acetamido)-5-oxohexanoate |
| 306 | isopropyl (S)-6-diazo-2-((R)-2-hydroxy-2-(5-methoxypyridin-3-yl)acetamido)-5-oxohexanoate |
| 307 | isopropyl (S)-2-((R)-2-(1H-imidazol-5-yl)-2-methoxyacetamido)-6-diazo-5-oxohexanoate |
| 308 | isopropyl (S)-6-diazo-2-((R)-2-hydroxy-2-(1H-imidazol-5-yl)acetamido)-5-oxohexanoate |
| 309 | isopropyl (S)-6-diazo-2-((R)-2-methoxy-2-(pyridin-2-yl)acetamido)-5-oxohexanoate |
| 310 | isopropyl (S)-6-diazo-2-((R)-2-hydroxy-2-(pyridin-2-yl)acetamido)-5-oxohexanoate |
| 311 | isopropyl (S)-6-diazo-2-((R)-2-methoxy-2-(pyrimidin-4-yl)acetamido)-5-oxohexanoate |
| 312 | isopropyl (S)-6-diazo-2-((R)-2-hydroxy-2-(pyrimidin-4-yl)acetamido)-5-oxohexanoate |
| 313 | isopropyl (S)-6-diazo-2-((R)-2-methoxy-2-(pyrimidin-2-yl)acetamido)-5-oxohexanoate |
| 314 | isopropyl (S)-6-diazo-2-((R)-2-hydroxy-2-(pyrimidin-2-yl)acetamido)-5-oxohexanoate |
| 315 | isopropyl (S)-6-diazo-2-((R)-2-(3-fluoropyridin-4-yl)-2-methoxyacetamido)-5-oxohexanoate |
| 316 | isopropyl (S)-6-diazo-2-((R)-2-(3-fluoropyridin-4-yl)-2-hydroxyacetamido)-5-oxohexanoate |
| 317 | isopropyl (S)-6-diazo-2-((R)-2-(5-fluoropyridin-2-yl)-2-methoxyacetamido)-5-oxohexanoate |
| 318 | isopropyl (S)-6-diazo-2-((R)-2-(5-fluoropyridin-2-yl)-2-hydroxyacetamido)-5-oxohexanoate |
| 319 | isopropyl (S)-6-diazo-2-((R)-2-(5-fluoropyridin-3-yl)-2-methoxyacetamido)-5-oxohexanoate |
| 320 | isopropyl (S)-6-diazo-2-((R)-2-(5-fluoropyridin-3-yl)-2-hydroxyacetamido)-5-oxohexanoate |
| 321 | isopropyl (S)-6-diazo-2-((R)-2-methoxy-2-(3-methoxypyridin-4-yl)acetamido)-5-oxohexanoate |
| 322 | isopropyl (S)-6-diazo-2-((R)-2-hydroxy-2-(3-methoxypyridin-4-yl)acetamido)-5-oxohexanoate |
| 323 | tert-butyl (S)-6-diazo-2-((S)-2-methoxypropanamido)-5-oxohexanoate |
| 324 | phenyl (S)-6-diazo-2-((S)-2-methoxypropanamido)-5-oxohexanoate |
| 325 | benzyl (S)-6-diazo-2-((S)-2-methoxypropanamido)-5-oxohexanoate |
| 326 | cyclohexyl (S)-6-diazo-2-((S)-2-methoxypropanamido)-5-oxohexanoate |
| 327 | cycloheptyl (S)-6-diazo-2-((S)-2-methoxypropanamido)-5-oxohexanoate |
| 328 | cyclooctyl (S)-6-diazo-2-((S)-2-methoxypropanamido)-5-oxohexanoate |
| 329 | cyclooctyl (S)-6-diazo-2-((R)-2-methoxypropanamido)-5-oxohexanoate |
| 330 | tert-butyl (S)-6-diazo-2-((R)-2-methoxypropanamido)-5-oxohexanoate |
| 331 | phenyl (S)-6-diazo-2-((R)-2-methoxypropanamido)-5-oxohexanoate |
| 332 | benzyl (S)-6-diazo-2-((R)-2-methoxypropanamido)-5-oxohexanoate |
| 333 | cyclohexyl (S)-6-diazo-2-((R)-2-methoxypropanamido)-5-oxohexanoate |
| 334 | cycloheptyl (S)-6-diazo-2-((R)-2-methoxypropanamido)-5-oxohexanoate |
| 335 | 1-methylpiperidin-4-yl (S)-6-diazo-2-((R)-2-methoxypropanamido)-5-oxohexanoate |
| 336 | pyridin-4-yl (S)-6-diazo-2-((S)-2-methoxypropanamido)-5-oxohexanoate |
| 337 | pyridin-4-ylmethyl (S)-6-diazo-2-((S)-2-methoxypropanamido)-5-oxohexanoate |
| 338 | tetrahydro-2H-pyran-4-yl (S)-6-diazo-2-((S)-2-methoxypropanamido)-5-oxohexanoate |
| 339 | piperidin-4-yl (S)-6-diazo-2-((S)-2-methoxypropanamido)-5-oxohexanoate |
| 340 | (R)-oxepan-4-yl (S)-6-diazo-2-((S)-2-methoxypropanamido)-5-oxohexanoate |
| 341 | (S)-oxepan-4-yl (S)-6-diazo-2-((S)-2-methoxypropanamido)-5-oxohexanoate |
| 342 | oxocan-5-yl (S)-6-diazo-2-((S)-2-methoxypropanamido)-5-oxohexanoate |
| 343 | pyridin-4-yl (S)-6-diazo-2-((R)-2-methoxypropanamido)-5-oxohexanoate |
| 344 | pyridin-4-ylmethyl (S)-6-diazo-2-((R)-2-methoxypropanamido)-5-oxohexanoate |

-continued

| | |
|---|---|
| 345 | tetrahydro-2H-pyran-4-yl (S)-6-diazo-2-((R)-2-methoxypropanamido)-5-oxohexanoate |
| 346 | piperidin-4-yl (S)-6-diazo-2-((R)-2-methoxypropanamido)-5-oxohexanoate |
| 347 | (R)-oxepan-4-yl (S)-6-diazo-2-((R)-2-methoxypropanamido)-5-oxohexanoate |
| 348 | (S)-oxepan-4-yl (S)-6-diazo-2-((R)-2-methoxypropanamido)-5-oxohexanoate |
| 349 | oxocan-5-yl (S)-6-diazo-2-((R)-2-methoxypropanamido)-5-oxohexanoate |
| 350 | trifluoromethyl (S)-6-diazo-2-((S)-2-methoxypropanamido)-5-oxohexanoate |
| 351 | 2,2,2-trifluoroethyl (S)-6-diazo-2-((S)-2-methoxypropanamido)-5-oxohexanoate |
| 352 | (S)-1,1,1-trifluoropropan-2-yl (S)-6-diazo-2-((S)-2-methoxypropanamido)-5-oxohexanoate |
| 353 | 3,3,3-trifluoropropyl (S)-6-diazo-2-((S)-2-methoxypropanamido)-5-oxohexanoate |
| 354 | (S)-4,4,4-trifluorobutan-2-yl (S)-6-diazo-2-((S)-2-methoxypropanamido)-5-oxohexanoate |
| 355 | 1,1,1-trifluoro-2-methylpropan-2-yl (S)-6-diazo-2-((S)-2-methoxypropanamido)-5-oxohexanoate |
| 356 | 4,4,4-trifluoro-2-methylbutan-2-yl (S)-6-diazo-2-((S)-2-methoxypropanamido)-5-oxohexanoate |
| 357 | cyanic (S)-6-diazo-2-((S)-2-methoxypropanamido)-5-oxohexanoic anhydride |
| 358 | cyanomethyl (S)-6-diazo-2-((S)-2-methoxypropanamido)-5-oxohexanoate |
| 359 | (S)-1-cyanoethyl (S)-6-diazo-2-((S)-2-methoxypropanamido)-5-oxohexanoate |
| 360 | 2-cyanoethyl (S)-6-diazo-2-((S)-2-methoxypropanamido)-5-oxohexanoate |
| 361 | 1-cyanopropan-2-yl (2S)-6-diazo-2-((S)-2-methoxypropanamido)-5-oxohexanoate |
| 362 | 2-cyanopropan-2-yl (S)-6-diazo-2-((S)-2-methoxypropanamido)-5-oxohexanoate |
| 363 | 1-cyano-2-methylpropan-2-yl (S)-6-diazo-2-((S)-2-methoxypropanamido)-5-oxohexanoate |
| 364 | hydroxymethyl (S)-6-diazo-2-((S)-2-methoxypropanamido)-5-oxohexanoate |
| 365 | methoxymethyl (S)-6-diazo-2-((S)-2-methoxypropanamido)-5-oxohexanoate |
| 366 | ethoxymethyl (S)-6-diazo-2-((S)-2-methoxypropanamido)-5-oxohexanoate |
| 367 | isopropoxymethyl (S)-6-diazo-2-((S)-2-methoxypropanamido)-5-oxohexanoate |
| 368 | cyclopropoxymethyl (S)-6-diazo-2-((S)-2-methoxypropanamido)-5-oxohexanoate |
| 369 | cyclobutoxymethyl (S)-6-diazo-2-((S)-2-methoxypropanamido)-5-oxohexanoate |
| 370 | trifluoromethyl (S)-6-diazo-2-((R)-2-methoxypropanamido)-5-oxohexanoate |
| 371 | 2,2,2-trifluoroethyl (S)-6-diazo-2-((R)-2-methoxypropanamido)-5-oxohexanoate |
| 372 | (S)-1,1,1-trifluoropropan-2-yl (S)-6-diazo-2-((R)-2-methoxypropanamido)-5-oxohexanoate |
| 373 | (R)-1,1,1-trifluoropropan-2-yl (S)-6-diazo-2-((S)-2-methoxypropanamido)-5-oxohexanoate |
| 374 | (R)-4,4,4-trifluorobutan-2-yl (S)-6-diazo-2-((S)-2-methoxypropanamido)-5-oxohexanoate |
| 375 | (R)-1-cyanoethyl (S)-6-diazo-2-((S)-2-methoxypropanamido)-5-oxohexanoate |
| 376 | (R)-1-cyanopropan-2-yl (S)-6-diazo-2-((S)-2-methoxypropanamido)-5-oxohexanoate |
| 377 | (R)-1,1,1-trifluoropropan-2-yl (S)-6-diazo-2-((R)-2-methoxypropanamido)-5-oxohexanoate |
| 378 | 3,3,3-trifluoropropyl (S)-6-diazo-2-((R)-2-methoxypropanamido)-5-oxohexanoate |
| 379 | (S)-4,4,4-trifluorobutan-2-yl (S)-6-diazo-2-((R)-2-methoxypropanamido)-5-oxohexanoate |
| 380 | (R)-4,4,4-trifluorobutan-2-yl (S)-6-diazo-2-((R)-2-methoxypropanamido)-5-oxohexanoate |
| 381 | 1,1,1-trifluoro-2-methylpropan-2-yl (S)-6-diazo-2-((R)-2-methoxypropanamido)-5-oxohexanoate |
| 382 | 4,4,4-trifluoro-2-methylbutan-2-yl (S)-6-diazo-2-((R)-2-methoxypropanamido)-5-oxohexanoate |
| 383 | cyanic (S)-6-diazo-2-((R)-2-methoxypropanamido)-5-oxohexanoic anhydride |
| 384 | cyanomethyl (S)-6-diazo-2-((R)-2-methoxypropanamido)-5-oxohexanoate |
| 385 | (S)-1-cyanoethyl (S)-6-diazo-2-((R)-2-methoxypropanamido)-5-oxohexanoate |
| 386 | (R)-1-cyanoethyl (S)-6-diazo-2-((R)-2-methoxypropanamido)-5-oxohexanoate |
| 387 | 2-cyanoethyl (S)-6-diazo-2-((R)-2-methoxypropanamido)-5-oxohexanoate |
| 388 | (S)-1-cyanopropan-2-yl (S)-6-diazo-2-((R)-2-methoxypropanamido)-5-oxohexanoate |
| 389 | (R)-1-cyanopropan-2-yl (S)-6-diazo-2-((R)-2-methoxypropanamido)-5-oxohexanoate |
| 390 | 2-cyanopropan-2-yl (S)-6-diazo-2-((R)-2-methoxypropanamido)-5-oxohexanoate |
| 391 | 1-cyano-2-methylpropan-2-yl (S)-6-diazo-2-((R)-2-methoxypropanamido)-5-oxohexanoate |
| 392 | hydroxymethyl (S)-6-diazo-2-((R)-2-methoxypropanamido)-5-oxohexanoate |
| 393 | methoxymethyl (S)-6-diazo-2-((R)-2-methoxypropanamido)-5-oxohexanoate |
| 394 | ethoxymethyl (S)-6-diazo-2-((R)-2-methoxypropanamido)-5-oxohexanoate |
| 395 | isopropoxymethyl (S)-6-diazo-2-((R)-2-methoxypropanamido)-5-oxohexanoate |
| 396 | cyclopropoxymethyl (S)-6-diazo-2-((R)-2-methoxypropanamido)-5-oxohexanoate |
| 397 | cyclobutoxymethyl (S)-6-diazo-2-((R)-2-methoxypropanamido)-5-oxohexanoate |
| 398 | 2-(pyrrolidin-1-yl)ethyl (S)-6-diazo-2-((R)-2-methoxypropanamido)-5-oxohexanoate |
| 399 | 2-methoxyethyl (S)-6-diazo-2-((S)-2-methoxypropanamido)-5-oxohexanoate |
| 400 | 2-ethoxyethyl (S)-6-diazo-2-((S)-2-methoxypropanamido)-5-oxohexanoate |
| 401 | 2-isopropoxyethyl (S)-6-diazo-2-((S)-2-methoxypropanamido)-5-oxohexanoate |
| 402 | 2-aminoethyl (S)-6-diazo-2-((S)-2-methoxypropanamido)-5-oxohexanoate |
| 403 | 2-(methylamino)ethyl (S)-6-diazo-2-((S)-2-methoxypropanamido)-5-oxohexanoate |
| 404 | 2-(dimethylamino)ethyl (S)-6-diazo-2-((S)-2-methoxypropanamido)-5-oxohexanoate |
| 405 | 2-(ethylamino)ethyl (S)-6-diazo-2-((S)-2-methoxypropanamido)-5-oxohexanoate |
| 406 | 2-(isopropylamino)ethyl (S)-6-diazo-2-((S)-2-methoxypropanamido)-5-oxohexanoate |
| 407 | 2-(cyclopropylamino)ethyl (S)-6-diazo-2-((S)-2-methoxypropanamido)-5-oxohexanoate |
| 408 | 2-(cyclobutylamino)ethyl (S)-6-diazo-2-((S)-2-methoxypropanamido)-5-oxohexanoate |
| 409 | 2-(cyclopentylamino)ethyl (S)-6-diazo-2-((S)-2-methoxypropanamido)-5-oxohexanoate |
| 410 | 2-(cyclohexylamino)ethyl (S)-6-diazo-2-((S)-2-methoxypropanamido)-5-oxohexanoate |
| 411 | 2-(azetidin-1-yl)ethyl (S)-6-diazo-2-((S)-2-methoxypropanamido)-5-oxohexanoate |
| 412 | 2-(piperidin-1-yl)ethyl (S)-6-diazo-2-((S)-2-methoxypropanamido)-5-oxohexanoate |
| 413 | 2-(azepan-1-yl)ethyl (S)-6-diazo-2-((S)-2-methoxypropanamido)-5-oxohexanoate |
| 414 | 2-(azocan-1-yl)ethyl (S)-6-diazo-2-((S)-2-methoxypropanamido)-5-oxohexanoate |
| 415 | 2-morpholinoethyl (S)-6-diazo-2-((S)-2-methoxypropanamido)-5-oxohexanoate |
| 416 | 2-(phenylamino)ethyl (S)-6-diazo-2-((S)-2-methoxypropanamido)-5-oxohexanoate |
| 417 | 2-(pyridin-4-ylamino)ethyl (S)-6-diazo-2-((S)-2-methoxypropanamido)-5-oxohexanoate |
| 418 | 2-(benzylamino)ethyl (S)-6-diazo-2-((S)-2-methoxypropanamido)-5-oxohexanoate |
| 419 | 2-((pyridin-4-ylmethyl)amino)ethyl (S)-6-diazo-2-((S)-2-methoxypropanamido)-5-oxohexanoate |
| 420 | 2-(4-methylpiperazin-1-yl)ethyl (S)-6-diazo-2-((S)-2-methoxypropanamido)-5-oxohexanoate |
| 421 | 2-methoxyethyl (S)-6-diazo-2-((R)-2-methoxypropanamido)-5-oxohexanoate |
| 422 | 2-ethoxyethyl (S)-6-diazo-2-((R)-2-methoxypropanamido)-5-oxohexanoate |
| 423 | 2-isopropoxyethyl (S)-6-diazo-2-((R)-2-methoxypropanamido)-5-oxohexanoate |

-continued

| | |
|---|---|
| 424 | 2-aminoethyl (S)-6-diazo-2-((R)-2-methoxypropanamido)-5-oxohexanoate |
| 425 | 2-(methylamino)ethyl (S)-6-diazo-2-((R)-2-methoxypropanamido)-5-oxohexanoate |
| 426 | 2-(dimethylamino)ethyl (S)-6-diazo-2-((R)-2-methoxypropanamido)-5-oxohexanoate |
| 427 | 2-(ethylamino)ethyl (S)-6-diazo-2-((R)-2-methoxypropanamido)-5-oxohexanoate |
| 428 | 2-(isopropylamino)ethyl (S)-6-diazo-2-((R)-2-methoxypropanamido)-5-oxohexanoate |
| 429 | 2-(cyclopropylamino)ethyl (S)-6-diazo-2-((R)-2-methoxypropanamido)-5-oxohexanoate |
| 430 | 2-(cyclobutylamino)ethyl (S)-6-diazo-2-((R)-2-methoxypropanamido)-5-oxohexanoate |
| 431 | 2-(cyclopentylamino)ethyl (S)-6-diazo-2-((R)-2-methoxypropanamido)-5-oxohexanoate |
| 432 | 2-(cyclohexylamino)ethyl (S)-6-diazo-2-((R)-2-methoxypropanamido)-5-oxohexanoate |
| 433 | 2-(azetidin-1-yl)ethyl (S)-6-diazo-2-((R)-2-methoxypropanamido)-5-oxohexanoate |
| 434 | 2-(piperidin-1-yl)ethyl (S)-6-diazo-2-((R)-2-methoxypropanamido)-5-oxohexanoate |
| 435 | 2-(azepan-1-yl)ethyl (S)-6-diazo-2-((R)-2-methoxypropanamido)-5-oxohexanoate |
| 436 | 2-(azocan-1-yl)ethyl (S)-6-diazo-2-((R)-2-methoxypropanamido)-5-oxohexanoate |
| 437 | 2-morpholinoethyl (S)-6-diazo-2-((R)-2-methoxypropanamido)-5-oxohexanoate |
| 438 | 2-(phenylamino)ethyl (S)-6-diazo-2-((R)-2-methoxypropanamido)-5-oxohexanoate |
| 439 | 2-(pyridin-4-ylamino)ethyl (S)-6-diazo-2-((R)-2-methoxypropanamido)-5-oxohexanoate |
| 440 | 2-(benzylamino)ethyl (S)-6-diazo-2-((R)-2-methoxypropanamido)-5-oxohexanoate |
| 441 | 2-((pyridin-4-ylmethyl)amino)ethyl (S)-6-diazo-2-((R)-2-methoxypropanamido)-5-oxohexanoate |
| 442 | 2-(4-methylpiperazin-1-yl)ethyl (S)-6-diazo-2-((R)-2-methoxypropanamido)-5-oxohexanoate |
| 443 | isopropyl (S)-6-diazo-2-((S)-2-methoxy-4-(methylthio)butanamido)-5-oxohexanoate |
| 444 | isopropyl (S)-6-diazo-2-(2-hydroxy-2-methylpropanamido)-5-oxohexanoate |
| 445 | methyl (S)-6-diazo-2-((S)-2-methoxy-4-(methylthio)butanamido)-5-oxohexanoate |
| 446 | methyl (S)-6-diazo-2-((S)-2-hydroxy-3-(1H-indol-3-yl)propanamido)-5-oxohexanoate |
| 447 | methyl (S)-6-diazo-2-((S)-2-hydroxy-3-methylbutanamido)-5-oxohexanoate |
| 448 | methyl (S)-6-diazo-2-(2-isopropoxyacetamido)-5-oxohexanoate |
| 449 | (S)-6-diazo-2-((S)-2-hydroxypropanamido)-5-oxohexanoic acid |
| 450 | isopropyl (S)-2-((S)-2-acetoxy-3-(1H-indol-3-yl)propanamido)-6-diazo-5-oxohexanoate |
| 451 | isopropyl (S)-2-((S)-3-(1H-indol-3-yl)-2-methoxypropanamido)-6-diazo-5-oxohexanoate |
| 452 | isopropyl (S)-6-diazo-2-(2-isopropoxyacetamido)-5-oxohexanoate |
| 453 | isopropyl (S)-6-diazo-2-((S)-2-methoxy-3-(1-methyl-1H-indol-3-yl)propanamido)-5-oxohexanoate |
| 454 | isopropyl (S)-6-diazo-2-((R)-2-methoxy-3-(1-methyl-1H-indol-3-yl)propanamido)-5-oxohexanoate |
| 455 | isopropyl (S)-6-diazo-2-((S)-2-(methoxy-d3)propanamido)-5-oxohexanoate |
| 456 | methyl (S)-6-diazo-2-((S)-2-hydroxy-2-phenylacetamido)-5-oxohexanoate |
| 457 | methyl (S)-6-diazo-2-((S)-2-methoxy-2-phenylacetamido)-5-oxohexanoate |
| 458 | methyl (S)-6-diazo-2-(2-methoxyacetamido)-5-oxohexanoate |
| 459 | S-isopropyl (S)-6-diazo-2-((S)-2-methoxypropanamido)-5-oxohexanethioate |
| 460 | (S)-6-diazo-2-((S)-2-methoxy-4-(methylthio)butanamido)-5-oxohexanoic acid |
| 461 | isopropyl (2S)-2-(2-acetoxy-3-(1H-indol-3-yl)propanamido)-6-diazo-5-oxohexanoate |
| 462 | isopropyl (2S)-2-(2-(2-cyanoacetoxy)-3-(1H-indol-3-yl)propanamido)-6-diazo-5-oxohexanoate |
| 463 | isopropyl (2S)-6-diazo-2-(2-((dimethylglycyl)oxy)-3-(1H-indol-3-yl)propanamido)-5-oxohexanoate |
| 464 | isopropyl (2S)-2-(3-(1H-indol-3-yl)-2-(2-(2-oxopyrrolidin-1-yl)acetoxy)propanamido)-6-diazo-5-oxohexanoate |
| 465 | isopropyl (2S)-6-diazo-2-(2-hydroxy-3-(1H-indol-3-yl)propanamido)-5-oxohexanoate |
| 466 | isopropyl (S)-6-diazo-2-((S)-2-(2-hydroxyethoxy)-3-(1H-indol-3-yl)propanamido)-5-oxohexanoate |
| 467 | isopropyl (S)-2-((S)-2-(2-acetamidoethoxy)-3-(1H-indol-3-yl)propanamido)-6-diazo-5-oxohexanoate |
| 468 | isopropyl (S)-2-((S)-2-(2-cyanoethoxy)-3-(1H-indol-3-yl)propanamido)-6-diazo-5-oxohexanoate |
| 469 | isopropyl (S)-2-((S)-2-(cyanomethoxy)-3-(1H-indol-3-yl)propanamido)-6-diazo-5-oxohexanoate |
| 470 | isopropyl (S)-6-diazo-2-((S)-2-(2-(dimethylamino)-2-oxoethoxy)-3-(1H-indol-3-yl)propanamido)-5-oxohexanoate |
| 471 | isopropyl (S)-2-((S)-3-(1H-indol-3-yl)-2-(2-(methylamino)-2-oxoethoxy)propanamido)-6-diazo-5-oxohexanoate |
| 472 | isopropyl (S)-2-((S)-3-(1H-indol-3-yl)-2-(2-oxopropoxy)propanamido)-6-diazo-5-oxohexanoate |
| 473 | isopropyl (S)-2-((S)-3-(1H-indol-3-yl)-2-((tetrahydro-2H-pyran-4-yl)oxy)propanamido)-6-diazo-5-oxohexanoate |
| 474 | isopropyl (S)-2-((S)-2-(3-amino-3-oxopropoxy)-3-(1H-indol-3-yl)propanamido)-6-diazo-5-oxohexanoate |
| 475 | isopropyl (S)-2-((S)-3-(1H-indol-3-yl)-2-(3-(methylamino)-3-oxopropoxy)propanamido)-6-diazo-5-oxohexanoate |
| 476 | isopropyl (S)-6-diazo-2-((S)-2-ethoxy-3-(1H-indol-3-yl)propanamido)-5-oxohexanoate |
| 477 | isopropyl (S)-6-diazo-2-((S)-2-methoxy-3-(1H-pyrrolo[3,2-b]pyridin-3-yl)propanamido)-5-oxohexanoate |
| 478 | isopropyl (S)-6-diazo-2-((S)-2-methoxy-3-(1H-pyrrolo[2,3-b]pyridin-3-yl)propanamido)-5-oxohexanoate |
| 479 | isopropyl (S)-6-diazo-2-((S)-2-hydroxy-3-(1-methyl-1H-pyrrolo[3,2-b]pyridin-3-yl)propanamido)-5-oxohexanoate |
| 480 | isopropyl (S)-6-diazo-2-((S)-2-hydroxy-3-(1-methyl-1H-pyrrolo[2,3-b]pyridin-3-yl)propanamido)-5-oxohexanoate |
| 481 | isopropyl (S)-6-diazo-2-((S)-2-ethoxy-3-(7-fluoro-1H-indol-3-yl)propanamido)-5-oxohexanoate |
| 482 | isopropyl (S)-6-diazo-2-((S)-3-(7-fluoro-1H-indol-3-yl)-2-isopropoxypropanamido)-5-oxohexanoate |
| 483 | isopropyl (S)-2-((S)-3-(1H-indol-3-yl)-2-phenoxypropanamido)-6-diazo-5-oxohexanoate |
| 484 | isopropyl (2S)-2-(3-(1H-indol-3-yl)-2-((methylglycyl)oxy)propanamido)-6-diazo-5-oxohexanoate |
| 485 | isopropyl (2S)-6-diazo-2-(2-(glycyloxy)-3-(1H-indol-3-yl)propanamido)-5-oxohexanoate |
| 486 | isopropyl (S)-6-diazo-2-((S)-2-(methoxy-d3)propanamido)-5-oxohexanoate |
| 487 | (S)-6-diazo-2-((S)-2-(methoxy-d3)propanamido)-5-oxohexanoic acid |
| 488 | methyl (S)-6-diazo-2-((S)-2-(methoxy-d3)propanamido)-5-oxohexanoate |
| 489 | ethyl (S)-6-diazo-2-((S)-2-(methoxy-d3)propanamido)-5-oxohexanoate |
| 490 | S-isopropyl (S)-6-diazo-2-((S)-2-(methoxy-d3)propanamido)-5-oxohexanethioate |
| 491 | isopropyl (S)-6-diazo-2-((S)-2-(methoxy-d3)-4-(methylthio)butanamido)-5-oxohexanoate |
| 492 | methyl-d3 (S)-6-diazo-2-((S)-2-methoxypropanamido)-5-oxohexanoate |
| 493 | ethyl-2,2,2-d3 (S)-6-diazo-2-((S)-2-methoxypropanamido)-5-oxohexanoate |
| 494 | isopropyl (S)-6-diazo-2-(2-(ethoxy-2,2,2-d3)acetamido)-5-oxohexanoate |
| 495 | isopropyl (S)-6-diazo-2-(2-(ethoxy-d5)acetamido)-5-oxohexanoate |
| 496 | ethyl-d5 (S)-6-diazo-2-((S)-2-methoxypropanamido)-5-oxohexanoate |
| 497 | propan-2-yl-d7 (S)-6-diazo-2-((S)-2-methoxypropanamido)-5-oxohexanoate |
| 498 | propan-2-yl-d7 (S)-6-diazo-2-((S)-2-hydroxypropanamido)-5-oxohexanoate |
| 499 | propan-2-yl-d7 (S)-6-diazo-2-((S)-2-hydroxy-3-methylbutanamido)-5-oxohexanoate |
| 500 | propan-2-yl-d7 (S)-6-diazo-2-(2-ethoxyacetamido)-5-oxohexanoate |
| 501 | S-(propan-2-yl-d7) (S)-6-diazo-2-((S)-2-methoxypropanamido)-5-oxohexanethioate |
| 502 | propan-2-yl-d7 (S)-6-diazo-2-((S)-2-methoxy-4-(methylthio)butanamido)-5-oxohexanoate |

-continued

| | |
|---|---|
| 503 | methyl-d3 (S)-6-diazo-2-((S)-2-(methoxy-d3)propanamido)-5-oxohexanoate |
| 504 | ethyl-2,2,2-d3 (S)-6-diazo-2-((S)-2-(methoxy-d3)propanamido)-5-oxohexanoate |
| 505 | ethyl-d5 (S)-6-diazo-2-((S)-2-(methoxy-d3)propanamido)-5-oxohexanoate |
| 506 | propan-2-yl-d7 (S)-6-diazo-2-((S)-2-(methoxy-d3)propanamido)-5-oxohexanoate |
| 507 | propan-2-yl-d7 (S)-6-diazo-2-(2-(ethoxy-2,2,2-d3)acetamido)-5-oxohexanoate |
| 508 | S-(propan-2-yl-d7) (S)-6-diazo-2-((S)-2-(methoxy-d3)propanamido)-5-oxohexanethioate |
| 509 | propan-2-yl-d7 (S)-6-diazo-2-((S)-2-(methoxy-d3)-4-(methylthio)butanamido)-5-oxohexanoate |
| 510 | propan-2-yl-d7 (S)-6-diazo-2-(2-(ethoxy-d5)acetamido)-5-oxohexanoate |
| 511 | methyl 6-diazo-2-((S)-2-methoxypropanamido)-5-oxohexanoate-2-d |
| 512 | ethyl 6-diazo-2-((S)-2-methoxypropanamido)-5-oxohexanoate-2-d |
| 513 | isopropyl 6-diazo-2-((S)-2-methoxypropanamido)-5-oxohexanoate-2-d |
| 514 | isopropyl 6-diazo-2-(2-ethoxyacetamido)-5-oxohexanoate-2-d |
| 515 | S-isopropyl 6-diazo-2-((S)-2-methoxypropanamido)-5-oxohexanethioate-2-d |
| 516 | isopropyl 6-diazo-2-((S)-2-methoxy-4-(methylthio)butanamido)-5-oxohexanoate-2-d |
| 517 | isopropyl 6-diazo-2-((S)-2-hydroxypropanamido)-5-oxohexanoate-2-d |
| 518 | isopropyl 6-diazo-2-((S)-2-hydroxy-3-methylbutanamido)-5-oxohexanoate-2-d |
| 519 | propan-2-yl-1,1,1,3,3,3-d6 (S)-6-diazo-2-((S)-2-(methoxy-d3)propanamido)-5-oxohexanoate |
| 520 | propan-2-yl-1,1,1,3,3,3-d6 (S)-6-diazo-2-(2-(ethoxy-2,2,2-d3)acetamido)-5-oxohexanoate |
| 521 | S-(propan-2-yl-1,1,1,3,3,3-d6) (S)-6-diazo-2-((S)-2-(methoxy-d3)propanamido)-5-oxohexanethioate |
| 522 | propan-2-yl-1,1,1,3,3,3-d6 (S)-6-diazo-2-((S)-2-(methoxy-d3)-4-(methylthio)butanamido)-5-oxohexanoate |
| 523 | propan-2-yl-1,1,1,3,3,3-d6 (S)-6-diazo-2-(2-(ethoxy-d5)acetamido)-5-oxohexanoate |
| 524 | propan-2-yl-1,1,1,3,3,3-d6 (S)-6-diazo-2-((S)-2-hydroxypropanamido)-5-oxohexanoate |
| 525 | propan-2-yl-1,1,1,3,3,3-d6 (S)-6-diazo-2-((S)-2-hydroxy-3-methylbutanamido)-5-oxohexanoate |
| 526 | propan-2-yl-1,1,1-d3 (2S)-6-diazo-2-((S)-2-(methoxy-d3)propanamido)-5-oxohexanoate |
| 527 | propan-2-yl-1,1,1-d3 (2S)-6-diazo-2-(2-(ethoxy-2,2,2-d3)acetamido)-5-oxohexanoate |
| 528 | S-(propan-2-yl-1,1,1-d3) (2S)-6-diazo-2-((S)-2-(methoxy-d3)propanamido)-5-oxohexanethioate |
| 529 | propan-2-yl-1,1,1-d3 (2S)-6-diazo-2-((S)-2-(methoxy-d3)-4-(methylthio)butanamido)-5-oxohexanoate |
| 530 | propan-2-yl-1,1,1-d3 (2S)-6-diazo-2-(2-(ethoxy-d5)acetamido)-5-oxohexanoate |
| 531 | propan-2-yl-1,1,1-d3 (2S)-6-diazo-2-((S)-2-hydroxypropanamido)-5-oxohexanoate |
| 532 | propan-2-yl-1,1,1-d3 (2S)-6-diazo-2-((S)-2-hydroxy-3-methylbutanamido)-5-oxohexanoate |
| 533 | propan-2-yl-1,1,1,3,3,3-d6 (S)-6-diazo-2-((S)-2-methoxypropanamido)-5-oxohexanoate |
| 534 | propan-2-yl-1,1,1,3,3,3-d6 (S)-6-diazo-2-(2-ethoxyacetamido)-5-oxohexanoate |
| 535 | S-(propan-2-yl-1,1,1,3,3,3-d6) (S)-6-diazo-2-((S)-2-methoxypropanamido)-5-oxohexanethioate |
| 536 | propan-2-yl-1,1,1,3,3,3-d6 (S)-6-diazo-2-((S)-2-methoxy-4-(methylthio)butanamido)-5-oxohexanoate |
| 537 | propan-2-yl-1,1,1-d3 (2S)-6-diazo-2-((S)-2-methoxypropanamido)-5-oxohexanoate |
| 538 | propan-2-yl-1,1,1-d3 (2S)-6-diazo-2-(2-ethoxyacetamido)-5-oxohexanoate |
| 539 | S-(propan-2-yl-1,1,1-d3) (2S)-6-diazo-2-((S)-2-methoxypropanamido)-5-oxohexanethioate |
| 540 | propan-2-yl-1,1,1-d3 (2S)-6-diazo-2-((S)-2-methoxy-4-(methylthio)butanamido)-5-oxohexanoate |
| 541 | methyl (S)-6-diazo-2-((S)-2-(methylthio)propanamido)-5-oxohexanoate |
| 542 | ethyl (S)-6-diazo-2-((S)-2-(methylthio)propanamido)-5-oxohexanoate |
| 543 | isopropyl (S)-6-diazo-2-((S)-2-(methylthio)propanamido)-5-oxohexanoate |
| 544 | isopropyl (S)-6-diazo-2-((S)-2-mercaptopropanamido)-5-oxohexanoate |
| 545 | isopropyl (S)-6-diazo-2-((S)-2-mercapto-3-methylbutanamido)-5-oxohexanoate |
| 546 | isopropyl (S)-6-diazo-2-(2-(ethylthio)acetamido)-5-oxohexanoate |
| 547 | S-isopropyl (S)-6-diazo-2-((S)-2-(methylthio)propanamido)-5-oxohexanethioate |
| 548 | isopropyl (S)-2-((S)-2,4-bis(methylthio)butanamido)-6-diazo-5-oxohexanoate |
| 549 | isopropyl (S)-6-diazo-2-((S)-2-(ethylthio)-3-(1H-indol-3-yl)propanamido)-5-oxohexanoate |
| 550 | isopropyl (S)-2-((S)-2-(acetylthio)-4-(methylthio)butanamido)-6-diazo-5-oxohexanoate |
| 551 | isopropyl (S)-2-((S)-3-(1H-indol-3-yl)-2-(methylthio)propanamido)-6-diazo-5-oxohexanoate |
| 552 | isopropyl (S)-6-diazo-2-(2-(isopropylthio)acetamido)-5-oxohexanoate |
| 553 | isopropyl (S)-6-diazo-2-((S)-2-(methylthio)-3-phenylpropanamido)-5-oxohexanoate |
| 554 | isopropyl (S)-6-diazo-2-((S)-2-(methylthio)-2-phenylacetamido)-5-oxohexanoate |
| 555 | isopropyl (S)-6-diazo-2-((S)-2-(methylthio)butanamido)-5-oxohexanoate |
| 556 | isopropyl (S)-6-diazo-2-((S)-3-methyl-2-(methylthio)butanamido)-5-oxohexanoate |
| 557 | cyclopentyl (S)-6-diazo-2-((S)-2-(methylthio)propanamido)-5-oxohexanoate |
| 558 | isopropyl (S)-6-diazo-5-oxo-2-((S)-thietane-2-carboxamido)hexanoate |
| 559 | methyl (2S)-6-diazo-2-((2S)-2-(methylsulfinyl)propanamido)-5-oxohexanoate |
| 560 | ethyl (2S)-6-diazo-2-((2S)-2-(methylsulfinyl)propanamido)-5-oxohexanoate |
| 561 | isopropyl (2S)-6-diazo-2-((2S)-2-(methylsulfinyl)propanamido)-5-oxohexanoate |
| 562 | isopropyl (2S)-6-diazo-2-(2-(ethylsulfinyl)acetamido)-5-oxohexanoate |
| 563 | S-isopropyl (2S)-6-diazo-2-((2S)-2-(methylsulfinyl)propanamido)-5-oxohexanethioate |
| 564 | isopropyl (2S)-6-diazo-2-((2S)-2-(methylsulfinyl)-4-(methylthio)butanamido)-5-oxohexanoate |
| 565 | isopropyl (2S)-6-diazo-2-((2S)-2-(ethylsulfinyl)-3-(1H-indol-3-yl)propanamido)-5-oxohexanoate |
| 566 | isopropyl (2S)-2-((2S)-3-(1H-indol-3-yl)-2-(methylsulfinyl)propanamido)-6-diazo-5-oxohexanoate |
| 567 | isopropyl (2S)-6-diazo-2-(2-(isopropylsulfinyl)acetamido)-5-oxohexanoate |
| 568 | isopropyl (2S)-6-diazo-2-((2S)-2-(methylsulfinyl)-3-phenylpropanamido)-5-oxohexanoate |
| 569 | isopropyl (2S)-6-diazo-2-((2S)-2-(methylsulfinyl)-2-phenylacetamido)-5-oxohexanoate |
| 570 | isopropyl (2S)-6-diazo-2-((2S)-2-(methylsulfinyl)butanamido)-5-oxohexanoate |
| 571 | isopropyl (2S)-6-diazo-2-((2S)-3-methyl-2-(methylsulfinyl)butanamido)-5-oxohexanoate |
| 572 | cyclopentyl (2S)-6-diazo-2-((2S)-2-(methylsulfinyl)propanamido)-5-oxohexanoate |
| 573 | methyl (S)-6-diazo-2-((S)-2-(methylsulfonyl)propanamido)-5-oxohexanoate |
| 574 | ethyl (S)-6-diazo-2-((S)-2-(methylsulfonyl)propanamido)-5-oxohexanoate |
| 575 | isopropyl (S)-6-diazo-2-((S)-2-(methylsulfonyl)propanamido)-5-oxohexanoate |
| 576 | isopropyl (S)-6-diazo-2-(2-(ethylsulfonyl)acetamido)-5-oxohexanoate |
| 577 | S-isopropyl (S)-6-diazo-2-((S)-2-(methylsulfonyl)propanamido)-5-oxohexanethioate |
| 578 | isopropyl (S)-6-diazo-2-((S)-2-(methylsulfonyl)-4-(methylthio)butanamido)-5-oxohexanoate |
| 579 | isopropyl (S)-6-diazo-2-((S)-2-(ethylsulfonyl)-3-(1H-indol-3-yl)propanamido)-5-oxohexanoate |
| 580 | isopropyl (S)-2-((S)-3-(1H-indol-3-yl)-2-(methylsulfonyl)propanamido)-6-diazo-5-oxohexanoate |
| 581 | isopropyl (S)-6-diazo-2-(2-(isopropylsulfonyl)acetamido)-5-oxohexanoate |

-continued

| | |
|---|---|
| 582 | isopropyl (S)-6-diazo-2-((S)-2-(methylsulfonyl)-3-phenylpropanamido)-5-oxohexanoate |
| 583 | isopropyl (S)-6-diazo-2-((S)-2-(methylsulfonyl)-2-phenylacetamido)-5-oxohexanoate |
| 584 | isopropyl (S)-6-diazo-2-((S)-2-(methylsulfonyl)butanamido)-5-oxohexanoate |
| 585 | isopropyl (S)-6-diazo-2-((S)-3-methyl-2-(methylsulfonyl)butanamido)-5-oxohexanoate |
| 586 | cyclopentyl (S)-6-diazo-2-((S)-2-(methylsulfonyl)propanamido)-5-oxohexanoate |

Methods of Preparation

The compounds of the present invention can be prepared in a number ways well known to one skilled in the art of organic synthesis using the methods described below or variations thereon as appreciated by those skilled in the art. The references cited herein are hereby incorporated by reference in their entirety.

The methods of synthesis described herein after are intended as an illustration of the invention, without restricting its subject matter and the scope of the compounds claimed to these examples. Where the preparation of starting compounds is not described, they are commercially obtainable or may be prepared analogously to known compounds or methods described herein. Compounds of any of the formulae described herein may be synthesized by reference to methods illustrated in the following schemes. As shown herein, the end compound is a product having the same structural formula depicted as any of formulas. It will be understood that any compound of the formulas may be prepared by the suitable selection of reagents with appropriate substitution. Solvents, temperature, pressures, and other reaction conditions may be readily selected by one of ordinary skill in the art.

For illustrative purposes, Scheme 1 and Scheme 2 show general synthetic methods for preparing the compounds described herein. For a more detailed description of the individual reaction steps, see the Examples section below. Those skilled in the art will appreciate that other synthetic routes may be used to synthesize the compounds. In addition, many of the compounds prepared by the methods described below can be further modified in light of this disclosure using conventional chemistry well known those skilled in the art.

Scheme 1

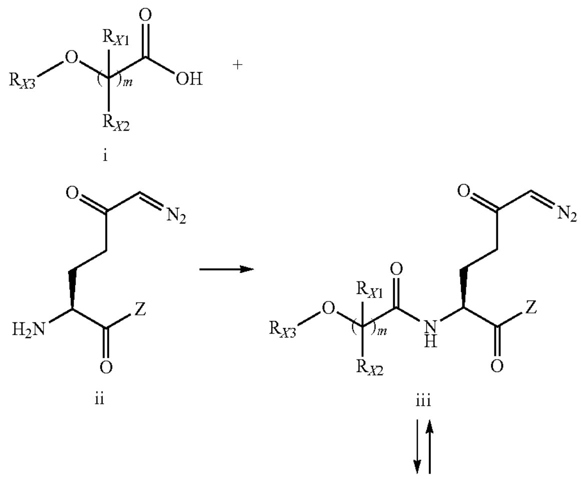

i ii iii

-continued

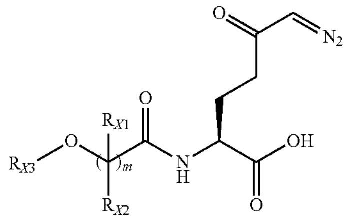

iv

Scheme 2

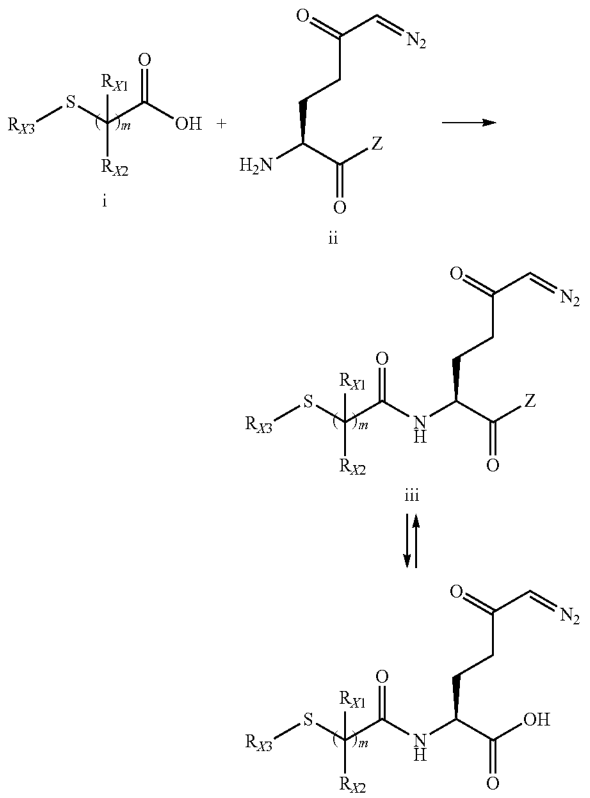

i ii iii iv

General routes to compounds illustrated in the invention is described in Scheme 1 and Scheme 2, where the Z, $R_{X1}$, $R_{X2}$, $R_{X3}$, and m etc. substituents are defined previously in the text or a functional group that can be converted to the desired final substituent.

As depicted in Scheme 1 and Scheme 2, condensation reaction of the acid i with the amine ii gives iii using organic base and condensation reagents. Hydrolysis reaction of iii can provide iv using LiOH, NaOH, etc. Under organic base and condensation reagents, condensation reaction between iv and alcohols or mercaptans gives iii as a different ester or thioester.

Wherein the organic base is preferably DIPEA, NMM, 1-Methylimidazole, 2,4,6-Collidine and so on. The condensation reagents is preferably HATU, TCFH, XtalFluor-E, N,N'-Diisopropylcarbodiimide and so on.

It will be appreciated that other synthetic routes may be available for practice of the present invention.

In another aspect, provided here is a pharmaceutical composition comprising the compound, the pharmaceutically acceptable salt thereof, the stereoisomer thereof, the tautomer thereof, and the isotopic substitution thereof of the present invention; and a pharmaceutically acceptable carrier, diluent or excipient.

In another aspect, provided here is a method for treating a disease or a condition, the method comprising administering to a subject in need of treatment of the compound, the pharmaceutically acceptable salt thereof, the stereoisomer thereof, the tautomer thereof, and the isotopic substitution thereof; or a pharmaceutical composition thereof, in an amount effective for treating the disease or condition. In still other aspects, the presently disclosed subject matter provides the use of the compound, the pharmaceutically acceptable salt thereof, the stereoisomer thereof, the tautomer thereof, and the isotopic substitution thereof, for treating a disease or condition. In some embodiments, the disease or condition is selected from the group consisting of an infection, cancer, an autoimmune disease, an inflammatory disease, and a neurodegenerative or neurological disease.

As used herein, a "cancer" in a patient refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within an animal, or circulate in the blood stream as independent cells, for example, leukemic cells. A "tumor," as used herein, refers to all neoplastic cell growth and proliferation, whether malignant or benign, and all precancerous and cancerous cells and tissues. A "solid tumor," as used herein, is an abnormal mass of tissue that generally does not contain cysts or liquid areas. A solid tumor may be in the brain, colon, breasts, prostate, liver, kidneys, lungs, esophagus, head and neck, ovaries, cervix, stomach, colon, rectum, bladder, uterus, testes, and pancreas, as non-limiting examples. In some embodiments, the solid tumor regresses or its growth is slowed or arrested after the solid tumor is treated with the presently disclosed methods. In other embodiments, the solid tumor is malignant. In some embodiments, the cancer comprises Stage 0 cancer. In some embodiments, the cancer comprises Stage I cancer. In some embodiments, the cancer comprises Stage II cancer. In some embodiments, the cancer comprises Stage III cancer. In some embodiments, the cancer comprises Stage IV cancer. In some embodiments, the cancer is refractory and/or metastatic. For example, the cancer may be refractory to treatment with radiotherapy, chemotherapy or monotreatment with immunotherapy. Cancer as used herein includes newly diagnosed or recurrent cancers, including without limitation, acute lymphoblastic leukemia, acute myelogenous leukemia, advanced soft tissue sarcoma, brain cancer, metastatic or aggressive breast cancer, breast carcinoma, bronchogenic carcinoma, choriocarcinoma, chronic myelocytic leukemia, colon carcinoma, colorectal carcinoma, Ewing's sarcoma, gastrointestinal tract carcinoma, glioma, glioblastoma multiforme, head and neck squamous cell carcinoma, hepatocellular carcinoma, Hodgkin's disease, intracranial ependymoblastoma, large bowel cancer, leukemia, liver cancer, lung carcinoma, Lewis lung carcinoma, lymphoma, malignant fibrous histiocytoma, a mammary tumor, melanoma, mesothelioma, neuroblastoma, osteosarcoma, ovarian cancer, pancreatic cancer, a pontine tumor, premenopausal breast cancer, prostate cancer, rhabdomyosarcoma, reticulum cell sarcoma, sarcoma, small cell lung cancer, a solid tumor, stomach cancer, testicular cancer, and uterine carcinoma.

In yet another aspect, provided here is a method of treating a subject having a cancer, said method comprising administering to the subject a therapeutically effective amount of the compound, the pharmaceutically acceptable salt thereof, the stereoisomer thereof, the tautomer thereof, and the isotopic substitution thereof of the present invention; or the pharmaceutical composition of the present invention.

In some embodiments, the cancer is selected from lung cancer, pancreatic cancer, liver cancer, breast cancer, colon cancer, leukemia, glioblastoma or head and neck cancer.

In another aspect, provided here is use of the compound, the pharmaceutically acceptable salt thereof, the stereoisomer thereof, the tautomer thereof, and the isotopic substitution thereof of the present invention; or the pharmaceutical composition of the present invention for the manufacture of a medicament for the treatment of a cancer.

In some embodiments, the cancer is selected from lung cancer, pancreatic cancer, liver cancer, breast cancer, colon cancer, leukemia, glioblastoma or head and neck cancer.

In some embodiments, the medicament is used as a glutamine antagonist.

As used herein, the term "glutamine antagonist" refers to a glutamine analog that interferes with a glutamine metabolic pathway, e.g., the inhibition or blocking of a metabolic pathway downstream of glutamine in which glutamine acts as a precursor of one or more non-glutamine compounds. Examples of such metabolic pathways are well known (see, e.g., Hensley et al, "Glutamine and cancer: cell biology, physiology, and clinical opportunities" J Clin Invest. 2013; 123(9):3678-3684; DeBerardinis et al, "Q's next: the diverse functions of glutamine in metabolism, cell biology and cancer" Oncogene. 2009; 29(3):313-324; and Medina et al, "Relevance of glutamine metabolism to tumor cell growth" Mol Cell Biochem. 1992; 113(1): 1-15). In some contexts, the term glutamine antagonist also includes glutamine analogs that inhibit glutamine uptake by cells, thereby reducing its biological activity. Diseases or conditions wherein excess and/or aberrant glutamine.

In yet another aspect, provided here is the compound, the pharmaceutically acceptable salt thereof, the stereoisomer thereof, the tautomer thereof, and the isotopic substitution thereof of the present invention; or the pharmaceutical composition of the present invention for use in therapy.

In yet another aspect, provided here is the compound, the pharmaceutically acceptable salt thereof, the stereoisomer thereof, the tautomer thereof, and the isotopic substitution thereof of the present invention; or the pharmaceutical composition of the present invention for use as a medicament.

In yet another aspect, provided here is the compound, the pharmaceutically acceptable salt thereof, the stereoisomer thereof, the tautomer thereof, and the isotopic substitution thereof of the present invention; or the pharmaceutical composition of the present invention, for use in treating the disease or condition. In some embodiments, the disease or condition is selected from the group consisting of an infection, cancer, an autoimmune disease, an inflammatory disease, and a neurodegenerative or neurological disease.

In yet another aspect, provided here is the compound, the pharmaceutically acceptable salt thereof, the stereoisomer thereof, the tautomer thereof, and the isotopic substitution thereof of the present invention; or the pharmaceutical composition of the present invention for use in the treatment of a cancer.

In some embodiments, the cancer is selected from lung cancer, pancreatic cancer, liver cancer, breast cancer, colon cancer, leukemia, glioblastoma or head and neck cancer.

The compounds provided herein used as active ingredient, are characterized by improved solubility, improved stability, improved safety, improved pKa properties, and high pharmacokinetics.

DEFINITION

Figure 1:
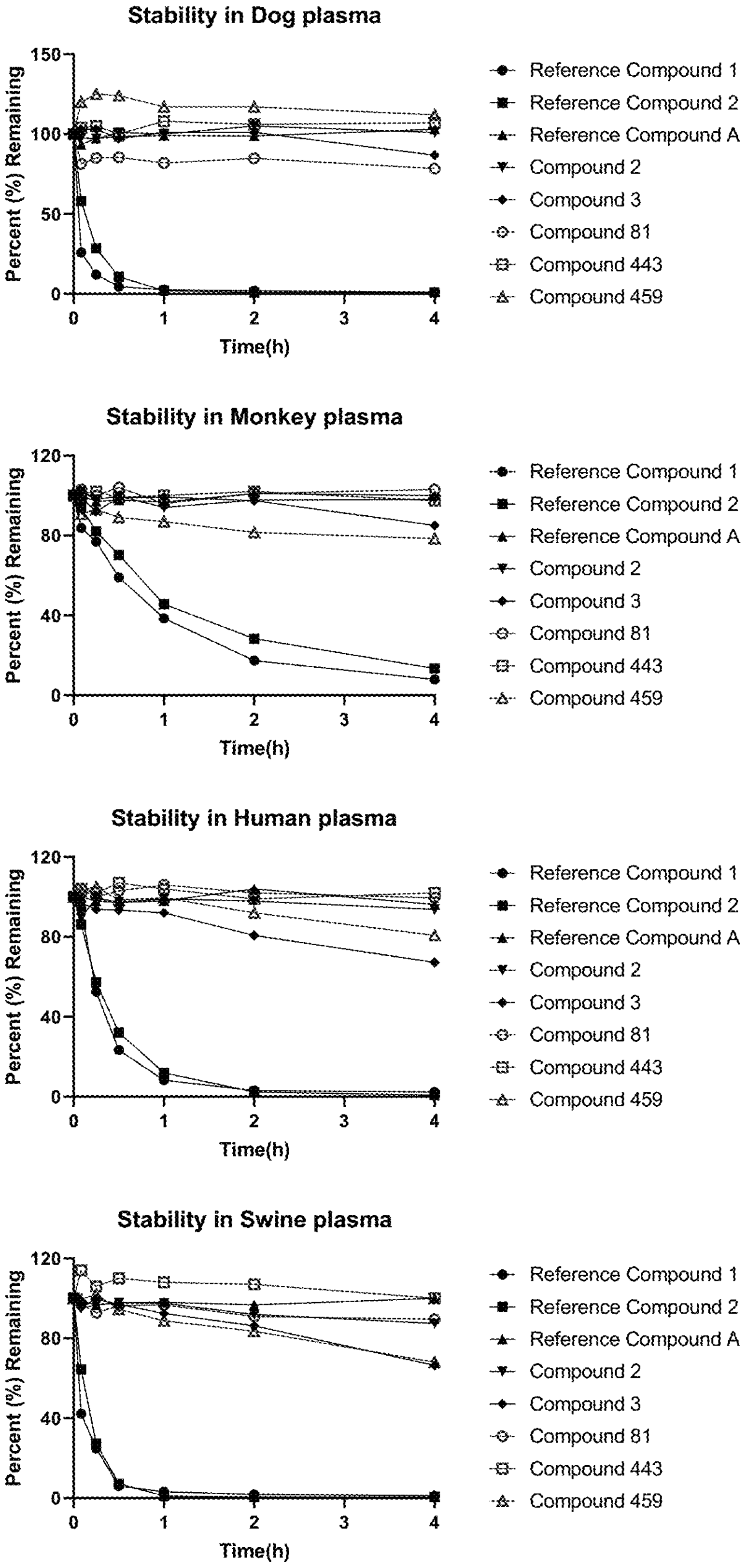
FIG. 1 shows the plasma stability of compounds after incubation for 4 hours in the presence of dog, monkey, swine and human plasma.

The term "halogen", as used herein, unless otherwise indicated, means fluoro, chloro, bromo or iodo. The preferred halogen groups include F, Cl and Br. The terms "halo$C_{1-6}$alkyl", "halo$C_{2-6}$alkenyl", "halo$C_{2-6}$alkynyl" and "halo$C_{1-6}$alkoxy" mean a $C_{1-6}$alkyl, $C_{2-6}$alkenyl, $C_{2-6}$alkynyl or $C_{1-6}$alkoxy in which one or more (in particular, 1 to 3) hydrogen atoms have been replaced by halogen atoms, especially fluorine or chlorine atoms. In some embodiment, preferred are fluoro$C_{1-6}$alkyl, fluoro$C_{2-6}$alkenyl, fluoro$C_{2-6}$alkynyl and fluoro$C_{1-6}$alkoxy groups, in particular fluoro$C_{1-3}$alkyl, for example, $CF_3$, $CHF_2$, $CH_2F$, $CH_2CH_2F$, $CH_2CHF_2$, $CH_2CF_3$ and fluoro$C_{1-3}$alkoxy groups, for example, $OCF_3$, $OCHF_2$, $OCH_2F$, $OCH_2CH_2F$, $OCH_2CHF_2$ or $OCH_2CF_3$, and most especially $CF_3$, $OCF_3$ and $OCHF_2$.

The term "alkyl", as used herein, unless otherwise indicated, includes saturated monovalent hydrocarbon radicals having straight branched or cyclic moieties. For example, alkyl radicals include methyl, ethyl, propyl, isopropyl, n-butyl, isobutyl, sec-butyl, t-butyl, n-pentyl, cyclobutyl, 3-(2-methyl)butyl, 2-pentyl, 2-methylbutyl, neopentyl, cyclopentyl, n-hexyl, 2-hexyl, 2-methylpentyl and cyclohexyl. Similarly, $C_{1-6}$, as in $C_{1-6}$alkyl is defined to identify the group as having 1, 2, 3, 4, 5 or 6 carbon atoms in a linear or branched arrangement.

The term "alkylene" means a difunctional group obtained by removal of a hydrogen atom from an alkyl group that is defined above. For example, methylene (i.e., $—CH_2—$), ethylene (i.e., $—CH_2—CH_2—$ or $—CH(CH_3)—$) and propylene (i.e., $—CH_2—CH_2—CH_2—$, $—CH(—CH_2—CH_3)—$ or $—CH_2—CH(CH_3)—$).

The term "alkenyl" means a straight or branch-chained hydrocarbon radical containing one or more double bonds and typically from 2 to 20 carbon atoms in length. For example, "$C_{2-6}$alkenyl" contains from 2 to 6 carbon atoms. Alkenyl group include, but are not limited to, for example, ethenyl, propenyl, butenyl, 2-methyl-2-buten-1-yl, hepetenyl, octenyl and the like.

The term "alkynyl" contains a straight or branch-chained hydrocarbon radical containing one or more triple bonds and typically from 2 to 20 carbon atoms in length. For example, "$C_{2-6}$alkynyl" contains from 2 to 6 carbon atoms. Representative alkynyl groups include, but are not limited to, for example, ethynyl, 1-propynyl, 1-butynyl, heptynyl, octynyl and the like.

The term "alkoxy" radicals are oxygen ethers formed from the previously described alkyl groups.

The term "aryl", as used herein, unless otherwise indicated, refers to an unsubstituted or substituted mono or polycyclic aromatic ring system containing carbon ring atoms. The preferred aryls are mono cyclic or bicyclic 6-10 membered aromatic ring systems. Phenyl and naphthyl are preferred aryls.

The term "heterocyclyl", as used herein, unless otherwise indicated, refers to unsubstituted and substituted mono or polycyclic non-aromatic ring system containing one or more heteroatoms, which comprising monocyclic heterocyclic ring, bicyclic heterocyclic ring, bridged heterocyclic ring, fused heterocyclic ring or spiro heterocyclic ring. Preferred heteroatoms include N, O, and S, including N-oxides, sulfur oxides, and dioxides. Preferably the ring is three to ten membered and is either fully saturated or has one or more degrees of unsaturation. Multiple degrees of substitution, preferably one, two or three, are included within the present definition. Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl", as used herein, unless otherwise indicated, represents an aromatic ring system containing carbon(s) and at least one heteroatom. Heteroaryl may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "cycloalkyl" refers to a substituted or unsubstituted monocyclic ring, bicyclic ring bridged ring, fused ring, spiro ring non-aromatic ring system one containing carbon atoms. Exemplary "cycloalkyl" groups includes but not limited to, cyclopropyl, cyclobutyl, cyclopentyl, cyclohexyl and so on.

wherein the term "substituted" refers to a group mentioned above in which one or more (preferably 1-6, more preferably 1-3) hydrogen atoms are each independently replaced with the same or different substituent(s). Typical substituents include, but are not limited to, T, $C_{1-6}$alkyl, $C_{1-6}$alkoxy, $C_{3-20}$ cycloalkyl, $-OR_{13}$, $SR_{13}$, $=O$, $=S$, $-C(O)R_{13}$, $-C(S)R_{13}$, $=NR_{13}$, $-C(O)OR_{13}$, $-C(S)OR_{13}$, $-NR_{13}R_{14}$, $-C(O)NR_{13}R_{14}$, cyano, nitro, $-S(O)_2R_{13}$, $-OS(O_2)OR_{13}$, $-OS(O)_2R_{13}$, or $-OP(O)(OR_{13})(OR_{14})$; wherein each T is independently a halogen (F, Cl, Br or I), and $R_{13}$ and $R_{14}$ is independently selected from —H, $C_{1-6}$ alkyl and $C_{1-6}$ haloalkyl. In some embodiments, the substituent(s) is independently selected from the group consisting of —F, —Cl, —Br, —I, —OH, trifluoromethoxy, methyl, ethyl, propyl, isopropyl, butyl, isobutyl, tert-butyl, sec-butyl, $CHF_2$, methoxy, ethoxy, propyloxy, iso-propyloxy, n-butyloxy, isobutyloxy, t-butyloxy, $-SCH_3$, $-SC_2H_5$, formaldehyde group, $-C(OCH_3)$, cyano, nitro, $CF_3$, $-OCF_3$, amino, dimethylamino, methyl thio, sulfonyl and acetyl. Particularly preferred substituent(s) is —F, —Cl or —Br.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention. Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

The compounds of the present invention may also be present in the form of pharmaceutically acceptable salt(s). For use in medicine, the salts of the compounds of this invention refer to non-toxic "pharmaceutically acceptable salt(s)". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic. Pharmaceutically acceptable basic/cationic salts include, and are not limited to aluminum, calcium, chloroprocaine, choline, diethanolamine, ethylenediamine, lithium, magnesium, potassium, sodium and zinc.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The present invention includes all stereoisomers of the compound and pharmaceutically acceptable salts thereof. Further, mixtures of stereoisomers as well as isolated specific stereoisomers are also included. During the course of the synthetic procedures used to prepare such compounds or in using racemization or epimerization procedures known to those skilled in the art, the products of such procedures can be a mixture of stereoisomers.

The term "stereoisomer" as used in the present invention refers to an isomer in which atoms or groups of atoms in the molecule are connected to each other in the same order but differ in spatial arrangement, including conformational isomers and conformational isomers. The configuration isomers include geometric isomers and optical isomers, and optical isomers mainly include enantiomers and diastereomers. The invention includes all possible stereoisomers of the compound.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^{1}H$(hydrogen), $^{2}H$(deuterium) and $^{3}H$(tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent.

When a tautomer of the compound exists, the present invention includes any possible tautomers and pharmaceutically acceptable salts thereof, and mixtures thereof, except where specifically stated otherwise.

When the compound and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. When the compound of the present invention is basic, its corresponding salt can be conveniently prepared from pharmaceutically acceptable non-toxic acids, including inorganic and organic acids. Since the compounds are intended for pharmaceutical use they are preferably provided in substantially pure form, for example at least 60% pure, more suitably at least 75% pure, especially at least 98% pure (% are on a weight for weight basis).

The pharmaceutical compositions of the present invention comprise a compound (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds or a prodrug or a metabolite or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt. The compounds or pharmaceutically acceptable salts thereof, can also be included in pharmaceutical compositions in combination with one or more other therapeutically active compounds.

The pharmaceutical carrier employed can be, for example, a solid, liquid or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 0.05 to about 95 percent of the total composition. Unit dosage forms will generally contain between from about 0.01 mg to about 2 g of the active ingredient, typically 0.01 mg, 0.02 mg, 1 mg, 2 mg, 3 mg, 4 mg, 5 mg, 6 mg, 7 mg, 8 mg, 9 mg, 10 mg, 25 mg, 50 mg, 100 mg, 200 mg, 300 mg, 400 mg, 500 mg, 600 mg, 800 mg or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder or the like. Further, the compositions can be in a form suitable for use in transdermal devices. These formulations may be prepared, utilizing a compound of this invention or a pharmaceutically acceptable salt thereof, via conventional processing methods. As an example, a cream or ointment is prepared by admixing hydrophilic material and water, together with about 0.05 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound or pharmaceutically acceptable salts thereof, may also be prepared in powder or liquid concentrate form.

Generally, dosage levels on the order of from about 0.001 mg/kg to about 150 mg/kg of body weight per day are useful in the treatment of the above-indicated conditions or alternatively about 0.05 mg to about 7 g per patient per day. For example, inflammation, cancer, psoriasis, allergy/asthma, disease and conditions of the immune system, disease and conditions of the central nervous system (CNS), may be effectively treated by the administration of from about 0.001 to 50 mg of the compound per kilogram of body weight per day or alternatively about 0.05 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

These and other aspects will become apparent from the following written description of the invention.

EXAMPLES

The following examples are provided to better illustrate the present invention. All parts and percentages are by weight and all temperatures are degrees Celsius, unless explicitly stated otherwise. The following abbreviations have been used in the examples:

| | |
|---|---|
| DMF | N,N-Dimethylformamide |
| EA | Ethyl acetate |
| MeONa | Sodium methanolate |
| MeOH | Methanol |
| DCM | Dichloromethane |
| DCE | 1,2-Dichloroethane |
| EtOH | Ethanol |
| THF | Tetrahydrofuran |
| MeCN | Acetonitrile |
| NMM | 4-Methylmorpholine |
| DIPEA | N,N-Diisopropylethylamine |
| TEA | Triethylamine |
| Ts | 4-methyl benzenesulfonyl |
| HATU | 2-(7-Azabenzotriazol-1-yl)-N,N,N',N'-tetramethyluronium hexafluorophosphate |

-continued

| | |
|---|---|
| XtalFluor-E | N,N-Diethyl-S,S-difluorosulfiliminium tetrafluoroborate |
| TCFH | N-(chloro(dimethylamino)methylene)-N-methylmethanaminium hexafluorophosphate(V) |
| BOP | 1H-Benzotriazol-1-yloxytris(dimethylamino)phosphonium Hexafluorophosphate |
| RT | Room temperature |
| min | minute(s) |
| h | hour(s) |
| aq | aqueous |
| sat | saturated |
| FLASH | Medium pressure chromatograph |
| Prep - TLC | Preparative thin layer chromatography |
| Pre-HPLC | High pressure chromatograph |

Intermediate A1

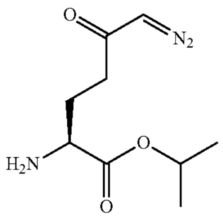

A1

Intermediate A1 was prepared referring to the compound 3 in WO2017023774 in Scheme 1 at page 82.

The following compounds were synthesized using the above procedure or modification procedure with the corresponding starting materials.

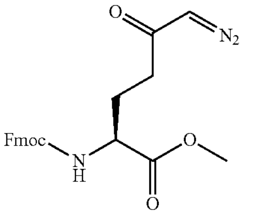

A2

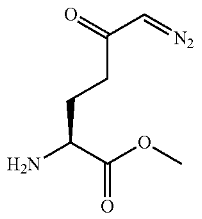

A3

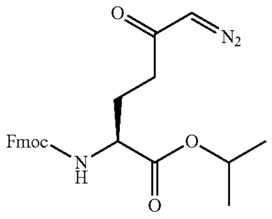

A4

-continued

A5

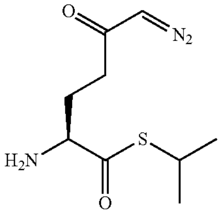

A6

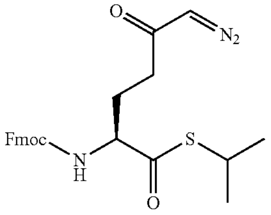

Intermediate B1

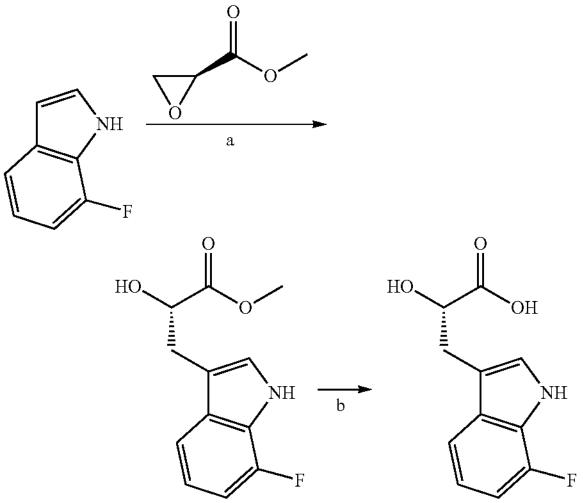

B1

Step a: To a solution of 7-Fluoroindole (308 mg, 2.279 mmol) and Ytterbium(III) triflate hydrate (219 mg, 343.119 µmol) in Chloroform (3 mL) was added (2S)-Methylglycidate (121 mg, 1.185 mmol) under $N_2$. The mixture was heated to 85° C. and stirred for 3 h. The reaction mixture was cooled to RT. The reaction mixture was quenched with $Na_2CO_3$ (aq) (10 mL), and adjusted the pH to 5-6 with 2M HCl. The aqueous layer was separated and extracted with DCM (2×10 mL). The combined organic layers were dried over anhydrous $Na_2SO_4$, filtered and concentrated under reduced pressure. The residue was purified by silica chromatography eluting with EtOAc/Hexane(1:2) to afford methyl (2S)-3-(7-fluoro-1H-indol-3-yl)-2-hydroxy-propanoate (136 mg, 573.292 µmol). MS: m/z 238$(M+H)^+$.

Step b: To a solution of methyl (2S)-3-(7-fluoro-1H-indol-3-yl)-2-hydroxy-propanoate (136 mg, 573.292 µmol) in water (1 mL) was added LiOH (2M solution in water, 1 mL). The mixture was stirred for overnight at RT-60° C., Citric acid(solid) was added, diluted with water (5 mL) and extracted with EA (2×10 mL). The combined organic layers were dried over anhydrous $Na_2SO_4$, filtered and concentrated under reduced pressure to afford (2S)-3-(7-fluoro-1H-indol-3-yl)-2-hydroxy-propanoic acid (165 mg, 739.247 mol) which was used in next step without any further purification. MS: m/z $(224)^+$.

Intermediate B2

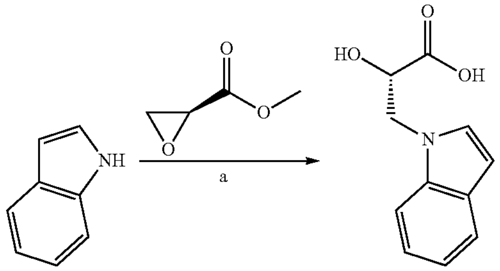

B2

Step a: To a solution of Indole (302 mg, 2.578 mmol) in DMF (3 mL) was added NaH (217 mg, 9.043 mmol) at ice-water bath for 1 h. (2S)-Methylglycidate (685 mg, 6.710 mmol) was added and the mixture was stirred over night at RT. The reaction mixture was quenched with $H_2O$, and adjusted the pH to 3-4 with citric acid. The aqueous layers were extracted with EA. The combined organic layers were dried over anhydrous $Na_2SO_4$, filtered and concentrated under reduced pressure. The residue was purified by FLASH with $H_2O$/MeCN (5%-~95%) to afford (S)-2-hydroxy-3-(1H-indol-1-yl)propanoic acid (222 mg, 1.082 mmol). MS: m/z 206$(M+H)^+$.

The following compounds were synthesized using the above procedure or modification procedure with the corresponding starting materials.

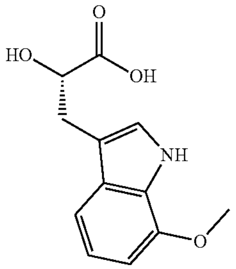

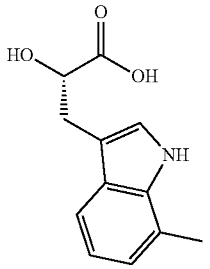

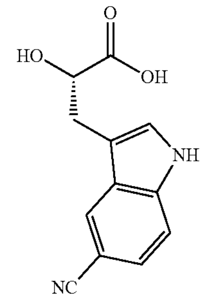

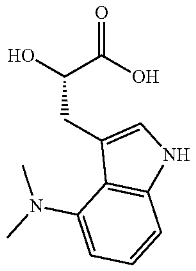

-continued
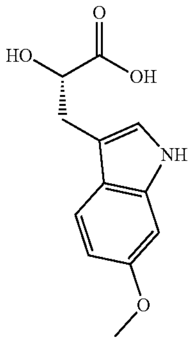
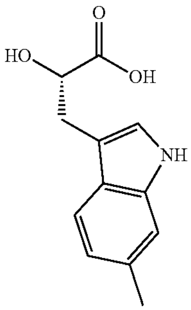
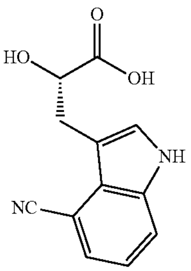
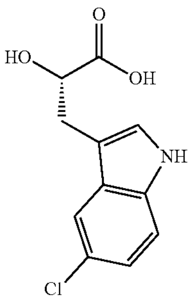
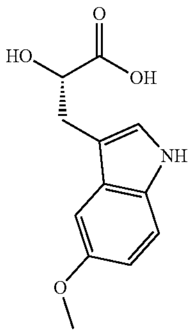
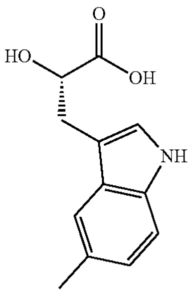
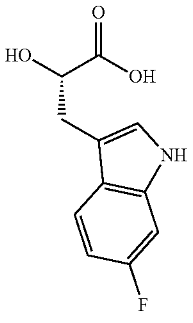
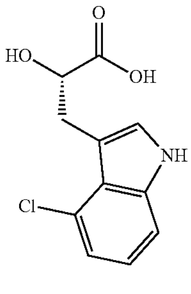
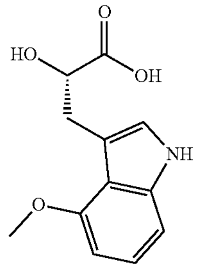
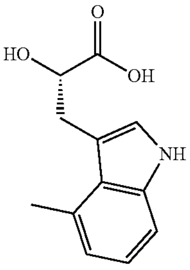
-continued
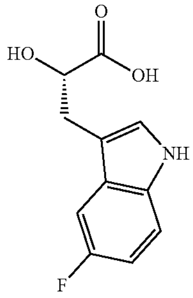
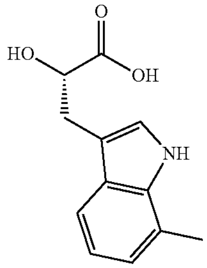
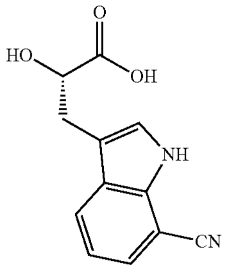
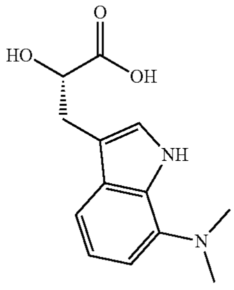
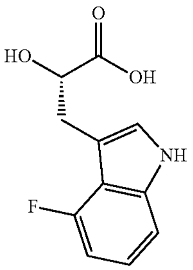
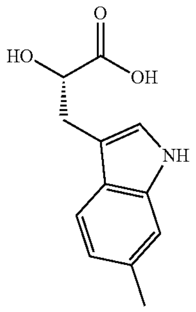
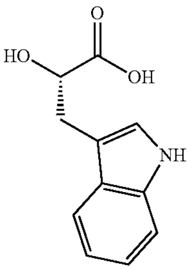
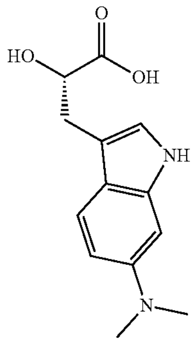
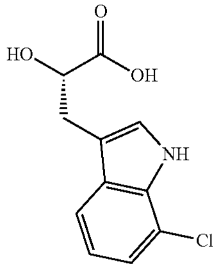
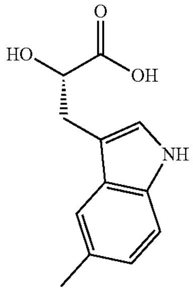

-continued

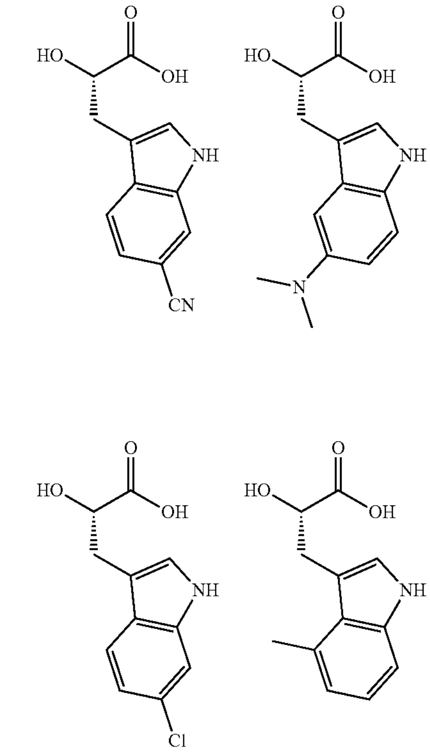

Intermediate C1

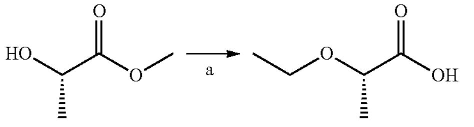

C1

Step a: To a solution of Methyl (S)-(−)-lactate (1099 mg, 10.5567 mmol), Iodoethane (3726 mg, 23.8900 mmol) in Diethyl ether (10 mL) was added $Ag_2O$ (4772 mg, 20.5925 mmol) under $N_2$. The reaction mixture was stirred over night at RT by light-avoiding. The reaction mixture was monitored by TLC. The reaction mixture was filtered and concentrated under reduced pressure. The residue was dissolved by THF (3 mL), MeOH (3 mL), $H_2O$ (3 mL) and then the reaction mixture was added LiOH (246 mg, 10.2721 mmol). The reaction mixture was stirred for 3 h at RT. The reaction mixture was monitored by TLC and adjusted the pH to 2 with 1N HCl. The reaction mixture was concentrated under reduced pressure to 5 mL. The aqueous layers were extracted with EA (3×10 mL). The combined organic layers were washed with saturated solution of NaCl (3×10 mL) and dried over anhydrous $Na_2SO_4$, filtered and concentrated under reduced pressure to afford (S)-2-ethoxypropanoic acid (772 mg, 6.5351 mmol). MS: m/z 119$(M+H)^+$.

Intermediate C2

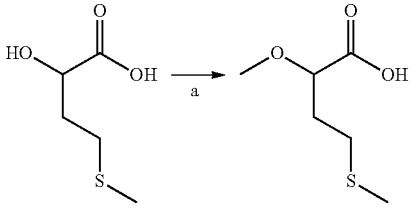

C2

Step a: To a solution of 2-hydroxy-4-(methylthio)butanoic acid (0.68 g, 4.5274 mmol), $CH_3I$ (3.35 g, 23.6019 mmol) in Diethyl ether (10 mL) was added $Ag_2O$ (4.41 g, 19.0303 mmol). The reaction mixture was stirred over night at RT. The reaction mixture was monitored by LC-MS. The reaction mixture was filtered and concentrated under reduced pressure. The residue was dissolved by MeOH (6 mL), $H_2O$ (2 mL) and then the reaction mixture was added NaOH (318 mg, 7.9506 mmol). The reaction mixture was stirred for 3 h at RT. The reaction mixture was monitored by TLC and adjusted the pH to 3 with 1M HCl. The reaction mixture was concentrated under reduced pressure to 5 mL. The aqueous layers were extracted with EA (3×10 mL). The combined organic layers were washed with saturated solution of NaCl (3×10 mL) and dried over anhydrous $Na_2SO_4$, filtered and concentrated under reduced pressure to afford 2-methoxy-4-(methylthio)butanoic acid (128 mg, 779.4318 μmol). MS: m/z 165$(M+H)^+$.

Intermediate C3

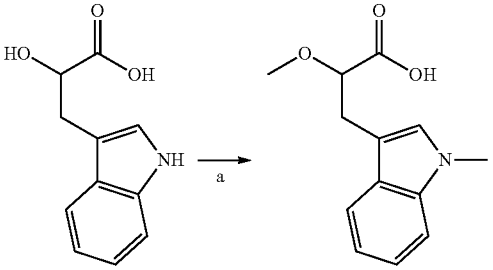

C3

Step a: To a solution of 2-hydroxy-3-(1H-indol-3-yl) propanoic acid (152 mg, 740.706 mol) in THF (10 mL) was added NaH (55 mg, 2.292 mmol). The reaction mixture was stirred for 20 min at RT and then $CH_3I$ (370 mg, 2.607 mmol) was added. The reaction mixture was monitored by LC-MS. $CH_3I$ (358 mg, 2.522 mmol) was added again. The reaction mixture was monitored by LC-MS. The reaction mixture was stirred for 3 h at 40° C. The reaction mixture was added $H_2O$ (5 mL) and extracted with EA (10 mL). The aqueous layers were combined and purified by FLASH with $H_2O$/MeCN (0%-100%, 40 min, C18). The product layers were concentrated under reduced pressure to afford 2-methoxy-3-(1-methyl-1H-indol-3-yl)propanoic acid (119 mg, 510.155 μmol). MS: m/z 234 $(M+H)^+$.

The following compounds were synthesized using the above procedure or modification procedure with the corresponding starting materials.

-continued
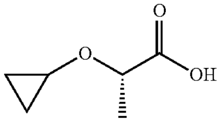
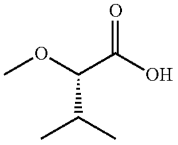
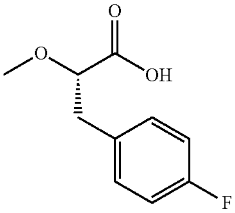
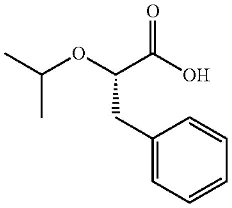
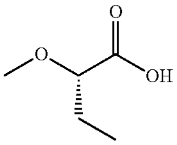
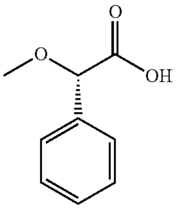
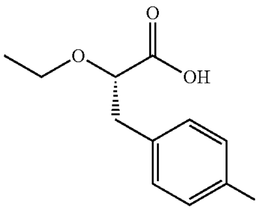
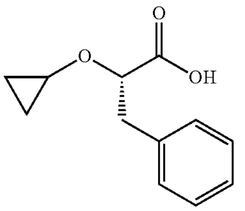
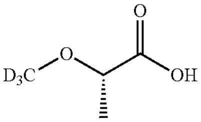
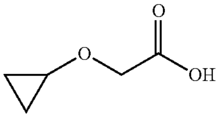
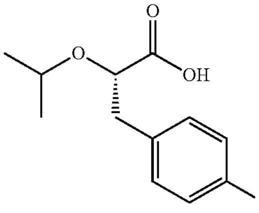
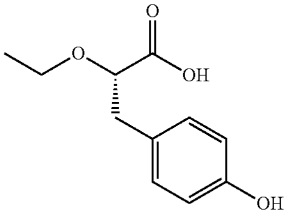
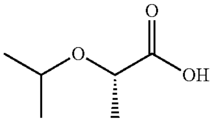
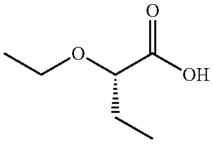
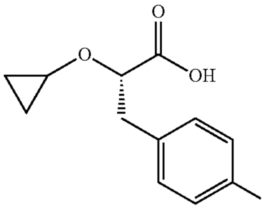
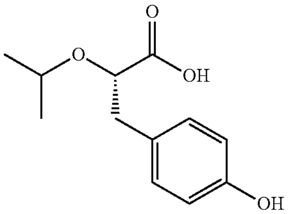
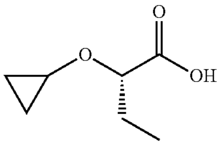
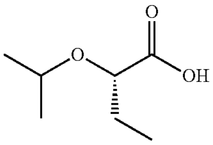
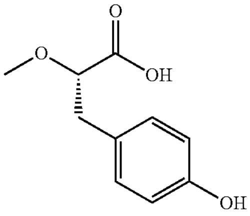
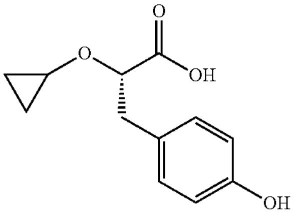
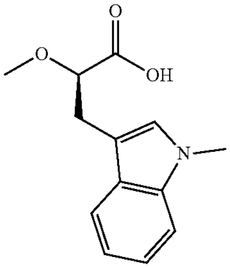
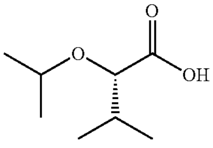
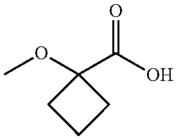
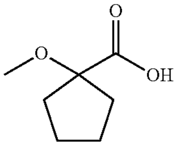
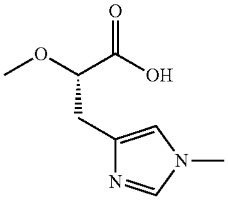
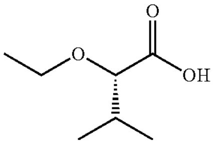
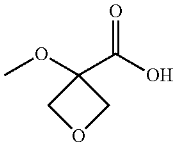
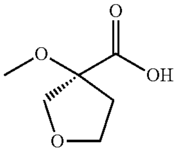
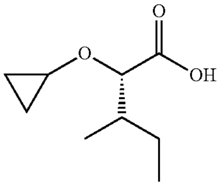
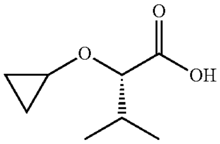
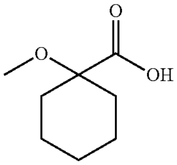
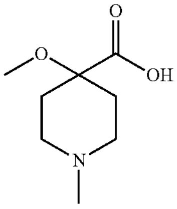
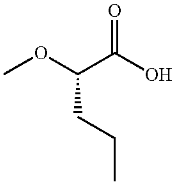
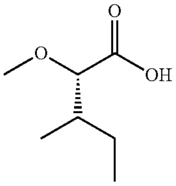
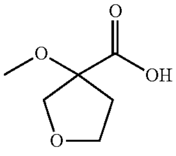

-continued
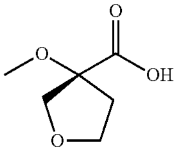
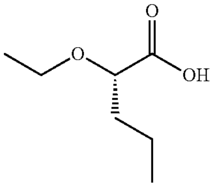
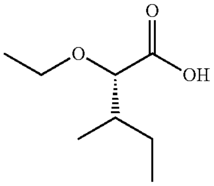
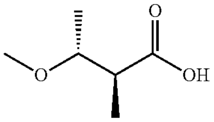
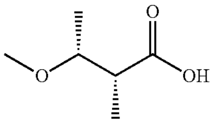
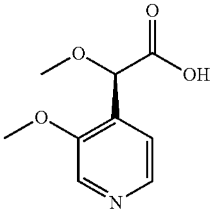
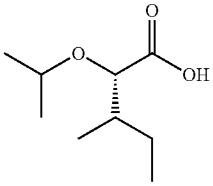
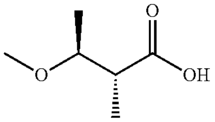
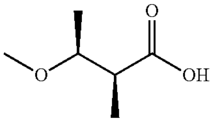
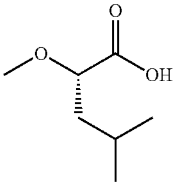
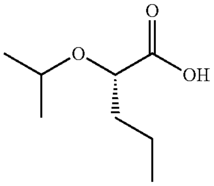
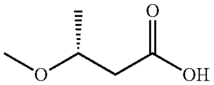
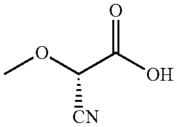
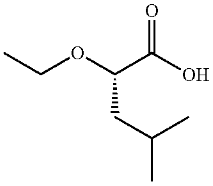
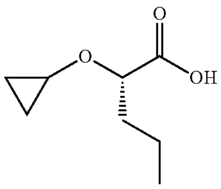
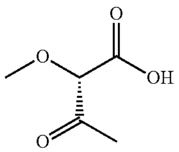
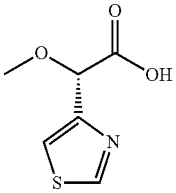
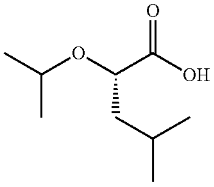
-continued
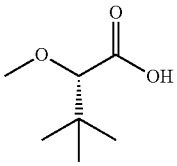
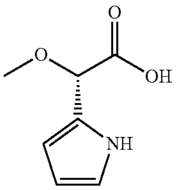
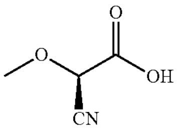
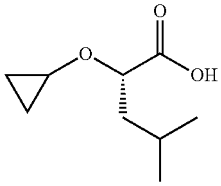
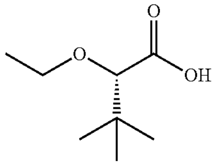
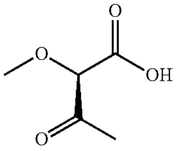
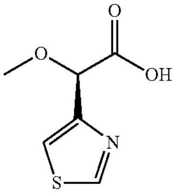
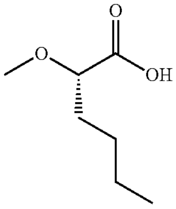
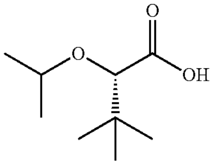
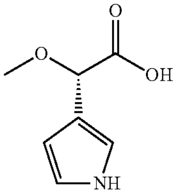
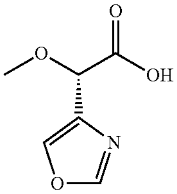
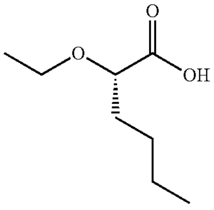
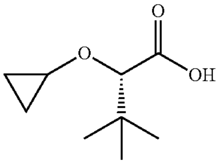
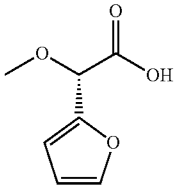
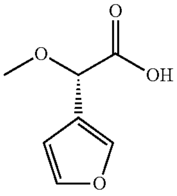
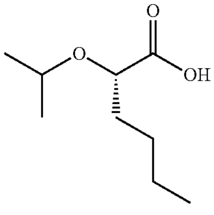
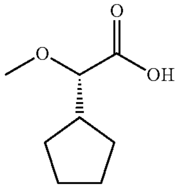
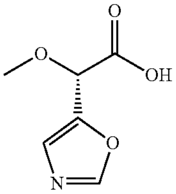
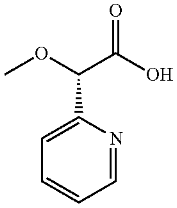

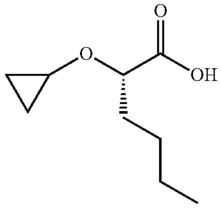
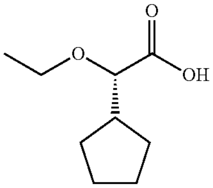
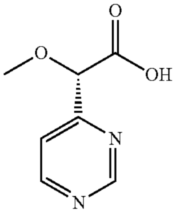
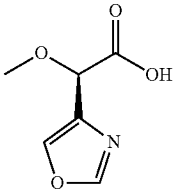
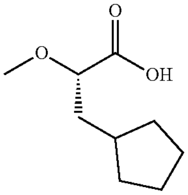
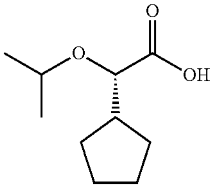
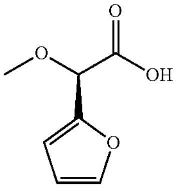
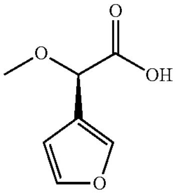
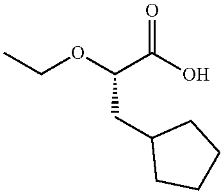
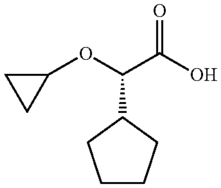
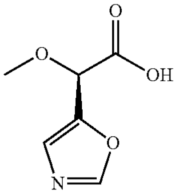
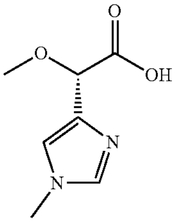
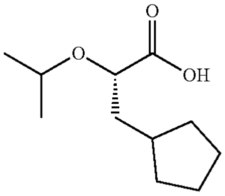
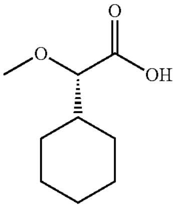
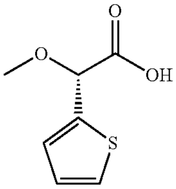
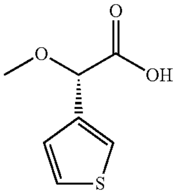
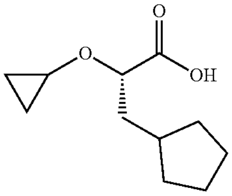
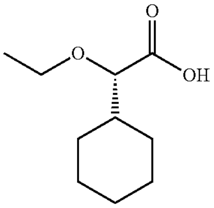
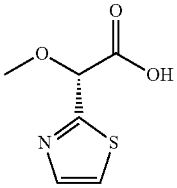
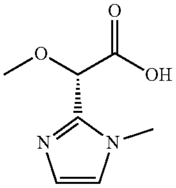
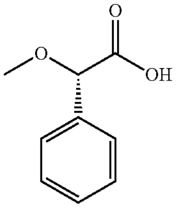
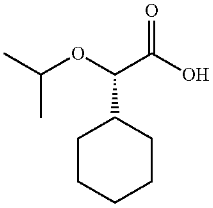
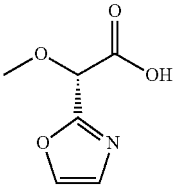
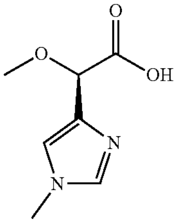
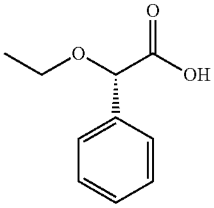
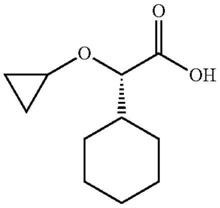
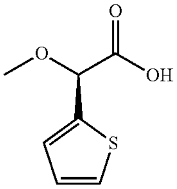
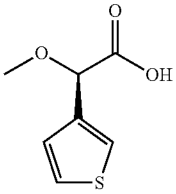
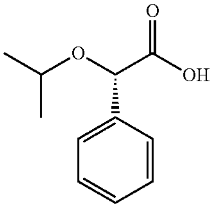
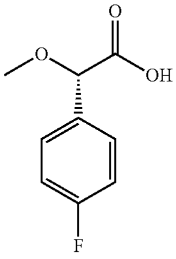
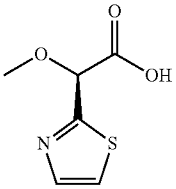
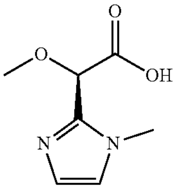
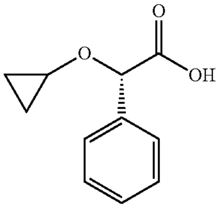
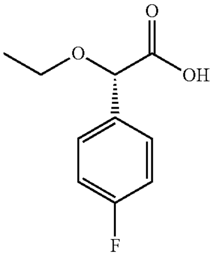

-continued
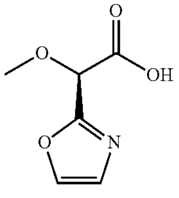
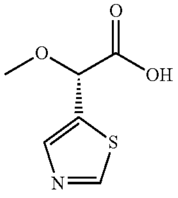
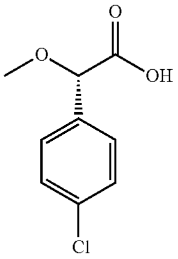
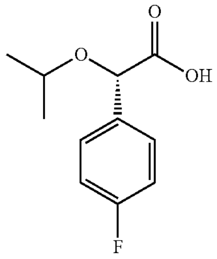
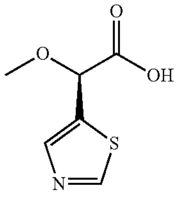
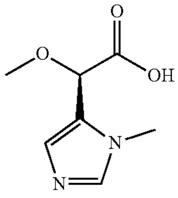
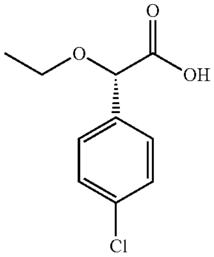
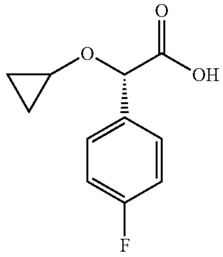
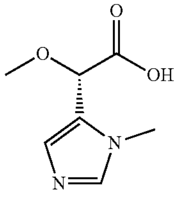
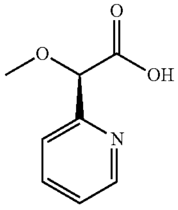
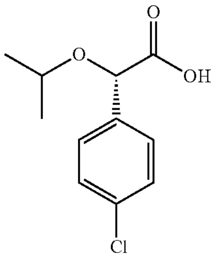
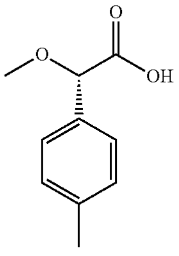
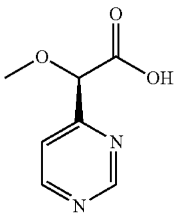
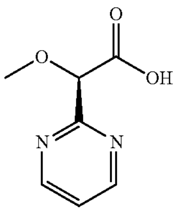
-continued
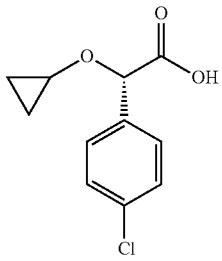
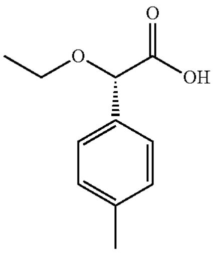
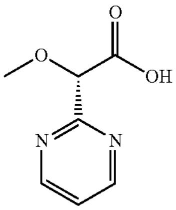
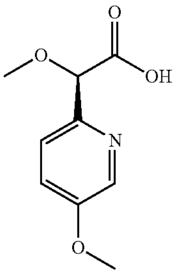
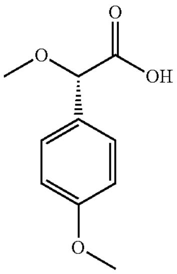
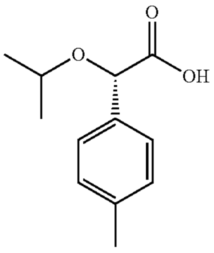
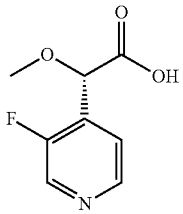
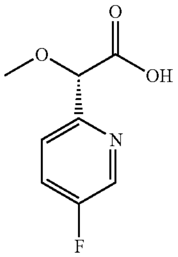
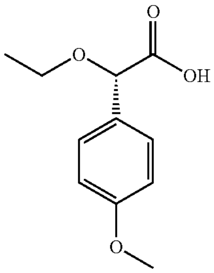
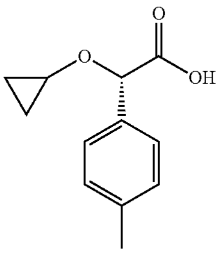
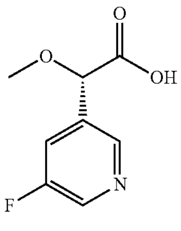
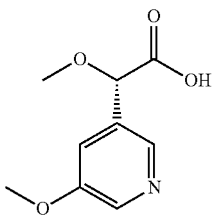
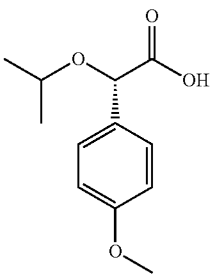

-continued

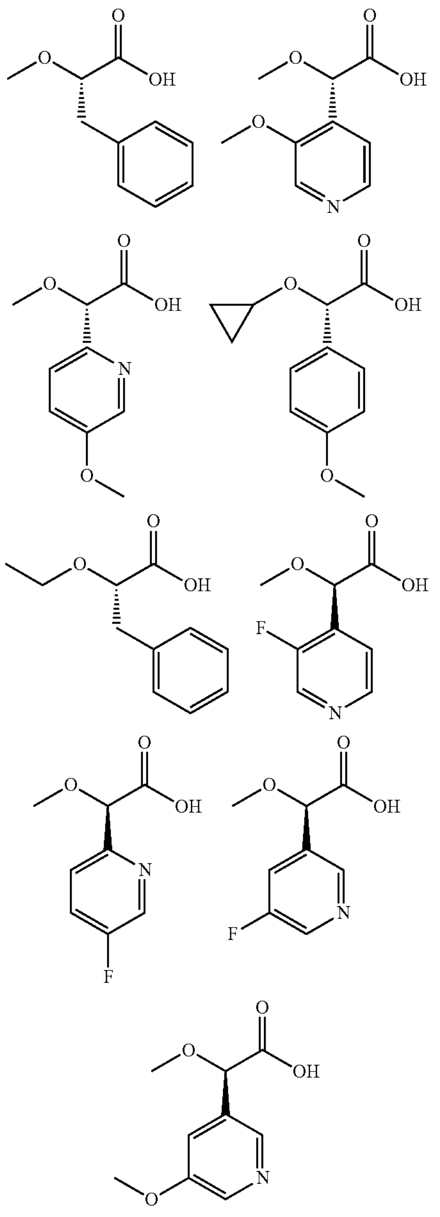

Intermediate D1

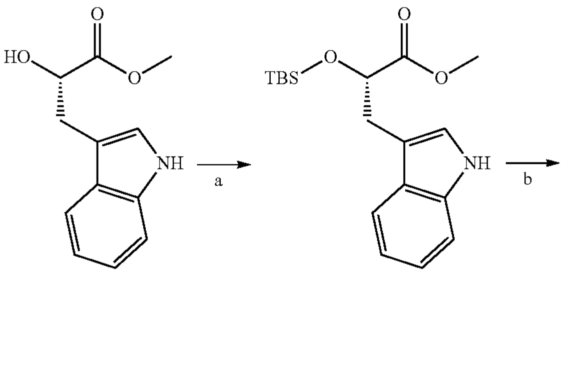

-continued

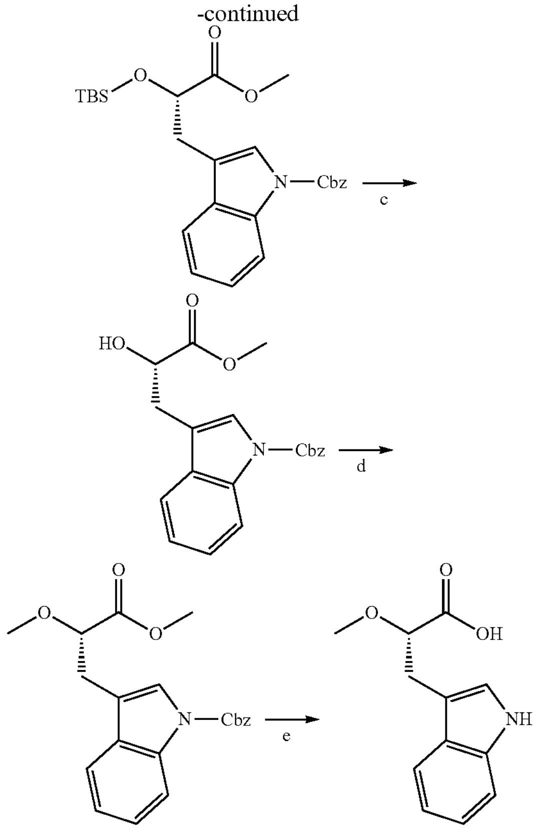

D1

Step a: To a solution of methyl (S)-2-hydroxy-3-(1H-indol-3-yl)propanoate(2 g, 9.123 mmol) in DCM (20 mL) was added Imidazole(2061 mg, 30.274 mmol) and TBDMS-Cl (2980 mg, 19.772 mmol). The mixture was stirred for overnight at RT. The reaction mixture was quenched with Water (10 mL) and extracted with DCM (10 mL). The reaction mixture was separated and organic extracts were collected. The aqueous solution was extracted with DCM (2×10 mL). The residue was purified by wet column chromatography with EA/Hex (0-20%). The product's solution was concentrated under reduced pressure. The methyl (S)-2-((tert-butyldimethylsilyl)oxy)-3-(1H-indol-3-yl)propanoate (3099 mg) was obtained. MS: m/z 334$(M+H)^+$.

Step b: To a −78° C. solution of methyl (S)-2-((tert-butyldimethylsilyl)oxy)-3-(1H-indol-3-yl)propanoate (3.099 g, 9.292 mmol) in THF (30 mL) was added LiHMDS (10.5 mL, 10.491 mmol). The mixture was stirred for 30 min at −78° C. Then Carbobenzyloxy chloride (4623 mg, 27.100 mmol) was dropped into the mixture at −78° C. The reaction mixture was stirred for 1 h at this temperature. Quenched the reaction with sat. $NH_4Cl$, and the aqueous solution was extracted with EA (2×10 mL). The combined organic extracts were washed with brine (3×10 mL), dried over anhydrous $Na_2SO_4$. The organic phase was concentrated under reduced pressure. The benzyl (S)-3-(2-((tert-butyldimethylsilyl)oxy)-3-methoxy-3-oxopropyl)-1H-indole-1-carboxylate (4345 mg) was obtained. MS: m/z 468$(M+H)^+$.

Step c: To a solution of benzyl(S)-3-(2-((tert-butyldimethylsilyl)oxy)-3-methoxy-3-oxopropyl)-1H-indole-1-carboxylate (4.345 g, 9.292 mmol) in THF (30 mL) was added Tetrabutylammonium fluoride (5 mL). The mixture was stirred for overnight at RT. The reaction mixture was concentrated under reduced pressure. The residue was purified by FLASH with EA/Hex(0-60%). The product's solution was concentrated under reduced pressure. The benzyl 3-[(2S)-2-hydroxy-3-methoxy-3-oxo-propyl]indole-1-carboxylate (2.21 g) was obtained. MS: m/z 354$(M+H)^+$.

Step d: To a solution of benzyl 3-[(2S)-2-hydroxy-3-methoxy-3-oxo-propyl]indole-1-carboxylate(103 mg, 291.481 µmol), and 4 Å molecular sieve in $CH_3I$ (1 mL) was added Silver oxide(216 mg, 932.098 µmol). The mixture was stirred for overnight at RT. The reaction mixture was concentrated under reduced pressure. The reaction mixture was diluted with EA (5 mL) and filtered, the filtrate was concentrated to afford benzyl (S)-3-(2,3-dimethoxy-3-oxo-propyl)-1H-indole-1-carboxylate (107.088 mg, 100.000% yield). MS: m/z 368$(M+H)^+$.

Step e: To a solution of benzyl(S)-3-(2,3-dimethoxy-3-oxopropyl)-1H-indole-1-carboxylate (0.107 g, 291.240 µmol) in THF (5 mL) and MeOH(5 mL) was added NaOH(3 mL, 3M/L). The mixture was stirred for 1 h at RT. The reaction mixture was adjusted the pH to 3 with 1M HCl. The aqueous solution was extracted with EA (2×10 mL). The combined organic extracts were washed with brine (3×10 mL), dried over anhydrous $Na_2SO_4$. The organic phase was concentrated under reduced pressure and (S)-3-(1H-indol-3-yl)-2-methoxypropanoic acid (71 mg) was obtained. MS: m/z 220$(M+H)^+$.

The following compounds were synthesized using intermediate D1 and the above procedure or modification procedure with the corresponding starting materials.

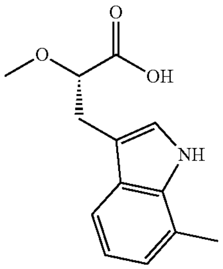
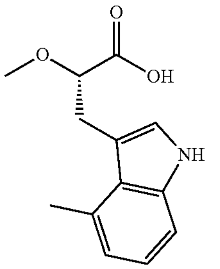
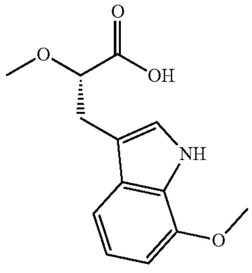
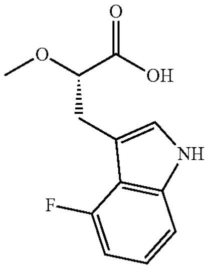
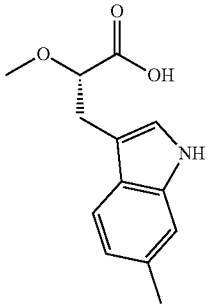
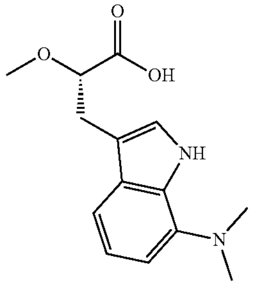

-continued

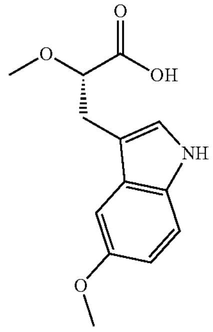
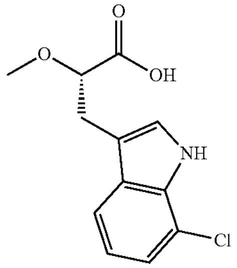
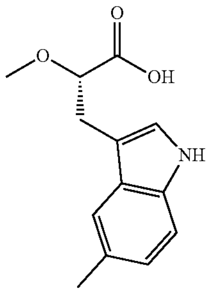
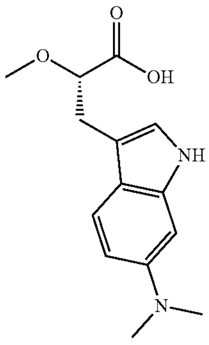
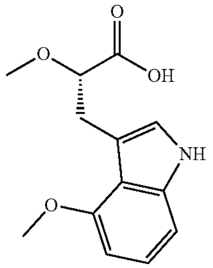
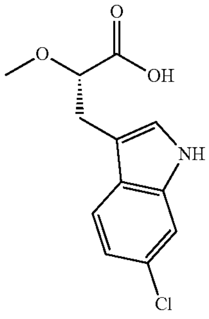
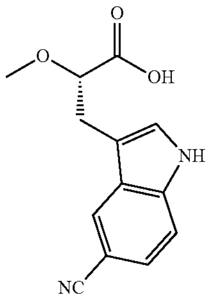
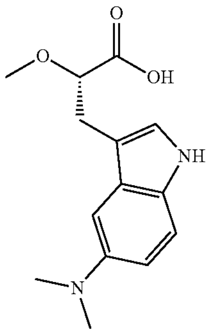
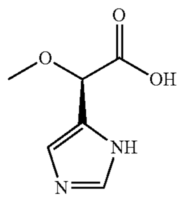
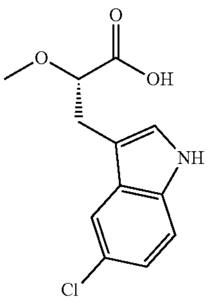

-continued
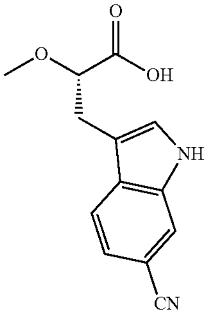
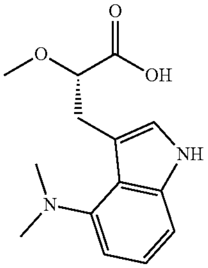
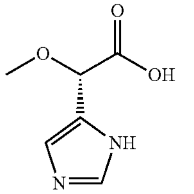
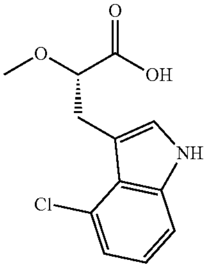
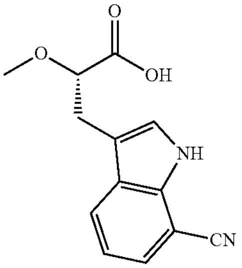
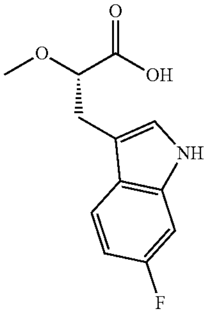
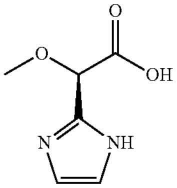
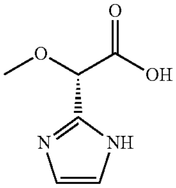
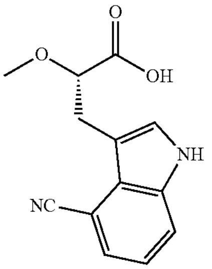
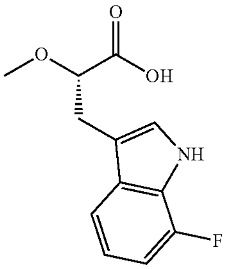
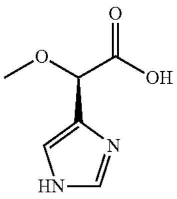
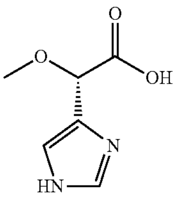
-continued
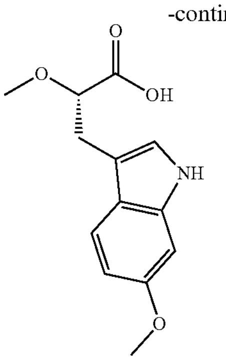
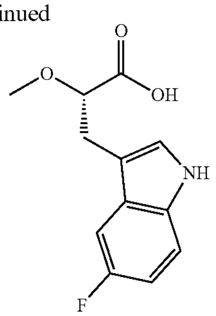
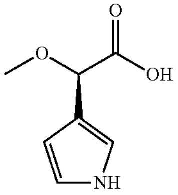
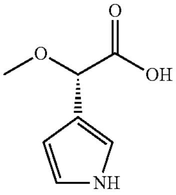
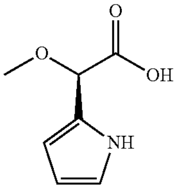
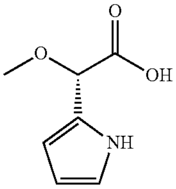
Example 1
Isopropyl (S)-6-diazo-2-((S)-3-(7-fluoro-1H-indol-3-yl)-2-hydroxypropanamido)-5-oxohexanoate (Compound 1)
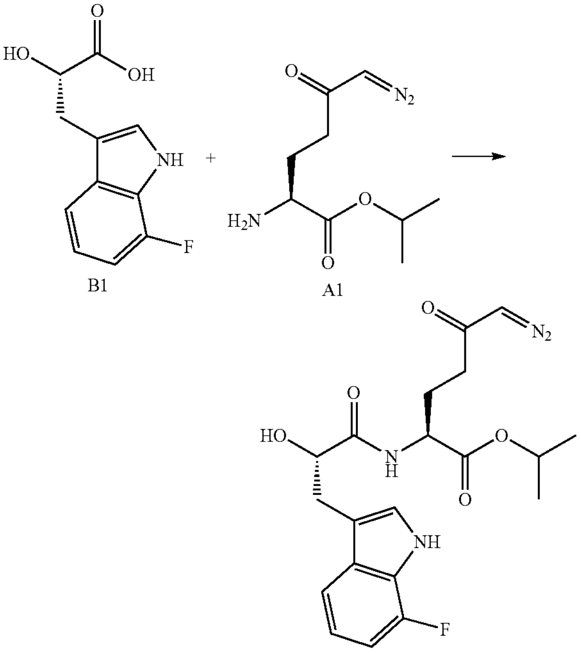
To a solution of (2S)-3-(7-fluoro-1H-indol-3-yl)-2-hydroxy-propanoic acid (0.165 g, 739.247 μmol) and isopropyl (2S)-2-amino-6-diazo-5-oxo-hexanoate(123 mg, 576.834

μmol) in DCM (2 mL) was added N,N'-Diisopropylcarbodiimide (95 mg, 752.779 μmol), 2,4,6-Collidine (115 mg, 949.008 μmol) and Ethyl cyanoglyoxylate-2-oxime (83 mg, 584.044 μmol) at 0° C. The mixture was stirred at RT for 16 h. The reaction mixture was concentrated under reduced pressure. The residue was purified by pre-HPLC, and concentrated under reduced pressure to afford isopropyl (2S)-6-diazo-2-[[(2S)-3-(7-fluoro-1H-indol-3-yl)-2-hydroxy-propanoyl]amino]-5-oxo-hexanoate (41.6 mg, 99.422 μmol) by lyophilization. MS: m/z 419(M+H)$^+$, $^1$H NMR (400 MHz, $CDCl_3$) δ 8.47-8.39 (m, 1H), 7.47 (d, J=7.9 Hz, 1H), 7.21-7.19 (m, 1H), 7.16 (d, J=7.8 Hz, 1H), 7.05 (td, J=7.9, 4.8 Hz, 1H), 6.93 (dd, J=10.8, 7.8 Hz, 1H), 5.09 (s, 1H), 5.03 (dt, J=12.5, 6.3 Hz, 1H), 4.53-4.45 (m, 1H), 4.43 (s, 1H), 3.29 (ddd, J=21.3, 14.8, 5.4 Hz, 2H), 2.73-2.60 (m, 1H), 2.43-2.25 (m, 1H), 2.18-1.98 (m, 2H), 1.97-1.80 (m, 1H), 1.30-1.22 (m, 6H).

Example 2

Isopropyl (S)-6-diazo-2-((S)-2-methoxypropanamido)-5-oxohexanoate (Compound 2)

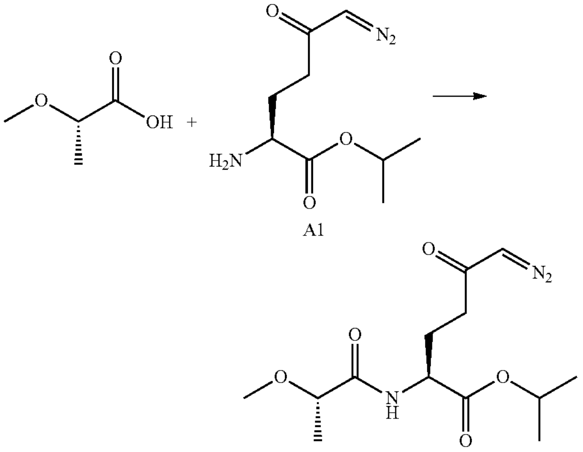

A1

To a solution of (S)-2-methoxypropanoic acid (267 mg, 2.565 mmol) and isopropyl (2S)-2-amino-6-diazo-5-oxo-hexanoate(0.152 g, 712.835 μmol) in DMF (5 mL) was added N,N'-Diisopropylcarbodiimide (327 mg, 2.591 mmol), 2,4,6-Collidine (412 mg, 3.400 mmol) and Ethyl cyanoglyoxylate-2-oxime (375 mg, 2.639 mmol) at 0° C. The mixture was stirred at RT for 15 h. The reaction mixture was quenched with saturated $NH_4Cl$ (50 mL) and extracted with EA (20 mL×3). The combined organic layers were washed with brine (50 mL×3) and concentrated under reduced pressure. The residue was purified by pre-HPLC (C18, MeCN/H2O=5-100%, 40 min) and concentrated under reduced pressure to afford isopropyl (S)-6-diazo-2-((S)-2-methoxypropanamido)-5-oxohexanoate (60.2 mg, 201.1211 μmol, easily dissolved in water). MS: m/z 300(M+H)$^+$, $^1$H NMR (400 MHz, $CDCl_3$) δ 7.22-7.08 (m, 1H), 5.12-5.01 (m, 1H), 4.57 (td, J=8.7, 4.8 Hz, 1H), 3.77 (dt, J=6.7, 5.7 Hz, 1H), 3.45 (s, 3H), 2.82-2.58 (m, 1H), 2.50-2.22 (m, 2H), 2.09-1.85 (m, 1H), 1.44-1.35 (m, 3H), 1.31-1.26 (m, 6H).

Example 3

Methyl (S)-6-diazo-2-((S)-2-methoxypropanamido)-5-oxohexanoate (Compound 3)

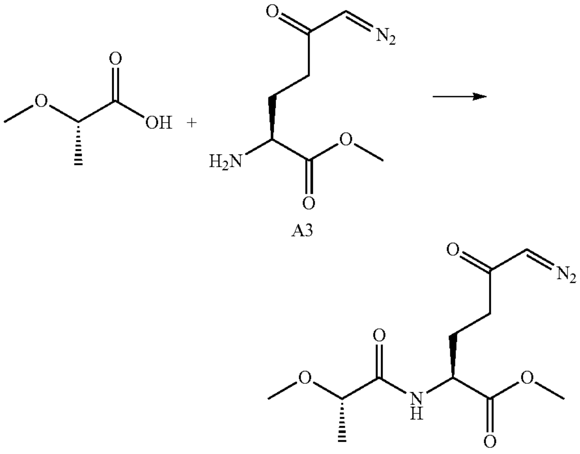

A3

To a solution of (S)-2-methoxypropanoic acid (2.06 g, 19.7879 mmol) and methyl (S)-2-amino-6-diazo-5-oxo-hexanoate (2308 mg, 12.4635 μmol) in DMF (5 mL) was added NMM (3.73 g, 36.8770 mmol) and HATU (6.26 g, 16.4637 mmol) at 0° C. The mixture was stirred at RT for 1 h. The reaction mixture was concentrated under reduced pressure. The residue was purified by pre-HPLC (C18, MeCN/$H_2O$=0-100%, min) and concentrated under reduced pressure to afford methyl (S)-6-diazo-2-((S)-2-methoxypropanamido)-5-oxohexanoate (2.87 g, 10.5799 mmol, easily dissolved in water). MS: m/z 272(M+H)$^+$, $^1$H NMR (400 MHz, $CD_3OD$) δ 5.82 (s, 1H), 4.46 (dd, J=8.9, 4.8 Hz, 1H), 3.79-3.74 (m, 1H), 3.72 (s, 3H), 3.40 (s, 3H), 2.43 (s, 2H), 2.33-2.15 (m, 1H), 2.08-1.90 (m, 1H), 1.33 (d, J=6.7 Hz, 3H).

Example 4

(S)-6-diazo-2-((S)-2-methoxypropanamido)-5-oxohexanoic acid (Compound 4)

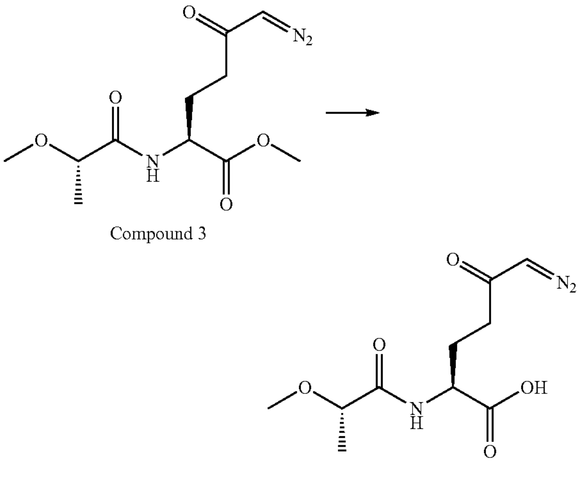

Compound 3

To a solution of methyl (S)-6-diazo-2-((S)-2-methoxypropanamido)-5-oxohexanoate (0.96 g, 3.5389 mmol) in THF (10 mL) was added a solution of NaOH (176 mg, 4.4003 mmol) in water (5 mL) at 0° C. The mixture was stirred at RT for 40 min. The reaction mixture was concentrated under reduced pressure. The residue was purified by pre-HPLC (C18, MeCN/$H_2O$=0-80%, 30 min) and concentrated under reduced pressure to afford (S)-6-diazo-2-((S)-2-methoxypropanamido)-5-oxohexanoic acid (866 mg, 3.3665 mmol, easily dissolved in water). MS: m/z 258$(M+H)^+$, $^1H$ NMR (400 MHz, $CD_3OD$) δ 5.82 (s, 1H), 4.27 (t, J=5.8 Hz, 1H), 3.72 (q, J=6.6 Hz, 1H), 3.40 (s, 3H), 2.46-2.27 (m, 2H), 2.28-2.13 (m, 1H), 2.06-1.91 (m, 1H), 1.33 (d, J=6.7 Hz, 3H).

Example 5

Isopropyl (S)-2-((S)-2-acetoxy-3-(7-fluoro-1H-indol-3-yl)propanamido)-6-diazo-5-oxohexanoate (Compound 5)

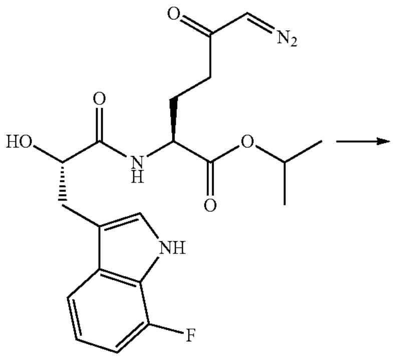

Compound 1

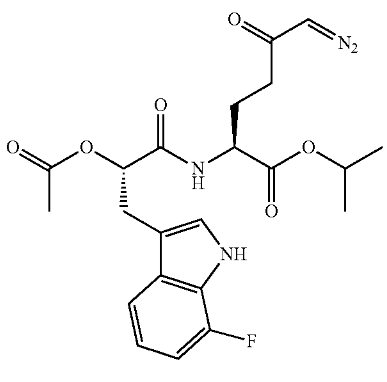

To a solution of isopropyl (S)-6-diazo-2-((S)-3-(7-fluoro-1H-indol-3-yl)-2-hydroxypropanamido)-5-oxohexanoate (0.166 g, 396.7325 mol) in DMF (3.5 mL) was added pyridine (189 mg, 2.3894 mmol) and acetic anhydride (104 mg, 1.0187 mmol) at RT. The mixture was stirred at RT for 1 h. The reaction mixture was concentrated under reduced pressure. The residue was purified by pre-HPLC (C18, MeCN/$H_2O$=2-80%) and concentrated under reduced pressure to afford isopropyl (S)-2-((S)-2-acetoxy-3-(7-fluoro-1H-indol-3-yl)propanamido)-6-diazo-5-oxohexanoate (75.2 mg, 163.3196 μmol). MS: m/z 461$(M+H)^+$, $^1H$ NMR (400 MHz, $CD_3OD$) δ 7.39 (d, J=7.9 Hz, 1H), 7.17 (s, 1H), 6.96 (dd, J=13.4, 6.4 Hz, 1H), 6.88-6.76 (m, 1H), 5.24 (t, J=5.4 Hz, 1H), 4.96 (dt, J=12.4, 6.3 Hz, 1H), 4.27 (d, J=8.7 Hz, 1H), 3.28 (d, J=5.6 Hz, 2H), 2.26-2.13 (m, 1H), 2.10 (s, 3H), 2.05 (d, J=10.2 Hz, 2H), 1.88-1.75 (m, 1H), 1.22 (t, J=6.8 Hz, 6H).

Example 6

Ethyl (S)-6-diazo-2-((S)-2-methoxypropanamido)-5-oxohexanoate (Compound 6)

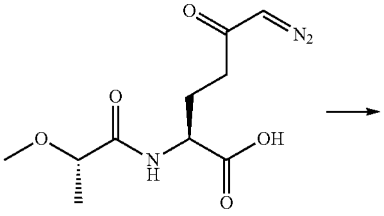

Compound 4

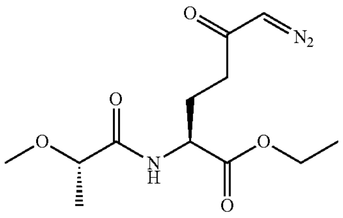

To a solution of (S)-6-diazo-2-((S)-2-methoxypropanamido)-5-oxohexanoic acid (104 mg, 404.2870 mol) and EtOH (96 mg, 2.0839 mmol) in DMF (5 mL) was added NMM (117 mg, 1.1567 mmol) and HATU (237 mg, 623.3081 μmol) at 0° C. The mixture was stirred at RT for 1 h. The reaction mixture was concentrated under reduced pressure. The residue was purified by pre-HPLC (C18, MeCN/$H_2O$=0-100%, min) and concentrated under reduced pressure to afford ethyl (S)-6-diazo-2-((S)-2-methoxypropanamido)-5-oxohexanoate (0.0332 g, 116.3705 mol, easily dissolved in water). MS: m/z 286$(M+H)^+$, $^1H$ NMR (400 MHz, $CD_3OD$) δ 4.49-4.35 (m, 1H), 4.23-4.13 (m, 2H), 3.83-3.71 (m, 1H), 3.44-3.35 (m, 3H), 2.43 (s, 2H), 2.30-2.15 (m, 1H), 2.08-1.93 (m, 1H), 1.36-1.31 (m, 3H), 1.29-1.24 (m, 3H).

The following compounds were synthesized using the above procedure or modification procedure of the above schemes with the corresponding starting materials.

| Compound | Structure | IUPAC Name | $^1$HNMR & MS: $(M + H)^+$ |
|---|---|---|---|
| 7 | 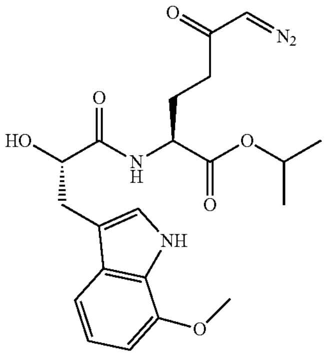 | isopropyl (S)-6-diazo-2-((S)-2-hydroxy-3-(7-methoxy-1H-indol-3-yl)propanamido)-5-oxohexanoate | MS: m/z 431 $(M + H)^+$, $^1$H NMR (400 MHz, $CDCl_3$) δ 8.41 (s, 1H), 7.28 (d, J = 8.0 Hz, 1H), 7.13 (d, J = 8.0 Hz, 1H), 7.10 (d, J = 2.2 Hz, 1H), 7.04 (t, J = 7.9 Hz, 1H), 6.65 (d, J = 7.7 Hz, 1H), 5.08-4.95 (m, 2H), 4.47 (td, J = 8.1, 4.3 Hz, 1H), 4.40 (dd, J = 10.6, 4.9 Hz, 1H), 3.94 (s, 3H), 3.26 (ddd, J = 21.3, 14.7, 5.5 Hz, 2H), 2.66 (d, J = 4.9 Hz, 1H), 2.15-2.01 (m, 2H), 2.01-1.80 (m, 2H), 1.24 (dd, J = 7.6, 6.4 Hz, 6H). |
| 8 | 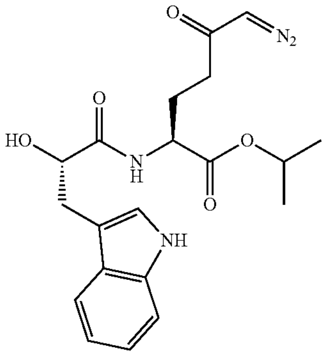 | isopropyl (S)-6-diazo-2-((S)-2-hydroxy-3-(1H-indol-3-yl)propanamido)-5-oxohexanoate | MS: m/z 401 $(M + H)^+$, $^1$H NMR (400 MHz, $CDCl_3$) δ 8.19 (d, J = 20.1 Hz, 1H), 7.70 (t, J = 8.6 Hz, 1H), 7.40 (d, J = 7.6 Hz, 1H), 7.24 (t, J = 7.5 Hz, 1H), 7.19-6.98 (m, 3H), 5.03 (dd, J = 13.1, 7.0 Hz, 2H), 4.54 (s, 1H), 4.44 (s, 1H), 3.33 (dd, J = 37.0, 16.6 Hz, 2H), 2.62-2.51 (m, 1H), 2.39-2.24 (m, 1H), 2.15-2.05 (m, 1H), 2.01-1.85 (m, 1H), 1.27 (t, J = 5.9 Hz, 6H). |
| 9 | 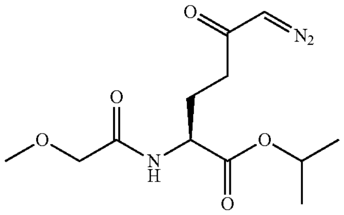 | isopropyl (S)-6-diazo-2-(2-methoxyacetamido)-5-oxohexanoate | 286 |
| 10 | 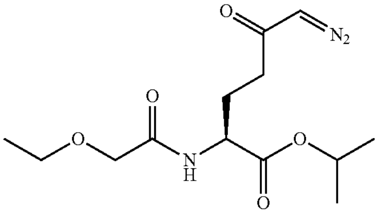 | isopropyl (S)-6-diazo-2-(2-ethoxyacetamido)-5-oxohexanoate | MS: m/z 300 $(M + H)^+$, $^1$H NMR (400 MHz, $CD_3OD$) δ 5.08-4.95 (m, 1H), 4.46-4.37 (m, 1H), 4.02-3.89 (m, 2H), 3.67-3.47 (m, 2H), 2.44 (s, 2H), 2.29-2.11 (m, 1H), 2.10-1.92 (m, 1H), 1.26 (s, 9H). |
| 11 | 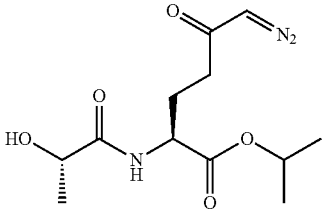 | isopropyl (S)-6-diazo-2-((S)-2-hydroxypropanamido)-5-oxohexanoate | MS: m/z 286 $(M + H)^+$, $^1$H NMR (400 MHz, $CD_3OD$) δ 5.09-4.95 (m, 1H), 4.42-4.32 (m, 1H), 4.18-4.08 (m, 1H), 2.42 (s, 2H), 2.30-2.13 (m, 1H), 2.08-1.88 (m, 1H), 1.40-1.31 (m, 3H), 1.26 (s, 6H). |

-continued

| Compound | Structure | IUPAC Name | $^1$HNMR & MS: $(M + H)^+$ |
|---|---|---|---|
| 12 | 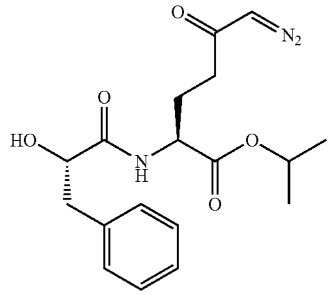 | isopropyl (S)-6-diazo-2-((S)-2-hydroxy-3-phenylpropanamido)-5-oxohexanoate | MS: m/z 362 $(M + H)^+$, $^1$H NMR (400 MHz, $CD_3OD$) δ 7.34-7.12 (m, 5H), 5.05-4.92 (m, 1H), 4.38-4.22 (m, 2H), 3.09 (d, 1H), 2.94-2.76 (m, 1H), 2.27-1.97 (m, 3H), 1.94-1.77 (m, 1H), 1.25 (d, J = 3.7 Hz, 6H). |
| 13 | 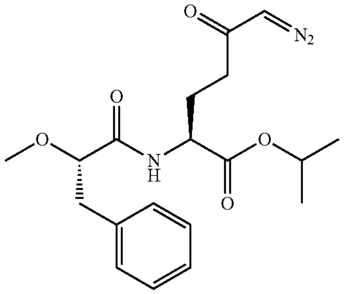 | isopropyl (S)-6-diazo-2-((S)-2-methoxy-3-phenylpropanamido)-5-oxohexanoate | MS: m/z 376 $(M + H)^+$, $^1$H NMR (400 MHz, $CDCl_3$) δ 7.35-7.17 (m, 9H), 7.02 (d, J = 8.5 Hz, 1H), 5.15 (s, 1H), 5.02 (dt, J = 12.3, 6.3 Hz, 1H), 4.55-4.44 (m, 1H), 3.95-3.87 (m, 1H), 3.46-3.38 (m, 3H), 3.21-3.09 (m, 1H), 3.01-2.89 (m, 1H), 2.19-1.91 (m, 3H), 1.89-1.76 (m, 1H), 1.24 (t, J = 6.2 Hz, 6H). |
| 14 | 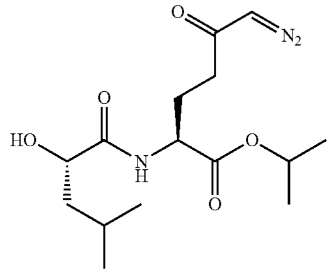 | isopropyl (S)-6-diazo-2-((S)-2-hydroxy-4-methylpentanamido)-5-oxohexanoate | MS: m/z 328 $(M + H)^+$, $^1$H NMR (400 MHz, $CDCl_3$) δ 7.08 (d, J = 7.9 Hz, 1H), 5.23 (s, 1H), 5.04-4.91 (m, 1H), 4.46 (td, J = 8.4, 4.7 Hz, 1H), 4.13-4.03 (m, 1H), 2.73-2.55 (m, 1H), 2.41-2.28 (m, 1H), 2.20-2.09 (m, 1H), 2.02-1.90 (m, 1H), 1.87-1.74 (m, 1H), 1.57-1.39 (m, 2H), 1.22-1.16 (m, 6H), 0.90 (dd, J = 6.6, 3.1 Hz, 6H). |
| 15 | 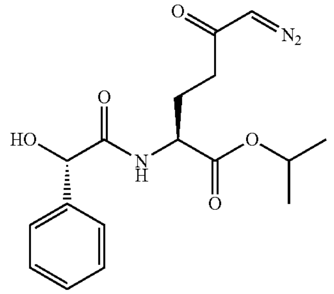 | isopropyl (S)-6-diazo-2-((S)-2-hydroxy-2-phenylacetamido)-5-oxohexanoate | MS: m/z 348 $(M + H)^+$, $^1$H NMR (400 MHz, $CD_3OD$) δ 7.48 (d, J = 6.8 Hz, 2H), 7.42-7.20 (m, 3H), 5.18-4.91 (m, 2H), 4.46-4.18 (m, 1H), 2.34 (s, 2H), 2.28-2.08 (m, 1H), 2.11-1.90 (m, 1H), 1.21 (s, 6H). |
| 16 | 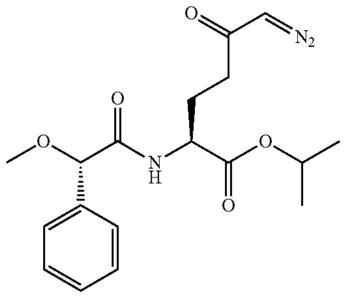 | isopropyl (S)-6-diazo-2-((S)-2-methoxy-2-phenylacetamido)-5-oxohexanoate | MS: m/z 362 $(M + H)^+$, $^1$H NMR (400 MHz, $CD_3OD$) δ 7.40 (d, J = 34.5 Hz, 5H), 4.99 (s, 1H), 4.67 (s, 1H), 4.35 (s, 1H), 3.43 (s, 3H), 2.33 (s, 2H), 2.18 (s, 1H), 1.99 (s, 1H), 1.24 (s, 6H). |

-continued

| Compound | Structure | IUPAC Name | $^1$HNMR & MS: (M + H)$^+$ |
|---|---|---|---|
| 17 | 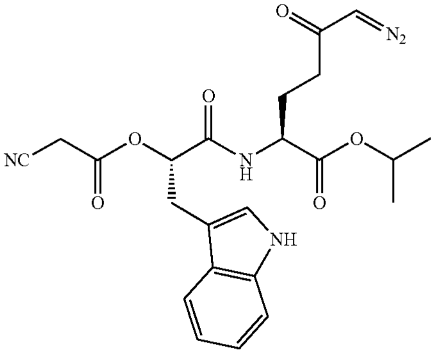 | isopropyl (S)-2-((S)-2-(2-cyanoacetoxy)-3-(1H-indol-3-yl)propanamido)-6-diazo-5-oxohexanoate | MS: m/z 468 (M + H)$^+$, $^1$H NMR (400 MHz, $CD_3OD$) δ 7.67-7.53 (m, 1H), 7.39-7.26 (m, 1H), 7.22-7.14 (m, 1H), 7.14-6.88 (m, 2H), 5.40-5.27 (m, 1H), 5.03-4.90 (m, 1H), 4.31-4.11 (m, 1H), 3.32 (s, 1H), 3.24-3.08 (m, 1H), 2.22-1.58 (m, 4H), 1.22 (s, 6H). |
| 18 | 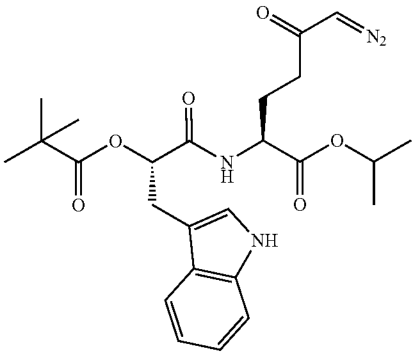 | isopropyl (S)-2-((S)-3-(1H-indol-3-yl)-2-(pivaloyloxy) propanamido)-6-diazo-5-oxohexanoate | MS: m/z 485 (M + H)$^+$, $^1$H NMR (400 MHz, $CD_3OD$) δ 7.62 (d, J = 7.8 Hz, 1H), 7.35 (d, J = 8.0 Hz, 1H), 7.15-7.08 (m, 2H), 7.03 (t, J = 7.4 Hz, 1H), 5.59 (s, 1H), 5.21 (t, J = 6.0 Hz, 1H), 4.99 (dt, J = 12.4, 6.1 Hz, 1H), 4.35-4.26 (m, 1H), 3.31-3.26 (m, 2H), 2.31-2.17 (m, 1H), 2.17-1.98 (m, 2H), 1.92-1.78 (m, 1H), 1.25 (t, J = 6.3 Hz, 6H), 1.18 (s, 9H). |
| 19 | 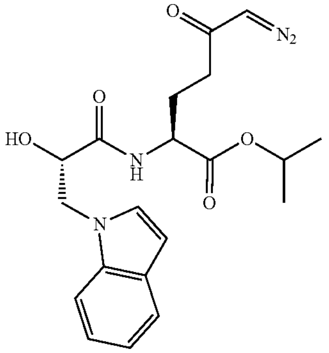 | isopropyl (S)-6-diazo-2-((S)-2-hydroxy-3-(1H-indol-1-yl)propanamido)-5-oxohexanoate | MS: m/z 401 (M + H)$^+$, $^1$H NMR (400 MHz, $CDCl_3$) δ 7.62 (d, J = 7.8 Hz, 1H), 7.45 (d, J = 8.2 Hz, 1H), 7.29 (d, J = 7.8 Hz, 1H), 7.21 (t, J = 7.6 Hz, 1H), 7.16 (s, 1H), 7.11 (t, J = 7.4 Hz, 1H), 6.52 (s, 1H), 5.22 (s, 1H), 5.02 (dt, J = 12.3, 6.3 Hz, 1H), 4.67-4.56 (m, 1H), 4.52-4.38 (m, 2H), 4.35-4.19 (m, 1H), 2.97-2.88 (m, 1H), 2.33-2.20 (m, 1H), 2.19-2.07 (m, 1H), 2.01-1.86 (m, 1H), 1.29-1.22 (m, 6H). |
| 20 | 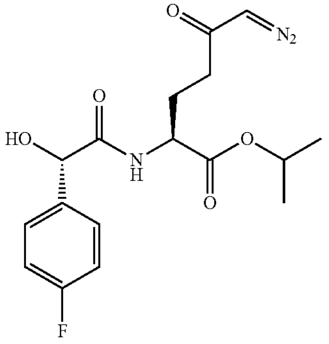 | isopropyl (S)-6-diazo-2-((S)-2-(4-fluorophenyl)-2-hydroxyacetamido)-5-oxohexanoate | MS: m/z 366 (M + H)$^+$, $^1$H NMR (400 MHz, $CD_3OD$) δ 7.52 (t, J = 6.1 Hz, 2H), 7.09 (td, J = 8.8, 3.0 Hz, 2H), 5.06 (s, 1H), 5.00 (dq, J = 12.9, 6.4 Hz, 1H), 4.38 (td, J = 9.5, 5.0 Hz, 1H), 2.56-2.32 (m, 2H), 2.30-2.14 (m, 1H), 2.12-1.89 (m, 1H), 1.27-1.09 (m, 6H). |

-continued

| Compound | Structure | IUPAC Name | $^1$HNMR & MS: $(M + H)^+$ |
|---|---|---|---|
| 21 | 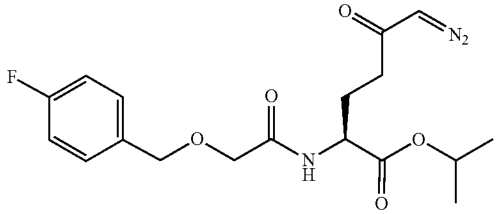 | isopropyl (S)-6-diazo-2-(2-((4-fluorobenzyl)oxy)acetamido)-5-oxohexanoate | MS: m/z 380 $(M + H)^+$, $^1$H NMR (400 MHz, $CDCl_3$) δ 7.40-7.30 (m, 2H), 7.06 (t, J = 8.4 Hz, 2H), 5.13-4.98 (m, 1H), 4.67-4.48 (m, 3H), 4.06-3.87 (m, 2H), 2.57-2.30 (m, 2H), 2.31-1.85 (m, 2H), 1.32-1.19 (m, 6H). |
| 22 | 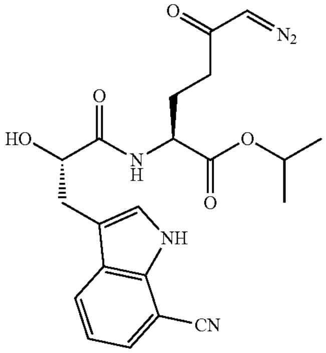 | isopropyl (S)-2-((S)-3-(7-cyano-1H-indol-3-yl)-2-hydroxypropanamido)-6-diazo-5-oxohexanoate | 426 |
| 23 | 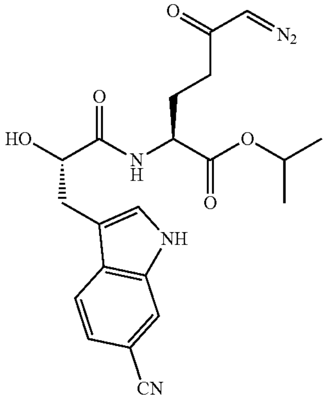 | isopropyl (S)-2-((S)-3-(6-cyano-1H-indol-3-yl)-2-hydroxypropanamido)-6-diazo-5-oxohexanoate | 426 |
| 24 | 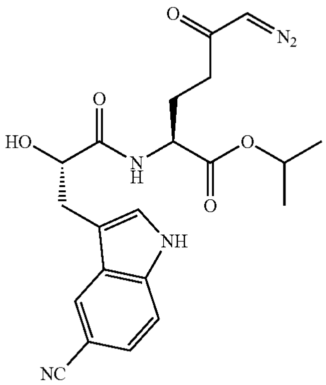 | isopropyl (S)-2-((S)-3-(5-cyano-1H-indol-3-yl)-2-hydroxypropanamido)-6-diazo-5-oxohexanoate | 426 |

-continued
| Compound | Structure | IUPAC Name | $^1$HNMR & MS: (M + H)$^+$ |
|---|---|---|---|
| 25 | 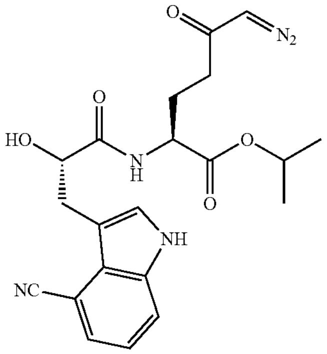 | isopropyl (S)-2-((S)-3-(4-cyano-1H-indol-3-yl)-2-hydroxypropanamido)-6-diazo-5-oxohexanoate | 426 |
| 26 | 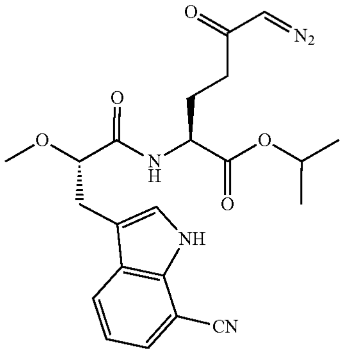 | isopropyl (S)-2-((S)-3-(6-cyano-1H-indol-3-yl)-2-methoxypropanamido)-6-diazo-5-oxohexanoate | 440 |
| 27 | 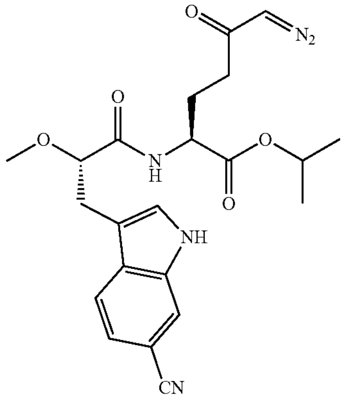 | isopropyl (S)-2-((S)-3-(6-cyano-1H-indol-3-yl)-2-methoxypropanamido)-6-diazo-5-oxohexanoate | 440 |
| 28 | 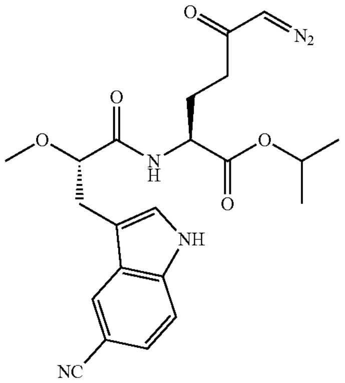 | isopropyl (S)-2-((S)-3-(5-cyano-1H-indol-3-yl)-2-methoxypropanamido)-6-diazo-5-oxohexanoate | 440 |

-continued
| Compound | Structure | IUPAC Name | ¹HNMR & MS: (M + H)⁺ |
|---|---|---|---|
| 29 | 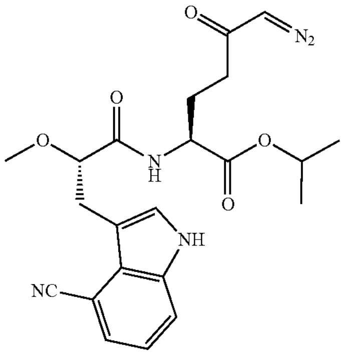 | isopropyl (S)-2-((S)-3-(4-cyano-1H-indol-3-yl)-2-methoxypropanamido)-6-diazo-5-oxohexanoate | 440 |
| 30 | 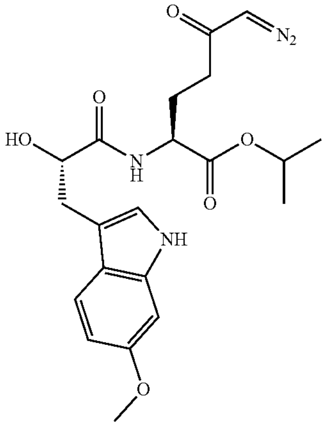 | isopropyl (S)-6-diazo-2-((S)-2-hydroxy-3-(6-methoxy-1H-indol-3-yl)propanamido)-5-oxohexanoate | 431 |
| 31 | 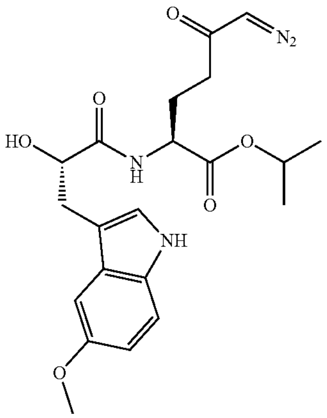 | isopropyl (S)-6-diazo-2-((S)-2-hydroxy-3-(5-methoxy-1H-indol-3-yl)propanamido)-5-oxohexanoate | 431 |
| 32 | 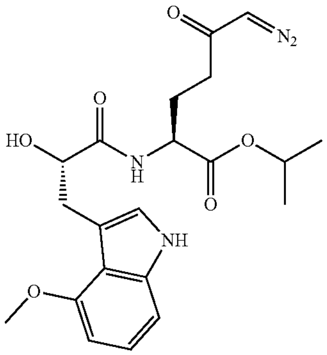 | isopropyl (S)-6-diazo-2-((S)-2-hydroxy-3-(4-methoxy-1H-indol-3-yl)propanamido)-5-oxohexanoate | 431 |

-continued
| Compound | Structure | IUPAC Name | $^{1}$HNMR & MS: $(M + H)^{+}$ |
|---|---|---|---|
| 33 | 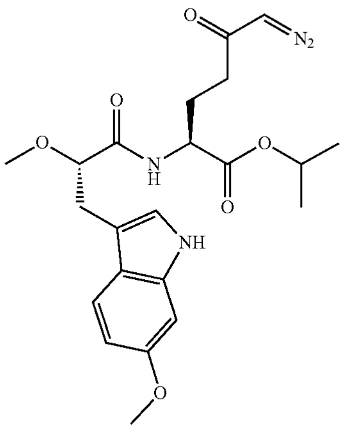 | isopropyl (S)-6-diazo-2-((S)-2-methoxy-3-(6-methoxy-1H-indol-3-yl)propanamido)-5-oxohexanoate | 445 |
| 34 | 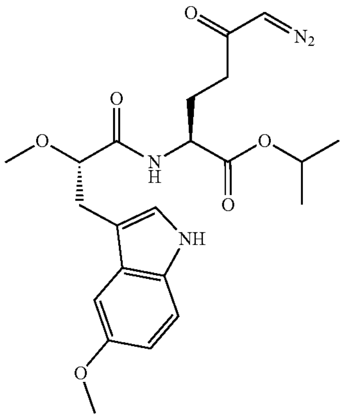 | isopropyl (S)-6-diazo-2-((S)-2-methoxy-3-(5-methoxy-1H-indol-3-yl)propanamido)-5-oxohexanoate | 445 |
| 35 | 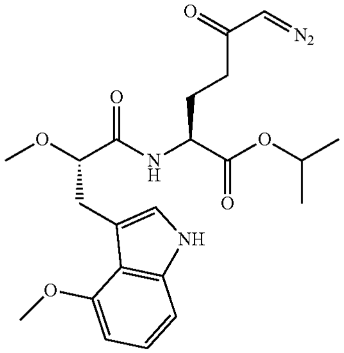 | isopropyl (S)-6-diazo-2-((S)-2-methoxy-3-(4-methoxy-1H-indol-3-yl)propanamido)-5-oxohexanoate | 445 |
| 36 | 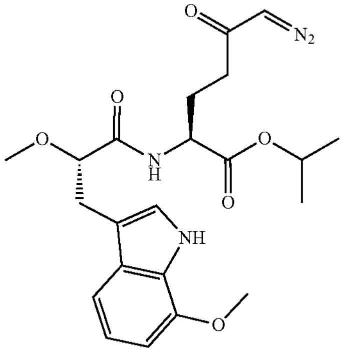 | isopropyl (S)-6-diazo-2-((S)-2-methoxy-3-(7-methoxy-1H-indol-3-yl)propanamido)-5-oxohexanoate | 445 |

-continued
| Compound | Structure | IUPAC Name | $^1$HNMR & MS: (M + H)$^+$ |
|---|---|---|---|
| 37 | 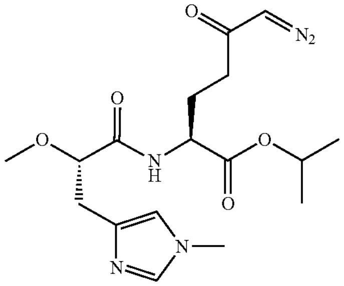 | isopropyl (S)-6-diazo-2-((S)-2-methoxy-3-(1-methyl-1H-imidazol-4-yl)propanamido)-5-oxohexanoate | 380 |
| 38 | 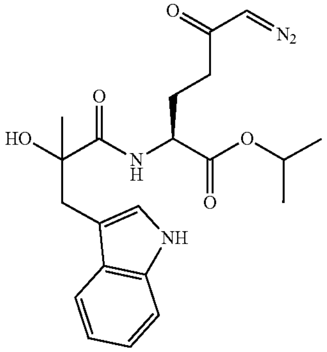 | isopropyl (2S)-6-diazo-2-(2-hydroxy-3-(1H-indol-3-yl)-2-methylpropanamido)-5-oxohexanoate | 415 |
| 39 | 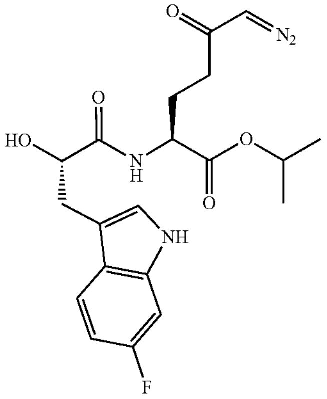 | isopropyl (S)-6-diazo-2-((S)-3-(6-fluoro-1H-indol-3-yl)-2-hydroxypropanamido)-5-oxohexanoate | 419 |
| 40 | 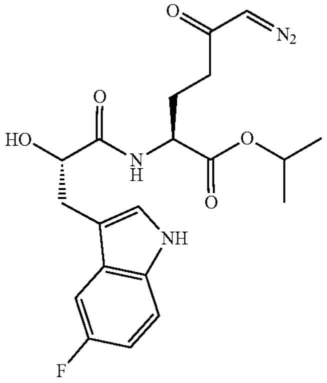 | isopropyl (S)-6-diazo-2-((S)-3-(5-fluoro-1H-indol-3-yl)-2-hydroxypropanamido)-5-oxohexanoate | 419 |

-continued
| Compound | Structure | IUPAC Name | $^1$HNMR & MS: (M + H)$^+$ |
|---|---|---|---|
| 41 | 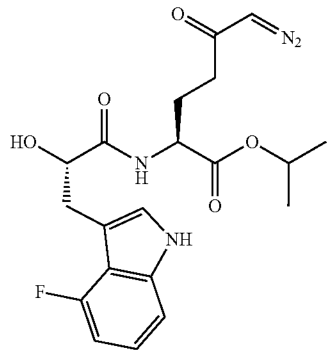 | isopropyl (S)-6-diazo-2-((S)-3-(4-fluoro-1H-indol-3-yl)-2-hydroxypropanamido)-5-oxohexanoate | 419 |
| 42 | 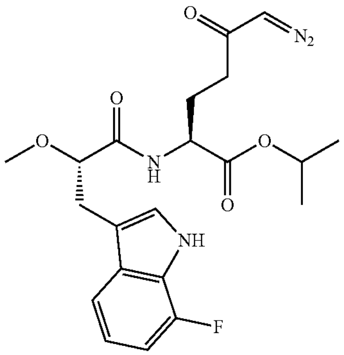 | isopropyl (S)-6-diazo-2-((S)-3-(7-fluoro-1H-indol-3-yl)-2-methoxypropanamido)-5-oxohexanoate | 433 |
| 43 | 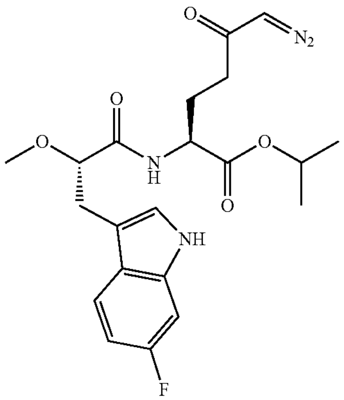 | isopropyl (S)-6-diazo-2-((S)-3-(6-fluoro-1H-indol-3-yl)-2-methoxypropanamido)-5-oxohexanoate | 433 |
| 44 | 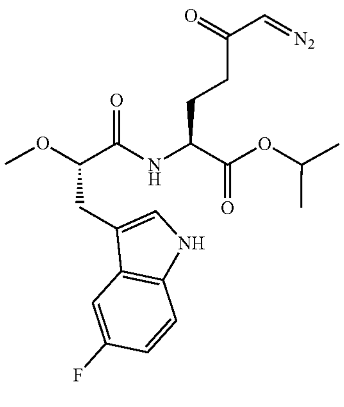 | isopropyl (S)-6-diazo-2-((S)-3-(5-fluoro-1H-indol-3-yl)-2-methoxypropanamido)-5-oxohexanoate | 433 |

-continued
| Compound | Structure | IUPAC Name | $^1$HNMR & MS: (M + H)$^+$ |
|---|---|---|---|
| 45 | 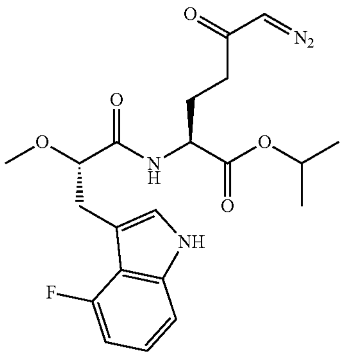 | isopropyl (S)-6-diazo-2-((S)-3-(4-fluoro-1H-indol-3-yl)-2-methoxypropanamido)-5-oxohexanoate | 433 |
| 46 | 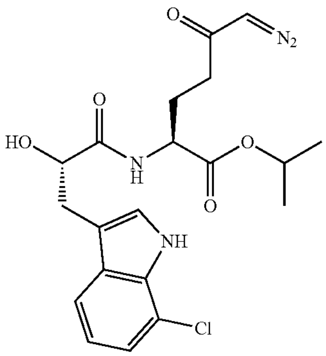 | isopropyl (S)-2-((S)-3-(7-chloro-1H-indol-3-yl)-2-hydroxypropanamido)-6-diazo-5-oxohexanoate | 435 |
| 47 | 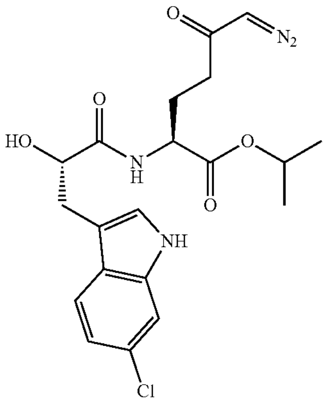 | isopropyl (S)-2-((S)-3-(6-chloro-1H-indol-3-yl)-2-hydroxypropanamido)-6-diazo-5-oxohexanoate | 435 |
| 48 | 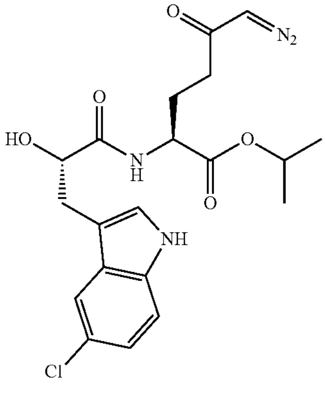 | isopropyl (S)-2-((S)-3-(5-chloro-1H-indol-3-yl)-2-hydroxypropanamido)-6-diazo-5-oxohexanoate | 435 |

-continued
| Compound | Structure | IUPAC Name | $^1$HNMR & MS: $(M + H)^+$ |
|---|---|---|---|
| 49 | 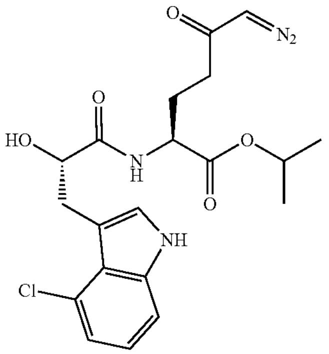 | isopropyl (S)-2-((S)-3-(4-chloro-1H-indol-3-yl)-2-hydroxypropanamido)-6-diazo-5-oxohexanoate | 435 |
| 50 | 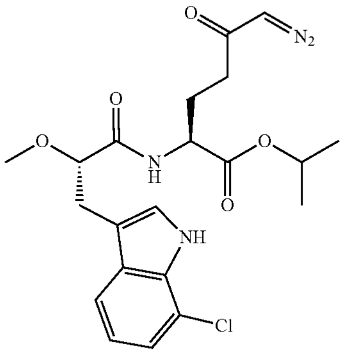 | isopropyl (S)-2-((S)-3-(7-chloro-1H-indol-3-yl)-2-methoxypropanamido)-6-diazo-5-oxohexanoate | 449 |
| 51 | 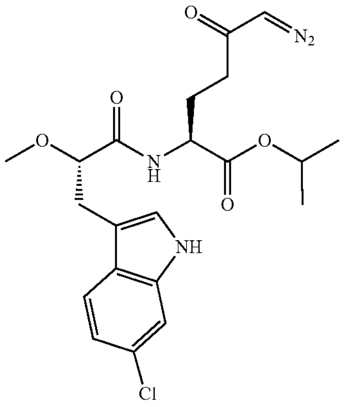 | isopropyl (S)-2-((S)-3-(6-chloro-1H-indol-3-yl)-2-methoxypropanamido)-6-diazo-5-oxohexanoate | 449 |
| 52 | 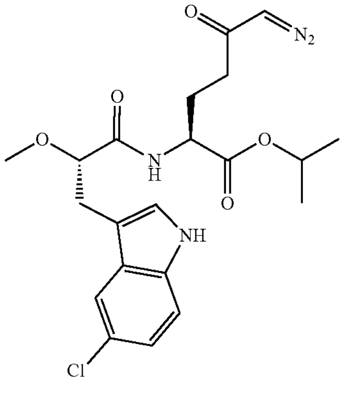 | isopropyl (S)-2-((S)-3-(5-chloro-1H-indol-3-yl)-2-methoxypropanamido)-6-diazo-5-oxohexanoate | 449 |

-continued
| Compound | Structure | IUPAC Name | $^1$HNMR & MS: (M + H)$^+$ |
|---|---|---|---|
| 53 | 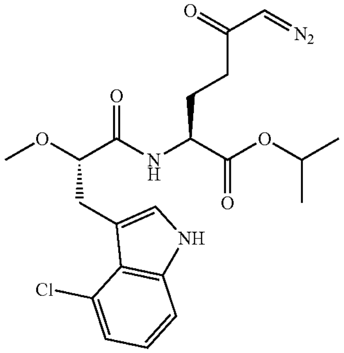 | isopropyl (S)-2-((S)-3-(4-chloro-1H-indol-3-yl)-2-methoxypropanamido)-6-diazo-5-oxohexanoate | 449 |
| 54 | 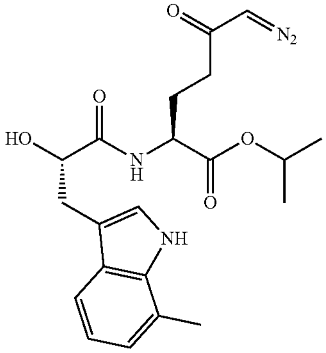 | isopropyl (S)-6-diazo-2-((S)-2-hydroxy-3-(7-methyl-1H-indol-3-yl)propanamido)-5-oxohexanoate | 415 |
| 55 | 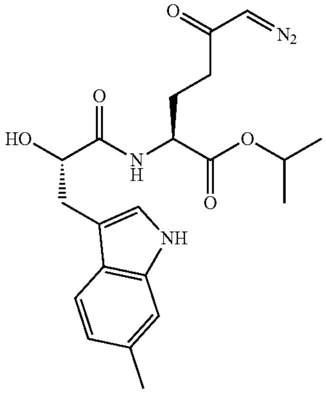 | isopropyl (S)-6-diazo-2-((S)-2-hydroxy-3-(6-methyl-1H-indol-3-yl)propanamido)-5-oxohexanoate | 415 |
| 56 | 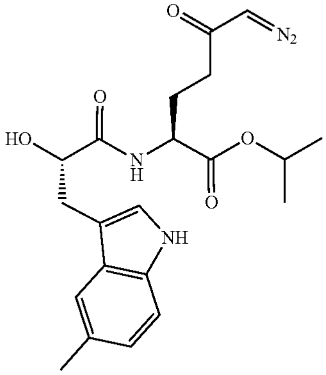 | isopropyl (S)-6-diazo-2-((S)-2-hydroxy-3-(5-methyl-1H-indol-3-yl)propanamido)-5-oxohexanoate | 415 |

-continued
| Compound | Structure | IUPAC Name | $^1$HNMR & MS: $(M + H)^+$ |
|---|---|---|---|
| 57 | 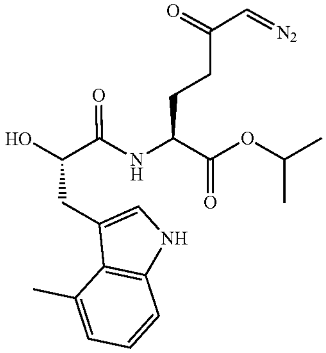 | isopropyl (S)-6-diazo-2-((S)-2-hydroxy-3-(4-methyl-1H-indol-3-yl)propanamido)-5-oxohexanoate | 415 |
| 58 | 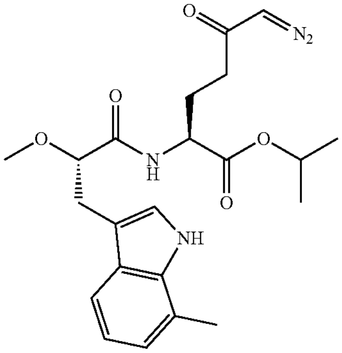 | isopropyl (S)-6-diazo-2-((S)-2-methoxy-3-(7-methyl-1H-indol-3-yl)propanamido)-5-oxohexanoate | 429 |
| 59 | 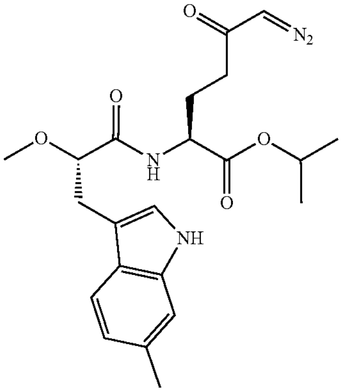 | isopropyl (S)-6-diazo-2-((S)-2-methoxy-3-(6-methyl-1H-indol-3-yl)propanamido)-5-oxohexanoate | 429 |
| 60 | 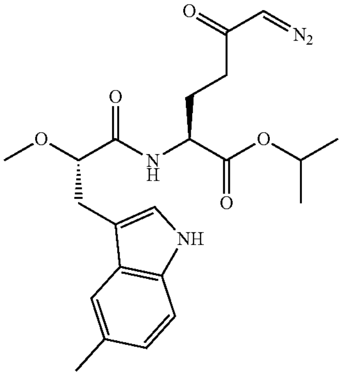 | isopropyl (S)-6-diazo-2-((S)-2-methoxy-3-(5-methyl-1H-indol-3-yl)propanamido)-5-oxohexanoate | 429 |

-continued

| Compound | Structure | IUPAC Name | $^1$HNMR & MS: (M + H)$^+$ |
|---|---|---|---|
| 61 | 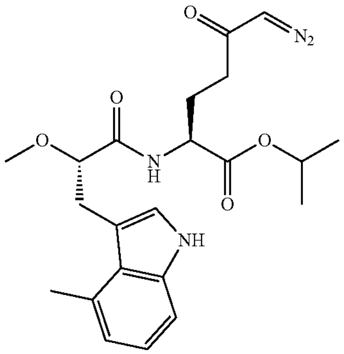 | isopropyl (S)-6-diazo-2-((S)-2-methoxy-3-(4-methyl-1H-indol-3-yl)propanamido)-5-oxohexanoate | 429 |
| 62 | 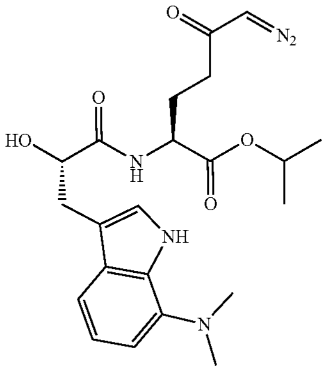 | isopropyl (S)-6-diazo-2-((S)-3-(7-(dimethylamino)-1H-indol-3-yl)-2-hydroxypropanamido)-5-oxohexanoate | 444 |
| 63 | 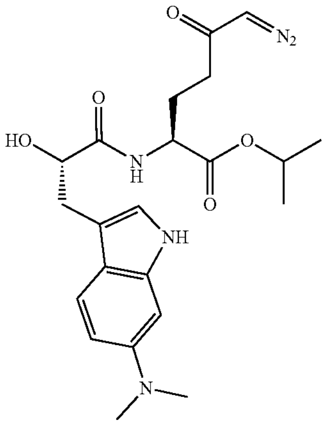 | isopropyl (S)-6-diazo-2-((S)-3-(6-(dimethylamino)-1H-indol-3-yl)-2-hydroxypropanamido)-5-oxohexanoate | 444 |
| 64 | 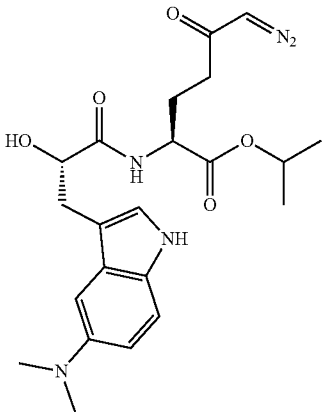 | isopropyl (S)-6-diazo-2-((S)-3-(5-(dimethylamino)-1H-indol-3-yl)-2-hydroxypropanamido)-5-oxohexanoate | 444 |

-continued

| Compound | Structure | IUPAC Name | ¹HNMR & MS: (M + H)⁺ |
|---|---|---|---|
| 65 | 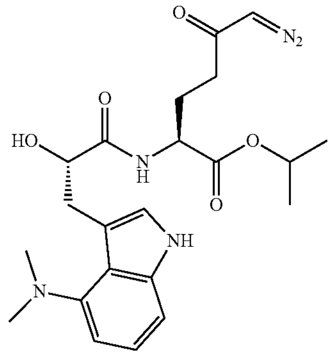 | isopropyl (S)-6-diazo-2-((S)-3-(4-(dimethylamino)-1H-indol-3-yl)-2-hydroxypropanamido)-5-oxohexanoate | 444 |
| 66 | 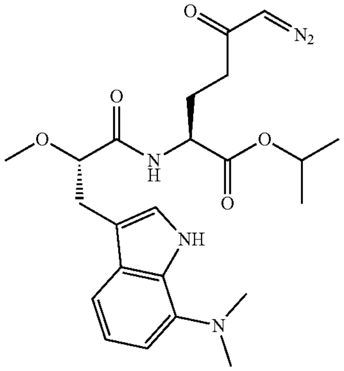 | isopropyl (S)-6-diazo-2-((S)-3-(7-(dimethylamino)-1H-indol-3-yl)-2-methoxypropanamido)-5-oxohexanoate | 458 |
| 67 | 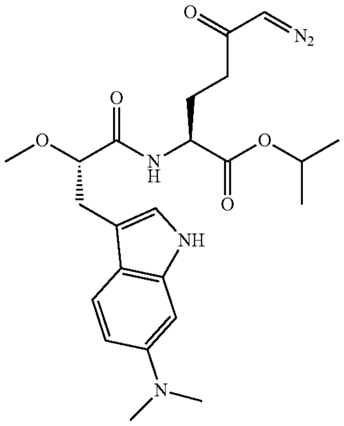 | isopropyl (S)-6-diazo-2-((S)-3-(6-(dimethylamino)-1H-indol-3-yl)-2-methoxypropanamido)-5-oxohexanoate | 458 |
| 68 | 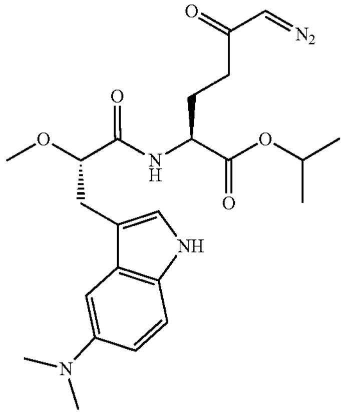 | isopropyl (S)-6-diazo-2-((S)-3-(5-(dimethylamino)-1H-indol-3-yl)-2-methoxypropanamido)-5-oxohexanoate | 458 |

-continued

| Compound | Structure | IUPAC Name | $^1$HNMR & MS: $(M + H)^+$ |
|---|---|---|---|
| 69 | 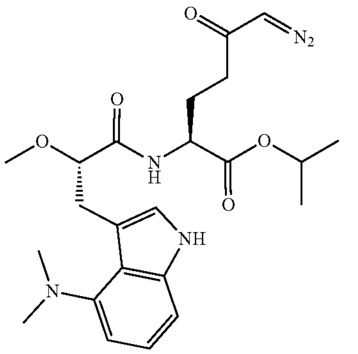 | isopropyl (S)-6-diazo-2-((S)-3-(4-(dimethylamino)-1H-indol-3-yl)-2-methoxypropanamido)-5-oxohexanoate | 458 |
| 70 | 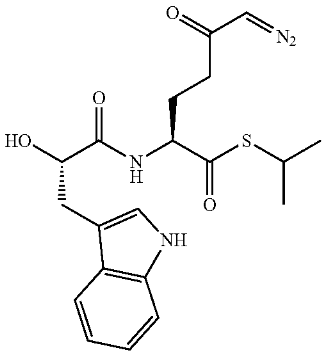 | S-isopropyl (S)-6-diazo-2-((S)-2-hydroxy-3-(1H-indol-3-yl)propanamido)-5-oxohexanethioate | MS: 417 $(M + H)^+$, $^1$H NMR (400 MHz, $CD_3OD$) δ 7.63 (d, J = 8.0 Hz, 1H), 7.33 (t, J = 8.8 Hz, 1H), 7.17 (s, 1H), 7.10 (t, J = 7.6 Hz, 1H), 7.01 (m, 1H), 5.24 (s, 1H), 4.44 (t, J = 4.8 Hz, 1H), 4.31 (m, 1H), 3.60-3.47 (m, 1H), 3.26-3.17 (m, 2H), 2.11 (s, 1H), 2.03-1.87 (m, 1H), 1.66 (m, 2H), 1.28 (m, 3H), 1.27 (d, J = 2.6 Hz, 3H). |
| 71 | 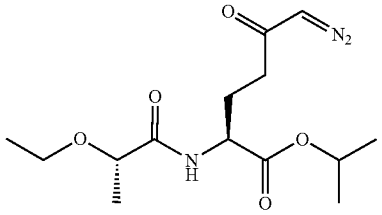 | isopropyl (S)-6-diazo-2-((S)-2-ethoxypropanamido)-5-oxohexanoate | MS: 314 $(M + H)^+$, $^1$H NMR (400 MHz, $CD_3OD$) δ 5.82 (s, 1H), 5.01 (dt, J = 12.5, 6.3 Hz, 1H), 4.39 (dd, J = 9.0, 4.9 Hz, 1H), 3.84 (q, J = 6.8 Hz, 1H), 3.66-3.45 (m, 2H), 2.43 (s, 2H), 2.27-1.92 (m, 2H), 1.33 (d, J = 6.8 Hz, 3H), 1.28-1.21 (m, 9H). |
| 72 | 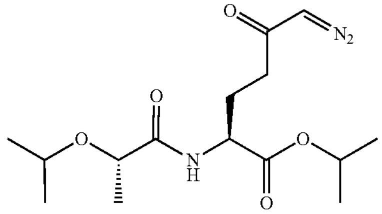 | isopropyl (S)-6-diazo-2-((S)-2-isopropoxypropanamido)-5-oxohexanoate | 328 |
| 73 | 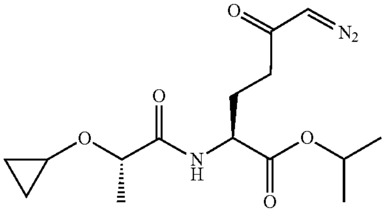 | isopropyl (S)-2-((S)-2-cyclopropoxypropanamido)-6-diazo-5-oxohexanoate | 326 |

-continued

| Compound | Structure | IUPAC Name | $^1$HNMR & MS: $(M + H)^+$ |
|---|---|---|---|
| 74 | 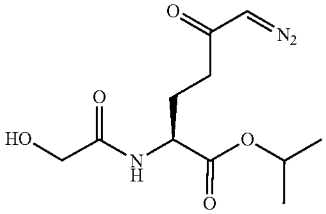 | isopropyl (S)-6-diazo-2-(2-hydroxyacetamido)-5-oxohexanoate | MS: 272 $(M + H)^+$, $^1$H NMR (400 MHz, $CD_3OD$) δ 5.02 (dt, J = 12.5, 6.2 Hz, 1H), 4.44 (dd, J = 8.7, 5.1 Hz, 1H), 4.01 (s, 2H), 2.44 (s, 2H), 2.30-1.95 (m, 2H), 1.26 (d, J = 6.2 Hz, 6H). |
| 75 | 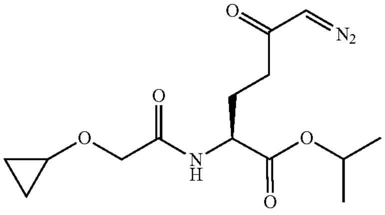 | isopropyl (S)-2-(2-cyclopropoxyacetamido)-6-diazo-5-oxohexanoate | 312 |
| 76 | 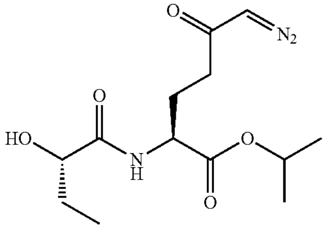 | isopropyl (S)-6-diazo-2-((S)-2-hydroxybutanamido)-5-oxohexanoate | 300 |
| 77 | 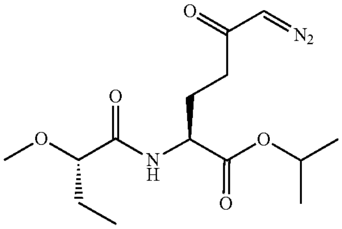 | isopropyl (S)-6-diazo-2-((S)-2-methoxybutanamido)-5-oxohexanoate | MS: 314 $(M + H)^+$, $^1$H NMR (400 MHz, $CD_3OD$) δ 5.81 (s, 1H), 5.02 (dt, J = 12.3, 6.3 Hz, 1H), 4.41 (dd, J = 9.3, 4.8 Hz, 1H), 3.62-3.55 (m, 1H), 3.41 (s, 3H), 2.44 (s, 2H), 2.27-1.91 (m, 2H), 1.86-1.59 (m, 2H), 1.26 (dd, J = 6.1, 3.4 Hz, 6H), 0.95 (t, J = 7.4 Hz, 3H). |
| 78 | 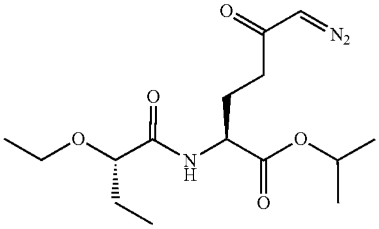 | isopropyl (S)-6-diazo-2-((S)-2-ethoxybutanamido)-5-oxohexanoate | 328 |
| 79 | 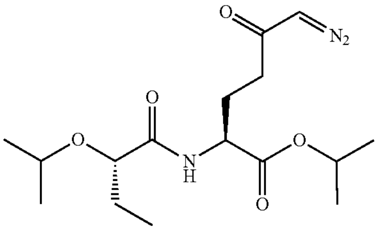 | isopropyl (S)-6-diazo-2-((S)-2-isopropoxybutanamido)-5-oxohexanoate | 342 |

-continued

| Compound | Structure | IUPAC Name | $^{1}$HNMR & MS: $(M + H)^+$ |
|---|---|---|---|
| 80 | 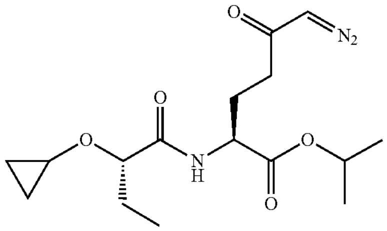 | isopropyl (S)-2-((S)-2-cyclopropoxybutanamido)-6-diazo-5-oxohexanoate | 340 |
| 81 | 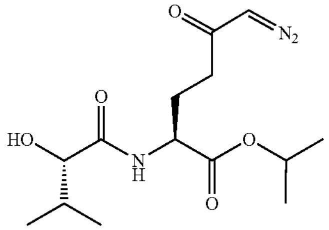 | isopropyl (S)-6-diazo-2-((S)-2-hydroxy-3-methylbutanamido)-5-oxohexanoate | MS: 314 $(M + H)^+$, $^{1}$H NMR (400 MHz, $CD_3OD$) δ 5.80 (s, 1H), 5.01 (dt, J = 12.5, 6.3 Hz, 1H), 4.39 (dd, J = 8.7, 5.1 Hz, 1H), 3.86 (d, J = 3.8 Hz, 1H), 2.43 (s, 2H), 2.25-1.91 (m, 3H), 1.30-1.21 (m, 6H), 1.01 (d, J = 6.9 Hz, 3H), 0.87 (d, J = 6.8 Hz, 3H). |
| 82 | 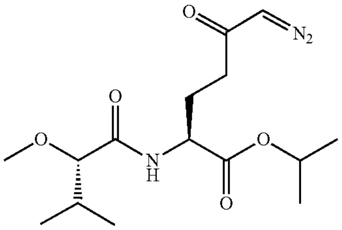 | isopropyl (S)-6-diazo-2-((S)-2-methoxy-3-methylbutanamido)-5-oxohexanoate | MS: 328 $(M + H)^+$, $^{1}$H NMR (400 MHz, $CD_3OD$) δ 5.02 (dt, J = 12.5, 6.2 Hz, 1H), 4.41 (dd, J = 9.2, 4.9 Hz, 1H), 3.41 (s, 3H), 3.38 (d, J = 5.2 Hz, 1H), 2.45 (s, 2H), 2.26-2.14 (m, 1H), 2.06-1.92 (m, 2H), 1.26 (dd, J = 6.1, 3.8 Hz, 6H), 0.98 (d, J = 6.9 Hz, 3H), 0.94 (d, J = 6.8 Hz, 3H). |
| 83 | 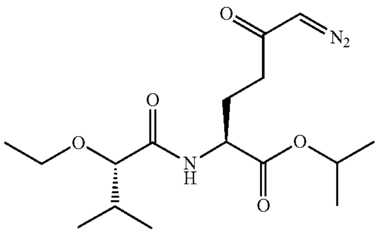 | isopropyl (S)-6-diazo-2-((S)-2-ethoxy-3-methylbutanamido)-5-oxohexanoate | 342 |
| 84 | 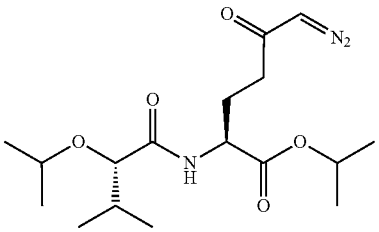 | isopropyl (S)-6-diazo-2-((S)-2-isopropoxy-3-methylbutanamido)-5-oxohexanoate | 356 |
| 85 | 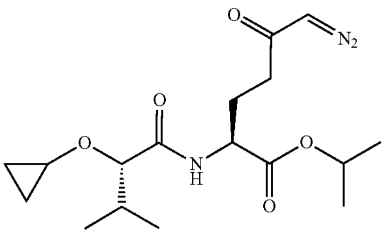 | isopropyl (S)-2-((S)-2-cyclopropoxy-3-methylbutanamido)-6-diazo-5-oxohexanoate | 354 |

-continued

| Compound | Structure | IUPAC Name | $^1$HNMR & MS: (M + H)$^+$ |
| --- | --- | --- | --- |
| 86 | 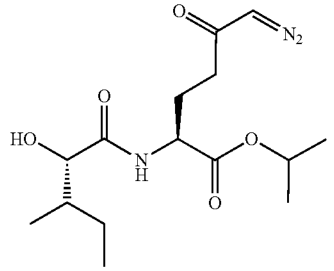 | isopropyl (S)-6-diazo-2-((2S,3R)-2-hydroxy-3-methylpentanamido)-5-oxohexanoate | 328 |
| 87 | 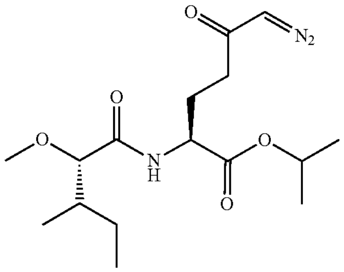 | isopropyl (S)-6-diazo-2-((2S,3R)-2-methoxy-3-methylpentanamido)-5-oxohexanoate | 342 |
| 88 | 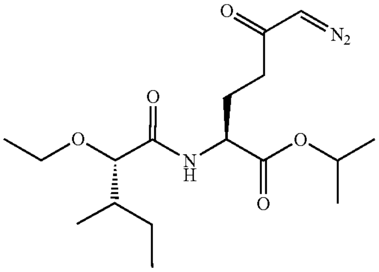 | isopropyl (S)-6-diazo-2-((2S,3R)-2-ethoxy-3-methylpentanamido)-5-oxohexanoate | 356 |
| 89 | 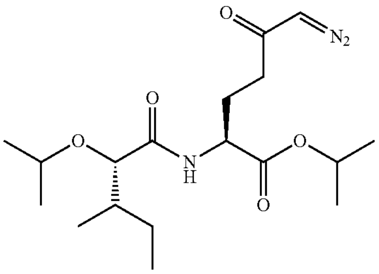 | isopropyl (S)-6-diazo-2-((2S,3R)-2-isopropoxy-3-methylpentanamido)-5-oxohexanoate | 370 |
| 90 | 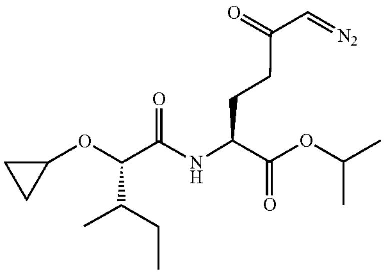 | isopropyl (S)-2-((2S,3R)-2-cyclopropoxy-3-methylpentanamido)-6-diazo-5-oxohexanoate | 368 |

-continued
| Compound | Structure | IUPAC Name | ¹HNMR & MS: $(M + H)^+$ |
|---|---|---|---|
| 91 | 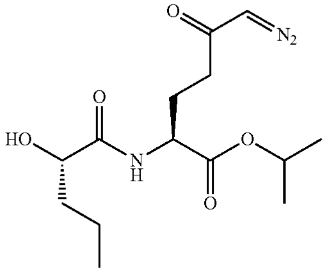 | isopropyl (S)-6-diazo-2-((S)-2-hydroxypentanamido)-5-oxohexanoate | 314 |
| 92 | 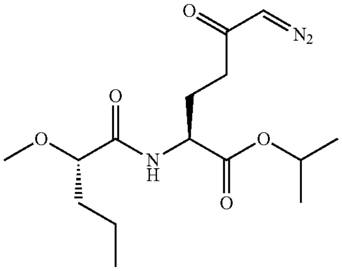 | isopropyl (S)-6-diazo-2-((S)-2-methoxypentanamido)-5-oxohexanoate | 328 |
| 93 | 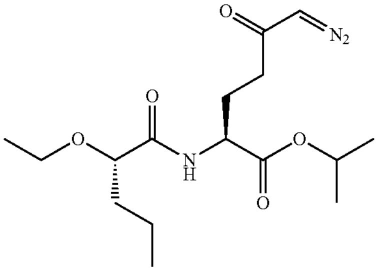 | isopropyl (S)-6-diazo-2-((S)-2-ethoxypentanamido)-5-oxohexanoate | 342 |
| 94 | 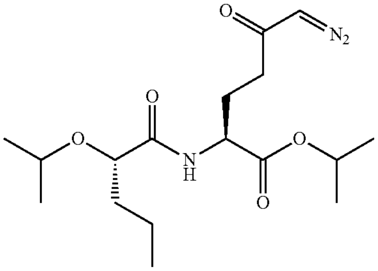 | isopropyl (S)-6-diazo-2-((S)-2-isopropoxypentanamido)-5-oxohexanoate | 356 |
| 95 | 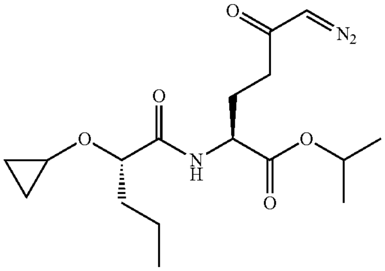 | isopropyl (S)-2-((S)-2-cyclopropoxypentanamido)-6-diazo-5-oxohexanoate | 354 |

-continued

| Compound | Structure | IUPAC Name | $^1$HNMR & MS: $(M + H)^+$ |
|---|---|---|---|
| 96 | 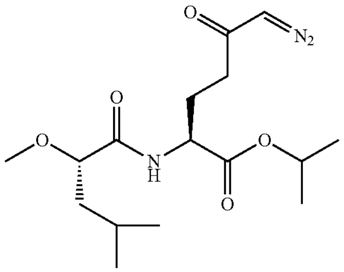 | isopropyl (S)-6-diazo-2-((S)-2-methoxy-4-methylpentanamido)-5-oxohexanoate | 342 |
| 97 | 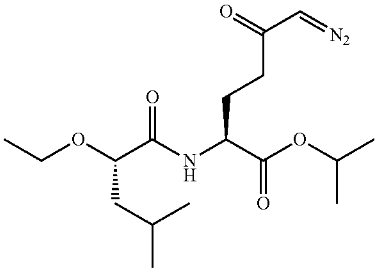 | isopropyl (S)-6-diazo-2-((S)-2-ethoxy-4-methylpentanamido)-5-oxohexanoate | 356 |
| 98 | 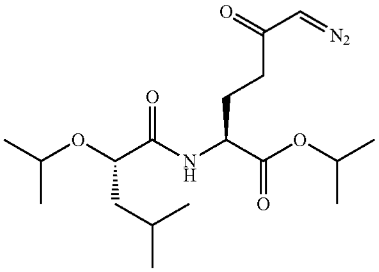 | isopropyl (S)-6-diazo-2-((S)-2-isopropoxy-4-methylpentanamido)-5-oxohexanoate | 370 |
| 99 | 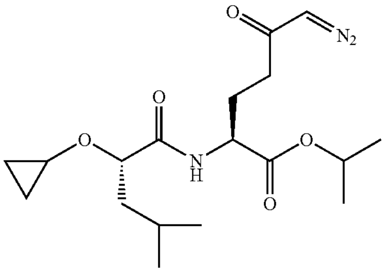 | isopropyl (S)-2-((S)-2-cyclopropoxy-4-methylpentanamido)-6-diazo-5-oxohexanoate | 368 |
| 100 | 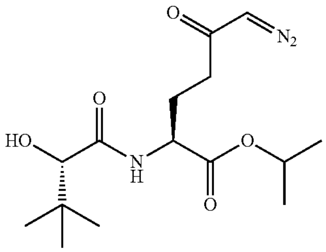 | isopropyl (S)-6-diazo-2-((S)-2-hydroxy-3,3-dimethylbutanamido)-5-oxohexanoate | 328 |

-continued

| Compound | Structure | IUPAC Name | $^1$HNMR & MS: (M + H)$^+$ |
|---|---|---|---|
| 101 | 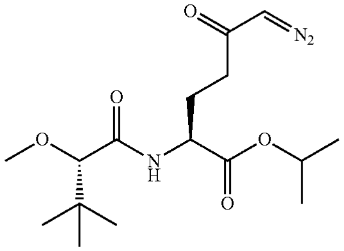 | isopropyl (S)-6-diazo-2-((S)-2-methoxy-3,3-dimethylbutanamido)-5-oxohexanoate | 342 |
| 102 | 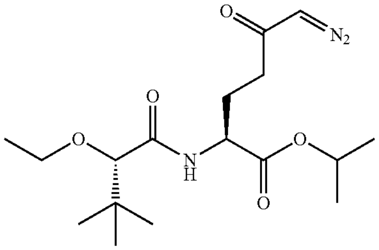 | isopropyl (S)-6-diazo-2-((S)-2-ethoxy-3,3-dimethylbutanamido)-5-oxohexanoate | 356 |
| 103 | 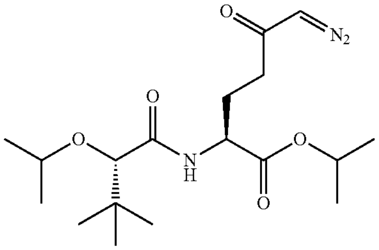 | isopropyl (S)-6-diazo-2-((S)-2-isopropoxy-3,3-dimethylbutanamido)-5-oxohexanoate | 370 |
| 104 | 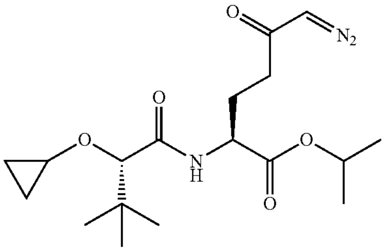 | isopropyl (S)-2-((S)-2-cyclopropoxy-3,3-dimethylbutanamido)-6-diazo-5-oxohexanoate | 368 |
| 105 | 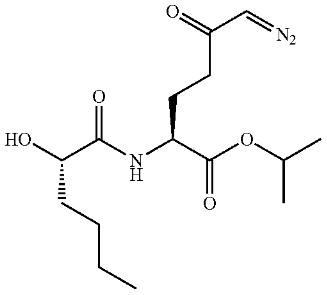 | isopropyl (S)-6-diazo-2-((S)-2-hydroxyhexanamido)-5-oxohexanoate | 328 |

-continued
| Compound | Structure | IUPAC Name | $^1$HNMR & MS: (M + H)+ |
|---|---|---|---|
| 106 | 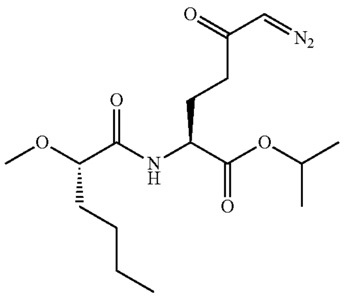 | isopropyl (S)-6-diazo-2-((S)-2-methoxyhexanamido)-5-oxohexanoate | 342 |
| 107 | 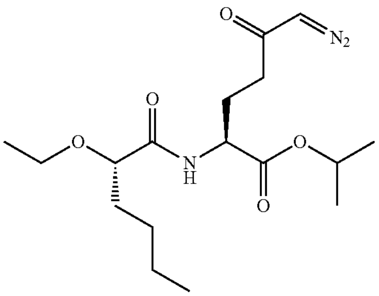 | isopropyl (S)-6-diazo-2-((S)-2-ethoxyhexanamido)-5-oxohexanoate | 356 |
| 108 | 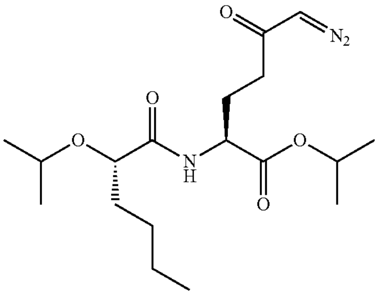 | isopropyl (S)-6-diazo-2-((S)-2-isopropoxyhexanamido)-5-oxohexanoate | 370 |
| 109 | 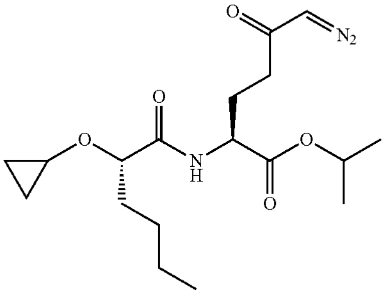 | isopropyl (S)-2-((S)-2-cyclopropoxyhexanamido)-6-diazo-5-oxohexanoate | 368 |
| 110 | 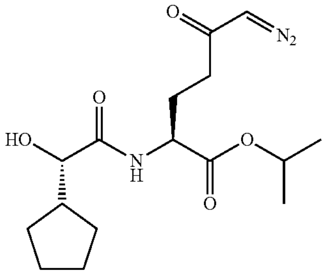 | isopropyl (S)-2-((S)-2-cyclopentyl-2-hydroxyacetamido)-6-diazo-5-oxohexanoate | 340 |

-continued

| Compound | Structure | IUPAC Name | $^1$HNMR & MS: (M + H)$^+$ |
|---|---|---|---|
| 111 | 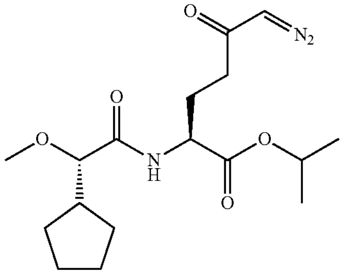 | isopropyl (S)-2-((S)-2-cyclopentyl-2-methoxyacetamido)-6-diazo-5-oxohexanoate | 354 |
| 112 | 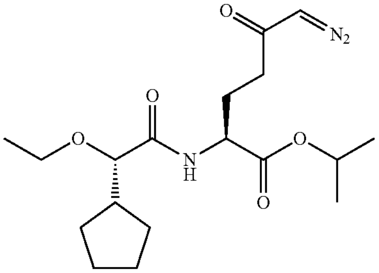 | isopropyl (S)-2-((S)-2-cyclopentyl-2-ethoxyacetamido)-6-diazo-5-oxohexanoate | 368 |
| 113 | 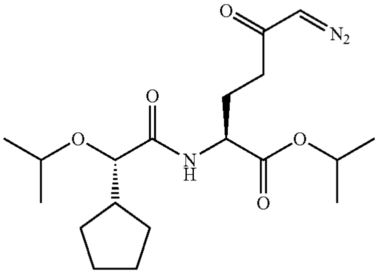 | isopropyl (S)-2-((S)-2-cyclopentyl-2-isopropoxyacetamido)-6-diazo-5-oxohexanoate | 382 |
| 114 | 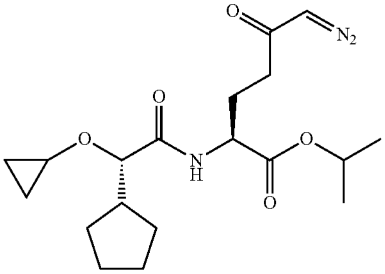 | isopropyl (S)-2-((S)-2-cyclopentyl-2-cyclopropoxyacetamido)-6-diazo-5-oxohexanoate | 380 |
| 115 | 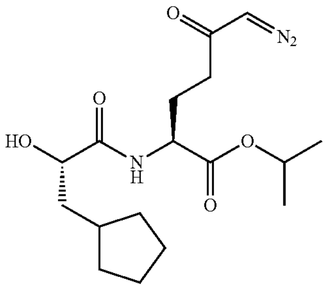 | isopropyl (S)-2-((S)-3-cyclopentyl-2-hydroxypropanamido)-6-diazo-5-oxohexanoate | 354 |

-continued

| Compound | Structure | IUPAC Name | $^1$HNMR & MS: (M + H)$^+$ |
|---|---|---|---|
| 116 | 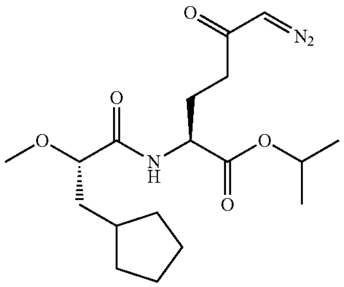 | isopropyl (S)-2-((S)-3-cyclopentyl-2-methoxypropanamido)-6-diazo-5-oxohexanoate | 368 |
| 117 | 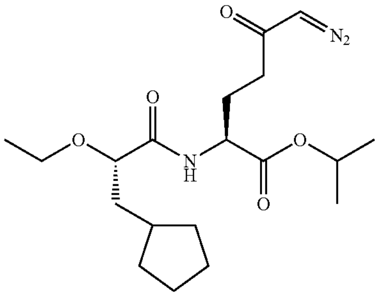 | isopropyl (S)-2-((S)-3-cyclopentyl-2-ethoxypropanamido)-6-diazo-5-oxohexanoate | 382 |
| 118 | 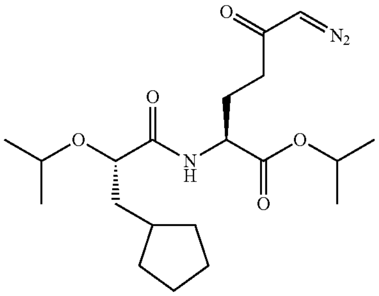 | isopropyl (S)-2-((S)-3-cyclopentyl-2-isopropoxypropanamido)-6-diazo-5-oxohexanoate | 396 |
| 119 | 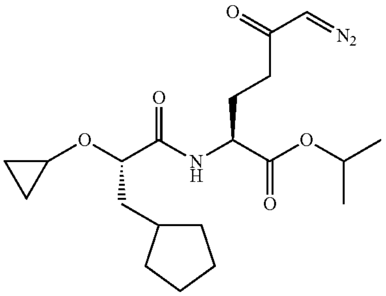 | isopropyl (S)-2-((S)-3-cyclopentyl-2-cyclopropoxypropanamido)-6-diazo-5-oxohexanoate | 394 |
| 120 | 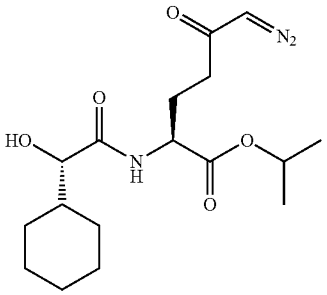 | isopropyl (S)-2-((S)-2-cyclohexyl-2-hydroxyacetamido)-6-diazo-5-oxohexanoate | 354 |

-continued

| Compound | Structure | IUPAC Name | $^1$HNMR & MS: (M + H)$^+$ |
|---|---|---|---|
| 121 | 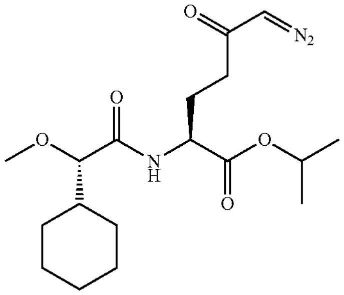 | isopropyl (S)-2-((S)-2-cyclohexyl-2-methoxyacetamido)-6-diazo-5-oxohexanoate | 368 |
| 122 | 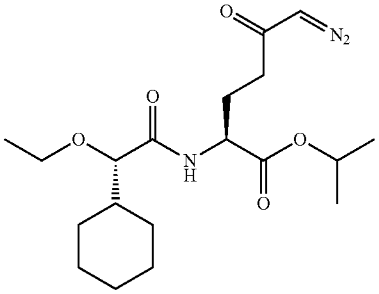 | isopropyl (S)-2-((S)-2-cyclohexyl-2-ethoxyacetamido)-6-diazo-5-oxohexanoate | 382 |
| 123 | 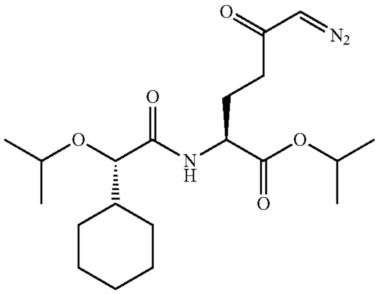 | isopropyl (S)-2-((S)-2-cyclohexyl-2-isopropoxyacetamido)-6-diazo-5-oxohexanoate | 396 |
| 124 | 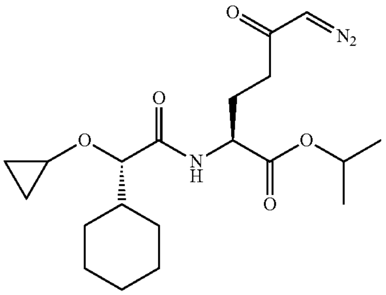 | isopropyl (S)-2-((S)-2-cyclohexyl-2-cyclopropoxyacetamido)-6-diazo-5-oxohexanoate | 394 |
| 125 | 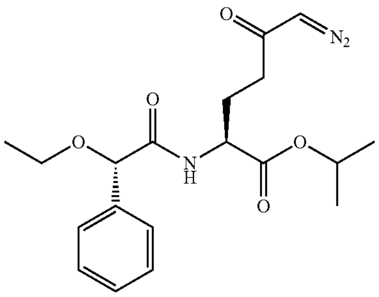 | isopropyl (S)-6-diazo-2-((S)-2-ethoxy-2-phenylacetamido)-5-oxohexanoate | 376 |

-continued
| Compound | Structure | IUPAC Name | $^1$HNMR & MS: $(M + H)^+$ |
|---|---|---|---|
| 126 | 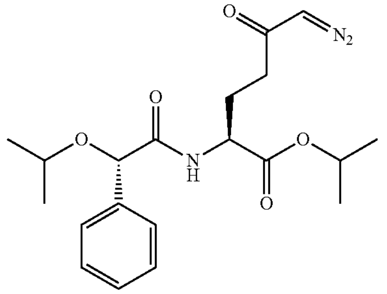 | isopropyl (S)-6-diazo-2-((S)-2-isopropoxy-2-phenylacetamido)-5-oxohexanoate | 390 |
| 127 | 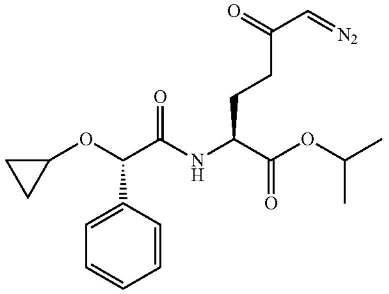 | isopropyl (S)-2-((S)-2-cyclopropoxy-2-phenylacetamido)-6-diazo-5-oxohexanoate | 388 |
| 128 | 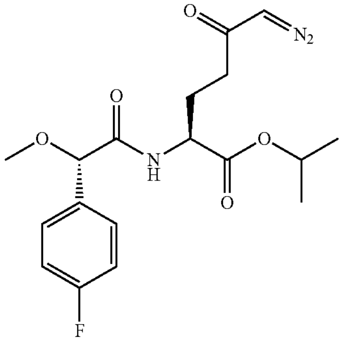 | isopropyl (S)-6-diazo-2-((S)-2-(4-fluorophenyl)-2-methoxyacetamido)-5-oxohexanoate | 380 |
| 129 | 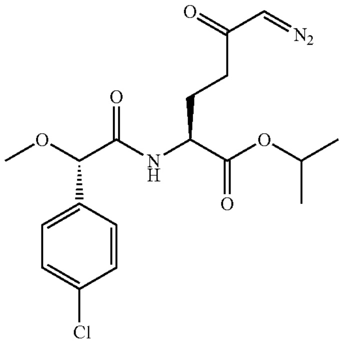 | isopropyl (S)-2-((S)-2-(4-chlorophenyl)-2-methoxyacetamido)-6-diazo-5-oxohexanoate | 396 |

-continued
| Compound | Structure | IUPAC Name | ¹HNMR & MS: (M + H)⁺ |
|---|---|---|---|
| 130 | 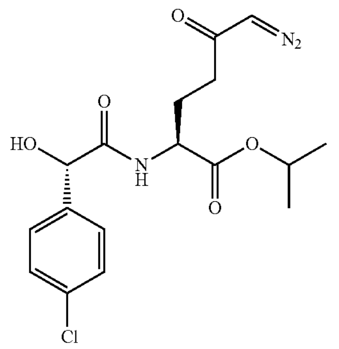 | isopropyl (S)-2-((S)-2-(4-chlorophenyl)-2-hydroxyacetamido)-6-diazo-5-oxohexanoate | 382 |
| 131 | 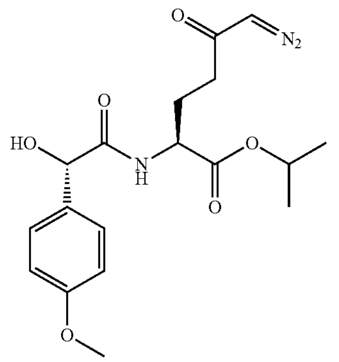 | isopropyl (S)-6-diazo-2-((S)-2-hydroxy-2-(4-methoxyphenyl) acetamido)-5-oxohexanoate | 378 |
| 132 | 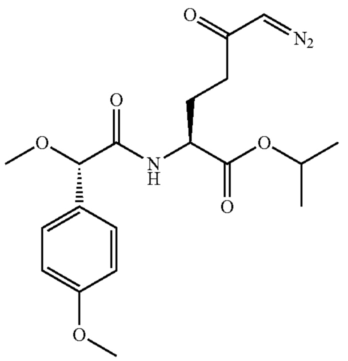 | isopropyl (S)-6-diazo-2-((S)-2-methoxy-2-(4-methoxyphenyl) acetamido)-5-oxohexanoate | 392 |
| 133 | 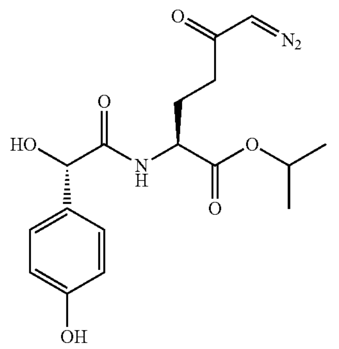 | isopropyl (S)-6-diazo-2-((S)-2-hydroxy-2-(4-hydroxyphenyl) acetamido)-5-oxohexanoate | 364 |

-continued
| Compound | Structure | IUPAC Name | $^1$HNMR & MS: (M + H)$^+$ |
|---|---|---|---|
| 134 | 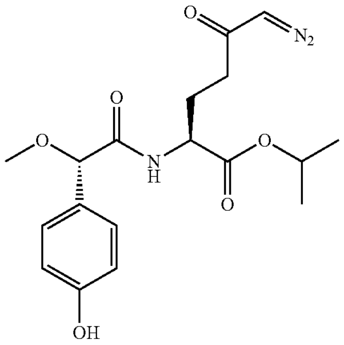 | isopropyl (S)-6-diazo-2-((S)-2-(4-hydroxyphenyl)-2-methoxyacetamido)-5-oxohexanoate | 378 |
| 135 | 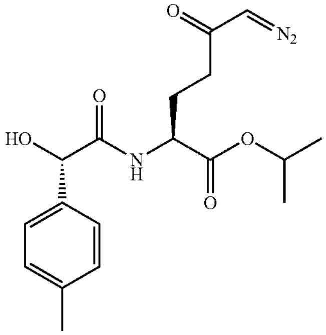 | isopropyl (S)-6-diazo-2-((S)-2-hydroxy-2-(p-tolyl)acetamido)-5-oxohexanoate | 362 |
| 136 | 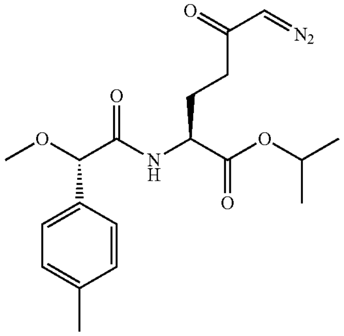 | isopropyl (S)-6-diazo-2-((S)-2-methoxy-2-(p-tolyl)acetamido)-5-oxohexanoate | 376 |
| 137 | 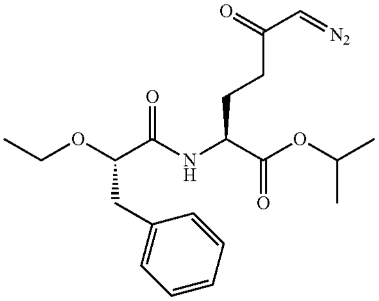 | isopropyl (S)-6-diazo-2-((S)-2-ethoxy-3-phenylpropanamido)-5-oxohexanoate | 390 |

-continued
| Compound | Structure | IUPAC Name | ¹HNMR & MS: (M + H)⁺ |
|---|---|---|---|
| 138 | 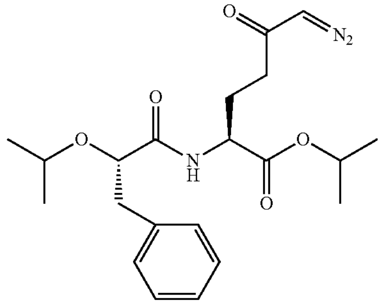 | isopropyl (S)-6-diazo-2-((S)-2-isopropoxy-3-phenylpropanamido)-5-oxohexanoate | 404 |
| 139 | 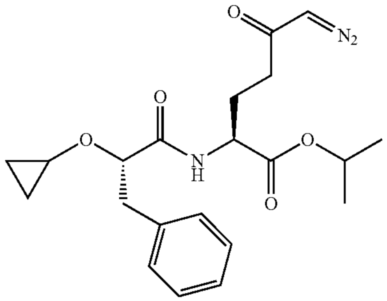 | isopropyl (S)-2-((S)-2-cyclopropoxy-3-phenylpropanamido)-6-diazo-5-oxohexanoate | 402 |
| 140 | 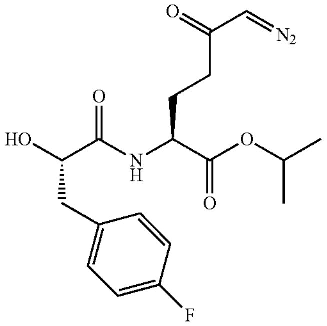 | isopropyl (S)-6-diazo-2-((S)-3-(4-fluorophenyl)-2-hydroxypropanamido)-5-oxohexanoate | 380 |
| 142 | 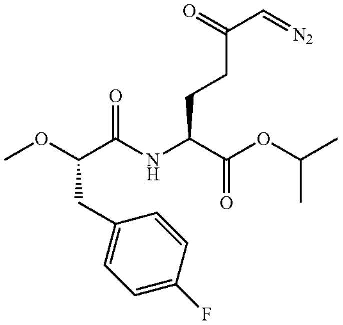 | isopropyl (S)-6-diazo-2-((S)-3-(4-fluorophenyl)-2-methoxypropanamido)-5-oxohexanoate | 394 |

-continued
| Compound | Structure | IUPAC Name | $^{1}$HNMR & MS: $(M + H)^{+}$ |
|---|---|---|---|
| 143 | 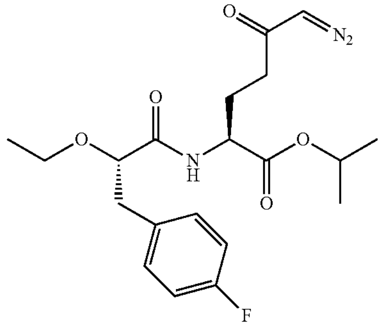 | isopropyl (S)-6-diazo-2-((S)-2-ethoxy-3-(4-fluorophenyl) propanamido)-5-oxohexanoate | 408 |
| 144 | 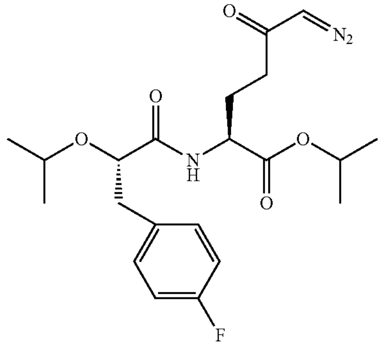 | isopropyl (S)-6-diazo-2-((S)-3-(4-fluorophenyl)-2-isopropoxypropanamido)-5-oxohexanoate | 422 |
| 145 | 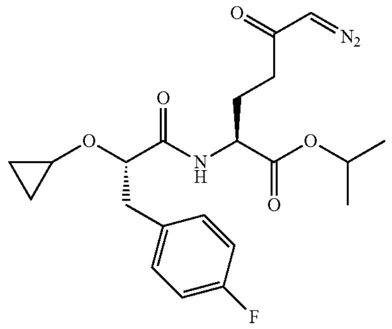 | isopropyl (S)-2-((S)-2-cyclopropoxy-3-(4-fluorophenyl) propanamido)-6-diazo-5-oxohexanoate | 420 |
| 146 | 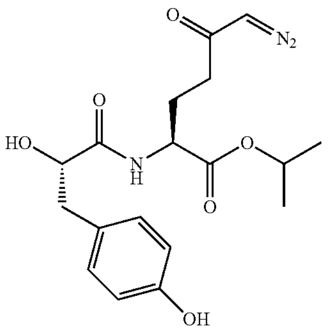 | isopropyl (S)-6-diazo-2-((S)-2-hydroxy-3-(4-hydroxyphenyl) propanamido)-5-oxohexanoate | 378 |

-continued

| Compound | Structure | IUPAC Name | $^1$HNMR & MS: $(M + H)^+$ |
|---|---|---|---|
| 147 | 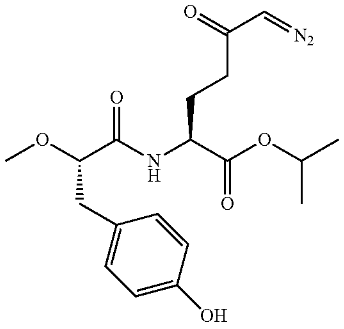 | isopropyl (S)-6-diazo-2-((S)-3-(4-hydroxyphenyl)-2-methoxypropanamido)-5-oxohexanoate | 392 |
| 148 | 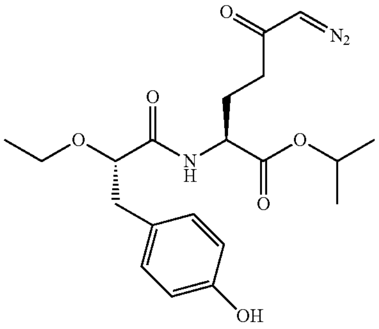 | isopropyl (S)-6-diazo-2-((S)-2-ethoxy-3-(4-hydroxyphenyl)propanamido)-5-oxohexanoate | 406 |
| 149 | 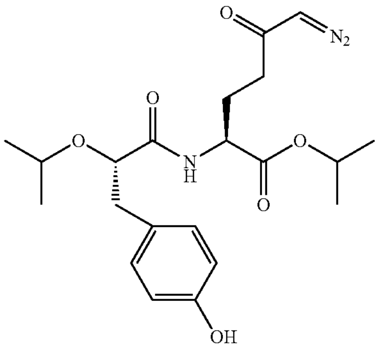 | isopropyl (S)-6-diazo-2-((S)-3-(4-hydroxyphenyl)-2-isopropoxypropanamido)-5-oxohexanoate | 420 |
| 150 | 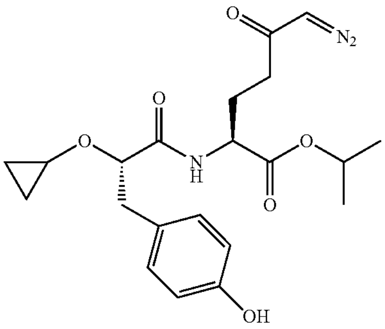 | isopropyl (S)-2-((S)-2-cyclopropoxy-3-(4-hydroxyphenyl)propanamido)-6-diazo-5-oxohexanoate | 418 |
| 151 | 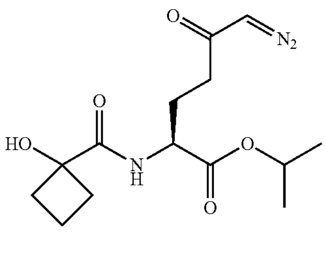 | isopropyl (S)-6-diazo-2-(1-hydroxycyclobutane-1-carboxamido)-5-oxohexanoate | 312 |

-continued

| Compound | Structure | IUPAC Name | $^1$HNMR & MS: $(M + H)^+$ |
|---|---|---|---|
| 152 | 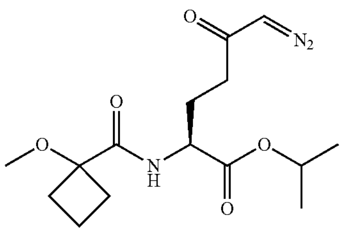 | isopropyl (S)-6-diazo-2-(1-methoxycyclobutane-1-carboxamido)-5-oxohexanoate | 326 |
| 153 | 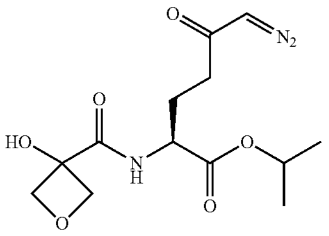 | isopropyl (S)-6-diazo-2-(3-hydroxyoxetane-3-carboxamido)-5-oxohexanoate | 314 |
| 154 | 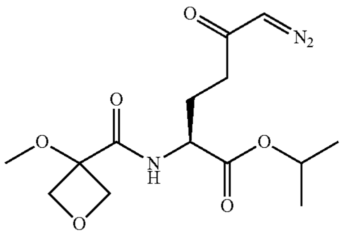 | isopropyl (S)-6-diazo-2-(3-methoxyoxetane-3-carboxamido)-5-oxohexanoate | 328 |
| 155 | 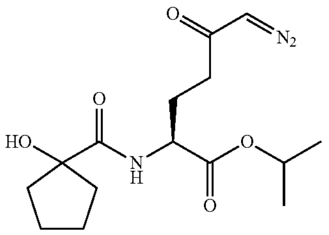 | isopropyl (S)-6-diazo-2-(1-hydroxycyclopentane-1-carboxamido)-5-oxohexanoate | 326 |
| 156 | 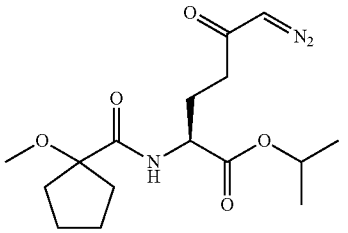 | isopropyl (S)-6-diazo-2-(1-methoxycyclopentane-1-carboxamido)-5-oxohexanoate | 340 |
| 157 | 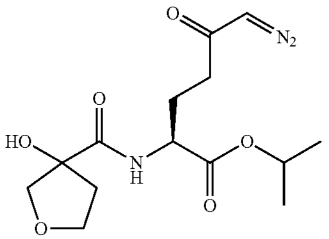 | isopropyl (2S)-6-diazo-2-(3-hydroxytetrahydrofuran-3-carboxamido)-5-oxohexanoate | 328 |

-continued

| Compound | Structure | IUPAC Name | ¹HNMR & MS: (M + H)⁺ |
|---|---|---|---|
| 158 | 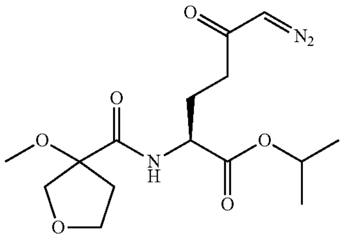 | isopropyl (2S)-6-diazo-2-(3-methoxytetrahydrofuran-3-carboxamido)-5-oxohexanoate | 342 |
| 159 | 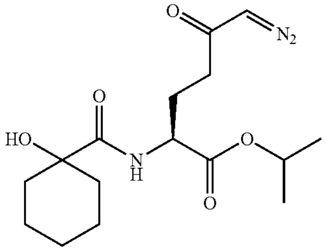 | isopropyl (S)-6-diazo-2-(1-hydroxycyclohexane-1-carboxamido)-5-oxohexanoate | 340 |
| 160 | 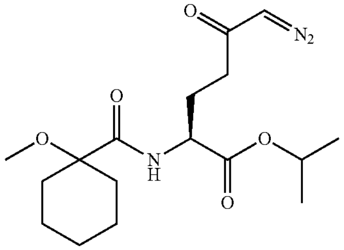 | isopropyl (S)-6-diazo-2-(1-methoxycyclohexane-1-carboxamido)-5-oxohexanoate | 354 |
| 161 | 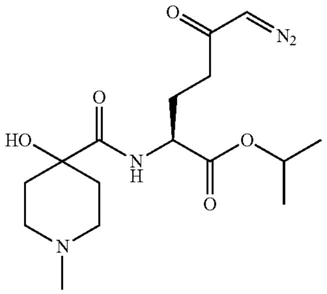 | isopropyl (S)-6-diazo-2-(4-hydroxy-1-methylpiperidine-4-carboxamido)-5-oxohexanoate | 355 |
| 162 | 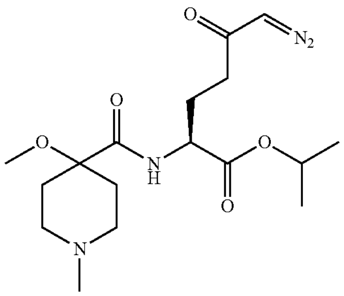 | isopropyl (S)-6-diazo-2-(4-methoxy-1-methylpiperidine-4-carboxamido)-5-oxohexanoate | 369 |

-continued

| Compound | Structure | IUPAC Name | $^1$HNMR & MS: $(M + H)^+$ |
|---|---|---|---|
| 163 | 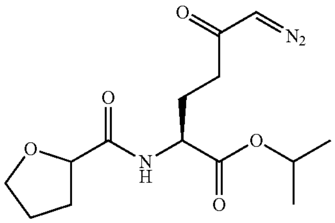 | isopropyl (2S)-6-diazo-5-oxo-2-(tetrahydrofuran-2-carboxamido) hexanoate | 312 |
| 164 | 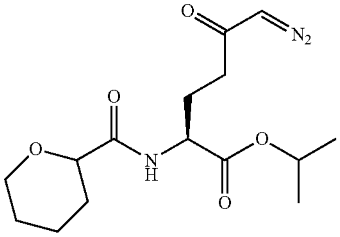 | isopropyl (2S)-6-diazo-5-oxo-2-(tetrahydro-2H-pyran-2-carboxamido) hexanoate | 326 |
| 165 | 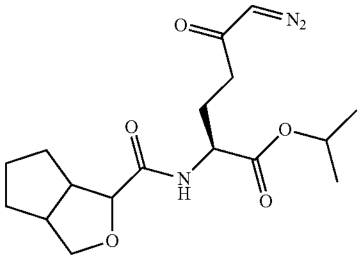 | isopropyl (2S)-6-diazo-2-(hexahydro-1H-cyclopenta[c]furan-1-carboxamido)-5-oxohexanoate | 352 |
| 166 | 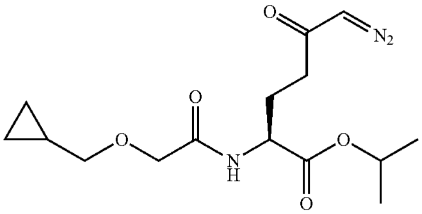 | isopropyl (S)-2-(2-(cyclopropylmethoxy) acetamido)-6-diazo-5-oxohexanoate | MS: 326 $(M + H)^+$, $^1$H NMR (400 MHz, $CD_3OD$) δ 5.82 (s, 1H), 5.02 (dt, J = 12.5, 6.3 Hz, 1H), 4.44 (dd, J = 8.8, 5.0 Hz, 1H), 4.09-3.89 (m, 2H), 3.40 (d, J = 6.9 Hz, 2H), 2.45 (s, 2H), 2.11 (ddq, J = 37.1, 14.6, 7.3 Hz, 2H), 1.34-1.20 (m, 6H), 1.12 (tt, J = 12.4, 6.2 Hz, 1H), 0.56 (d, J = 8.0 Hz, 2H), 0.26 (d, J = 3.7 Hz, 2H). |
| 167 | 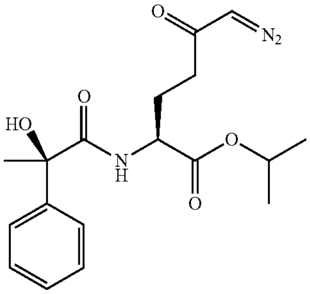 | isopropyl (S)-6-diazo-2-((R)-2-hydroxy-2-phenylpropanamido)-5-oxohexanoate | MS: 362 $(M + H)^+$, $^1$H NMR (400 MHz, $CD_3OD$) δ 7.62-7.56 (m, 2H), 7.35-7.28 (m, 2H), 7.28-7.22 (m, 1H), 4.93 (dt, J = 12.5, 6.3 Hz, 1H), 4.31 (dd, J = 8.9, 5.1 Hz, 1H), 2.42 (s, 2H), 2.29-1.94 (m, 2H), 1.75 (s, 3H), 1.13 (dd, J = 19.5, 6.3 Hz, 6H). |

-continued

| Compound | Structure | IUPAC Name | $^1$HNMR & MS: (M + H)$^+$ |
|---|---|---|---|
| 168 | 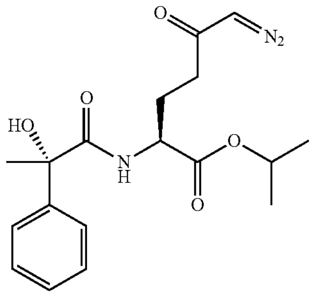 | isopropyl (S)-6-diazo-2-((S)-2-hydroxy-2-phenylpropanamido)-5-oxohexanoate | MS: 362 (M + H)$^+$, $^1$H NMR (400 MHz, $CD_3OD$) δ 7.63-7.58 (m, 2H), 7.37-7.30 (m, 2H), 7.28-7.23 (m, 1H), 5.01 (dt, J = 12.5, 6.3 Hz, 1H), 4.29 (dd, J = 9.2, 4.5 Hz, 1H), 2.29-2.09 (m, 3H), 1.99-1.87 (m, 1H), 1.73 (s, 3H), 1.24 (dd, J = 6.2, 3.2 Hz, 5H). |
| 169 | 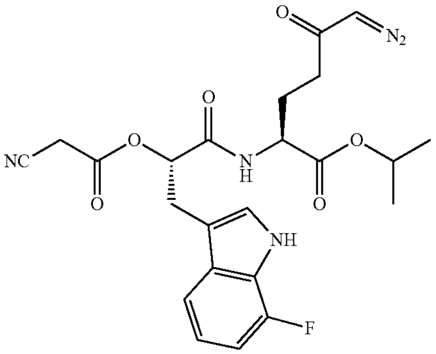 | isopropyl (S)-2-((S)-2-(2-cyanoacetoxy)-3-(7-fluoro-1H-indol-3-yl)propanamido)-6-diazo-5-oxohexanoate | MS: 486 (M + H)$^+$, $^1$H NMR (400 MHz, $CD_3OD$) δ 7.47-7.35 (m, 1H), 7.24-7.13 (m, 1H), 6.93 (td, J = 7.8, 4.0 Hz, 1H), 6.84-6.72 (m, 1H), 5.36 (s, 1H), 5.07-4.91 (m, 1H), 4.43-4.32 (m, 1H), 4.43-4.19 (m, 2H), 4.32-4.19 (m, 1H), 3.23-3.09 (m, 2H), 2.12-1.60 (m, 4H), 1.27-1.13 (m, 6H). |
| 170 | 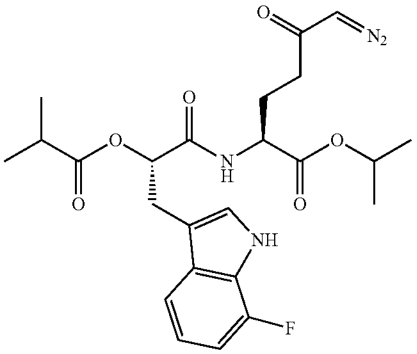 | isopropyl (S)-6-diazo-2-((S)-3-(7-fluoro-1H-indol-3-yl)-2-(isobutyryloxy) propanamido)-5-oxohexanoate | 489 |
| 171 | 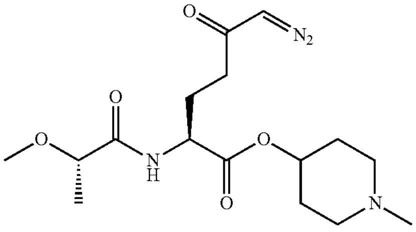 | 1-methylpiperidin-4-yl (S)-6-diazo-2-((S)-2-methoxypropanamido)-5-oxohexanoate | 355 |
| 172 | 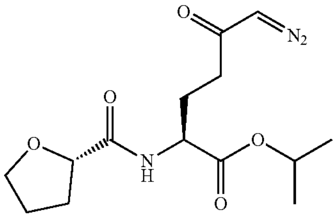 | isopropyl (S)-6-diazo-5-oxo-2-((S)-tetrahydrofuran-2-carboxamido)hexanoate | MS: 312 (M + H)$^+$, $^1$H NMR (400 MHz, $CD_3OD$) δ 5.83 (s, 1H), 5.01 (dt, J = 12.6, 6.2 Hz, 1H), 4.38-4.27 (m, 2H), 4.07-3.97 (m, 1H), 3.93-3.82 (m, 1H), 2.43 (s, 2H), 2.31-2.12 (m, 2H), 2.07-1.83 (m, 4H), 1.29-1.23 (m, 6H). |

-continued

| Compound | Structure | IUPAC Name | $^1$HNMR & MS: $(M + H)^+$ |
|---|---|---|---|
| 173 | 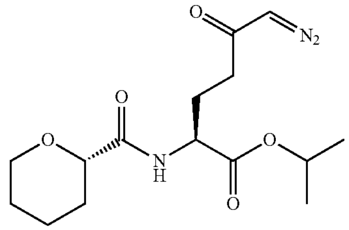 | isopropyl (S)-6-diazo-5-oxo-2-((S)-tetrahydro-2H-pyran-2-carboxamido)hexanoate | 326 |
| 174 | 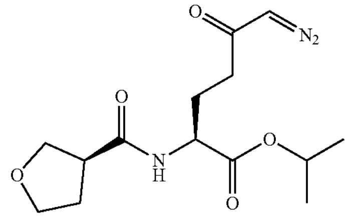 | isopropyl (S)-6-diazo-5-oxo-2-((S)-tetrahydrofuran-3-carboxamido)hexanoate | MS: 312 $(M + H)^+$, $^1$H NMR (400 MHz, $CD_3OD$) δ 5.82 (s, 1H), 5.00 (dt, J = 12.5, 6.2 Hz, 1H), 4.32 (dd, J = 9.1, 5.2 Hz, 1H), 3.97-3.90 (m, 1H), 3.91-3.74 (m, 3H), 3.14-3.03 (m, 1H), 2.44 (s, 2H), 2.22-2.06 (m, 3H), 2.00-1.88 (m, 1H), 1.25 (dd, J = 6.2, 4.1 Hz, 6H). |
| 175 | 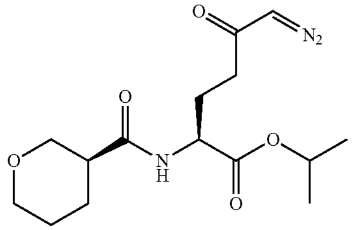 | isopropyl (S)-6-diazo-5-oxo-2-((S)-tetrahydro-2H-pyran-3-carboxamido)hexanoate | 326 |
| 176 | 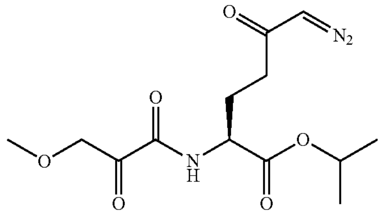 | isopropyl (S)-6-diazo-2-(3-methoxy-2-oxopropanamido)-5-oxohexanoate | 314 |
| 177 | 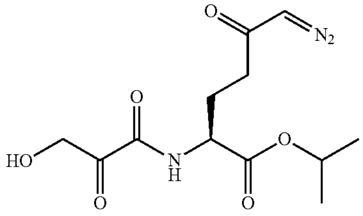 | isopropyl (S)-6-diazo-2-(3-hydroxy-2-oxopropanamido)-5-oxohexanoate | 300 |
| 178 | 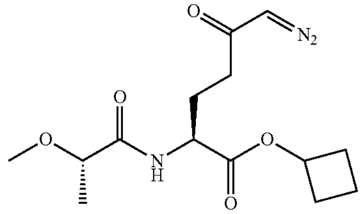 | cyclobutyl (S)-6-diazo-2-((S)-2-methoxypropanamido)-5-oxohexanoate | MS: 312 $(M + H)^+$, $^1$H NMR (400 MHz, $CD_3OD$) δ 5.82 (s, 1H), 5.04-4.91 (m, 1H), 4.49-4.29 (m, 1H), 3.76 (p, J = 6.8 Hz, 1H), 3.44-3.34 (m, 3H), 2.51-2.29 (m, 4H), 2.25-1.98 (m, 4H), 1.88-1.76 (m, 1H), 1.73-1.62 (m, 1H), 1.33 (d, J = 6.8 Hz, 3H). |

-continued

| Compound | Structure | IUPAC Name | $^1$HNMR & MS: (M + H)$^+$ |
|---|---|---|---|
| 179 | 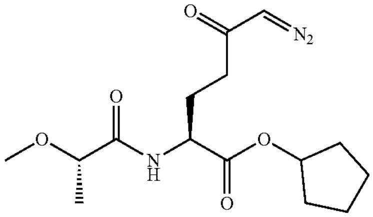 | cyclopentyl (S)-6-diazo-2-((S)-2-methoxypropanamido)-5-oxohexanoate | MS: 326 (M + H)$^+$, $^1$H NMR (400 MHz, $CD_3OD$) δ 5.27-5.07 (m, 1H), 4.43-4.30 (m, 1H), 3.76 (p, J = 6.6 Hz, 1H), 3.46-3.34 (m, 3H), 2.57-2.34 (m, 2H), 2.26-2.12 (m, 1H), 2.06-1.93 (m, 1H), 1.94-1.82 (m, 2H), 1.81-1.56 (m, 6H), 1.34 (d, J = 6.8 Hz, 3H). |
| 180 | 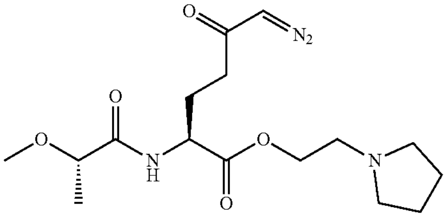 | 2-(pyrrolidin-1-yl)ethyl (S)-6-diazo-2-((S)-2-methoxypropanamido)-5-oxohexanoate | 355 |
| 181 | 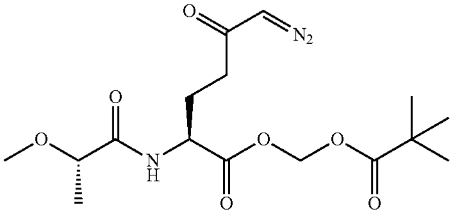 | (pivaloyloxy)methyl (S)-6-diazo-2-((S)-2-methoxypropanamido)-5-oxohexanoate | 372 |
| 182 | 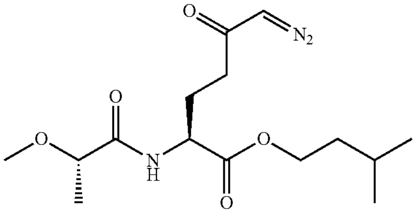 | isopentyl (S)-6-diazo-2-((S)-2-methoxypropanamido)-5-oxohexanoate | MS: 328 (M + H)$^+$, $^1$H NMR (400 MHz, $CD_3OD$) δ 4.48-4.36 (m, 1H), 4.17 (dt, J = 6.6, 4.3 Hz, 2H), 3.76 (p, J = 6.8 Hz, 1H), 3.45-3.33 (m, 3H), 2.51-2.37 (m, 2H), 2.28-2.15 (m, 1H), 2.07-1.93 (m, 1H), 1.71 (dt, J = 13.4, 6.7 Hz, 1H), 1.62-1.49 (m, 2H), 1.37-1.29 (m, 3H), 0.93 (d, J = 6.6 Hz, 6H). |
| 183 | 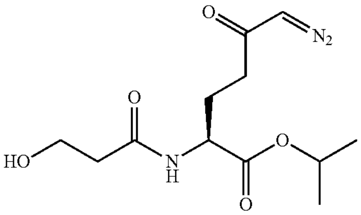 | isopropyl (S)-6-diazo-2-(3-hydroxypropanamido)-5-oxohexanoate | MS: 286 (M + H)+, $^1$H NMR (400 MHz, $CD_3OD$) δ 5.00 (dt, J = 12.7, 6.5 Hz, 1H), 4.37 (dd, J = 9.0, 5.1 Hz, 1H), 3.81 (dd, J = 10.2, 5.3 Hz, 2H), 2.55-2.37 (m, 4H), 2.22-2.08 (m, 1H), 1.99-1.83 (m, 1H), 1.37-1.17 (m, 6H). |
| 184 | 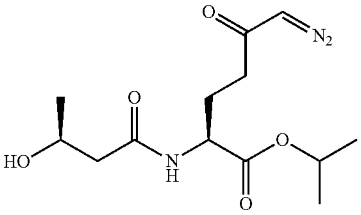 | isopropyl (S)-6-diazo-2-((S)-3-hydroxybutanamido)-5-oxohexanoate | MS: 286 (M + H)$^+$, $^1$H NMR (400 MHz, $CD_3OD$) δ 5.00 (dt, J = 12.5, 6.2 Hz, 1H), 4.35 (dd, J = 8.6, 5.2 Hz, 1H), 4.14 (dd, J = 12.6, 6.3 Hz, 1H), 2.50-2.28 (m, 4H), 2.15 (td, J = 13.6, 6.9 Hz, 1H), 1.93 (td, J = 15.2, 7.9 Hz, 1H), 1.25 (d, J = 6.2 Hz, 6H), 1.21 (d, J = 6.1 Hz, 3H). |

-continued

| Compound | Structure | IUPAC Name | $^1$HNMR & MS: $(M + H)^+$ |
|---|---|---|---|
| 185 | 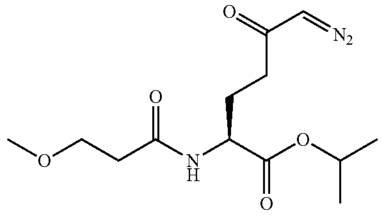 | isopropyl (S)-6-diazo-2-(3-methoxypropanamido)-5-oxohexanoate | MS: 300 $(M + H)^+$, $^1$H NMR (400 MHz, $CD_3OD$) δ 5.00 (dt, J = 12.4, 6.2 Hz, 1H), 4.36 (dd, J = 8.9, 5.1 Hz, 1H), 3.70-3.55 (m, 2H), 3.33 (s, 3H), 2.58-2.35 (m, 4H), 2.14 (td, J = 13.5, 7.2 Hz, 1H), 1.91 (td, J = 15.1, 7.8 Hz, 1H), 1.30-1.20 (m, 6H). |
| 186 | 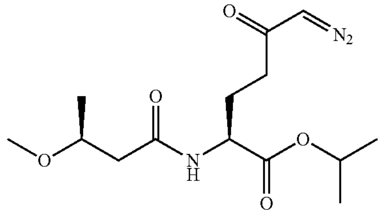 | isopropyl (S)-6-diazo-2-((S)-3-methoxybutanamido)-5-oxohexanoate | 314 |
| 187 | 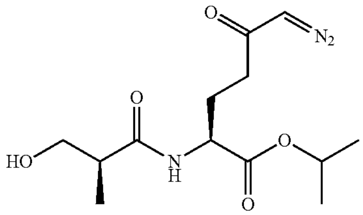 | isopropyl (S)-6-diazo-2-((S)-3-hydroxy-2-methylpropanamido)-5-oxohexanoate | MS: 300 $(M + H)^+$, $^1$H NMR (400 MHz, $CD_3OD$) δ 5.81 (s, 1H), 5.00 (dt, J = 12.4, 6.3 Hz, 1H), 4.34 (dd, J = 8.7, 5.1 Hz, 1H), 3.73-3.63 (m, 1H), 3.56-3.45 (m, 1H), 2.56 (dd, J = 13.6, 6.7 Hz, 1H), 2.44 (s, 2H), 2.22-2.08 (m, 1H), 2.02-1.88 (m, 1H), 1.25 (d, J = 6.2 Hz, 6H), 1.11 (d, J = 6.9 Hz, 3H). |
| 188 | 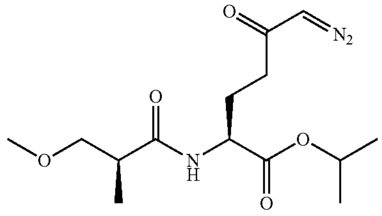 | isopropyl (S)-6-diazo-2-((S)-3-methoxy-2-methylpropanamido)-5-oxohexanoate | MS: 314 $(M + H)^+$, $^1$H NMR (400 MHz, $CD_3OD$) δ 5.81 (s, 1H), 5.00 (dt, J = 12.5, 6.3 Hz, 1H), 4.33 (dd, J = 9.0, 5.2 Hz, 1H), 3.53 (dd, J = 9.3, 8.1 Hz, 1H), 3.38-3.33 (m, 1H), 3.33 (s, 3H), 2.68 (dd, J = 13.4, 7.1 Hz, 1H), 2.43 (s, 2H), 2.25-2.08 (m, 1H), 2.02-1.86 (m, 1H), 1.25 (dd, J = 6.2, 2.7 Hz, 6H), 1.10 (d, J = 7.0 Hz, 3H). |
| 189 | 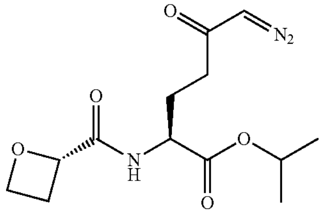 | isopropyl (S)-6-diazo-2-((S)-oxetane-2-carboxamido)-5-oxohexanoate | MS: 298 $(M + H)^+$, $^1$H NMR (400 MHz, $CD_3OD$) δ 5.81 (s, 1H), 5.12-4.98 (m, 2H), 4.83-4.64 (m, 2H), 4.45 (dd, J = 9.2, 4.9 Hz, 1H), 3.11-2.95 (m, 1H), 2.70-2.55 (m, 1H), 2.45 (s, 2H), 2.30-2.18 (m, 1H), 2.10-1.94 (m, 1H), 1.31-1.27 (m, 6H). |
| 190 | 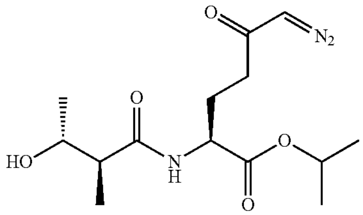 | isopropyl (S)-6-diazo-2-((2S,3R)-3-hydroxy-2-methylbutanamido)-5-oxohexanoate | 314 |

-continued

| Compound | Structure | IUPAC Name | $^1$HNMR & MS: (M + H)$^+$ |
|---|---|---|---|
| 191 | 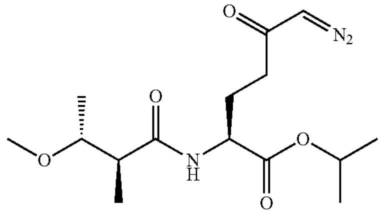 | isopropyl (S)-6-diazo-2-((2S,3R)-3-methoxy-2-methylbutanamido)-5-oxohexanoate | 328 |
| 192 | 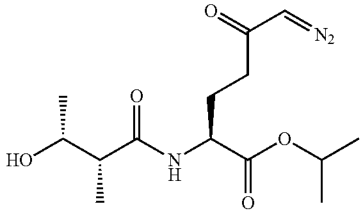 | isopropyl (S)-6-diazo-2-((2R,3R)-3-hydroxy-2-methylbutanamido)-5-oxohexanoate | 314 |
| 193 | 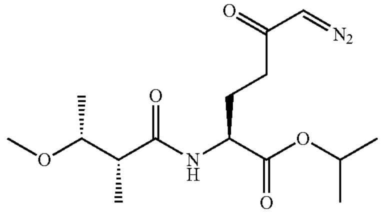 | isopropyl (S)-6-diazo-2-((2R,3R)-3-methoxy-2-methylbutanamido)-5-oxohexanoate | 328 |
| 194 | 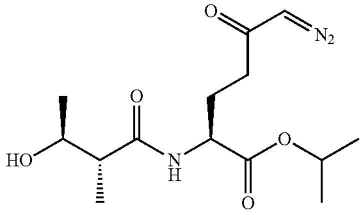 | isopropyl (S)-6-diazo-2-((2R,3S)-3-hydroxy-2-methylbutanamido)-5-oxohexanoate | 314 |
| 195 | 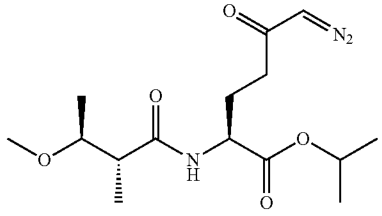 | isopropyl (S)-6-diazo-2-((2R,3S)-3-methoxy-2-methylbutanamido)-5-oxohexanoate | 328 |
| 196 | 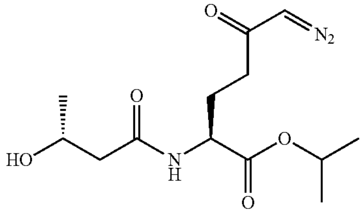 | isopropyl (S)-6-diazo-2-((R)-3-hydroxybutanamido)-5-oxohexanoate | 300 |
| 197 | 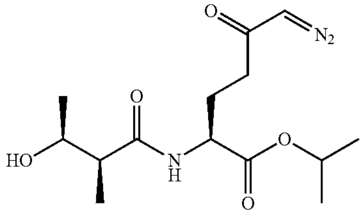 | isopropyl (S)-6-diazo-2-((2S,3S)-3-hydroxy-2-methylbutanamido)-5-oxohexanoate | 314 |

-continued

| Compound | Structure | IUPAC Name | $^1$HNMR & MS: $(M + H)^+$ |
|---|---|---|---|
| 198 | 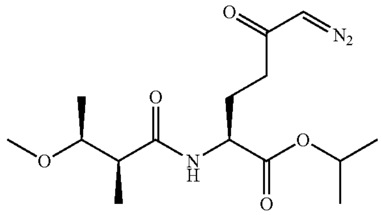 | isopropyl (S)-6-diazo-2-((2S,3S)-3-methoxy-2-methylbutanamido)-5-oxohexanoate | 328 |
| 199 | 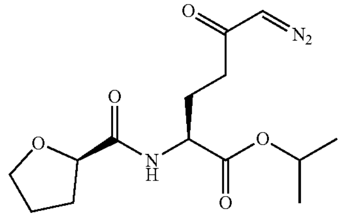 | isopropyl (S)-6-diazo-5-oxo-2-((R)-tetrahydrofuran-2-carboxamido)hexanoate | 312 |
| 200 | 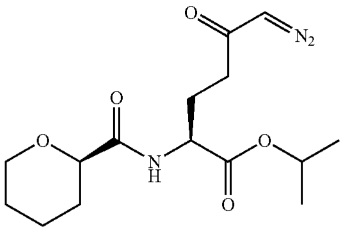 | isopropyl (S)-6-diazo-5-oxo-2-((R)-tetrahydro-2H-pyran-2-carboxamido)hexanoate | 326 |
| 201 | 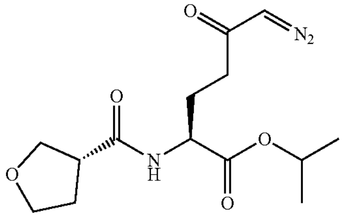 | isopropyl (S)-6-diazo-5-oxo-2-((R)-tetrahydrofuran-3-carboxamido)hexanoate | MS: 312 $(M + H)^+$, $^1$H NMR (400 MHz, $CD_3OD$) δ 5.82 (s, 1H), 4.99 (dt, J = 12.5, 6.2 Hz, 1H), 4.32 (dd, J = 9.1, 5.2 Hz, 1H), 3.99-3.93 (m, 1H), 3.91-3.84 (m, 1H), 3.83-3.74 (m, 2H), 3.14-2.98 (m, 1H), 2.45 (s, 2H), 2.21-2.06 (m, 3H), 1.93 (dt, J = 14.4, 7.5 Hz, 1H), 1.24 (dd, J = 6.2, 4.3 Hz, 6H). |
| 202 | 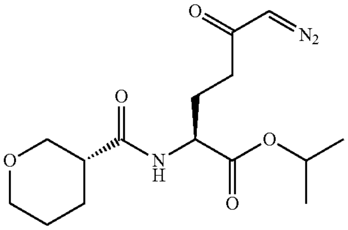 | isopropyl (S)-6-diazo-5-oxo-2-((R)-tetrahydro-2H-pyran-3-carboxamido)hexanoate | 326 |
| 203 | 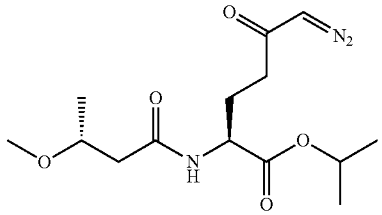 | isopropyl (S)-6-diazo-2-((R)-3-methoxybutanamido)-5-oxohexanoate | 314 |

-continued

| Compound | Structure | IUPAC Name | $^1$HNMR & MS: (M + H)$^+$ |
|---|---|---|---|
| 204 | 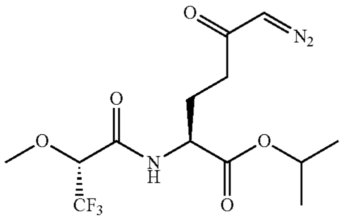 | isopropyl (S)-6-diazo-5-oxo-2-((R)-3,3,3-trifluoro-2-methoxypropanamido) hexanoate | 354 |
| 205 | 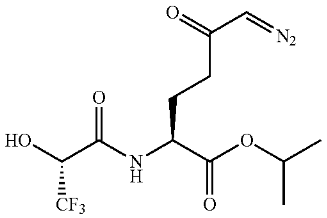 | isopropyl (S)-6-diazo-5-oxo-2-((R)-3,3,3-trifluoro-2-hydroxypropanamido) hexanoate | 340 |
| 206 | 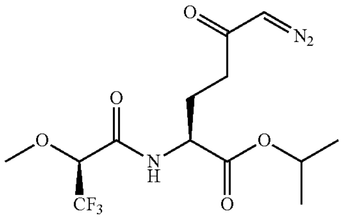 | isopropyl (S)-6-diazo-5-oxo-2-((S)-3,3,3-trifluoro-2-methoxypropanamido) hexanoate | 354 |
| 207 | 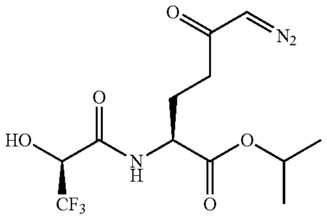 | isopropyl (S)-6-diazo-5-oxo-2-((S)-3,3,3-trifluoro-2-hydroxypropanamido) hexanoate | 340 |
| 208 | 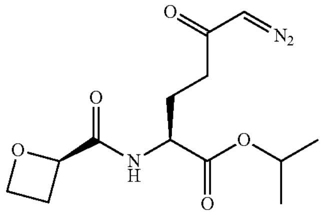 | isopropyl (S)-6-diazo-2-((R)-oxetane-2-carboxamido)-5-oxohexanoate | MS: 298 (M + H)$^+$, $^1$H NMR (400 MHz, $CD_3OD$) δ 5.85 (s, 1H), 5.09-4.96 (m, 2H), 4.80-4.60 (m, 2H), 4.43 (dd, J = 9.0, 5.0 Hz, 1H), 3.11-2.97 (m, 1H), 2.70-2.56 (m, 1H), 2.50 (s, 2H), 2.35-2.19 (m, 1H), 2.17-1.99 (m, 1H), 1.26 (d, J = 6.3 Hz, 6H). |
| 209 | 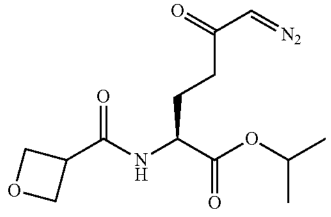 | isopropyl (S)-6-diazo-2-(oxetane-3-carboxamido)-5-oxohexanoate | 298 |

-continued

| Compound | Structure | IUPAC Name | $^1$HNMR & MS: (M + H)$^+$ |
|---|---|---|---|
| 210 | 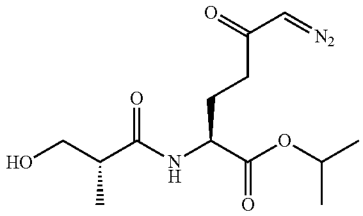 | isopropyl (S)-6-diazo-2-((R)-3-hydroxy-2-methylpropanamido)-5-oxohexanoate | 300 |
| 211 | 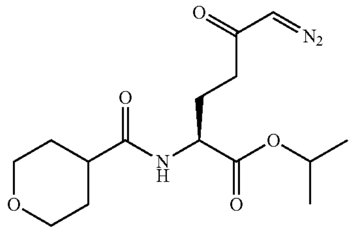 | isopropyl (S)-6-diazo-5-oxo-2-(tetrahydro-2H-pyran-4-carboxamido)hexanoate | 326 |
| 212 | 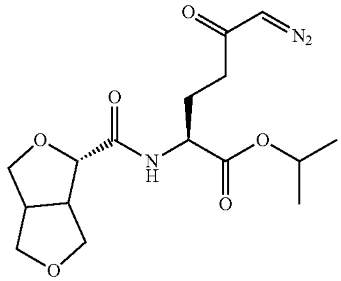 | isopropyl (2S)-6-diazo-5-oxo-2-((1S)-tetrahydro-1H,3H-furo[3,4-c]furan-1-carboxamido)hexanoate | 354 |
| 213 | 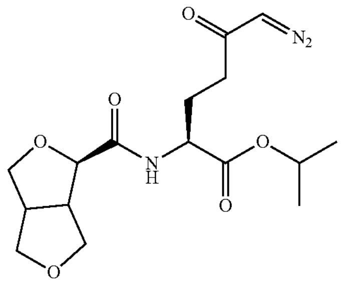 | isopropyl (2S)-6-diazo-5-oxo-2-((1R)-tetrahydro-1H,3H-furo[3,4-c]furan-1-carboxamido)hexanoate | 354 |
| 214 | 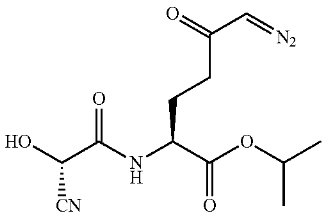 | isopropyl (S)-2-((S)-2-cyano-2-hydroxyacetamido)-6-diazo-5-oxohexanoate | 297 |
| 215 | 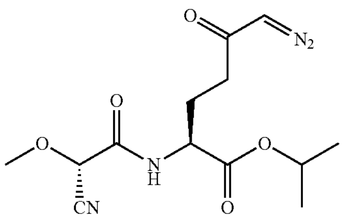 | isopropyl (S)-2-((S)-2-cyano-2-methoxyacetamido)-6-diazo-5-oxohexanoate | 311 |

-continued

| Compound | Structure | IUPAC Name | $^1$HNMR & MS: (M + H)$^+$ |
|---|---|---|---|
| 216 | 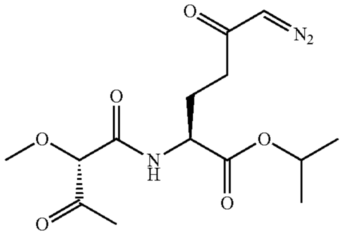 | isopropyl (S)-6-diazo-2-((S)-2-methoxy-3-oxobutanamido)-5-oxohexanoate | 328 |
| 217 | 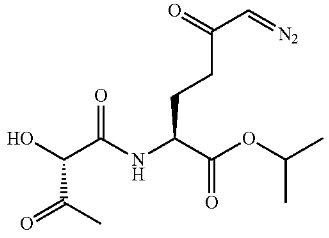 | isopropyl (S)-6-diazo-2-((S)-2-hydroxy-3-oxobutanamido)-5-oxohexanoate | 314 |
| 218 | 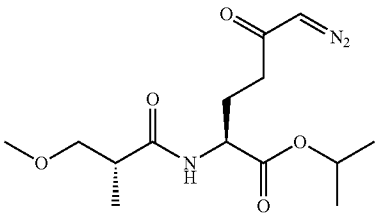 | isopropyl (S)-6-diazo-2-((R)-3-methoxy-2-methylpropanamido)-5-oxohexanoate | MS: 298 (M + H)$^+$, $^1$H NMR (400 MHz, $CD_3OD$) δ 5.78 (s, 1H), 5.00 (dt, J = 12.5, 6.3 Hz, 1H), 4.36 (dd, J = 9.5, 4.9 Hz, 1H), 3.52 (t, J = 9.1 Hz, 1H), 3.35-3.32 (m, 4H), 2.74-2.59 (m, 1H), 2.45 (s, 2H), 2.23-2.08 (m, 1H), 1.98-1.82 (m, 1H), 1.25 (dd, J = 6.1, 4.7 Hz, 6H), 1.08 (d, J = 7.0 Hz, 3H). |
| 219 | 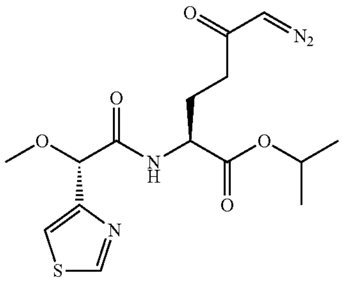 | isopropyl (S)-6-diazo-2-((S)-2-methoxy-2-(thiazol-4-yl)acetamido)-5-oxohexanoate | 367 |
| 220 | 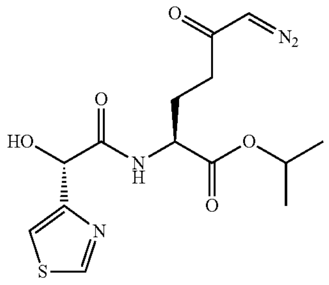 | isopropyl (S)-6-diazo-2-((S)-2-hydroxy-2-(thiazol-4-yl)acetamido)-5-oxohexanoate | 355 |
| 221 | 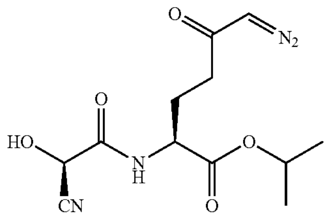 | isopropyl (S)-2-((R)-2-cyano-2-hydroxyacetamido)-6-diazo-5-oxohexanoate | 297 |

-continued

| Compound | Structure | IUPAC Name | $^1$HNMR & MS: (M + H)$^+$ |
|---|---|---|---|
| 222 | 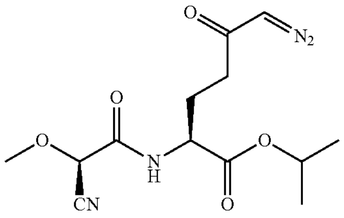 | isopropyl (S)-2-((R)-2-cyano-2-methoxyacetamido)-6-diazo-5-oxohexanoate | 311 |
| 223 | 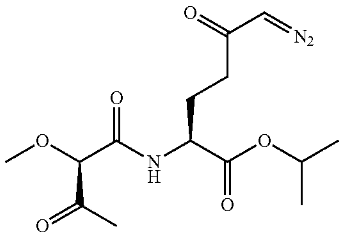 | isopropyl (S)-6-diazo-2-((R)-2-methoxy-3-oxobutanamido)-5-oxohexanoate | 328 |
| 224 | 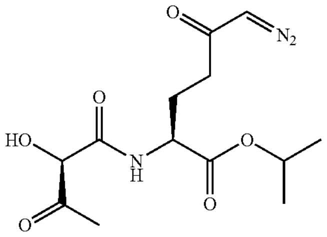 | isopropyl (S)-6-diazo-2-((R)-2-hydroxy-3-oxobutanamido)-5-oxohexanoate | 314 |
| 225 | 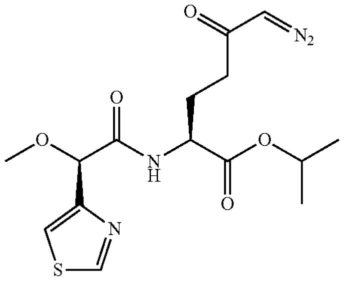 | isopropyl (S)-6-diazo-2-((R)-2-methoxy-2-(thiazol-4-yl)acetamido)-5-oxohexanoate | 369 |
| 226 | 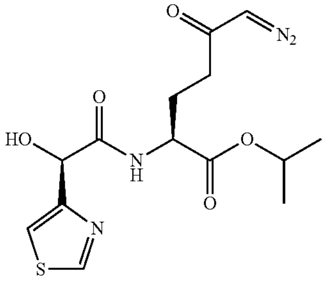 | isopropyl (S)-6-diazo-2-((R)-2-hydroxy-2-(thiazol-4-yl)acetamido)-5-oxohexanoate | 355 |
| 227 | 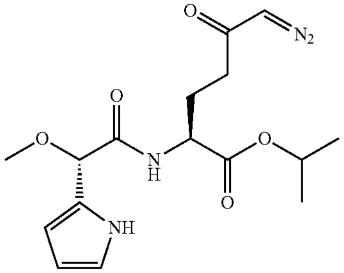 | isopropyl (S)-6-diazo-2-((S)-2-methoxy-2-(1H-pyrrol-2-yl)acetamido)-5-oxohexanoate | 351 |

-continued

| Compound | Structure | IUPAC Name | $^1$HNMR & MS: $(M + H)^+$ |
|---|---|---|---|
| 228 | 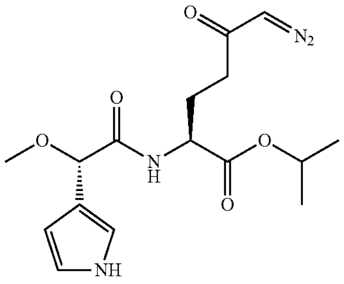 | isopropyl (S)-6-diazo-2-((S)-2-methoxy-2-(1H-pyrrol-3-yl)acetamido)-5-oxohexanoate | 351 |
| 229 | 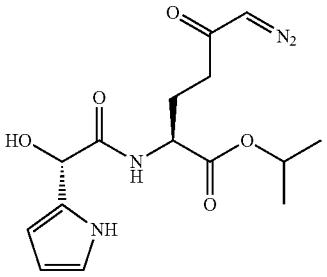 | isopropyl (S)-6-diazo-2-((S)-2-hydroxy-2-(1H-pyrrol-2-yl)acetamido)-5-oxohexanoate | 337 |
| 230 | 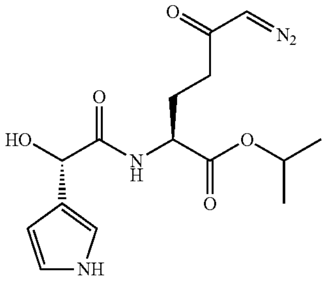 | isopropyl (S)-6-diazo-2-((S)-2-hydroxy-2-(1H-pyrrol-3-yl)acetamido)-5-oxohexanoate | 337 |
| 231 | 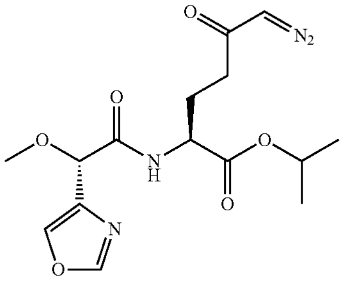 | isopropyl (S)-6-diazo-2-((S)-2-methoxy-2-(oxazol-4-yl)acetamido)-5-oxohexanoate | 353 |
| 232 | 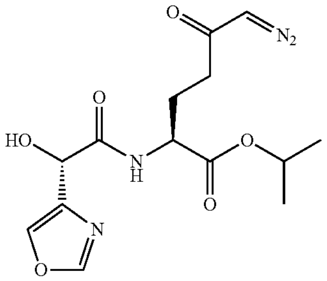 | isopropyl (S)-6-diazo-2-((S)-2-hydroxy-2-(oxazol-4-yl)acetamido)-5-oxohexanoate | 339 |

-continued

| Compound | Structure | IUPAC Name | ¹HNMR & MS: (M + H)⁺ |
|---|---|---|---|
| 233 | 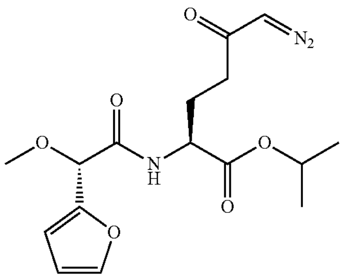 | isopropyl (S)-6-diazo-2-((S)-2-(furan-2-yl)-2-methoxyacetamido)-5-oxohexanoate | 352 |
| 234 | 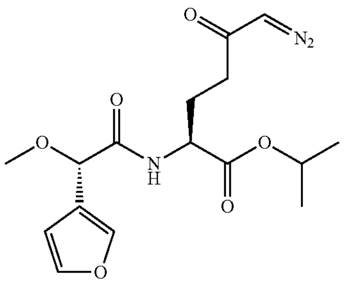 | isopropyl (S)-6-diazo-2-((S)-2-(furan-3-yl)-2-methoxyacetamido)-5-oxohexanoate | 352 |
| 235 | 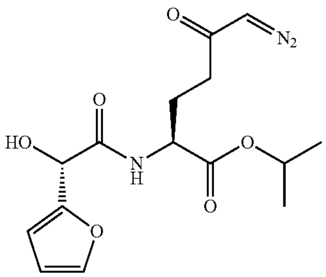 | isopropyl (S)-6-diazo-2-((S)-2-(furan-2-yl)-2-hydroxyacetamido)-5-oxohexanoate | 338 |
| 236 | 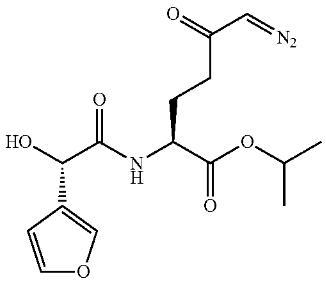 | isopropyl (S)-6-diazo-2-((S)-2-(furan-3-yl)-2-hydroxyacetamido)-5-oxohexanoate | 338 |
| 237 | 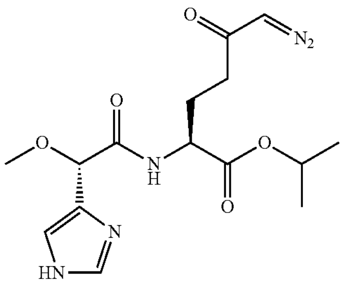 | isopropyl (S)-2-((S)-2-(1H-imidazol-4-yl)-2-methoxyacetamido)-6-diazo-5-oxohexanoate | 352 |

-continued

| Compound | Structure | IUPAC Name | ¹HNMR & MS: (M + H)⁺ |
| --- | --- | --- | --- |
| 238 | 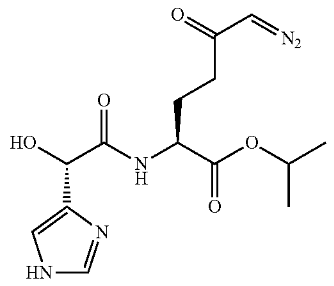 | isopropyl (S)-6-diazo-2-((S)-2-hydroxy-2-(1H-imidazol-4-yl)acetamido)-5-oxohexanoate | 338 |
| 239 | 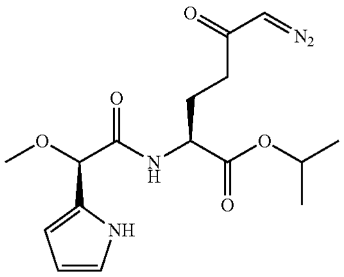 | isopropyl (S)-6-diazo-2-((R)-2-methoxy-2-(1H-pyrrol-2-yl)acetamido)-5-oxohexanoate | 351 |
| 240 | 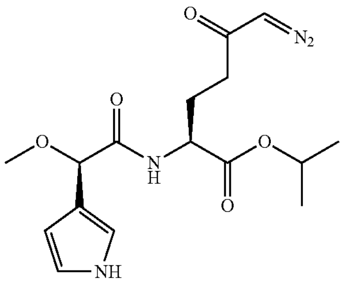 | isopropyl (S)-6-diazo-2-((R)-2-methoxy-2-(1H-pyrrol-3-yl)acetamido)-5-oxohexanoate | 351 |
| 241 | 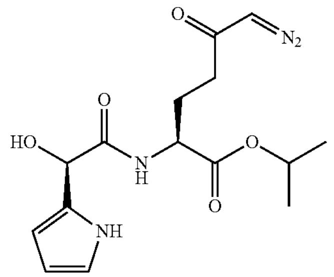 | isopropyl (S)-6-diazo-2-((R)-2-hydroxy-2-(1H-pyrrol-2-yl)acetamido)-5-oxohexanoate | 337 |
| 242 | 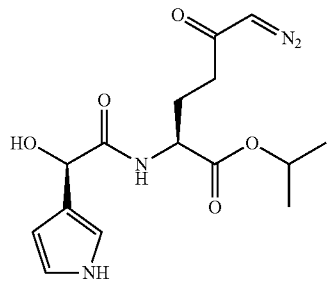 | isopropyl (S)-6-diazo-2-((R)-2-hydroxy-2-(1H-pyrrol-3-yl)acetamido)-5-oxohexanoate | 337 |

-continued

| Compound | Structure | IUPAC Name | $^1$HNMR & MS: (M + H)$^+$ |
|---|---|---|---|
| 243 | 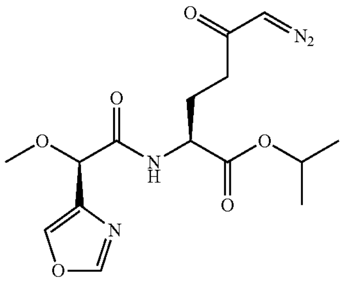 | isopropyl (S)-6-diazo-2-((R)-2-methoxy-2-(oxazol-4-yl)acetamido)-5-oxohexanoate | 353 |
| 244 | 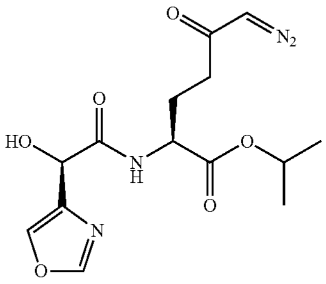 | isopropyl (S)-6-diazo-2-((R)-2-hydroxy-2-(oxazol-4-yl)acetamido)-5-oxohexanoate | 339 |
| 245 | 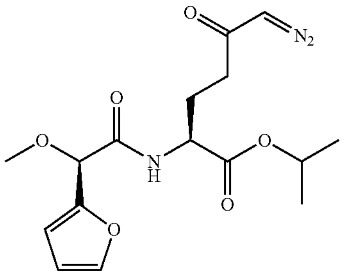 | isopropyl (S)-6-diazo-2-((R)-2-(furan-2-yl)-2-methoxyacetamido)-5-oxohexanoate | 352 |
| 246 | 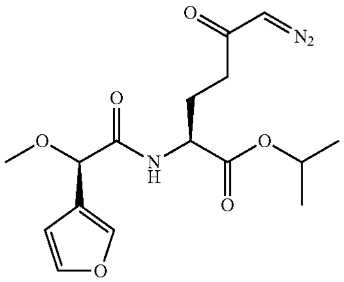 | isopropyl (S)-6-diazo-2-((R)-2-(furan-3-yl)-2-methoxyacetamido)-5-oxohexanoate | 352 |
| 247 | 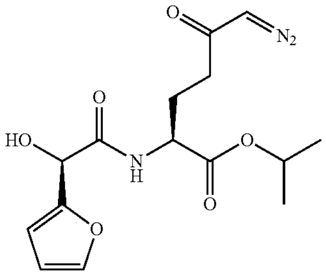 | isopropyl (S)-6-diazo-2-((R)-2-(furan-2-yl)-2-hydroxyacetamido)-5-oxohexanoate | 338 |

-continued

| Compound | Structure | IUPAC Name | $^1$HNMR & MS: (M + H)$^+$ |
|---|---|---|---|
| 248 | 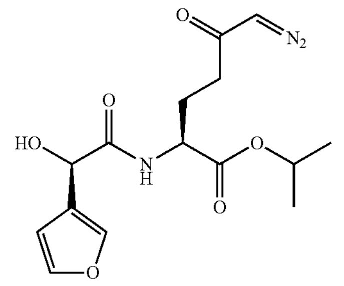 | isopropyl (S)-6-diazo-2-((R)-2-(furan-3-yl)-2-hydroxyacetamido)-5-oxohexanoate | 338 |
| 249 | 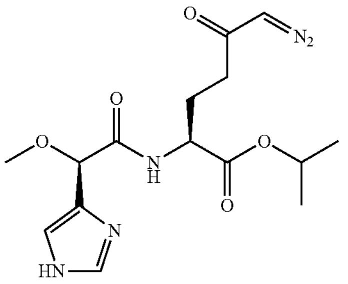 | isopropyl (S)-2-((R)-2-(1H-imidazol-4-yl)-2-methoxyacetamido)-6-diazo-5-oxohexanoate | 352 |
| 250 | 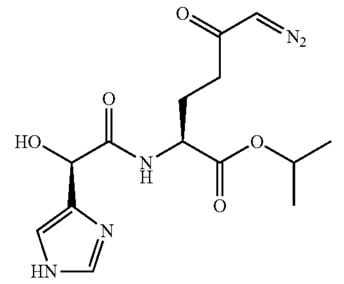 | isopropyl (S)-6-diazo-2-((R)-2-hydroxy-2-(1H-imidazol-4-yl)acetamido)-5-oxohexanoate | 338 |
| 251 | 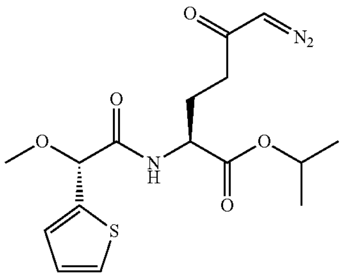 | isopropyl (S)-6-diazo-2-((R)-2-methoxy-2-(thiophen-2-yl)acetamido)-5-oxohexanoate | 368 |
| 252 | 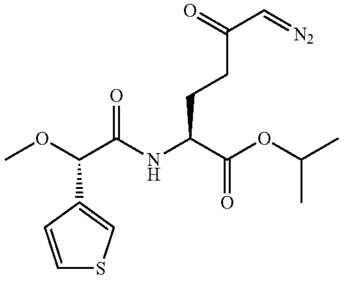 | isopropyl (S)-6-diazo-2-((S)-2-methoxy-2-(thiophen-3-yl)acetamido)-5-oxohexanoate | 368 |

-continued

| Compound | Structure | IUPAC Name | $^1$HNMR & MS: (M + H)$^+$ |
|---|---|---|---|
| 253 | 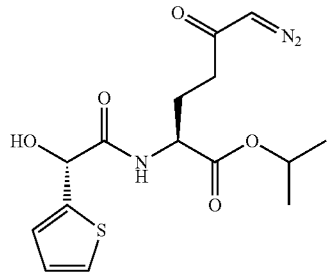 | isopropyl (S)-6-diazo-2-((R)-2-hydroxy-2-(thiophen-2-yl)acetamido)-5-oxohexanoate | 354 |
| 254 | 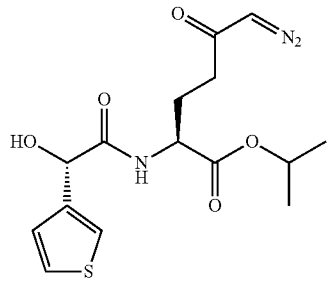 | isopropyl (S)-6-diazo-2-((S)-2-hydroxy-2-(thiophen-3-yl)acetamido)-5-oxohexanoate | 354 |
| 255 | 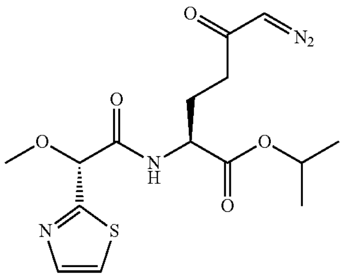 | isopropyl (S)-6-diazo-2-((R)-2-methoxy-2-(thiazol-2-yl)acetamido)-5-oxohexanoate | 369 |
| 256 | 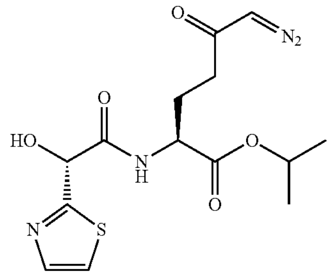 | isopropyl (S)-6-diazo-2-((R)-2-hydroxy-2-(thiazol-2-yl)acetamido)-5-oxohexanoate | 355 |
| 257 | 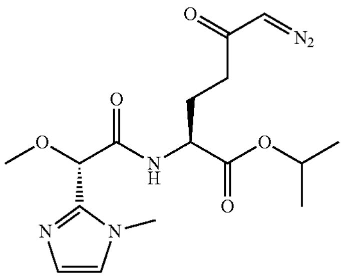 | isopropyl (S)-6-diazo-2-((S)-2-methoxy-2-(1-methyl-1H-imidazol-2-yl)acetamido)-5-oxohexanoate | 366 |

-continued

| Compound | Structure | IUPAC Name | $^1$HNMR & MS: $(M + H)^+$ |
| --- | --- | --- | --- |
| 258 | 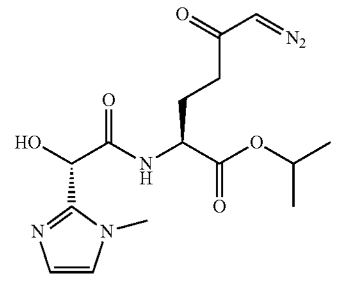 | isopropyl (S)-6-diazo-2-((S)-2-hydroxy-2-(1-methyl-1H-imidazol-2-yl)acetamido)-5-oxohexanoate | 352 |
| 259 | 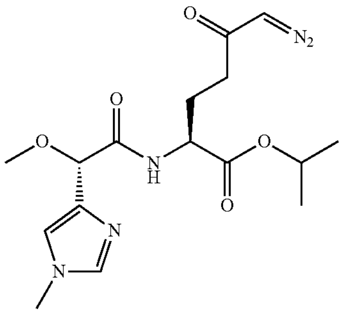 | isopropyl (S)-6-diazo-2-((S)-2-methoxy-2-(1-methyl-1H-imidazol-4-yl)acetamido)-5-oxohexanoate | 366 |
| 260 | 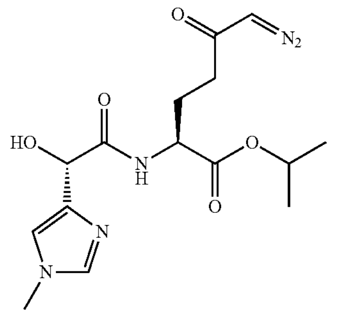 | isopropyl (S)-6-diazo-2-((S)-2-hydroxy-2-(1-methyl-1H-imidazol-4-yl)acetamido)-5-oxohexanoate | 352 |
| 261 | 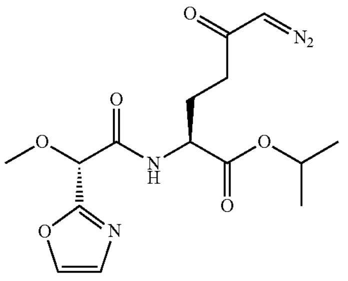 | isopropyl (S)-6-diazo-2-((S)-2-methoxy-2-(oxazol-2-yl)acetamido)-5-oxohexanoate | 353 |
| 262 | 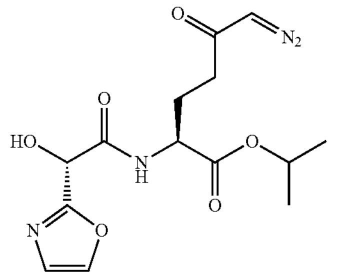 | isopropyl (S)-6-diazo-2-((S)-2-hydroxy-2-(oxazol-2-yl)acetamido)-5-oxohexanoate | 339 |

-continued

| Compound | Structure | IUPAC Name | $^1$HNMR & MS: (M + H)$^+$ |
|---|---|---|---|
| 263 | 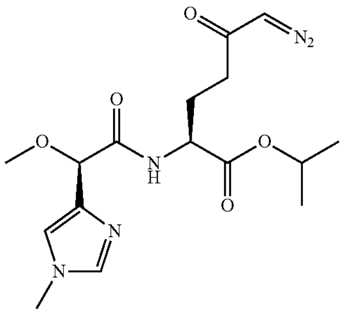 | isopropyl (S)-6-diazo-2-((R)-2-methoxy-2-(1-methyl-1H-imidazol-4-yl)acetamido)-5-oxohexanoate | 366 |
| 264 | 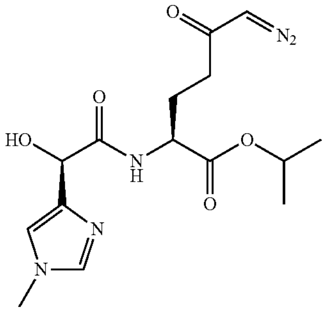 | isopropyl (S)-6-diazo-2-((R)-2-hydroxy-2-(1-methyl-1H-imidazol-4-yl)acetamido)-5-oxohexanoate | 352 |
| 265 | 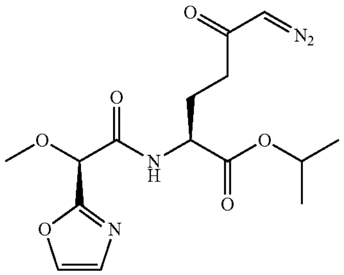 | isopropyl (S)-6-diazo-2-((R)-2-methoxy-2-(oxazol-2-yl)acetamido)-5-oxohexanoate | 353 |
| 266 | 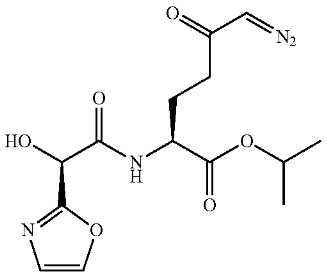 | isopropyl (S)-6-diazo-2-((R)-2-hydroxy-2-(oxazol-2-yl)acetamido)-5-oxohexanoate | 339 |
| 267 | 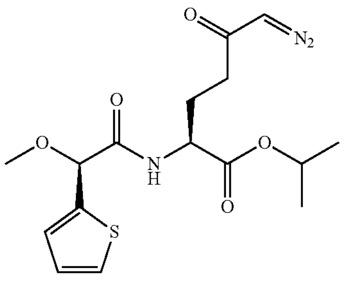 | isopropyl (S)-6-diazo-2-((S)-2-methoxy-2-(thiophen-2-yl)acetamido)-5-oxohexanoate | 368 |

-continued

| Compound | Structure | IUPAC Name | $^1$HNMR & MS: (M + H)$^+$ |
|---|---|---|---|
| 268 | 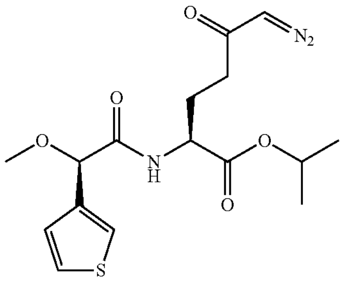 | isopropyl (S)-6-diazo-2-((R)-2-methoxy-2-(thiophen-3-yl)acetamido)-5-oxohexanoate | 368 |
| 269 | 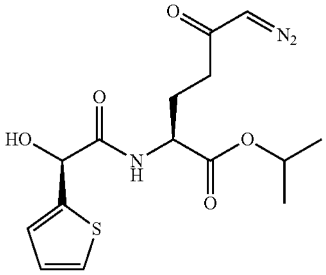 | isopropyl (S)-6-diazo-2-((S)-2-hydroxy-2-(thiophen-2-yl)acetamido)-5-oxohexanoate | 354 |
| 270 | 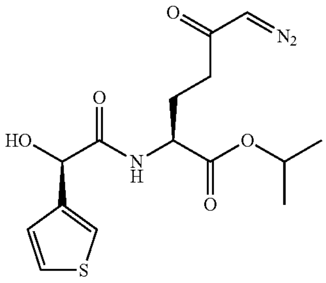 | isopropyl (S)-6-diazo-2-((R)-2-hydroxy-2-(thiophen-3-yl)acetamido)-5-oxohexanoate | 354 |
| 271 | 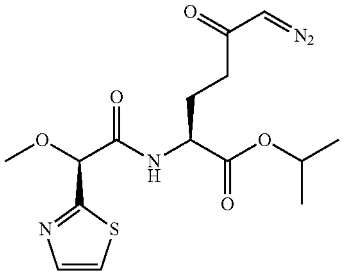 | isopropyl (S)-6-diazo-2-((S)-2-methoxy-2-(thiazol-2-yl)acetamido)-5-oxohexanoate | 369 |
| 272 | 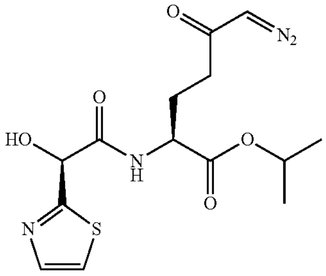 | isopropyl (S)-6-diazo-2-((S)-2-hydroxy-2-(thiazol-2-yl)acetamido)-5-oxohexanoate | 355 |

-continued

| Compound | Structure | IUPAC Name | $^1$HNMR & MS: $(M + H)^+$ |
|---|---|---|---|
| 273 | 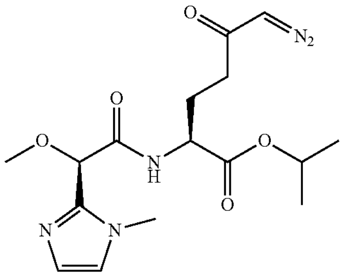 | isopropyl (S)-6-diazo-2-((R)-2-methoxy-2-(1-methyl-1H-imidazol-2-yl)acetamido)-5-oxohexanoate | 366 |
| 274 | 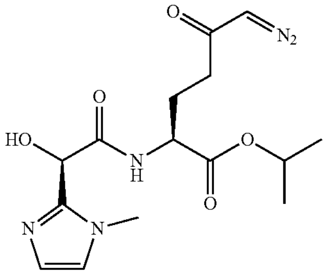 | isopropyl (S)-6-diazo-2-((R)-2-hydroxy-2-(1-methyl-1H-imidazol-2-yl)acetamido)-5-oxohexanoate | 352 |
| 275 | 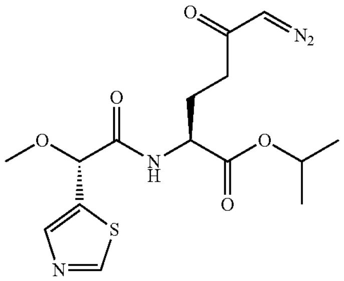 | isopropyl (S)-6-diazo-2-((R)-2-methoxy-2-(thiazol-5-yl)acetamido)-5-oxohexanoate | 369 |
| 276 | 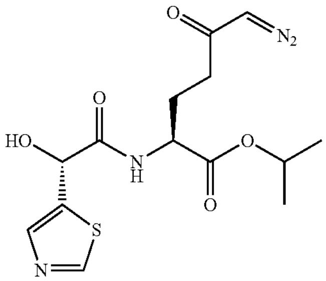 | isopropyl (S)-6-diazo-2-((R)-2-hydroxy-2-(thiazol-5-yl)acetamido)-5-oxohexanoate | 355 |
| 277 | 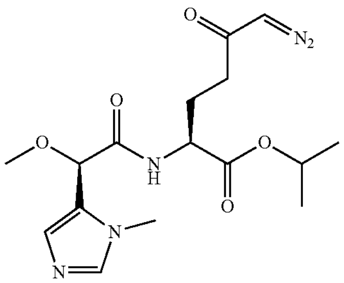 | isopropyl (S)-6-diazo-2-((R)-2-methoxy-2-(1-methyl-1H-imidazol-5-yl)acetamido)-5-oxohexanoate | 366 |

-continued

| Compound | Structure | IUPAC Name | $^1$HNMR & MS: $(M + H)^+$ |
|---|---|---|---|
| 278 | 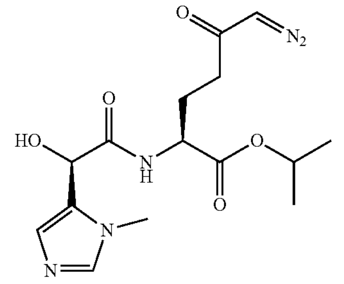 | isopropyl (S)-6-diazo-2-((R)-2-hydroxy-2-(1-methyl-1H-imidazol-5-yl)acetamido)-5-oxohexanoate | 352 |
| 279 | 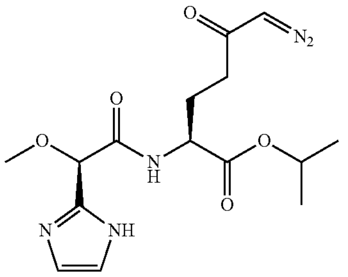 | isopropyl (S)-2-((R)-2-(1H-imidazol-2-yl)-2-methoxyacetamido)-6-diazo-5-oxohexanoate | 352 |
| 280 | 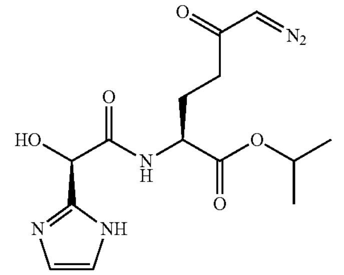 | isopropyl (S)-6-diazo-2-((R)-2-hydroxy-2-(1H-imidazol-2-yl)acetamido)-5-oxohexanoate | 338 |
| 281 | 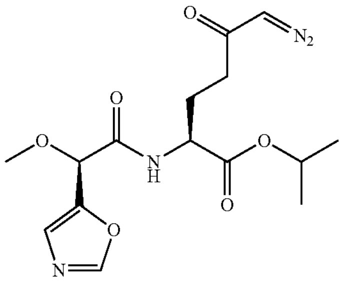 | isopropyl (S)-6-diazo-2-((R)-2-methoxy-2-(oxazol-5-yl)acetamido)-5-oxohexanoate | 353 |
| 282 | 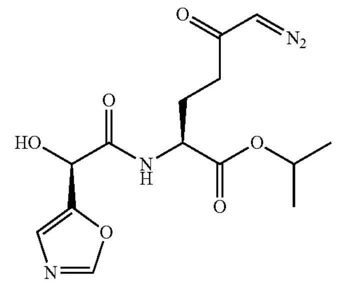 | isopropyl (S)-6-diazo-2-((R)-2-hydroxy-2-(oxazol-5-yl)acetamido)-5-oxohexanoate | 339 |

-continued

| Compound | Structure | IUPAC Name | $^1$HNMR & MS: (M + H)+ |
| --- | --- | --- | --- |
| 283 | 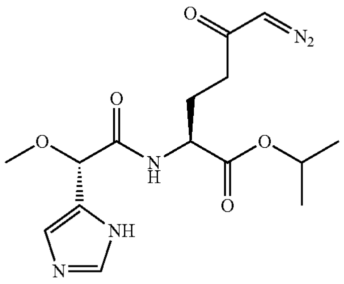 | isopropyl (S)-2-((S)-2-(1H-imidazol-5-yl)-2-methoxyacetamido)-6-diazo-5-oxohexanoate | 352 |
| 284 | 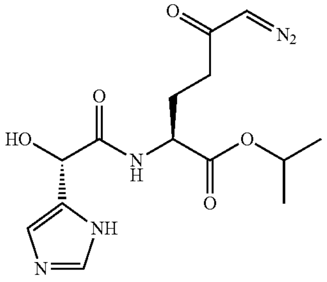 | isopropyl (S)-6-diazo-2-((S)-2-hydroxy-2-(1H-imidazol-5-yl)acetamido)-5-oxohexanoate | 338 |
| 285 | 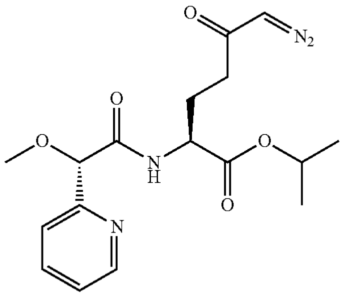 | isopropyl (S)-6-diazo-2-((S)-2-methoxy-2-(pyridin-2-yl)acetamido)-5-oxohexanoate | 363 |
| 286 | 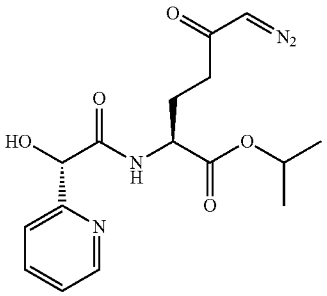 | isopropyl (S)-6-diazo-2-((S)-2-hydroxy-2-(pyridin-2-yl)acetamido)-5-oxohexanoate | 349 |
| 287 | 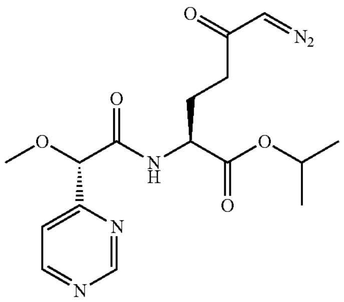 | isopropyl (S)-6-diazo-2-((S)-2-methoxy-2-(pyrimidin-4-yl)acetamido)-5-oxohexanoate | 364 |

-continued

| Compound | Structure | IUPAC Name | $^1$HNMR & MS: $(M + H)^+$ |
|---|---|---|---|
| 288 | 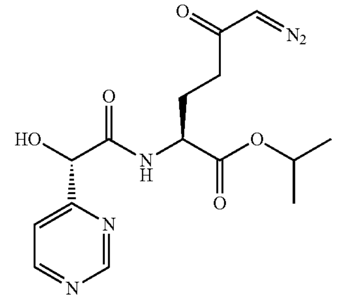 | isopropyl (S)-6-diazo-2-((S)-2-hydroxy-2-(pyrimidin-4-yl)acetamido)-5-oxohexanoate | 350 |
| 289 | 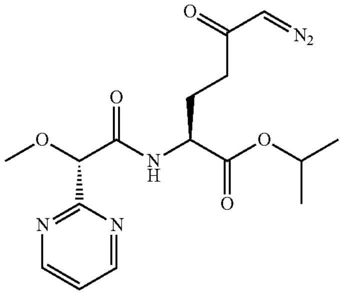 | isopropyl (S)-6-diazo-2-((S)-2-methoxy-2-(pyrimidin-2-yl)acetamido)-5-oxohexanoate | 364 |
| 290 | 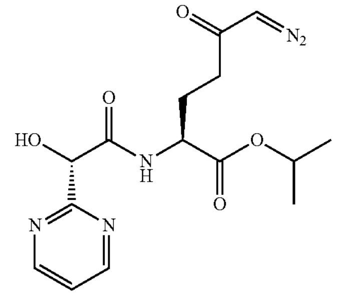 | isopropyl (S)-6-diazo-2-((S)-2-hydroxy-2-(pyrimidin-2-yl)acetamido)-5-oxohexanoate | 350 |
| 291 | 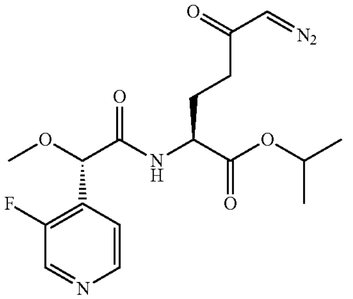 | isopropyl (S)-6-diazo-2-((S)-2-(3-fluoropyridin-4-yl)-2-methoxyacetamido)-5-oxohexanoate | 381 |
| 292 | 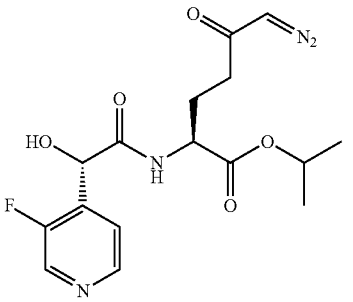 | isopropyl (S)-6-diazo-2-((S)-2-(3-fluoropyridin-4-yl)-2-hydroxyacetamido)-5-oxohexanoate | 367 |

-continued
| Compound | Structure | IUPAC Name | $^1$HNMR & MS: $(M + H)^+$ |
|---|---|---|---|
| 293 | 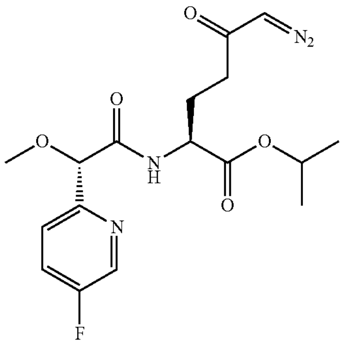 | isopropyl (S)-6-diazo-2-((S)-2-(5-fluoropyridin-2-yl)-2-methoxyacetamido)-5-oxohexanoate | 381 |
| 294 | 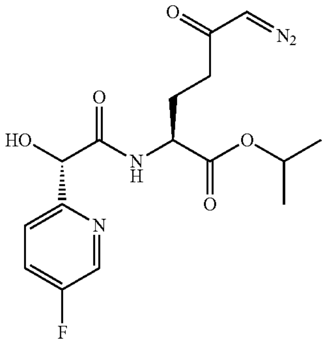 | isopropyl (S)-6-diazo-2-((S)-2-(5-fluoropyridin-2-yl)-2-hydroxyacetamido)-5-oxohexanoate | 367 |
| 295 | 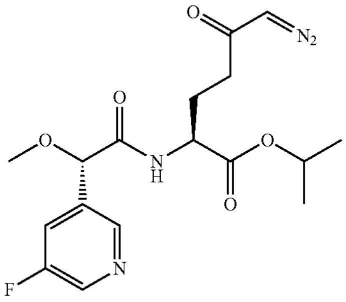 | isopropyl (S)-6-diazo-2-((S)-2-(5-fluoropyridin-3-yl)-2-methoxyacetamido)-5-oxohexanoate | 381 |
| 296 | 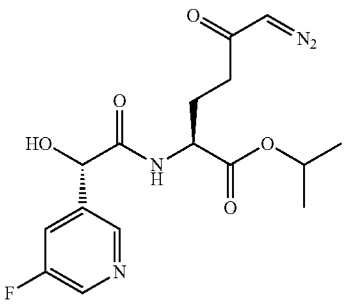 | isopropyl (S)-6-diazo-2-((S)-2-(5-fluoropyridin-3-yl)-2-hydroxyacetamido)-5-oxohexanoate | 367 |

-continued
| Compound | Structure | IUPAC Name | $^1$HNMR & MS: $(M + H)^+$ |
|---|---|---|---|
| 297 | 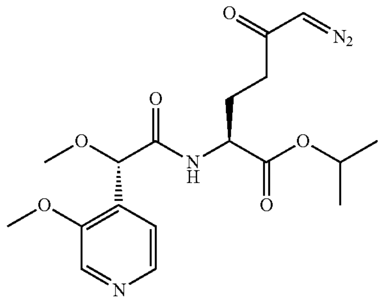 | isopropyl (S)-6-diazo-2-((S)-2-methoxy-2-(3-methoxypyridin-4-yl)acetamido)-5-oxohexanoate | 393 |
| 298 | 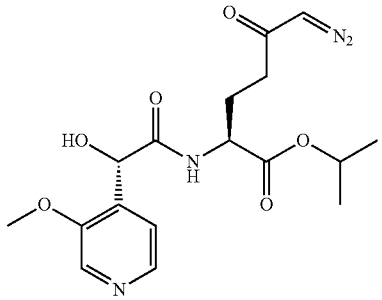 | isopropyl (S)-6-diazo-2-((S)-2-hydroxy-2-(3-methoxypyridin-4-yl)acetamido)-5-oxohexanoate | 379 |
| 299 | 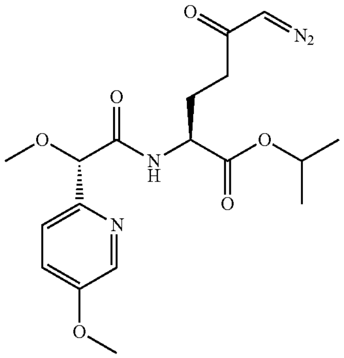 | isopropyl (S)-6-diazo-2-((S)-2-methoxy-2-(5-methoxypyridin-2-yl)acetamido)-5-oxohexanoate | 393 |
| 300 | 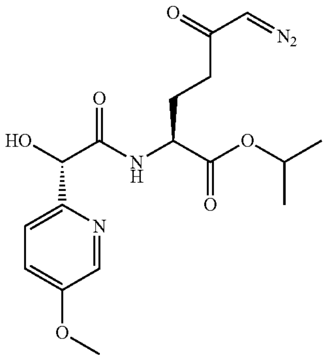 | isopropyl (S)-6-diazo-2-((S)-2-hydroxy-2-(5-methoxypyridin-2-yl)acetamido)-5-oxohexanoate | 379 |

-continued
| Compound | Structure | IUPAC Name | ¹HNMR & MS: (M + H)⁺ |
|---|---|---|---|
| 301 | 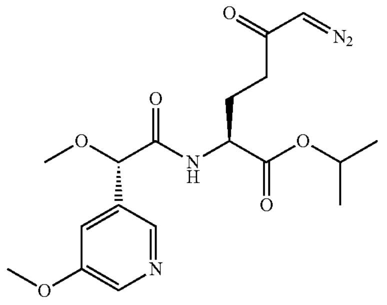 | isopropyl (S)-6-diazo-2-((S)-2-methoxy-2-(5-methoxypyridin-3-yl)acetamido)-5-oxohexanoate | 393 |
| 302 | 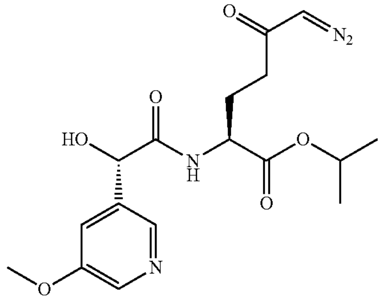 | isopropyl (S)-6-diazo-2-((S)-2-hydroxy-2-(5-methoxypyridin-3-yl)acetamido)-5-oxohexanoate | 379 |
| 303 | 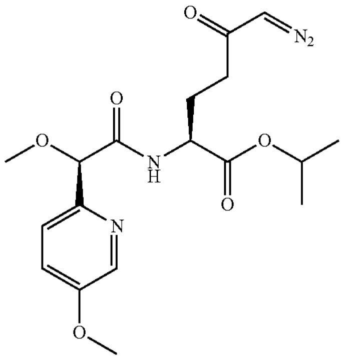 | isopropyl (S)-6-diazo-2-((R)-2-methoxy-2-(5-methoxypyridin-2-yl)acetamido)-5-oxohexanoate | 393 |
| 304 | 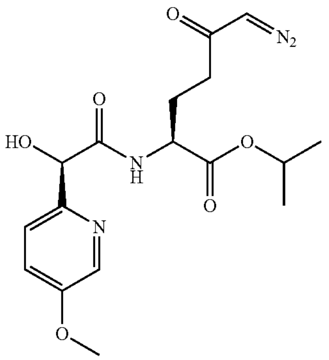 | isopropyl (S)-6-diazo-2-((R)-2-hydroxy-2-(5-methoxypyridin-2-yl)acetamido)-5-oxohexanoate | 379 |

-continued

| Compound | Structure | IUPAC Name | $^1$HNMR & MS: (M + H)$^+$ |
|---|---|---|---|
| 305 | 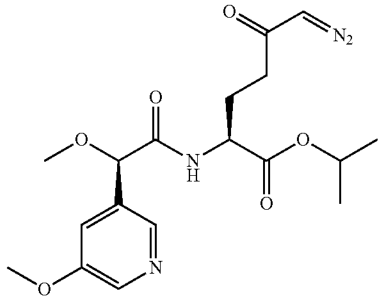 | isopropyl (S)-6-diazo-2-((R)-2-methoxy-2-(5-methoxypyridin-3-yl)acetamido)-5-oxohexanoate | 393 |
| 306 | 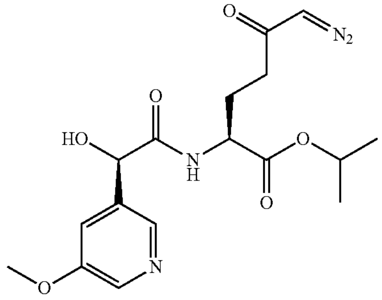 | isopropyl (S)-6-diazo-2-((R)-2-hydroxy-2-(5-methoxypyridin-3-yl)acetamido)-5-oxohexanoate | 379 |
| 307 | 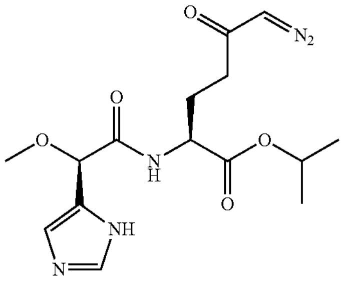 | isopropyl (S)-2-((R)-2-(1H-imidazol-5-yl)-2-methoxyacetamido)-6-diazo-5-oxohexanoate | 352 |
| 308 | 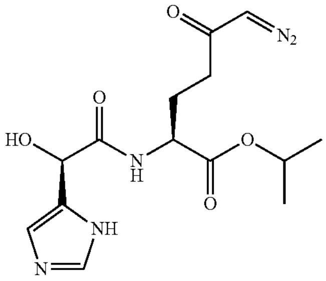 | isopropyl (S)-6-diazo-2-((R)-2-hydroxy-2-(1H-imidazol-5-yl)acetamido)-5-oxohexanoate | 338 |
| 309 | 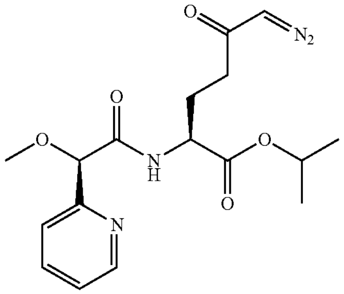 | isopropyl (S)-6-diazo-2-((R)-2-methoxy-2-(pyridin-2-yl)acetamido)-5-oxohexanoate | 363 |

-continued

| Com-pound | Structure | IUPAC Name | $^1$HNMR & MS: (M + H)$^+$ |
|---|---|---|---|
| 310 | 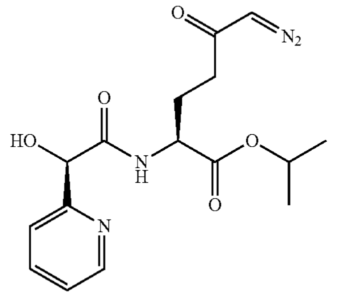 | isopropyl (S)-6-diazo-2-((R)-2-hydroxy-2-(pyridin-2-yl)acetamido)-5-oxohexanoate | 349 |
| 311 | 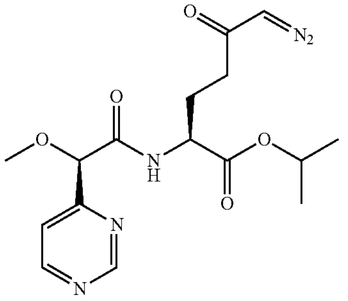 | isopropyl (S)-6-diazo-2-((R)-2-methoxy-2-(pyrimidin-4-yl)acetamido)-5-oxohexanoate | 364 |
| 312 | 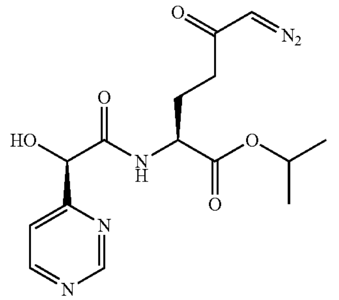 | isopropyl (S)-6-diazo-2-((R)-2-hydroxy-2-(pyrimidin-4-yl)acetamido)-5-oxohexanoate | 350 |
| 313 | 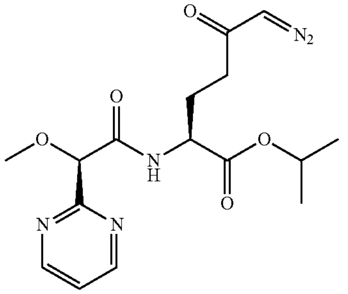 | isopropyl (S)-6-diazo-2-((R)-2-methoxy-2-(pyrimidin-2-yl)acetamido)-5-oxohexanoate | 364 |
| 314 | 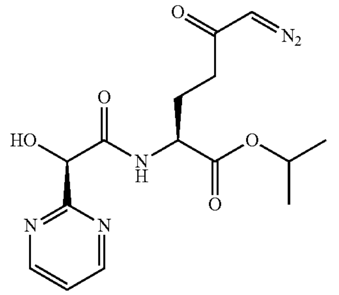 | isopropyl (S)-6-diazo-2-((R)-2-hydroxy-2-(pyrimidin-2-yl)acetamido)-5-oxohexanoate | 350 |

-continued
| Compound | Structure | IUPAC Name | $^1$HNMR & MS: (M + H)$^+$ |
|---|---|---|---|
| 315 | 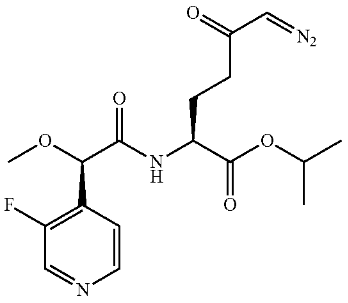 | isopropyl (S)-6-diazo-2-((R)-2-(3-fluoropyridin-4-yl)-2-methoxyacetamido)-5-oxohexanoate | 381 |
| 316 | 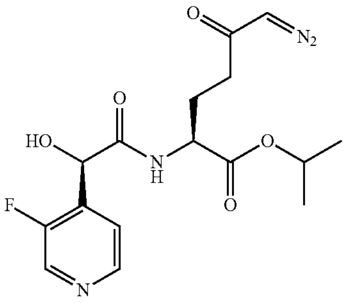 | isopropyl (S)-6-diazo-2-((R)-2-(3-fluoropyridin-4-yl)-2-hydroxyacetamido)-5-oxohexanoate | 367 |
| 317 | 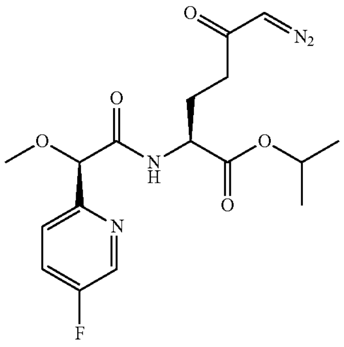 | isopropyl (S)-6-diazo-2-((R)-2-(5-fluoropyridin-2-yl)-2-methoxyacetamido)-5-oxohexanoate | 381 |
| 318 | 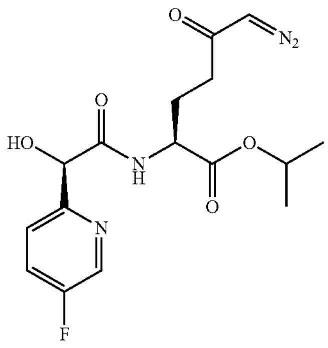 | isopropyl (S)-6-diazo-2-((R)-2-(5-fluoropyridin-2-yl)-2-hydroxyacetamido)-5-oxohexanoate | 367 |

-continued

| Compound | Structure | IUPAC Name | ¹HNMR & MS: (M + H)⁺ |
|---|---|---|---|
| 319 | 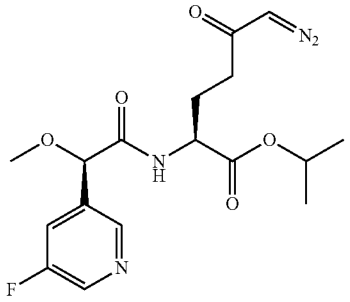 | isopropyl (S)-6-diazo-2-((R)-2-(5-fluoropyridin-3-yl)-2-methoxyacetamido)-5-oxohexanoate | 381 |
| 320 | 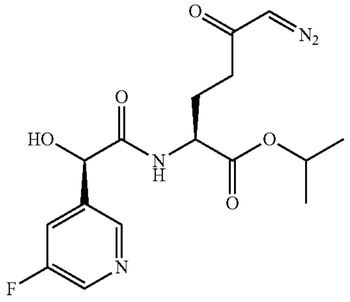 | isopropyl (S)-6-diazo-2-((R)-2-(5-fluoropyridin-3-yl)-2-hydroxyacetamido)-5-oxohexanoate | 367 |
| 321 | 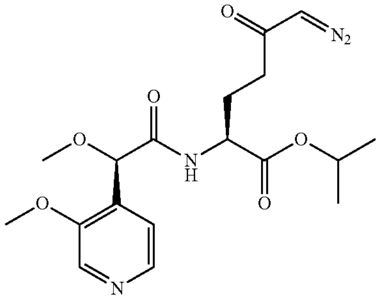 | isopropyl (S)-6-diazo-2-((R)-2-methoxy-2-(3-methoxypyridin-4-yl)acetamido)-5-oxohexanoate | 393 |
| 322 | 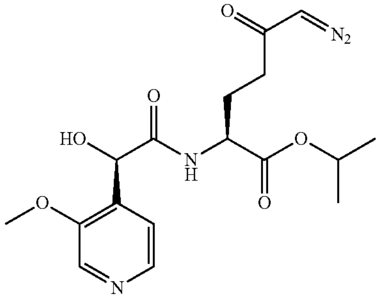 | isopropyl (S)-6-diazo-2-((R)-2-hydroxy-2-(3-methoxypyridin-4-yl)acetamido)-5-oxohexanoate | 379 |
| 323 | 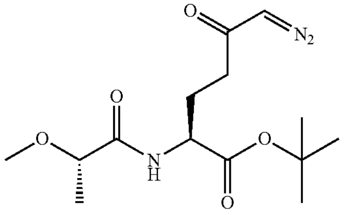 | tert-butyl (S)-6-diazo-2-((S)-2-methoxypropanamido)-5-oxohexanoate | 314 |

-continued

| Compound | Structure | IUPAC Name | ¹HNMR & MS: (M + H)⁺ |
|---|---|---|---|
| 324 | 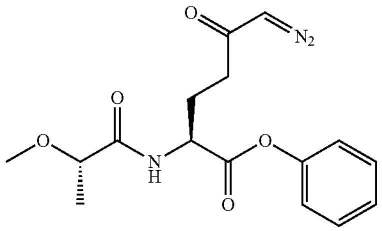 | phenyl (S)-6-diazo-2-((S)-2-methoxypropanamido)-5-oxohexanoate | 334 |
| 325 | 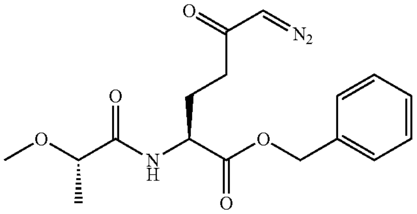 | benzyl (S)-6-diazo-2-((S)-2-methoxypropanamido)-5-oxohexanoate | 348 |
| 326 | 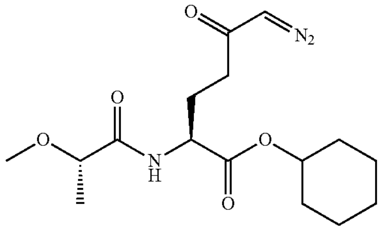 | cyclohexyl (S)-6-diazo-2-((S)-2-methoxypropanamido)-5-oxohexanoate | 340 |
| 327 | 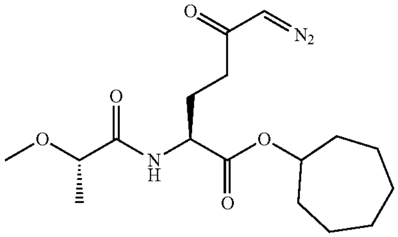 | cycloheptyl (S)-6-diazo-2-((S)-2-methoxypropanamido)-5-oxohexanoate | 354 |
| 328 | 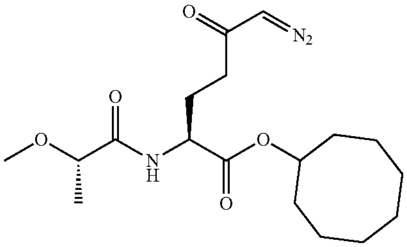 | cyclooctyl (S)-6-diazo-2-((S)-2-methoxypropanamido)-5-oxohexanoate | 368 |
| 329 | 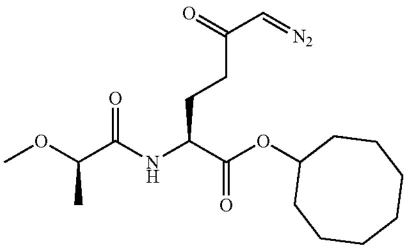 | cyclooctyl (S)-6-diazo-2-((R)-2-methoxypropanamido)-5-oxohexanoate | 368 |

-continued

| Compound | Structure | IUPAC Name | $^1$HNMR & MS: (M + H)$^+$ |
|---|---|---|---|
| 330 | 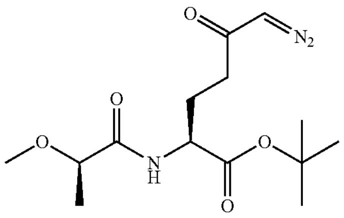 | tert-butyl (S)-6-diazo-2-((R)-2-methoxypropanamido)-5-oxohexanoate | 314 |
| 331 | 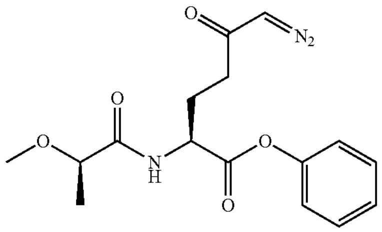 | phenyl (S)-6-diazo-2-((R)-2-methoxypropanamido)-5-oxohexanoate | 334 |
| 332 | 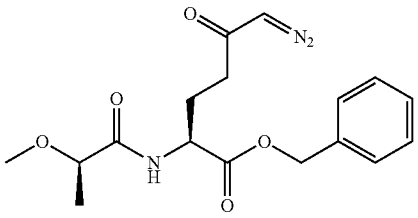 | benzyl (S)-6-diazo-2-((R)-2-methoxypropanamido)-5-oxohexanoate | 348 |
| 333 | 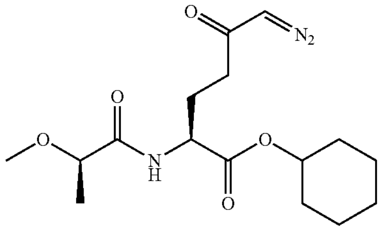 | cyclohexyl (S)-6-diazo-2-((R)-2-methoxypropanamido)-5-oxohexanoate | 340 |
| 334 | 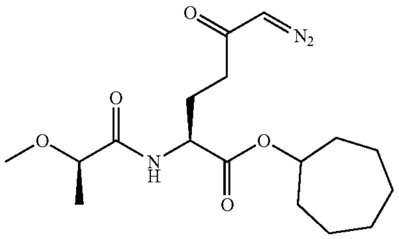 | cycloheptyl (S)-6-diazo-2-((R)-2-methoxypropanamido)-5-oxohexanoate | 354 |
| 335 | 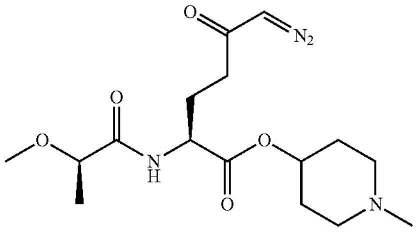 | 1-methylpiperidin-4-yl (S)-6-diazo-2-((R)-2-methoxypropanamido)-5-oxohexanoate | 355 |

-continued

| Compound | Structure | IUPAC Name | $^1$HNMR & MS: (M + H)$^+$ |
| --- | --- | --- | --- |
| 336 | 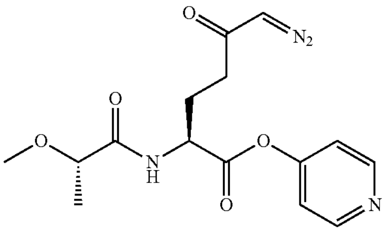 | pyridin-4-yl (S)-6-diazo-2-((S)-2-methoxypropanamido)-5-oxohexanoate | 335 |
| 337 | 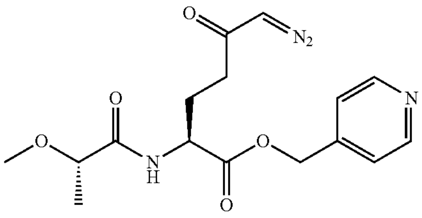 | pyridin-4-ylmethyl (S)-6-diazo-2-((S)-2-methoxypropanamido)-5-oxohexanoate | 349 |
| 338 | 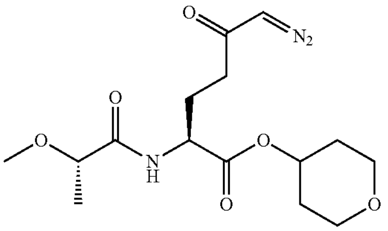 | tetrahydro-2H-pyran-4-yl (S)-6-diazo-2-((S)-2-methoxypropanamido)-5-oxohexanoate | 342 |
| 339 | 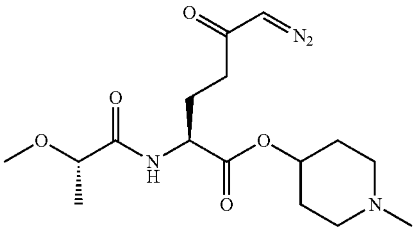 | 1-methylpiperidin-4-yl (S)-6-diazo-2-((S)-2-methoxypropanamido)-5-oxohexanoate | 355 |
| 340 | 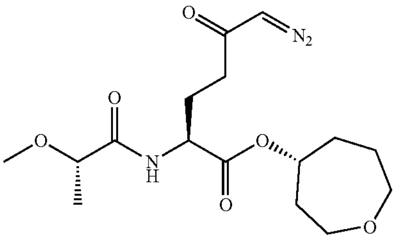 | (R)-oxepan-4-yl (S)-6-diazo-2-((S)-2-methoxypropanamido)-5-oxohexanoate | 356 |
| 341 | 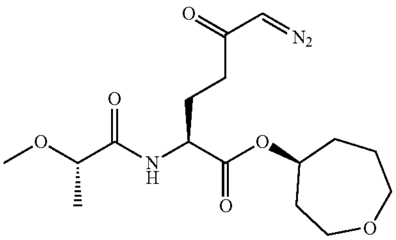 | (S)-oxepan-4-yl (S)-6-diazo-2-((S)-2-methoxypropanamido)-5-oxohexanoate | 356 |

-continued

| Compound | Structure | IUPAC Name | $^1$HNMR & MS: (M + H)$^+$ |
|---|---|---|---|
| 342 | 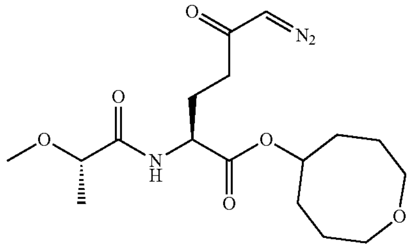 | oxocan-5-yl (S)-6-diazo-2-((S)-2-methoxypropanamido)-5-oxohexanoate | 370 |
| 343 | 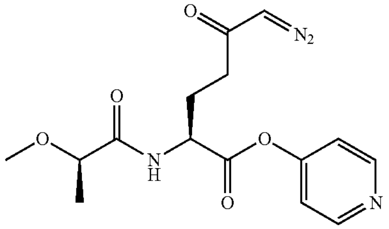 | pyridin-4-yl (S)-6-diazo-2-((R)-2-methoxypropanamido)-5-oxohexanoate | 335 |
| 344 | 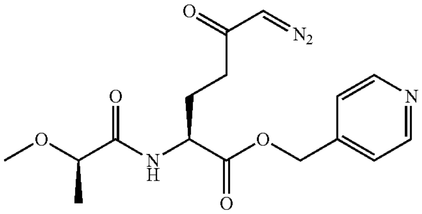 | pyridin-4-ylmethyl (S)-6-diazo-2-((R)-2-methoxypropanamido)-5-oxohexanoate | 349 |
| 345 | 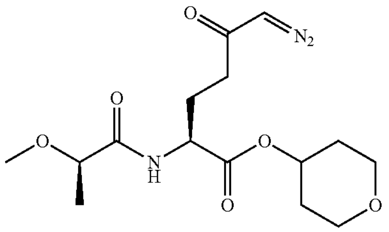 | tetrahydro-2H-pyran-4-yl (S)-6-diazo-2-((R)-2-methoxypropanamido)-5-oxohexanoate | 342 |
| 346 | 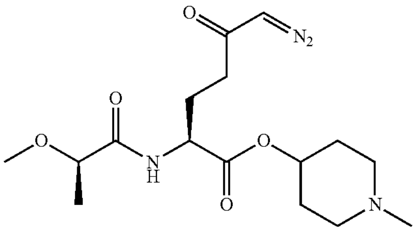 | 1-methylpiperidin-4-yl (S)-6-diazo-2-((R)-2-methoxypropanamido)-5-oxohexanoate | 355 |
| 347 | 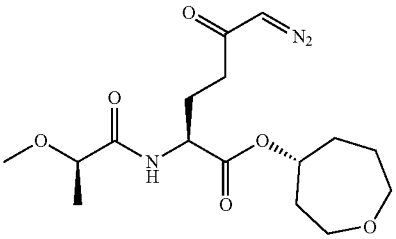 | (R)-oxepan-4-yl (S)-6-diazo-2-((R)-2-methoxypropanamido)-5-oxohexanoate | 356 |

-continued

| Compound | Structure | IUPAC Name | $^1$HNMR & MS: (M + H)$^+$ |
|---|---|---|---|
| 348 | 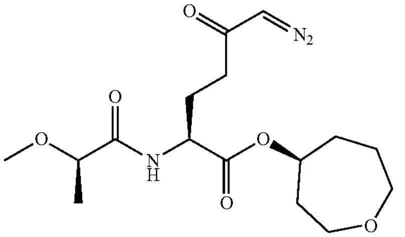 | (S)-oxepan-4-yl (S)-6-diazo-2-((R)-2-methoxypropanamido)-5-oxohexanoate | 356 |
| 349 | 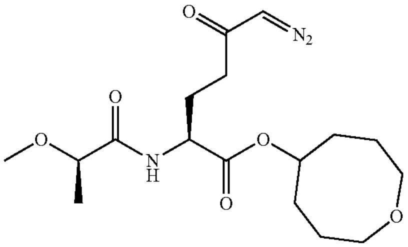 | oxocan-5-yl (S)-6-diazo-2-((R)-2-methoxypropanamido)-5-oxohexanoate | 370 |
| 350 | 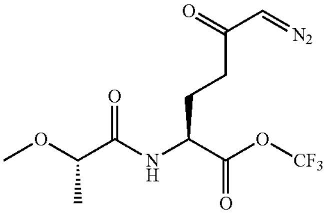 | trifluoromethyl (S)-6-diazo-2-((S)-2-methoxypropanamido)-5-oxohexanoate | 326 |
| 351 | 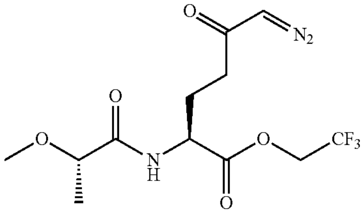 | 2,2,2-trifluoroethyl (S)-6-diazo-2-((S)-2-methoxypropanamido)-5-oxohexanoate | 340 |
| 352 | 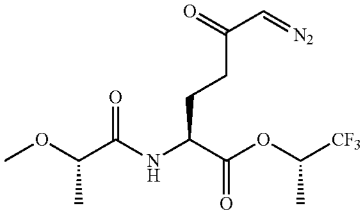 | (S)-1,1,1-trifluoropropan-2-yl (S)-6-diazo-2-((S)-2-methoxypropanamido)-5-oxohexanoate | 354 |
| 353 | 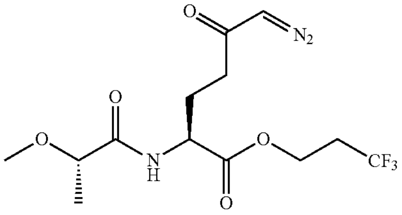 | 3,3,3-trifluoropropyl (S)-6-diazo-2-((S)-2-methoxypropanamido)-5-oxohexanoate | 354 |

-continued

| Compound | Structure | IUPAC Name | $^1$HNMR & MS: (M + H)+ |
|---|---|---|---|
| 354 | 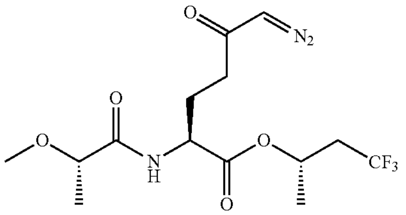 | (S)-4,4,4-trifluorobutan-2-yl (S)-6-diazo-2-((S)-2-methoxypropanamido)-5-oxohexanoate | 368 |
| 355 | 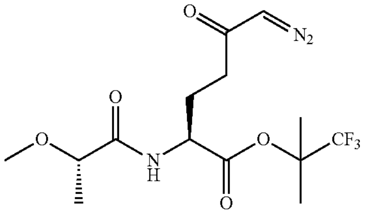 | 1,1,1-trifluoro-2-methylpropan-2-yl (S)-6-diazo-2-((S)-2-methoxypropanamido)-5-oxohexanoate | 368 |
| 356 | 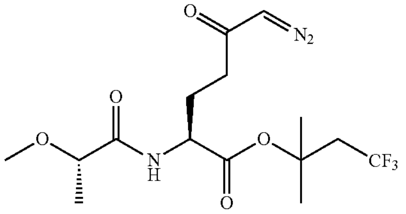 | 4,4,4-trifluoro-2-methylbutan-2-yl (S)-6-diazo-2-((S)-2-methoxypropanamido)-5-oxohexanoate | 382 |
| 357 | 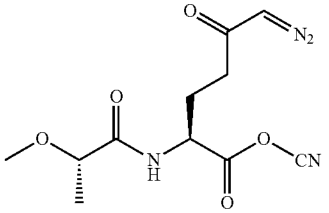 | cyanic (S)-6-diazo-2-((S)-2-methoxypropanamido)-5-oxohexanoic anhydride | 283 |
| 358 | 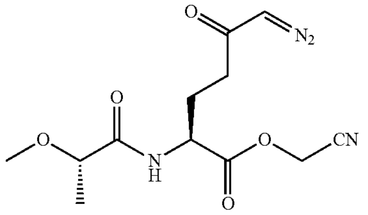 | cyanomethyl (S)-6-diazo-2-((S)-2-methoxypropanamido)-5-oxohexanoate | 297 |
| 359 | 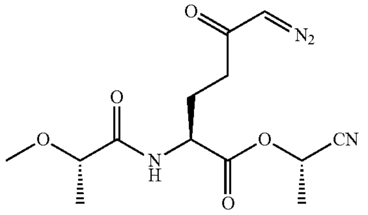 | (S)-1-cyanoethyl (S)-6-diazo-2-((S)-2-methoxypropanamido)-5-oxohexanoate | 311 |
| 360 | 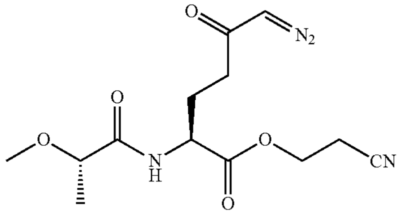 | 2-cyanoethyl (S)-6-diazo-2-((S)-2-methoxypropanamido)-5-oxohexanoate | 311 |

-continued

| Com-pound | Structure | IUPAC Name | $^1$HNMR & MS: (M + H)$^+$ |
|---|---|---|---|
| 361 | 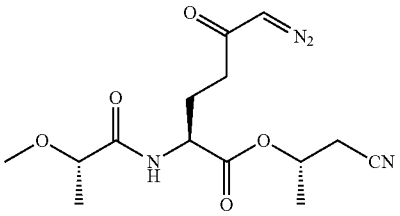 | 1-cyanopropan-2-yl (2S)-6-diazo-2-((S)-2-methoxypropanamido)-5-oxohexanoate | 325 |
| 362 | 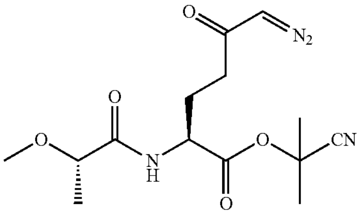 | 2-cyanopropan-2-yl (S)-6-diazo-2-((S)-2-methoxypropanamido)-5-oxohexanoate | 325 |
| 363 | 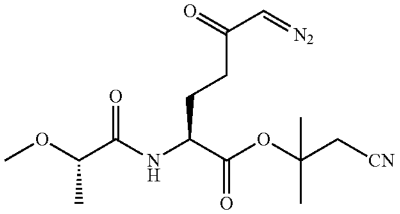 | 1-cyano-2-methylpropan-2-yl (S)-6-diazo-2-((S)-2-methoxypropanamido)-5-oxohexanoate | 339 |
| 364 | 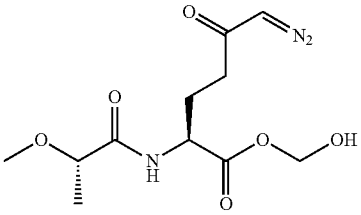 | hydroxymethyl (S)-6-diazo-2-((S)-2-methoxypropanamido)-5-oxohexanoate | 288 |
| 365 | 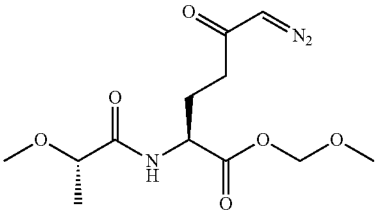 | methoxymethyl (S)-6-diazo-2-((S)-2-methoxypropanamido)-5-oxohexanoate | 302 |
| 366 | 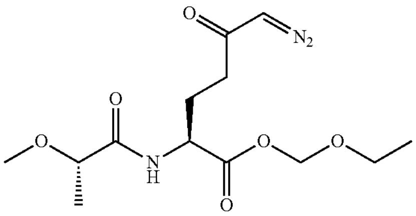 | ethoxymethyl (S)-6-diazo-2-((S)-2-methoxypropanamido)-5-oxohexanoate | 316 |

-continued

| Compound | Structure | IUPAC Name | $^{1}$HNMR & MS: $(M + H)^{+}$ |
|---|---|---|---|
| 367 | 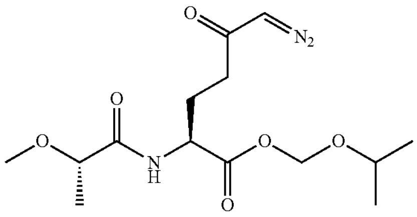 | isopropoxymethyl (S)-6-diazo-2-((S)-2-methoxypropanamido)-5-oxohexanoate | 330 |
| 368 | 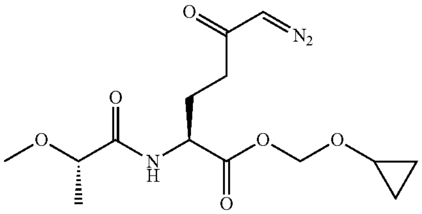 | cyclopropoxymethyl (S)-6-diazo-2-((S)-2-methoxypropanamido)-5-oxohexanoate | 328 |
| 369 | 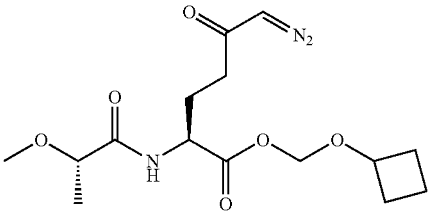 | cyclobutoxymethyl (S)-6-diazo-2-((S)-2-methoxypropanamido)-5-oxohexanoate | 342 |
| 370 | 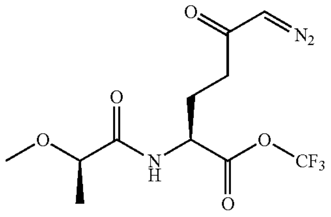 | trifluoromethyl (S)-6-diazo-2-((R)-2-methoxypropanamido)-5-oxohexanoate | 326 |
| 371 | 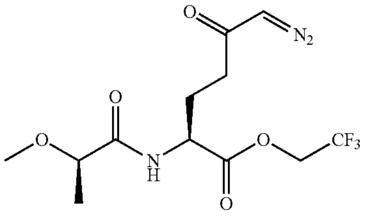 | 2,2,2-trifluoroethyl (S)-6-diazo-2-((R)-2-methoxypropanamido)-5-oxohexanoate | 340 |
| 372 | 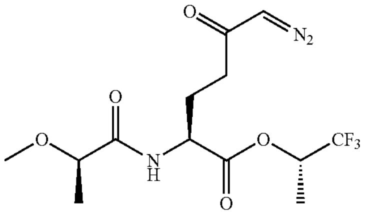 | (S)-1,1,1-trifluoropropan-2-yl (S)-6-diazo-2-((R)-2-methoxypropanamido)-5-oxohexanoate | 354 |
| 373 | 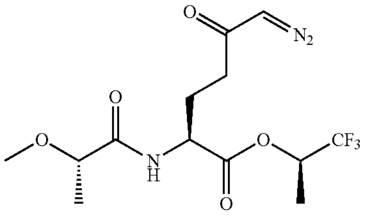 | (R)-1,1,1-trifluoropropan-2-yl (S)-6-diazo-2-((S)-2-methoxypropanamido)-5-oxohexanoate | 354 |

-continued

| Compound | Structure | IUPAC Name | $^1$HNMR & MS: (M + H)$^+$ |
|---|---|---|---|
| 374 | 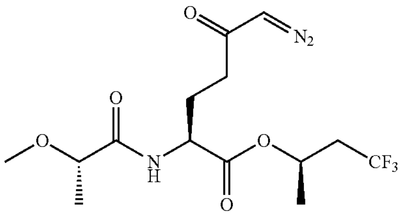 | (R)-4,4,4-trifluorobutan-2-yl (S)-6-diazo-2-((S)-2-methoxypropanamido)-5-oxohexanoate | 368 |
| 375 | 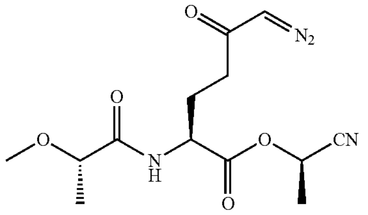 | (R)-1-cyanoethyl (S)-6-diazo-2-((S)-2-methoxypropanamido)-5-oxohexanoate | 311 |
| 376 | 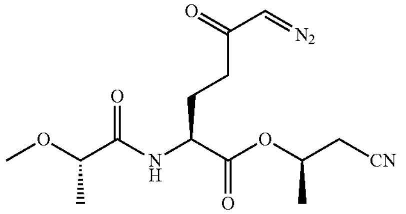 | (R)-1-cyanopropan-2-yl (S)-6-diazo-2-((S)-2-methoxypropanamido)-5-oxohexanoate | 325 |
| 377 | 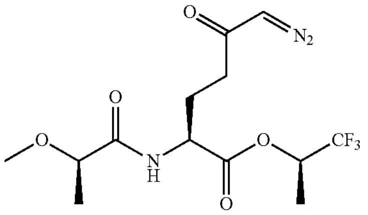 | (R)-1,1,1-trifluoropropan-2-yl (S)-6-diazo-2-((R)-2-methoxypropanamido)-5-oxohexanoate | 354 |
| 378 | 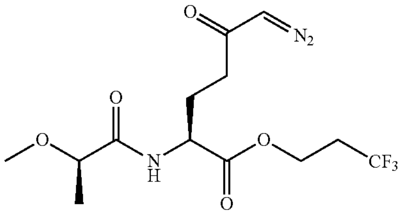 | 3,3,3-trifluoropropyl (S)-6-diazo-2-((R)-2-methoxypropanamido)-5-oxohexanoate | 354 |
| 379 | 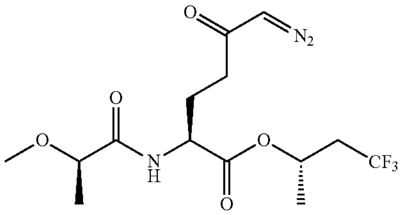 | (S)-4,4,4-trifluorobutan-2-yl (S)-6-diazo-2-((R)-2-methoxypropanamido)-5-oxohexanoate | 368 |

-continued

| Com-pound | Structure | IUPAC Name | $^1$HNMR & MS: (M + H)$^+$ |
|---|---|---|---|
| 380 | 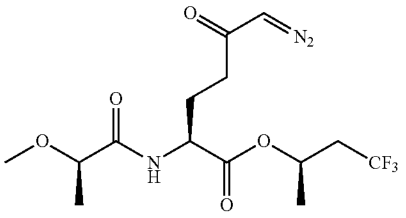 | (R)-4,4,4-trifluorobutan-2-yl (S)-6-diazo-2-((R)-2-methoxypropanamido)-5-oxohexanoate | 368 |
| 381 | 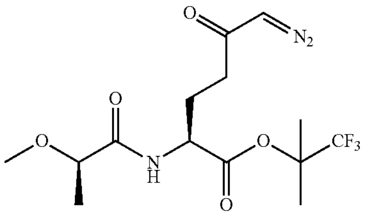 | 1,1,1-trifluoro-2-methylpropan-2-yl (S)-6-diazo-2-((R)-2-methoxypropanamido)-5-oxohexanoate | 368 |
| 382 | 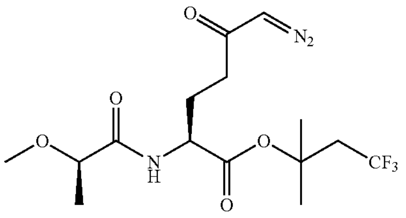 | 4,4,4-trifluoro-2-methylbutan-2-yl (S)-6-diazo-2-((R)-2-methoxypropanamido)-5-oxohexanoate | 382 |
| 383 | 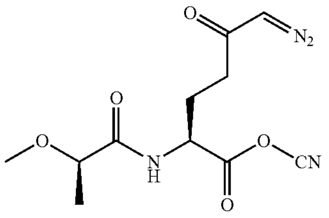 | cyanic (S)-6-diazo-2-((R)-2-methoxypropanamido)-5-oxohexanoic anhydride | 283 |
| 384 | 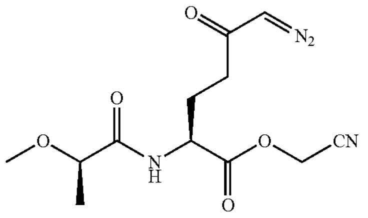 | cyanomethyl (S)-6-diazo-2-((R)-2-methoxypropanamido)-5-oxohexanoate | 297 |
| 385 | 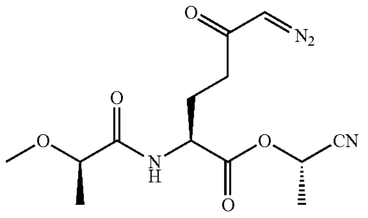 | (S)-1-cyanoethyl (S)-6-diazo-2-((R)-2-methoxypropanamido)-5-oxohexanoate | 311 |
| 386 | 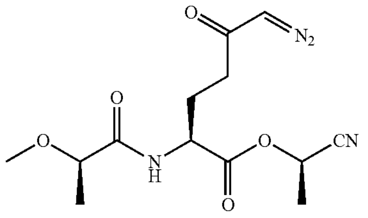 | (R)-1-cyanoethyl (S)-6-diazo-2-((R)-2-methoxypropanamido)-5-oxohexanoate | 311 |

-continued

| Compound | Structure | IUPAC Name | $^1$HNMR & MS: $(M + H)^+$ |
|---|---|---|---|
| 387 | 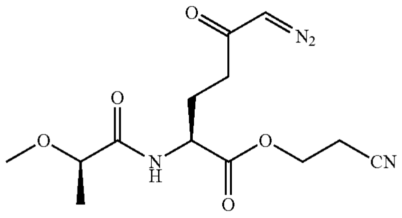 | 2-cyanoethyl (S)-6-diazo-2-((R)-2-methoxypropanamido)-5-oxohexanoate | 311 |
| 388 | 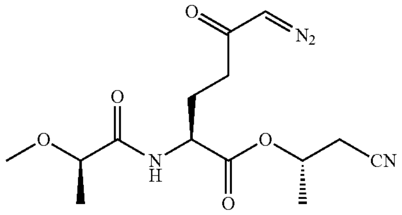 | (S)-1-cyanopropan-2-yl (S)-6-diazo-2-((R)-2-methoxypropanamido)-5-oxohexanoate | 325 |
| 389 | 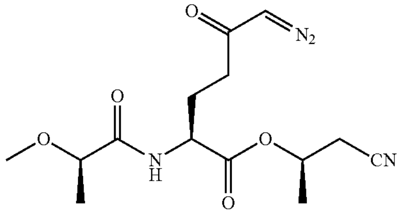 | (R)-1-cyanopropan-2-yl (S)-6-diazo-2-((R)-2-methoxypropanamido)-5-oxohexanoate | 325 |
| 390 | 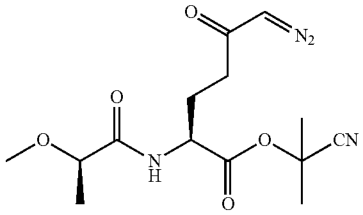 | 2-cyanopropan-2-yl (S)-6-diazo-2-((R)-2-methoxypropanamido)-5-oxohexanoate | 325 |
| 391 | 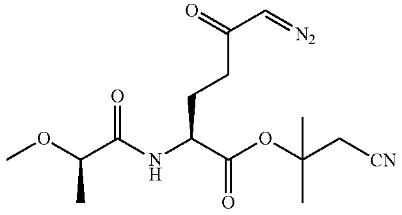 | 1-cyano-2-methylpropan-2-yl (S)-6-diazo-2-((R)-2-methoxypropanamido)-5-oxohexanoate | 339 |
| 392 | 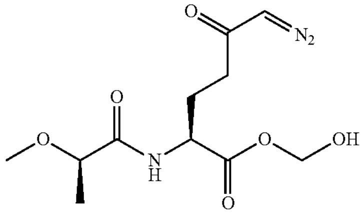 | hydroxymethyl (S)-6-diazo-2-((R)-2-methoxypropanamido)-5-oxohexanoate | 288 |

-continued

| Compound | Structure | IUPAC Name | $^{1}$HNMR & MS: $(M + H)^+$ |
|---|---|---|---|
| 393 | 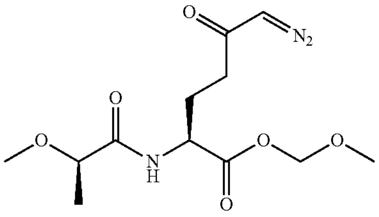 | methoxymethyl (S)-6-diazo-2-((R)-2-methoxypropanamido)-5-oxohexanoate | 302 |
| 394 | 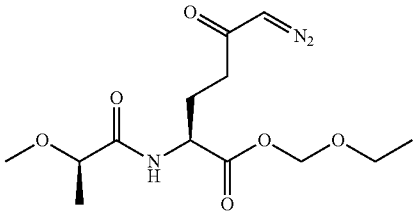 | ethoxymethyl (S)-6-diazo-2-((R)-2-methoxypropanamido)-5-oxohexanoate | 316 |
| 395 | 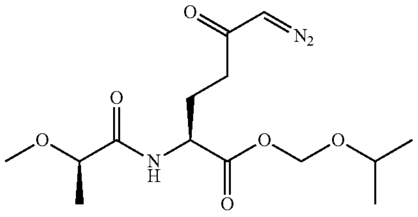 | isopropoxymethyl (S)-6-diazo-2-((R)-2-methoxypropanamido)-5-oxohexanoate | 330 |
| 396 | 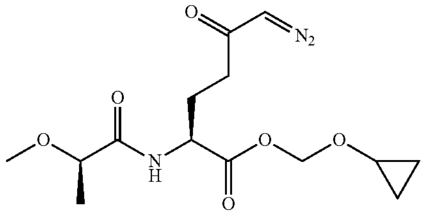 | cyclopropoxymethy (S)-6-diazo-2-((R)-2-methoxypropanamido)-5-oxohexanoate | 328 |
| 397 | 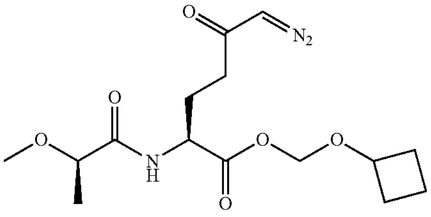 | cyclobutoxymethyl (S)-6-diazo-2-((R)-2-methoxypropanamido)-5-oxohexanoate | 342 |
| 398 | 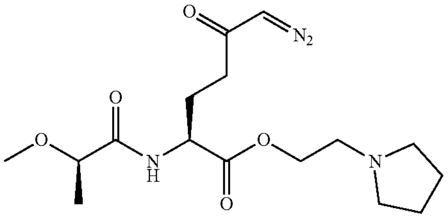 | 2-(pyrrolidin-1-yl)ethyl (S)-6-diazo-2-((R)-2-methoxypropanamido)-5-oxohexanoate | 355 |
| 399 | 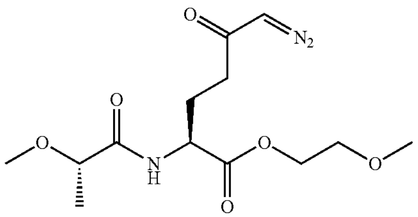 | 2-methoxyethyl (S)-6-diazo-2-((S)-2-methoxypropanamido)-5-oxohexanoate | 316 |

-continued

| Compound | Structure | IUPAC Name | $^{1}$HNMR & MS: (M + H)$^{+}$ |
|---|---|---|---|
| 400 | 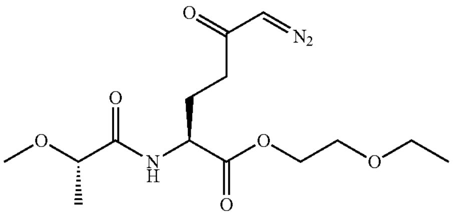 | 2-ethoxyethyl (S)-6-diazo-2-((S)-2-methoxypropanamido)-5-oxohexanoate | 330 |
| 401 | 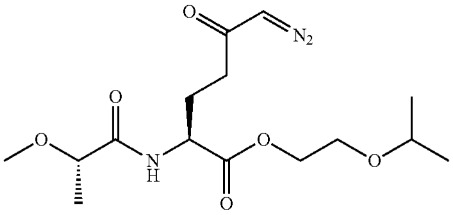 | 2-isopropoxyethyl (S)-6-diazo-2-((S)-2-methoxypropanamido)-5-oxohexanoate | 344 |
| 402 | 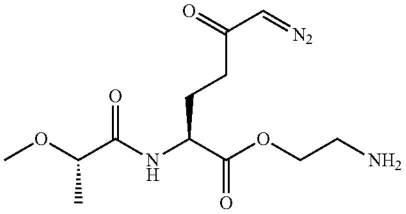 | 2-aminoethyl (S)-6-diazo-2-((S)-2-methoxypropanamido)-5-oxohexanoate | 301 |
| 403 | 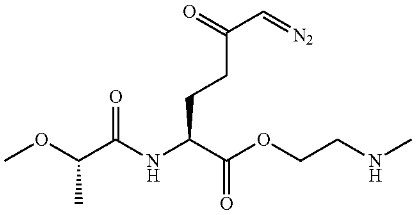 | 2-(methylamino)ethyl (S)-6-diazo-2-((S)-2-methoxypropanamido)-5-oxohexanoate | 315 |
| 404 | 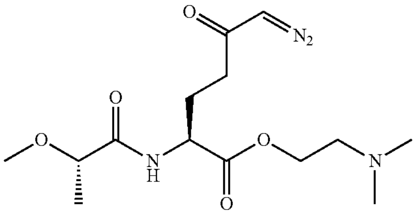 | 2-(dimethylamino)ethyl (S)-6-diazo-2-((S)-2-methoxypropanamido)-5-oxohexanoate | 329 |
| 405 | 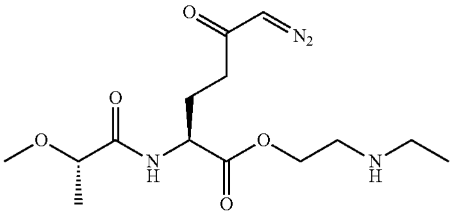 | 2-(ethylamino)ethyl (S)-6-diazo-2-((S)-2-methoxypropanamido)-5-oxohexanoate | 329 |

-continued

| Compound | Structure | IUPAC Name | ¹HNMR & MS: (M + H)⁺ |
|---|---|---|---|
| 406 | 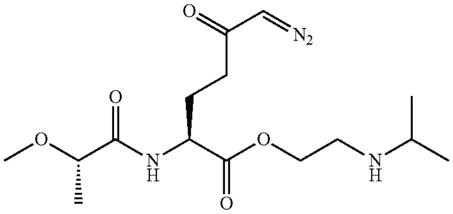 | 2-(isopropylamino)ethyl (S)-6-diazo-2-((S)-2-methoxypropanamido)-5-oxohexanoate | 343 |
| 407 | 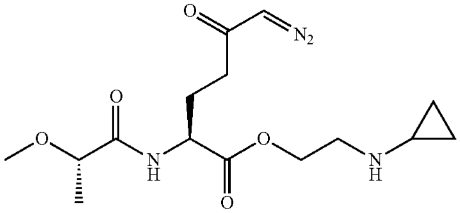 | 2-(cyclopropylamino) ethyl (S)-6-diazo-2-((S)-2-methoxypropanamido)-5-oxohexanoate | 341 |
| 408 | 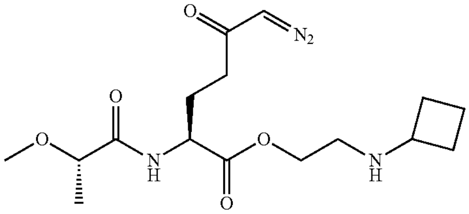 | 2-(cyclobutylamino) ethyl (S)-6-diazo-2-((S)-2-methoxypropanamido)-5-oxohexanoate | 355 |
| 409 | 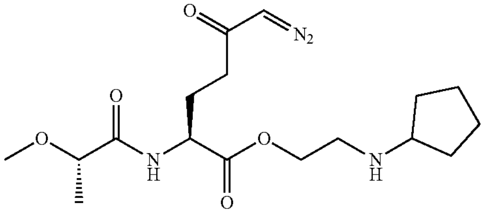 | 2-(cyclopentylamino) ethyl (S)-6-diazo-2-((S)-2-methoxypropanamido)-5-oxohexanoate | 369 |
| 410 | 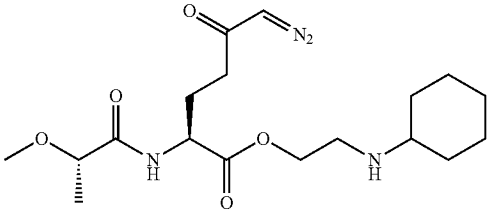 | 2-(cyclohexylamino) ethyl (S)-6-diazo-2-((S)-2-methoxypropanamido)-5-oxohexanoate | 383 |
| 411 | 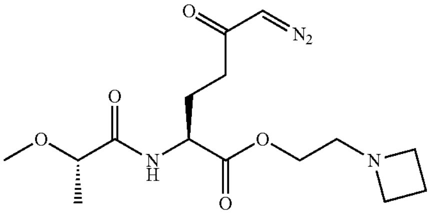 | 2-(azetidin-1-yl)ethyl (S)-6-diazo-2-((S)-2-methoxypropanamido)-5-oxohexanoate | 341 |
| 412 | 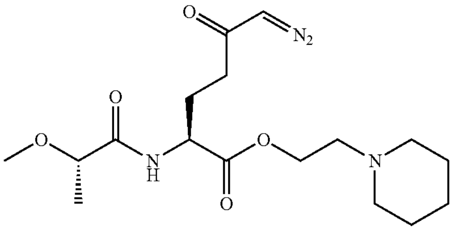 | 2-(piperidin-1-yl)ethyl (S)-6-diazo-2-((S)-2-methoxypropanamido)-5-oxohexanoate | 369 |

-continued

| Compound | Structure | IUPAC Name | $^1$HNMR & MS: $(M + H)^+$ |
|---|---|---|---|
| 413 | 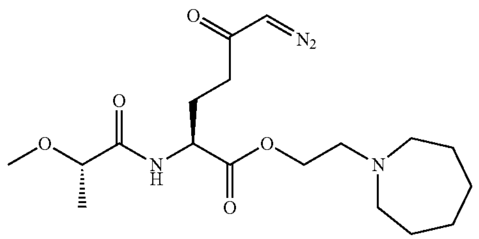 | 2-(azepan-1-yl)ethyl (S)-6-diazo-2-((S)-2-methoxypropanamido)-5-oxohexanoate | 383 |
| 414 | 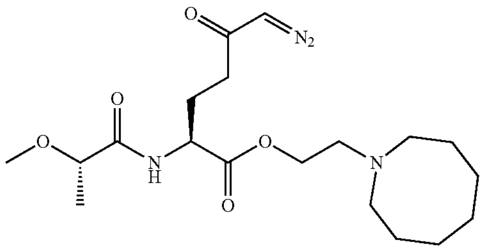 | 2-(azocan-1-yl)ethyl (S)-6-diazo-2-((S)-2-methoxypropanamido)-5-oxohexanoate | 397 |
| 415 | 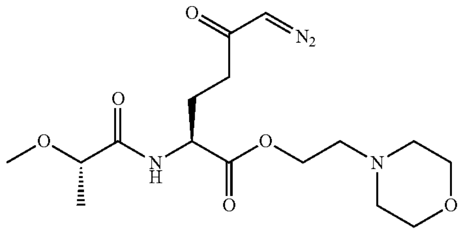 | 2-morpholinoethyl (S)-6-diazo-2-((S)-2-methoxypropanamido)-5-oxohexanoate | 371 |
| 416 | 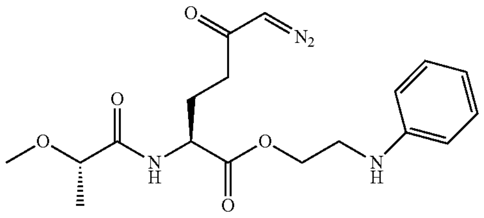 | 2-(phenylamino)ethyl (S)-6-diazo-2-((S)-2-methoxypropanamido)-5-oxohexanoate | 377 |
| 417 | 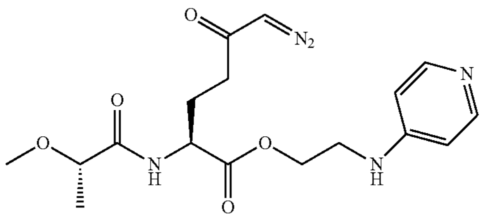 | 2-(pyridin-4-ylamino)ethyl (S)-6-diazo-2-((S)-2-methoxypropanamido)-5-oxohexanoate | 378 |
| 418 | 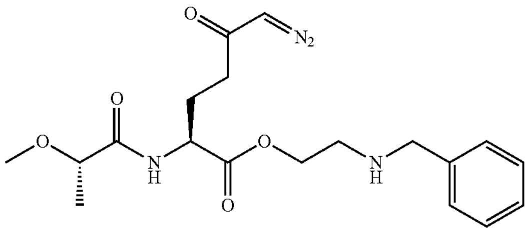 | 2-(benzylamino)ethyl (S)-6-diazo-2-((S)-2-methoxypropanamido)-5-oxohexanoate | 391 |

-continued

| Compound | Structure | IUPAC Name | ¹HNMR & MS: (M + H)⁺ |
|---|---|---|---|
| 419 | 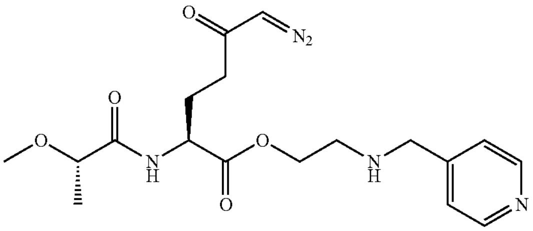 | 2-((pyridin-4-ylmethyl)amino)ethyl (S)-6-diazo-2-((S)-2-methoxypropanamido)-5-oxohexanoate | 392 |
| 420 | 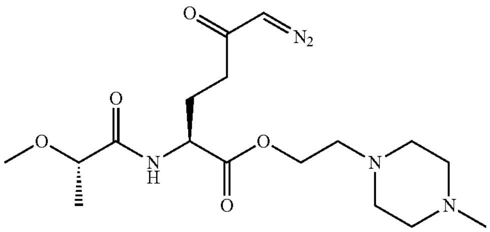 | 2-(4-methylpiperazin-1-yl)ethyl (S)-6-diazo-2-((S)-2-methoxypropanamido)-5-oxohexanoate | 384 |
| 421 | 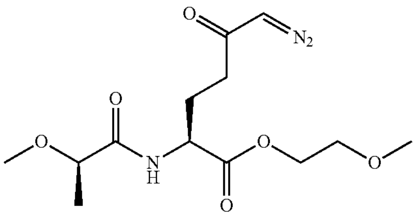 | 2-methoxyethyl (S)-6-diazo-2-((R)-2-methoxypropanamido)-5-oxohexanoate | 316 |
| 422 | 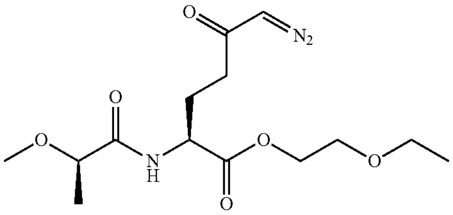 | 2-ethoxyethyl (S)-6-diazo-2-((R)-2-methoxypropanamido)-5-oxohexanoate | 330 |
| 423 | 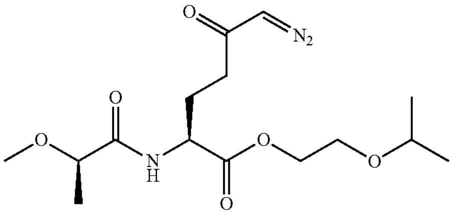 | 2-isopropoxyethyl (S)-6-diazo-2-((R)-2-methoxypropanamido)-5-oxohexanoate | 344 |
| 424 | 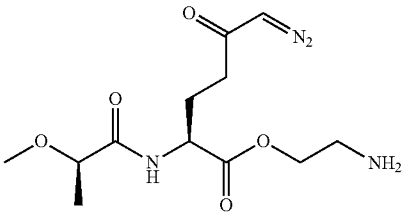 | 2-aminoethyl (S)-6-diazo-2-((R)-2-methoxypropanamido)-5-oxohexanoate | 301 |

-continued

| Compound | Structure | IUPAC Name | ¹HNMR & MS: (M + H)⁺ |
|---|---|---|---|
| 425 | 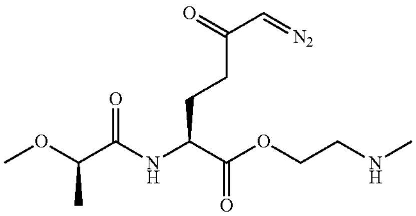 | 2-(methylamino)ethyl (S)-6-diazo-2-((R)-2-methoxypropanamido)-5-oxohexanoate | 315 |
| 426 | 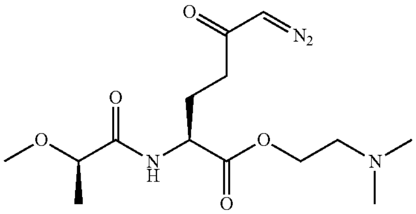 | 2-(dimethylamino) ethyl (S)-6-diazo-2-((R)-2-methoxypropanamido)-5-oxohexanoate | 329 |
| 427 | 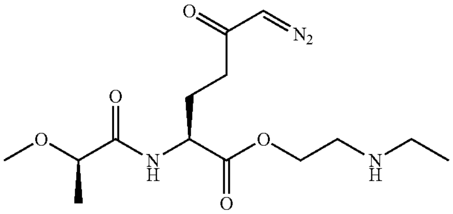 | 2-(ethylamino)ethyl (S)-6-diazo-2-((R)-2-methoxypropanamido)-5-oxohexanoate | 329 |
| 428 | 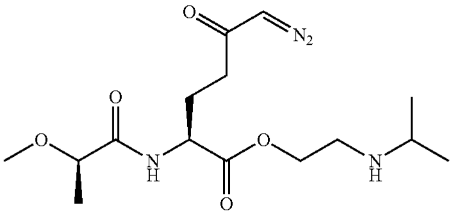 | 2-(isopropylamino) ethyl (S)-6-diazo-2-((R)-2-methoxypropanamido)-5-oxohexanoate | 343 |
| 429 | 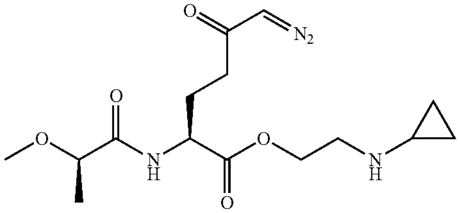 | 2-(cyclopropylamino) ethyl (S)-6-diazo-2-((R)-2-methoxypropanamido)-5-oxohexanoate | 341 |
| 430 | 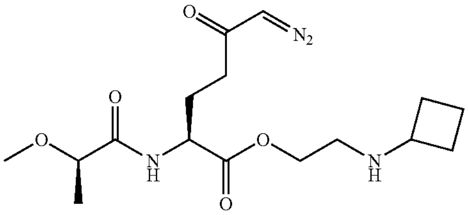 | 2-(cyclobutylamino) ethyl (S)-6-diazo-2-((R)-2-methoxypropanamido)-5-oxohexanoate | 355 |
| 431 | 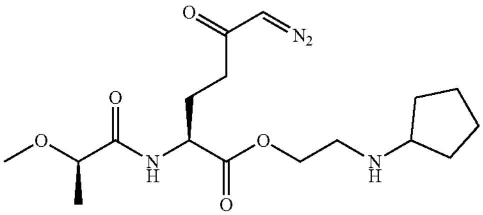 | 2-(cyclopentylamino) ethyl (S)-6-diazo-2-((R)-2-methoxypropanamido)-5-oxohexanoate | 369 |

-continued

| Compound | Structure | IUPAC Name | $^1$HNMR & MS: (M + H)$^+$ |
|---|---|---|---|
| 432 | 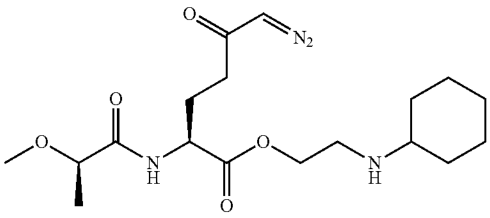 | 2-(cyclohexylamino) ethyl (S)-6-diazo-2-((R)-2-methoxypropanamido)-5-oxohexanoate | 383 |
| 433 | 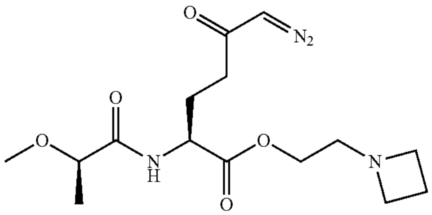 | 2-(azetidin-1-yl)ethyl (S)-6-diazo-2-((R)-2-methoxypropanamido)-5-oxohexanoate | 341 |
| 434 | 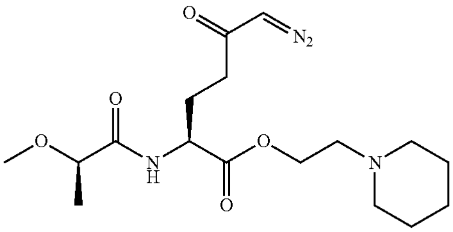 | 2-(piperidin-1-yl)ethyl (S)-6-diazo-2-((R)-2-methoxypropanamido)-5-oxohexanoate | 369 |
| 435 | 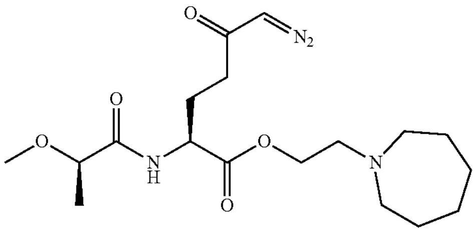 | 2-(azepan-1-yl)ethyl (S)-6-diazo-2-((R)-2-methoxypropanamido)-5-oxohexanoate | 383 |
| 436 | 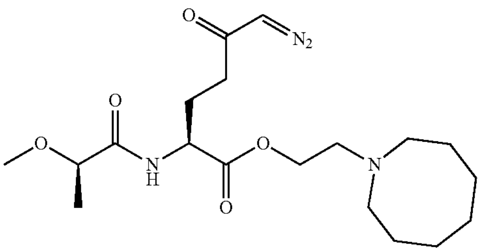 | 2-(azocan-1-yl)ethyl (S)-6-diazo-2-((R)-2-methoxypropanamido)-5-oxohexanoate | 397 |
| 437 | 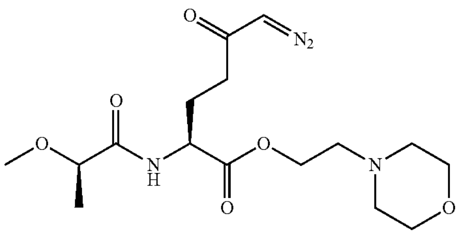 | 2-morpholinoethyl (S)-6-diazo-2-((R)-2-methoxypropanamido)-5-oxohexanoate | 371 |

-continued

| Compound | Structure | IUPAC Name | $^{1}$HNMR & MS: $(M + H)^{+}$ |
|---|---|---|---|
| 438 | 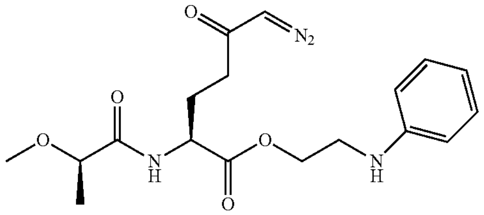 | 2-(phenylamino)ethyl (S)-6-diazo-2-((R)-2-methoxypropanamido)-5-oxohexanoate | 377 |
| 439 | 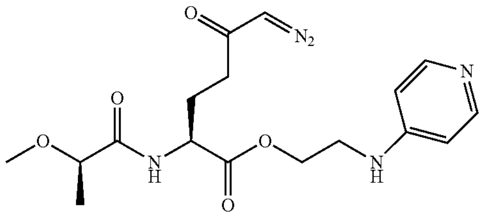 | 2-(pyridin-4-ylamino)ethyl (S)-6-diazo-2-((R)-2-methoxypropanamido)-5-oxohexanoate | 378 |
| 440 | 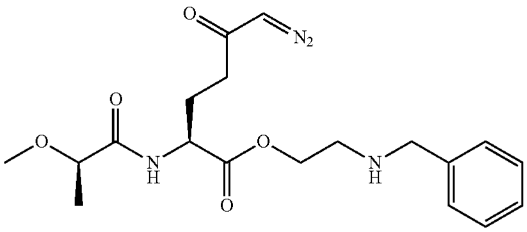 | 2-(benzylamino)ethyl (S)-6-diazo-2-((R)-2-methoxypropanamido)-5-oxohexanoate | 391 |
| 441 | 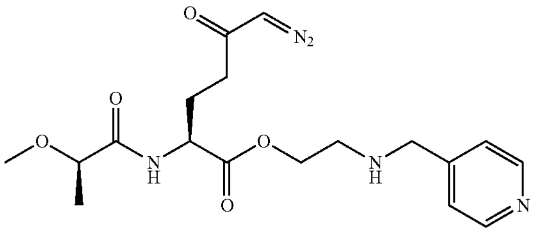 | 2-((pyridin-4-ylmethyl)amino) ethyl (S)-6-diazo-2-((R)-2-methoxypropanamido)-5-oxohexanoate | 392 |
| 442 | 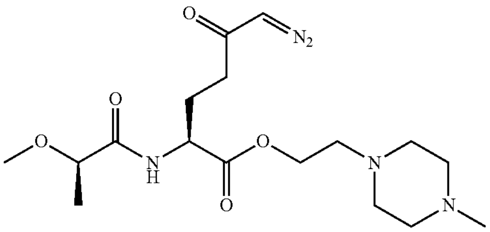 | 2-(4-methylpiperazin-1-yl)ethyl (S)-6-diazo-2-((R)-2-methoxypropanamido)-5-oxohexanoate | 384 |
| 443 | 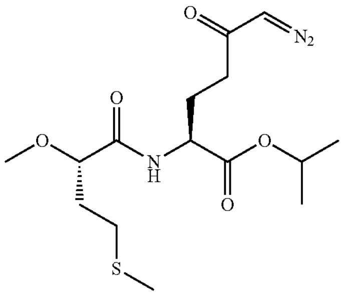 | isopropyl (S)-6-diazo-2-((S)-2-methoxy-4-(methylthio) butanamido)-5-oxohexanoate | MS: 360 $(M + H)^{+}$, $^{1}$H NMR (400 MHz, $CDCl_3$) δ 7.23-7.04 (m, 1H), 5.26 (s, 1H), 5.11-4.95 (m, 1H), 4.58-4.44 (m, 1H), 3.86-3.68 (m, 1H), 3.50-3.35 (m, 3H), 2.64-2.50 (m, 2H), 2.40 (s, 2H), 2.26-2.15 (m, 1H), 2.10-2.05 (m, 3H), 2.06-1.86 (m, 3H), 1.29-1.19 (m, 6H). |

-continued

| Compound | Structure | IUPAC Name | $^1$HNMR & MS: $(M + H)^+$ |
|---|---|---|---|
| 444 | 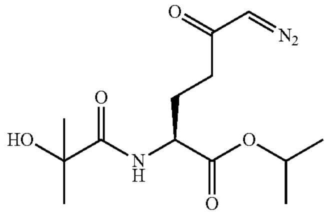 | isopropyl (S)-6-diazo-2-(2-hydroxy-2-methylpropanamido)-5-oxohexanoate | MS: 300 $(M + H)^+$, $^1$H NMR (400 MHz, $CD_3OD$) δ 5.81 (s, 1H), 5.01 (dt, J = 12.5, 6.3 Hz, 1H), 4.33 (dd, J = 8.7, 5.1 Hz, 1H), 2.43 (s, 2H), 2.29-2.11 (m, 1H), 2.10-1.90 (m, 1H), 1.36 (d, J = 3.3 Hz, 6H), 1.26 (dd, J = 6.2, 2.9 Hz, 6H). |
| 445 | 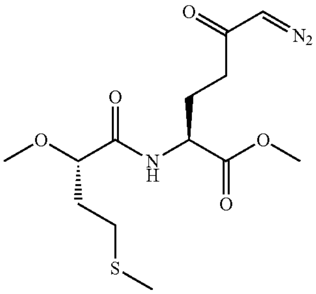 | methyl (S)-6-diazo-2-((S)-2-methoxy-4-(methylthio) butanamido)-5-oxohexanoate | 332 |
| 446 | 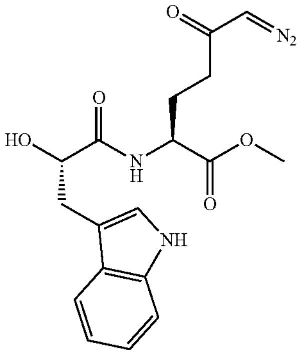 | methyl (S)-6-diazo-2-((S)-2-hydroxy-3-(1H-indol-3-yl)propanamido)-5-oxohexanoate | MS: 373 $(M + H)^+$ $^1$H NMR (400 MHz, $CD_3OD$) δ 7.61 (d, J = 7.9 Hz, 1H), 7.32 (d, J = 8.1 Hz, 1H), 7.14 (s, 1H), 7.11-7.03 (m, 1H), 7.03-6.94 (m, 1H), 5.23 (s, 1H), 4.38 (t, J = 4.9 Hz, 1H), 4.32-4.22 (m, 1H), 3.67 (s, 3H), 3.25-3.12 (m, 2H), 1.96-1.84 (m, 1H), 1.81-1.60 (m, 3H). |
| 447 | 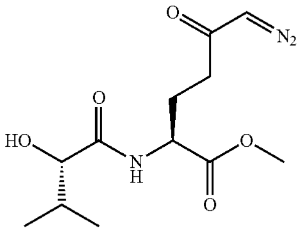 | methyl (S)-6-diazo-2-((S)-2-hydroxy-3-methylbutanamido)-5-oxohexanoate | MS: 286 $(M + H)^+$, $^1$H NMR (400 MHz, $CD_3OD$) δ 4.46 (dd, J = 8.5, 5.1 Hz, 1H), 3.87 (d, J = 3.4 Hz, 1H), 3.73 (s, 3H), 2.54-2.33 (m, 2H), 2.29-2.14 (m, 1H), 2.15-1.92 (m, 2H), 1.01 (d, J = 6.9 Hz, 3H), 0.87 (d, J = 6.8 Hz, 3H). |
| 448 | 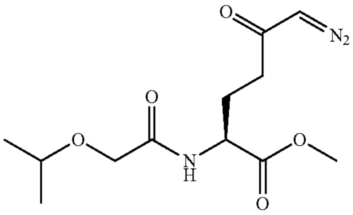 | methyl (S)-6-diazo-2-(2-isopropoxyacetamido)-5-oxohexanoate | MS: 286 $(M + H)^+$, $^1$H NMR (400 MHz, $CD_3OD$) δ 5.82 (s, 1H), 4.50 (dd, J = 8.7, 5.0 Hz, 1H), 4.05-3.88 (m, 2H), 3.74 (s, 3H), 3.72-3.66 (m, 1H), 2.45 (s, 2H), 2.31-2.15 (m, 1H), 2.13-1.92 (m, 1H), 1.30-1.15 (m, 6H). |
| 449 | 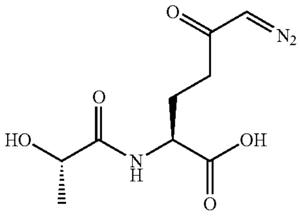 | (S)-6-diazo-2-((S)-2-hydroxypropanamido)-5-oxohexanoic acid | 244 |

-continued

| Compound | Structure | IUPAC Name | $^1$HNMR & MS: (M + H)$^+$ |
|---|---|---|---|
| 450 | 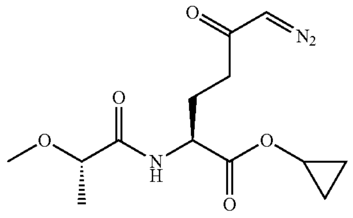 | cyclopropyl (S)-6-diazo-2-((S)-2-methoxypropanamido)-5-oxohexanoate | MS: 298 (M + H)$^+$, $^1$H NMR (400 MHz, $CD_3OD$) δ 5.81 (s, 1H), 4.44-4.29 (m, 1H), 4.15 (dt, J = 8.8, 2.8 Hz, 1H), 3.82-3.70 (m, 1H), 3.42-3.34 (m, 3H), 2.44 (s, 2H), 2.28-2.10 (m, 1H), 2.06-1.91 (m, 1H), 1.35-1.31 (m, 3H), 0.78-0.63 (m, 4H). |
| 451 | 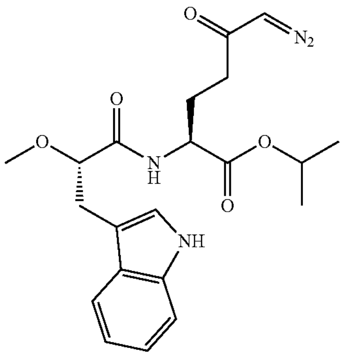 | isopropyl (S)-2-((S)-3-(1H-indol-3-yl)-2-methoxypropanamido)-6-diazo-5-oxohexanoate | MS: 415 (M + H)$^+$, $^1$H NMR (400 MHz, $CDCl_3$) δ 8.12-8.00 (m, 1H), 7.65 (d, J = 7.8 Hz, 1H), 7.29 (d, J = 7.9 Hz, 1H), 7.17-7.05 (m, 3H), 6.92-6.83 (m, 1H), 4.96 (dt, J = 12.6, 6.3 Hz, 1H), 4.76 (s, 1H), 4.46-4.34 (m, 1H), 4.00-3.92 (m, 1H), 3.50-3.41 (m, 3H), 3.29-3.19 (m, 2H), 1.94-1.69 (m, 2H), 1.70-1.59 (m, 2H), 1.21-1.16 (m, 6H). |
| 452 | 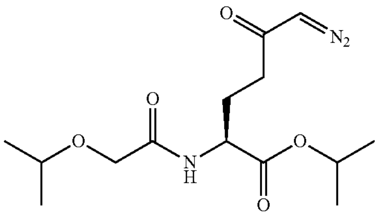 | isopropyl (S)-6-diazo-2-(2-isopropoxyacetamido)-5-oxohexanoate | MS: 314 (M + H)$^+$, $^1$H NMR (400 MHz, $CD_3OD$) δ 5.81 (s, 1H), 5.02 (dt, J = 12.5, 6.3 Hz, 1H), 4.42 (dd, J = 8.7, 5.0 Hz, 1H), 4.03-3.87 (m, 2H), 3.70 (dt, J = 12.2, 6.1 Hz, 1H), 2.44 (s, 2H), 2.27-2.14 (m, 1H), 2.10-1.93 (m, 1H), 1.26 (dd, J = 6.3, 2.1 Hz, 6H), 1.22 (dd, J = 6.1, 3.4 Hz, 6H). |
| 453 | 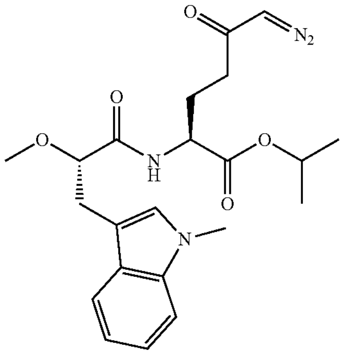 | isopropyl (S)-6-diazo-2-((S)-2-methoxy-3-(1-methyl-1H-indol-3-yl)propanamido)-5-oxohexanoate | MS: 429 (M + H)$^+$, $^1$H NMR (400 MHz, $CD_3OD$) δ 7.57 (d, J = 8.0 Hz, 1H), 7.31 (d, J = 8.2 Hz, 1H), 7.15 (t, J = 7.1 Hz, 1H), 7.08-6.99 (m, 2H), 5.26 (s, 1H), 4.26-4.18 (m, 1H), 3.96 (t, J = 5.0 Hz, 1H), 3.75 (s, 3H), 3.48 (s, 3H), 3.22-3.16 (m, 2H), 1.95-1.83 (m, 1H), 1.80-1.61 (m, 3H), 1.22 (dd, J = 8.6, 6.3 Hz, 6H). |
| 454 | 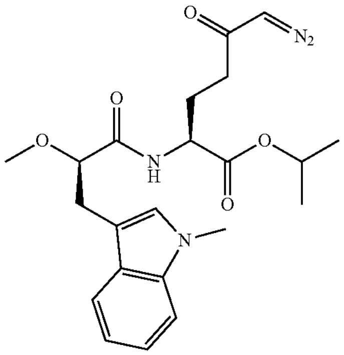 | isopropyl (S)-6-diazo-2-((R)-2-methoxy-3-(1-methyl-1H-indol-3-yl)propanamido)-5-oxohexanoate | MS: 429 (M + H)$^+$, $^1$H NMR (400 MHz, $CD_3OD$) δ 7.55 (d, J = 8.0 Hz, 1H), 7.30 (d, J = 8.2 Hz, 1H), 7.14 (t, J = 7.5 Hz, 1H), 7.06-6.99 (m, 2H), 5.49 (s, 1H), 4.94 (dt, J = 12.5, 6.2 Hz, 1H), 4.21-4.09 (m, 1H), 3.94 (t, J = 6.4 Hz, 1H), 3.74 (s, 3H), 3.37 (s, 3H), 3.13 (ddd, J = 34.8, 14.5, 6.4 Hz, 2H), 2.06-1.85 (m, 3H), 1.82-1.69 (m, 1H), 1.20 (dd, J = 8.8, 6.3 Hz, 6H). |

-continued

| Compound | Structure | IUPAC Name | $^1$HNMR & MS: (M + H)$^+$ |
|---|---|---|---|
| 456 | 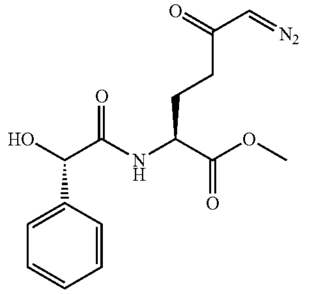 | methyl (S)-6-diazo-2-((S)-2-hydroxy-2-phenylacetamido)-5-oxohexanoate | MS: 320 (M + H)$^+$, $^1$H NMR (400 MHz, $CD_3OD$) δ 7.53-7.43 (m, 2H), 7.42-7.22 (m, 3H), 5.05 (s, 1H), 4.45 (dd, J = 8.9, 4.8 Hz, 1H), 3.71 (s, 3H), 2.33 (s, 2H), 2.27-2.12 (m, 1H), 2.07-1.91 (m, 1H). |
| 457 | 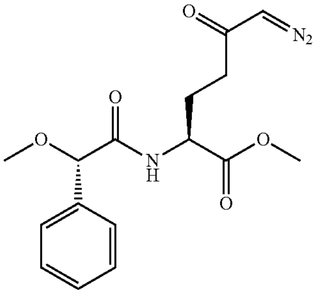 | methyl (S)-6-diazo-2-((S)-2-methoxy-2-phenylacetamido)-5-oxohexanoate | MS: 334 (M + H)$^+$, $^1$H NMR (400 MHz, $CD_3OD$) δ 7.47-7.42 (m, 2H), 7.40-7.32 (m, 3H), 5.57 (s, 1H), 4.68 (s, 1H), 4.44 (dd, J = 9.4, 4.8 Hz, 1H), 3.71 (s, 3H), 3.42 (s, 3H), 2.32 (s, 2H), 2.26-2.12 (m, 1H), 2.05-1.97 (m, 1H). |
| 458 | 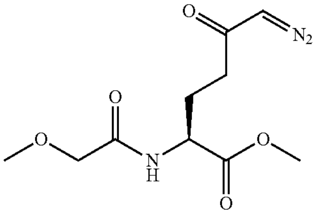 | methyl (S)-6-diazo-2-(2-methoxyacetamido)-5-oxohexanoate | MS: 258 (M + H)$^+$, $^1$H NMR (400 MHz, $CD_3OD$) δ 5.82 (s, 1H), 4.50 (dd, J = 8.8, 5.0 Hz, 1H), 3.93 (d, J = 4.0 Hz, 2H), 3.73 (s, 3H), 3.43 (s, 3H), 2.44 (s, 2H), 2.30-2.16 (m, 1H), 2.11-1.93 (m, 1H). |
| 459 | 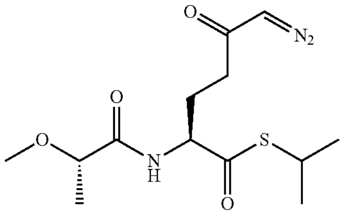 | S-isopropyl (S)-6-diazo-2-((S)-2-methoxypropanamido)-5-oxohexanethioate | MS: 316 (M + H)$^+$, $^1$H NMR (400 MHz, $CD_3OD$) δ 5.81 (s, 1H), 4.51 (dd, J = 9.9, 4.6 Hz, 1H), 3.80 (q, J = 6.7 Hz, 1H), 3.59 (dt, J = 13.7, 6.9 Hz, 1H), 3.44 (s, 3H), 2.43 (s, 2H), 2.31-2.16 (m, 1H), 2.04-1.87 (m, 1H), 1.35 (d, J = 6.8 Hz, 3H), 1.30 (d, J = 6.9 Hz, 6H). |
| 460 | 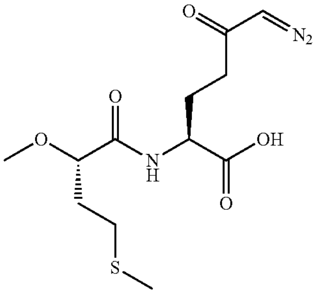 | (S)-6-diazo-2-((S)-2-methoxy-4-(methylthio) butanamido)-5-oxohexanoic acid | 318 |

-continued
| Compound | Structure | IUPAC Name | $^1$HNMR & MS: (M + H)$^+$ |
|---|---|---|---|
| 461 | 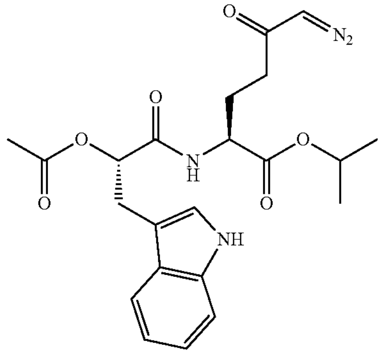 | isopropyl (2S)-2-(2-acetoxy-3-(1H-indol-3-yl)propanamido)-6-diazo-5-oxohexanoate | 442 |
| 462 | 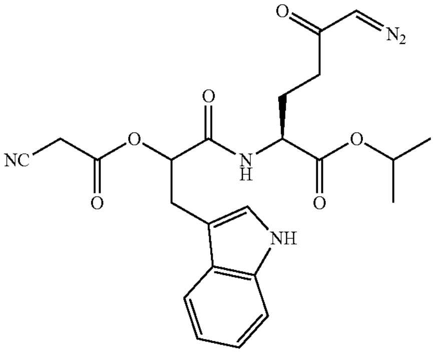 | isopropyl (2S)-2-(2-(2-cyanoacetoxy)-3-(1H-indol-3-yl)propanamido)-6-diazo-5-oxohexanoate | 467 |
| 463 | 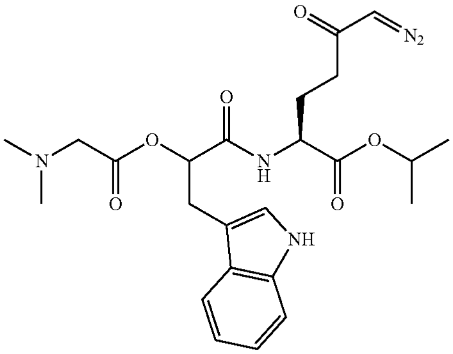 | isopropyl (2S)-6-diazo-2-(2-((dimethylglycyl)oxy)-3-(1H-indol-3-yl)propanamido)-5-oxohexanoate | 486 |
| 464 | 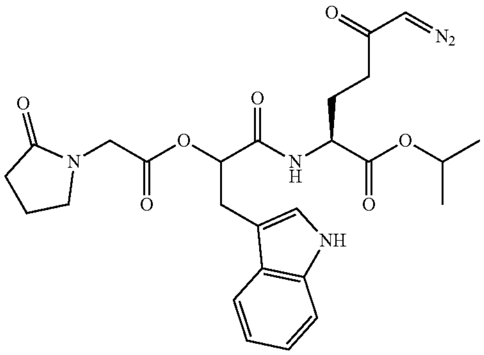 | isopropyl (2S)-2-(3-(1H-indol-3-yl)-2-(2-(2-oxopyrrolidin-1-yl)acetoxy)propanamido)-6-diazo-5-oxohexanoate | 526 |

-continued
| Compound | Structure | IUPAC Name | $^1$HNMR & MS: (M + H)$^+$ |
|---|---|---|---|
| 465 | 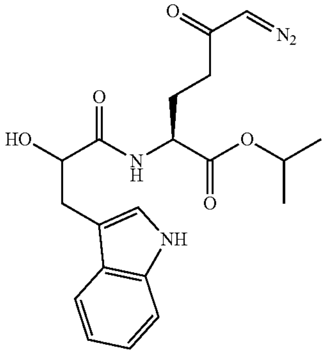 | isopropyl (2S)-6-diazo-2-(2-hydroxy-3-(1H-indol-3-yl)propanamido)-5-oxohexanoate | 400 |
| 466 | 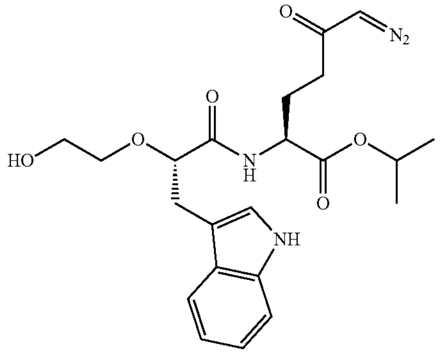 | isopropyl (S)-6-diazo-2-((S)-2-(2-hydroxyethoxy)-3-(1H-indol-3-yl)propanamido)-5-oxohexanoate | 444 |
| 467 | 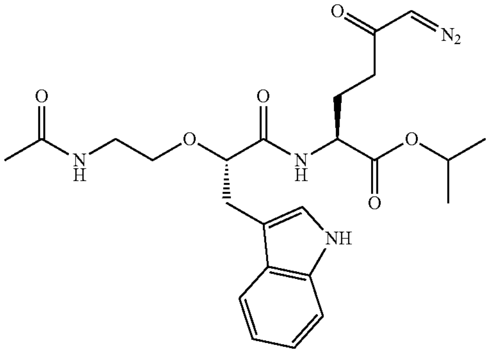 | isopropyl (S)-2-((S)-2-(2-acetamidoethoxy)-3-(1H-indol-3-yl)propanamido)-6-diazo-5-oxohexanoate | 486 |
| 468 | 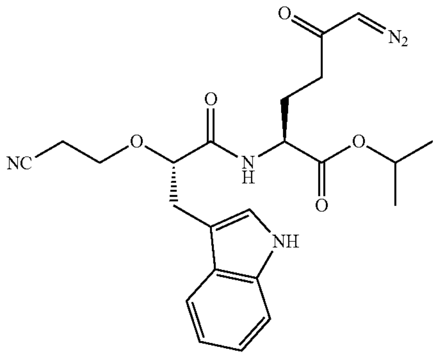 | isopropyl (S)-2-((S)-2-(2-cyanoethoxy)-3-(1H-indol-3-yl)propanamido)-6-diazo-5-oxohexanoate | 454 |

-continued

| Compound | Structure | IUPAC Name | $^{1}$HNMR & MS: (M + H)$^{+}$ |
|---|---|---|---|
| 469 | 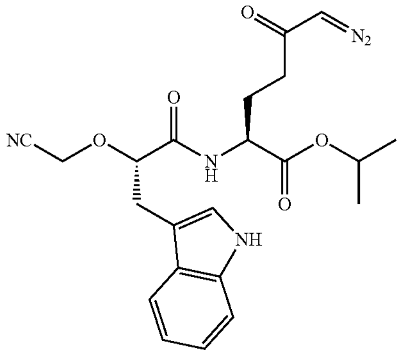 | isopropyl (S)-2-((S)-2-(cyanomethoxy)-3-(1H-indol-3-yl)propanamido)-6-diazo-5-oxohexanoate | 439 |
| 470 | 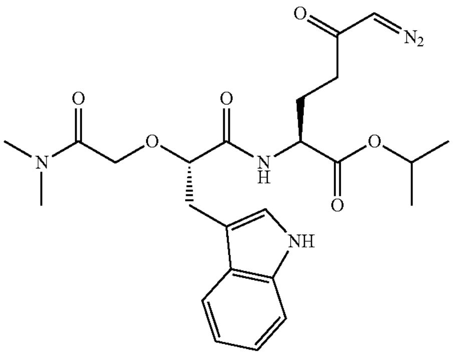 | isopropyl (S)-6-diazo-2-((S)-2-(2-(dimethylamino)-2-oxoethoxy)-3-(1H-indol-3-yl)propanamido)-5-oxohexanoate | 486 |
| 471 | 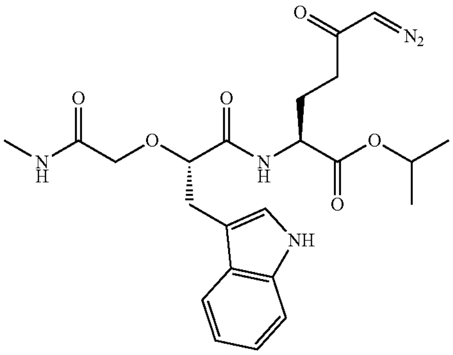 | isopropyl (S)-2-((S)-3-(1H-indol-3-yl)-2-(2-(methylamino)-2-oxoethoxy)propanamido)-6-diazo-5-oxohexanoate | 472 |
| 472 | 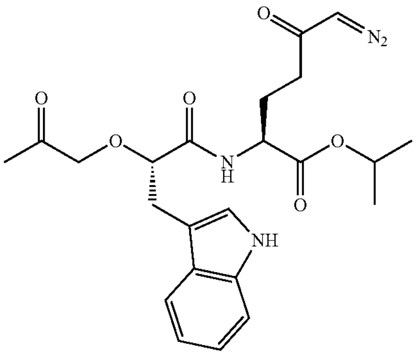 | isopropyl (S)-2-((S)-3-(1H-indol-3-yl)-2-(2-oxopropoxy)propanamido)-6-diazo-5-oxohexanoate | 457 |

-continued

| Compound | Structure | IUPAC Name | $^1$HNMR & MS: (M + H)$^+$ |
| --- | --- | --- | --- |
| 473 | 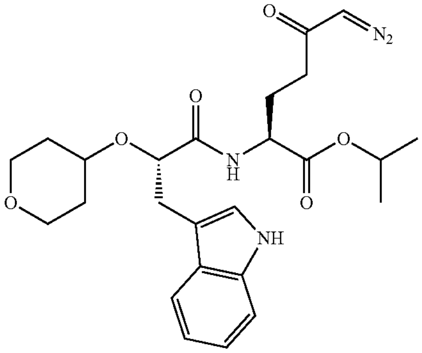 | isopropyl (S)-2-((S)-3-(1H-indol-3-yl)-2-((tetrahydro-2H-pyran-4-yl)oxy)propanamido)-6-diazo-5-oxohexanoate | 485 |
| 474 | 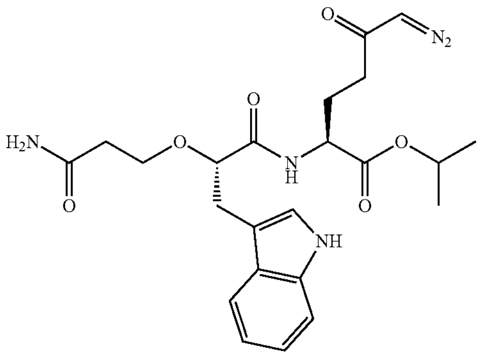 | isopropyl (S)-2-((S)-2-(3-amino-3-oxopropoxy)-3-(1H-indol-3-yl)propanamido)-6-diazo-5-oxohexanoate | 472 |
| 475 | 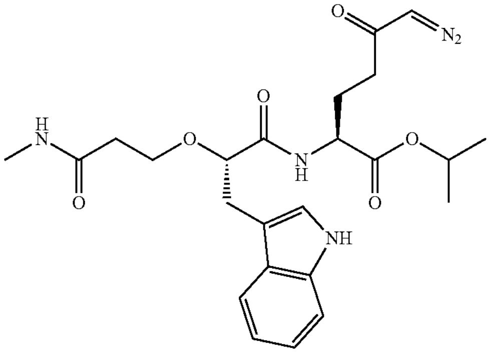 | isopropyl (S)-2-((S)-3-(1H-indol-3-yl)-2-(3-(methylamino)-3-oxopropoxy)propanamido)-6-diazo-5-oxohexanoate | 486 |
| 476 | 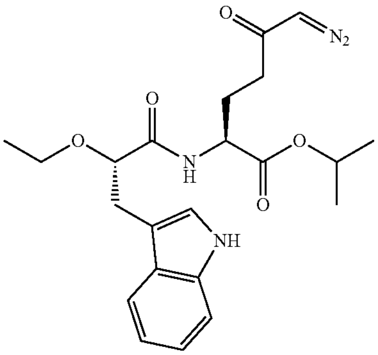 | isopropyl (S)-6-diazo-2-((S)-2-ethoxy-3-(1H-indol-3-yl)propanamido)-5-oxohexanoate | 428 |

-continued

| Compound | Structure | IUPAC Name | $^1$HNMR & MS: (M + H)$^+$ |
| --- | --- | --- | --- |
| 477 | 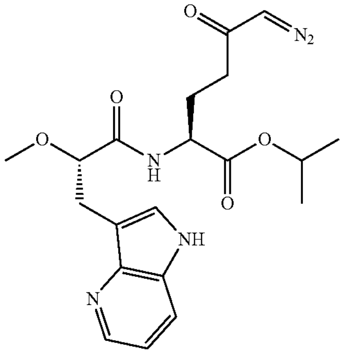 | isopropyl (S)-6-diazo-2-((S)-2-methoxy-3-(1H-pyrrolo[3,2-b]pyridin-3-yl)propanamido)-5-oxohexanoate | 415 |
| 478 | 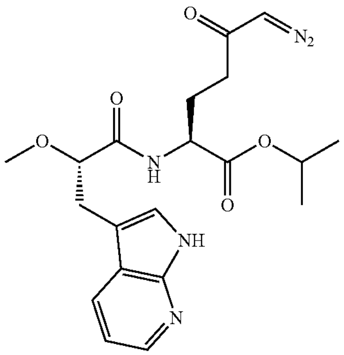 | isopropyl (S)-6-diazo-2-((S)-2-methoxy-3-(1H-pyrrolo[2,3-b]pyridin-3-yl)propanamido)-5-oxohexanoate | 415 |
| 479 | 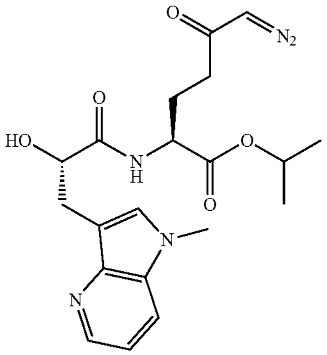 | isopropyl (S)-6-diazo-2-((S)-2-hydroxy-3-(1-methyl-1H-pyrrolo[3,2-b]pyridin-3-yl)propanamido)-5-oxohexanoate | 415 |
| 480 | 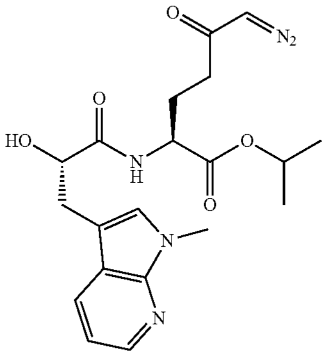 | isopropyl (S)-6-diazo-2-((S)-2-hydroxy-3-(1-methyl-1H-pyrrolo[2,3-b]pyridin-3-yl)propanamido)-5-oxohexanoate | 415 |

-continued
| Compound | Structure | IUPAC Name | $^1$HNMR & MS: (M + H)$^+$ |
|---|---|---|---|
| 481 | 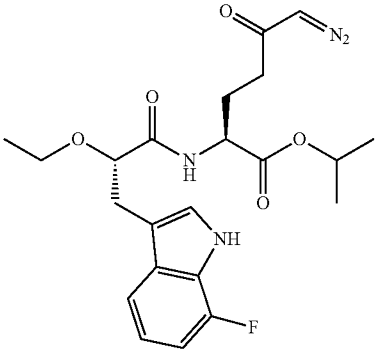 | isopropyl (S)-6-diazo-2-((S)-2-ethoxy-3-(7-fluoro-1H-indol-3-yl)propanamido)-5-oxohexanoate | 447 |
| 482 | 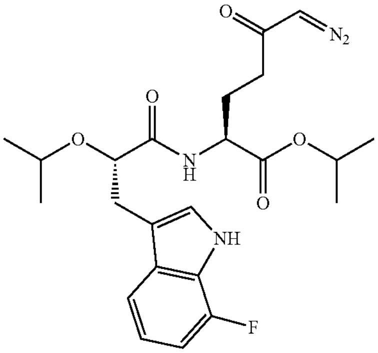 | isopropyl (S)-6-diazo-2-((S)-3-(7-fluoro-1H-indol-3-yl)-2-isopropoxypropanamido)-5-oxohexanoate | 461 |
| 483 | 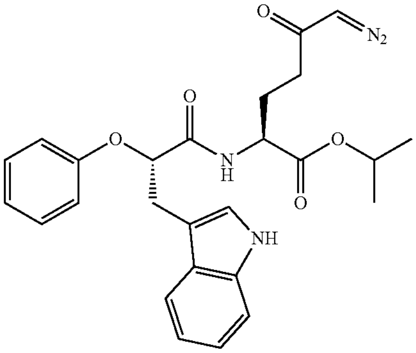 | isopropyl (S)-2-((S)-3-(1H-indol-3-yl)-2-phenoxypropanamido)-6-diazo-5-oxohexanoate | 477 |
| 484 | 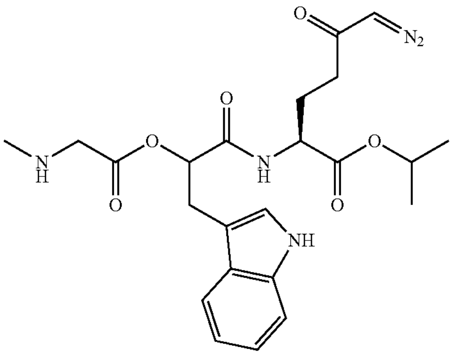 | isopropyl (2S)-2-(3-(1H-indol-3-yl)-2-((methylglycyl)oxy)propanamido)-6-diazo-5-oxohexanoate | 472 |

-continued

| Compound | Structure | IUPAC Name | $^1$HNMR & MS: $(M + H)^+$ |
|---|---|---|---|
| 485 | 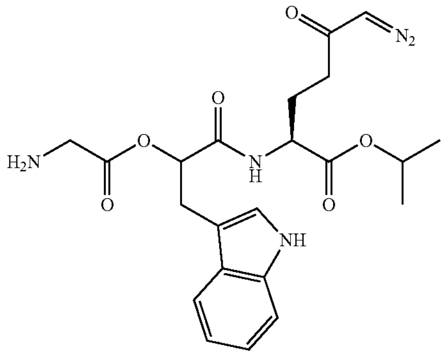 | isopropyl (2S)-6-diazo-2-(2-(glycyloxy)-3-(1H-indol-3-yl)propanamido)-5-oxohexanoate | 457 |
| 486 | 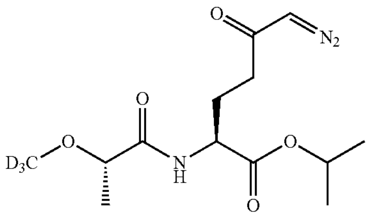 | isopropyl (S)-6-diazo-2-((S)-2-(methoxy-d3)propanamido)-5-oxohexanoate | 303 |
| 487 | 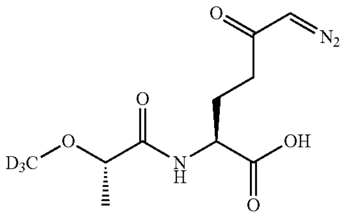 | (S)-6-diazo-2-((S)-2-(methoxy-d3)propanamido)-5-oxohexanoic acid | 261 |
| 488 | 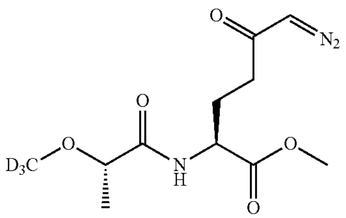 | methyl (S)-6-diazo-2-((S)-2-(methoxy-d3)propanamido)-5-oxohexanoate | 275 |
| 489 | 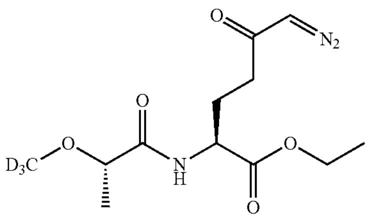 | ethyl (S)-6-diazo-2-((S)-2-(methoxy-d3)propanamido)-5-oxohexanoate | 289 |
| 490 | 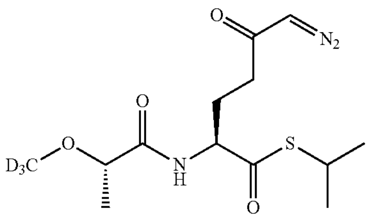 | S-isopropyl (S)-6-diazo-2-((S)-2-(methoxy-d3)propanamido)-5-oxohexanethioate | 319 |

-continued

| Compound | Structure | IUPAC Name | $^1$HNMR & MS: $(M + H)^+$ |
|---|---|---|---|
| 491 | 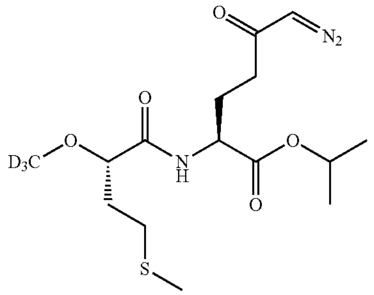 | isopropyl (S)-6-diazo-2-((S)-2-(methoxy-d3)-4-(methylthio) butanamido)-5-oxohexanoate | 363 |
| 492 | 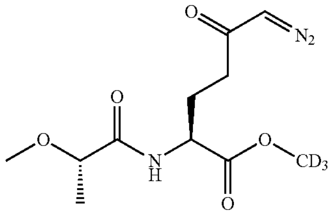 | methyl-d3 (S)-6-diazo-2-((S)-2-methoxypropanamido)-5-oxohexanoate | 275 |
| 493 | 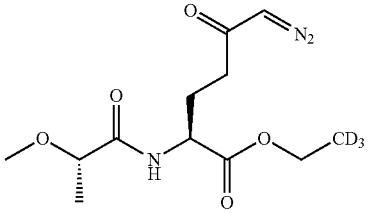 | ethyl-2,2,2-d3 (S)-6-diazo-2-((S)-2-methoxypropanamido)-5-oxohexanoate | 289 |
| 494 | 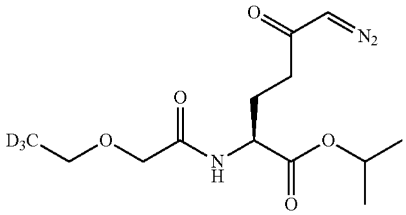 | isopropyl (S)-6-diazo-2-(2-(ethoxy-2,2,2-d3)acetamido)-5-oxohexanoate | 303 |
| 495 | 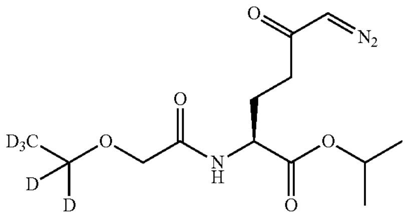 | isopropyl (S)-6-diazo-2-(2-(ethoxy-d5)acetamido)-5-oxohexanoate | 305 |
| 496 | 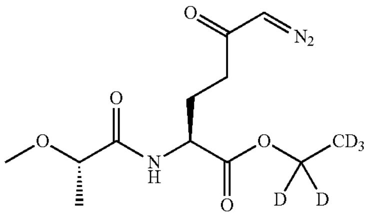 | ethyl-d5 (S)-6-diazo-2-((S)-2-methoxypropanamido)-5-oxohexanoate | 291 |

-continued

| Compound | Structure | IUPAC Name | ¹HNMR & MS: (M + H)⁺ |
|---|---|---|---|
| 497 | 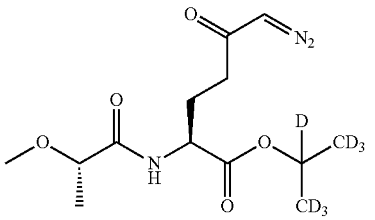 | propan-2-yl-d7 (S)-6-diazo-2-((S)-2-methoxypropanamido)-5-oxohexanoate | 307 |
| 498 | 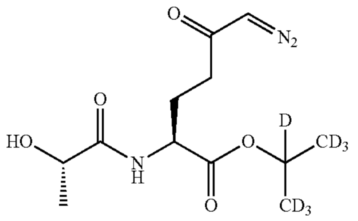 | propan-2-yl-d7 (S)-6-diazo-2-((S)-2-hydroxypropanamido)-5-oxohexanoate | 293 |
| 499 | 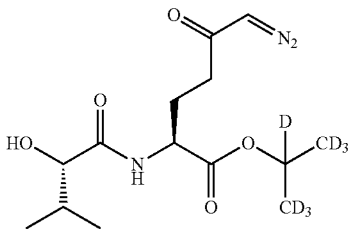 | propan-2-yl-d7 (S)-6-diazo-2-((S)-2-hydroxy-3-methylbutanamido)-5-oxohexanoate | 321 |
| 500 | 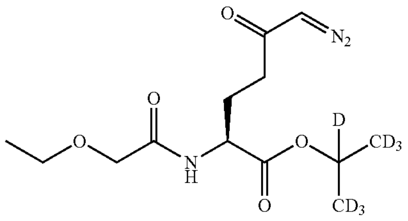 | propan-2-yl-d7 (S)-6-diazo-2-(2-ethoxyacetamido)-5-oxohexanoate | 307 |
| 501 | 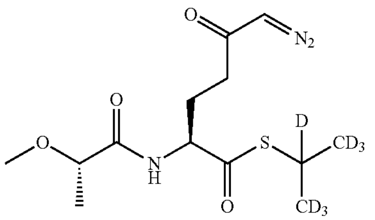 | S-(propan-2-yl-d7) (S)-6-diazo-2-((S)-2-methoxypropanamido)-5-oxohexanethioate | 323 |
| 502 | 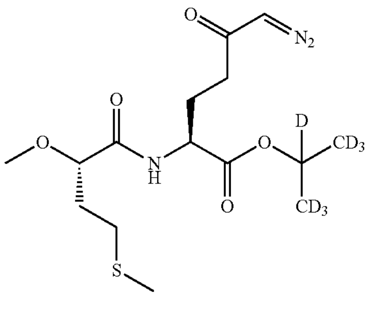 | propan-2-yl-d7 (S)-6-diazo-2-((S)-2-methoxy-4-(methylthio)butanamido)-5-oxohexanoate | 367 |

-continued

| Compound | Structure | IUPAC Name | $^1$HNMR & MS: (M + H)$^+$ |
|---|---|---|---|
| 503 | 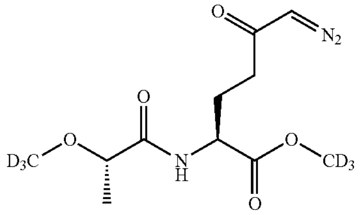 | methyl-d3 (S)-6-diazo-2-((S)-2-(methoxy-d3)propanamido)-5-oxohexanoate | 278 |
| 504 | 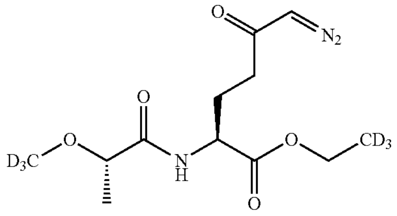 | ethyl-2,2,2-d3 (S)-6-diazo-2-((S)-2-(methoxy-d3)propanamido)-5-oxohexanoate | 292 |
| 505 | 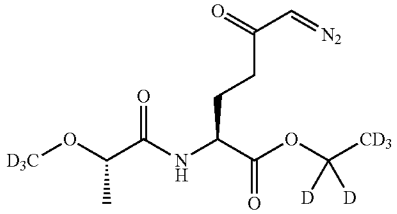 | ethyl-d5 (S)-6-diazo-2-((S)-2-(methoxy-d3)propanamido)-5-oxohexanoate | 294 |
| 506 | 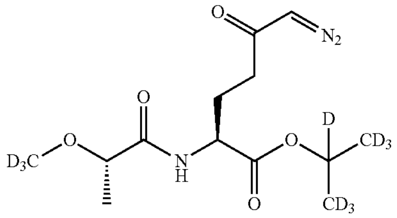 | propan-2-yl-d7 (S)-6-diazo-2-((S)-2-(methoxy-d3)propanamido)-5-oxohexanoate | 310 |
| 507 | 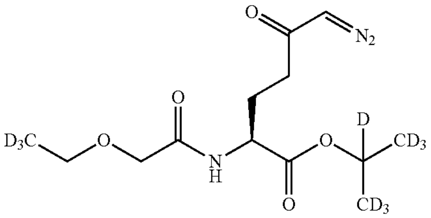 | propan-2-yl-d7 (S)-6-diazo-2-(2-(ethoxy-2,2,2-d3)acetamido)-5-oxohexanoate | 310 |
| 508 | 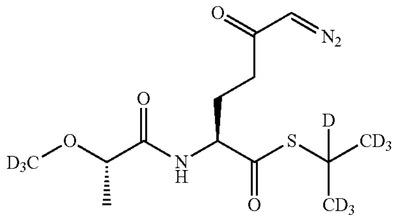 | S-(propan-2-yl-d7) (S)-6-diazo-2-((S)-2-(methoxy-d3)propanamido)-5-oxohexanethioate | 326 |

-continued

| Compound | Structure | IUPAC Name | ¹HNMR & MS: (M + H)⁺ |
|---|---|---|---|
| 509 | 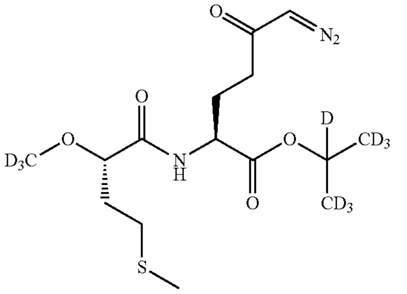 | propan-2-yl-d7 (S)-6-diazo-2-((S)-2-(methoxy-d3)-4-(methylthio) butanamido)-5-oxohexanoate | 370 |
| 510 | 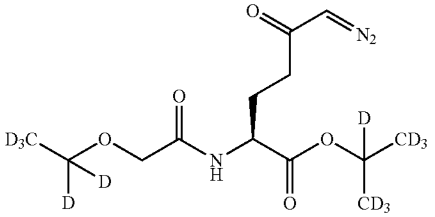 | propan-2-yl-d7 (S)-6-diazo-2-(2-(ethoxy-d5)acetamido)-5-oxohexanoate | 312 |
| 511 | 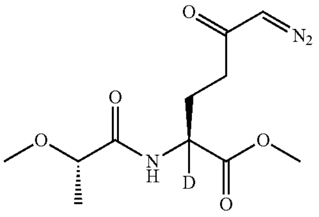 | methyl 6-diazo-2-((S)-2-methoxypropanamido)-5-oxohexanoate-2-d | 273 |
| 512 | 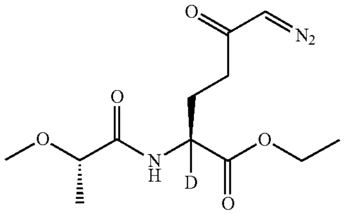 | ethyl 6-diazo-2-((S)-2-methoxypropanamido)-5-oxohexanoate-2-d | 287 |
| 513 | 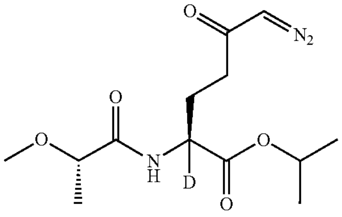 | isopropyl 6-diazo-2-((S)-2-methoxypropanamido)-5-oxohexanoate-2-d | 301 |
| 514 | 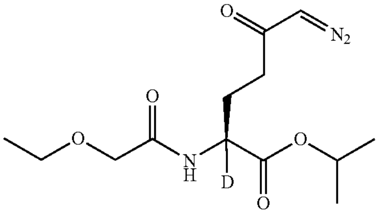 | isopropyl 6-diazo-2-(2-ethoxyacetamido)-5-oxohexanoate-2-d | 301 |

-continued

| Compound | Structure | IUPAC Name | $^1$HNMR & MS: (M + H)$^+$ |
|---|---|---|---|
| 515 | 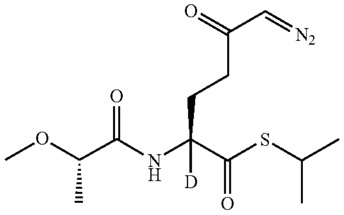 | S-isopropyl 6-diazo-2-((S)-2-methoxypropanamido)-5-oxohexanethioate-2-d | 317 |
| 516 | 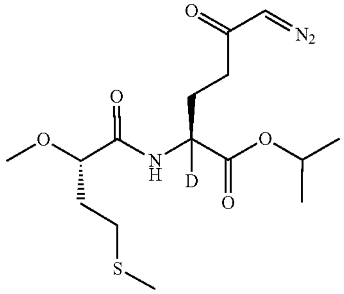 | isopropyl 6-diazo-2-((S)-2-methoxy-4-(methylthio) butanamido)-5-oxohexanoate-2-d | 361 |
| 517 | 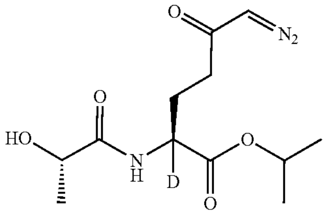 | isopropyl 6-diazo-2-((S)-2-hydroxypropanamido)-5-oxohexanoate-2-d | 287 |
| 518 | 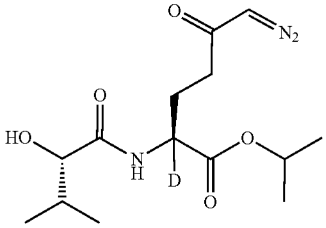 | isopropyl 6-diazo-2-((S)-2-hydroxy-3-methylbutanamido)-5-oxohexanoate-2-d | 315 |
| 519 | 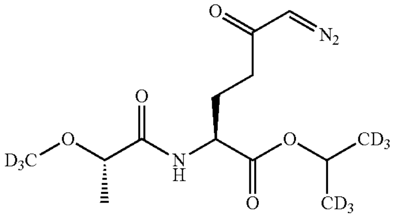 | propan-2-yl-1,1,1,3,3,3-d6 (S)-6-diazo-2-((S)-2-(methoxy-d3)propanamido)-5-oxohexanoate | 309 |
| 520 | 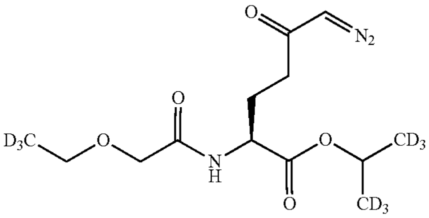 | propan-2-yl-1,1,1,3,3,3-d6 (S)-6-diazo-2-(2-(ethoxy-2,2,2-d3)acetamido)-5-oxohexanoate | 309 |

-continued

| Compound | Structure | IUPAC Name | $^1$HNMR & MS: $(M+H)^+$ |
|---|---|---|---|
| 521 | 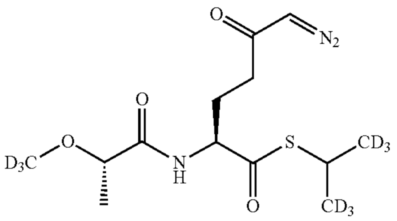 | S-(propan-2-yl-1,1,1,3,3,3-d6) (S)-6-diazo-2-((S)-2-(methoxy-d3)propanamido)-5-oxohexanethioate | 325 |
| 522 | 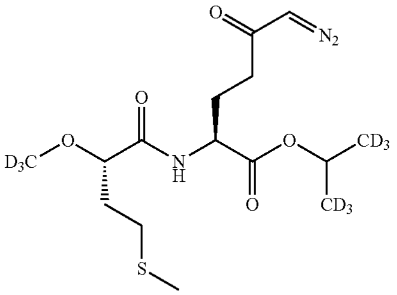 | propan-2-yl-1,1,1,3,3,3-d6 (S)-6-diazo-2-((S)-2-(methoxy-d3)-4-(methylthio) butanamido)-5-oxohexanoate | 369 |
| 523 | 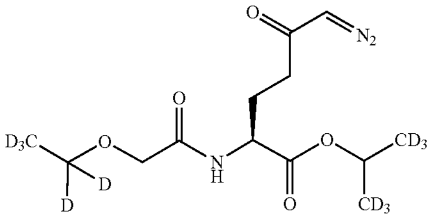 | propan-2-yl-1,1,1,3,3,3-d6 (S)-6-diazo-2-(2-(ethoxy-d5)acetamido)-5-oxohexanoate | 311 |
| 524 | 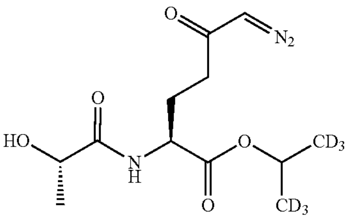 | propan-2-yl-1,1,1,3,3,3-d6 (S)-6-diazo-2-((S)-2-hydroxypropanamido)-5-oxohexanoate | 292 |
| 525 | 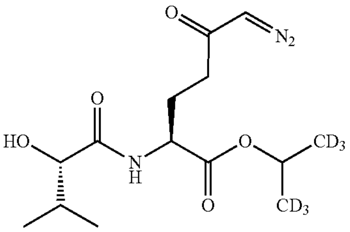 | propan-2-yl-1,1,1,3,3,3-d6 (S)-6-diazo-2-((S)-2-hydroxy-3-methylbutanamido)-5-oxohexanoate | 320 |
| 526 | 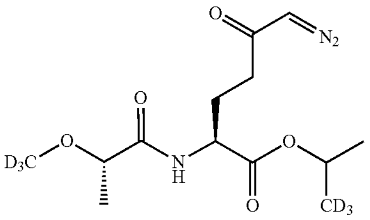 | propan-2-yl-1,1,1-d3 (2S)-6-diazo-2-((S)-2-(methoxy-d3)propanamido)-5-oxohexanoate | 306 |

-continued

| Compound | Structure | IUPAC Name | ¹HNMR & MS: (M + H)⁺ |
|---|---|---|---|
| 527 | 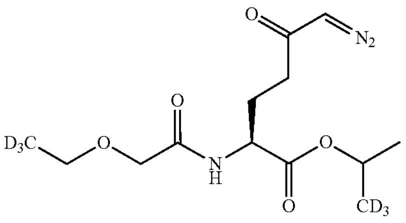 | propan-2-yl-1,1,1-d3 (2S)-6-diazo-2-(2-(ethoxy-2,2,2-d3)acetamido)-5-oxohexanoate | 306 |
| 528 | 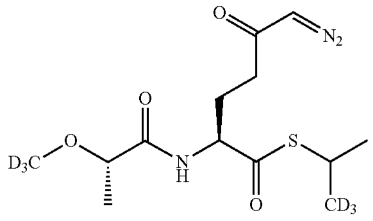 | S-(propan-2-yl-1,1,1-d3) (2S)-6-diazo-2-((S)-2-(methoxy-d3)propanamido)-5-oxohexanethioate | 322 |
| 529 | 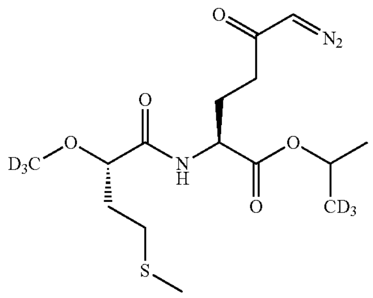 | propan-2-yl-1,1,1-d3 (2S)-6-diazo-2-((S)-2-(methoxy-d3)-4-(methylthio) butanamido)-5-oxohexanoate | 366 |
| 530 | 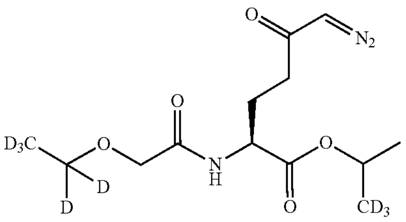 | propan-2-yl-1,1,1-d3 (2S)-6-diazo-2-(2-(ethoxy-d5)acetamido)-5-oxohexanoate | 308 |
| 531 | 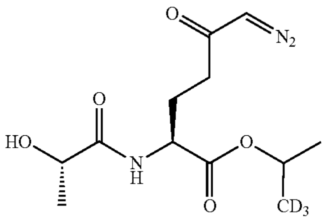 | propan-2-yl-1,1,1-d3 (2S)-6-diazo-2-((S)-2-hydroxypropanamido)-5-oxohexanoate | 289 |
| 532 | 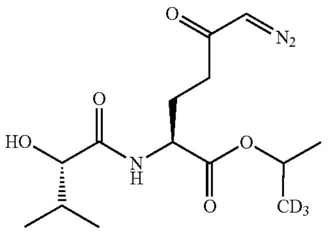 | propan-2-yl-1,1,1-d3 (2S)-6-diazo-2-((S)-2-hydroxy-3-methylbutanamido)-5-oxohexanoate | 317 |

-continued

| Compound | Structure | IUPAC Name | $^1$HNMR & MS: (M + H)$^+$ |
|---|---|---|---|
| 533 | 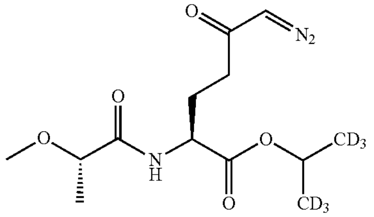 | propan-2-yl-1,1,1,3,3,3-d6 (S)-6-diazo-2-((S)-2-methoxypropanamido)-5-oxohexanoate | 306 |
| 534 | 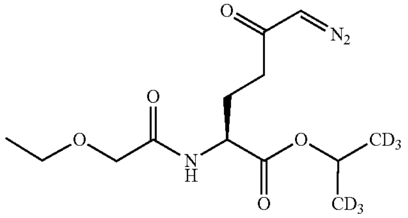 | propan-2-yl-1,1,1,3,3,3-d6 (S)-6-diazo-2-(2-ethoxyacetamido)-5-oxohexanoate | 306 |
| 535 | 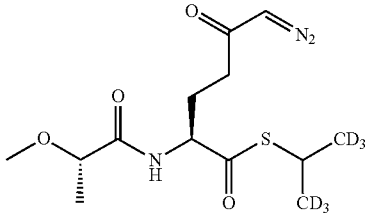 | S-(propan-2-yl-1,1,1,3,3,3-d6) (S)-6-diazo-2-((S)-2-methoxypropanamido)-5-oxohexanethioate | 322 |
| 536 | 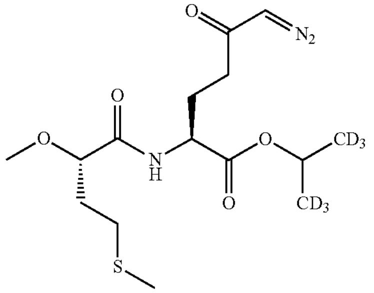 | propan-2-yl-1,1,1,3,3,3-d6 (S)-6-diazo-2-((S)-2-methoxy-4-(methylthio) butanamido)-5-oxohexanoate | 366 |
| 537 | 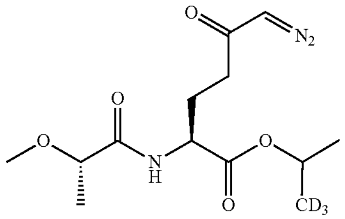 | propan-2-yl-1,1,1-d3 (2S)-6-diazo-2-((S)-2-methoxypropanamido)-5-oxohexanoate | 303 |
| 538 | 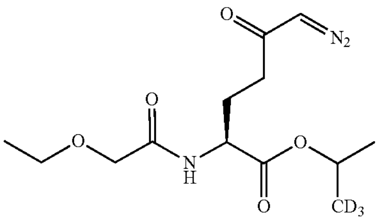 | propan-2-yl-1,1,1-d3 (2S)-6-diazo-2-(2-ethoxyacetamido)-5-oxohexanoate | 303 |

-continued

| Compound | Structure | IUPAC Name | $^1$HNMR & MS: $(M + H)^+$ |
|---|---|---|---|
| 539 | 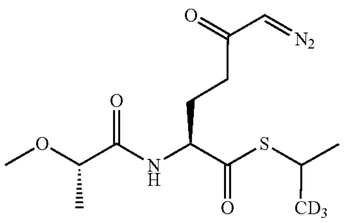 | S-(propan-2-yl-1,1,1-d3) (2S)-6-diazo-2-((S)-2-methoxypropanamido)-5-oxohexanethioate | 319 |
| 540 | 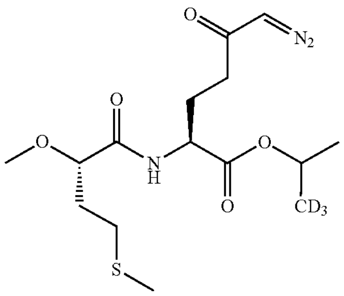 | propan-2-yl-1,1,1-d3 (2S)-6-diazo-2-((S)-2-methoxy-4-(methylthio) butanamido)-5-oxohexanoate | 363 |
| 541 | 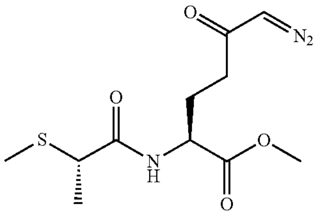 | methyl (S)-6-diazo-2-((S)-2-(methylthio) propanamido)-5-oxohexanoate | 288 |
| 542 | 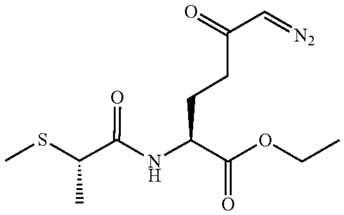 | ethyl (S)-6-diazo-2-((S)-2-(methylthio) propanamido)-5-oxohexanoate | 302 |
| 543 | 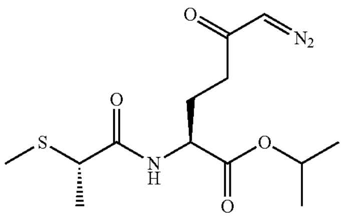 | isopropyl (S)-6-diazo-2-((S)-2-(methylthio) propanamido)-5-oxohexanoate | 316 |
| 544 | 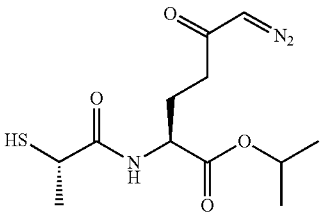 | isopropyl (S)-6-diazo-2-((S)-2-mercaptopropanamido)-5-oxohexanoate | 302 |

-continued

| Compound | Structure | IUPAC Name | ¹HNMR & MS: (M + H)⁺ |
| --- | --- | --- | --- |
| 545 | 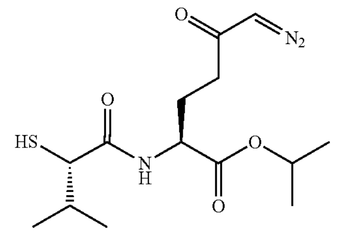 | isopropyl (S)-6-diazo-2-((S)-2-mercapto-3-methylbutanamido)-5-oxohexanoate | 330 |
| 546 | 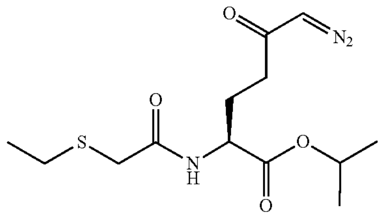 | isopropyl (S)-6-diazo-2-(2-(ethylthio)acetamido)-5-oxohexanoate | 316 |
| 547 | 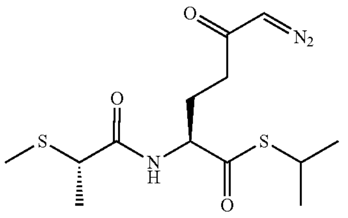 | S-isopropyl (S)-6-diazo-2-((S)-2-(methylthio) propanamido)-5-oxohexanethioate | 332 |
| 548 | 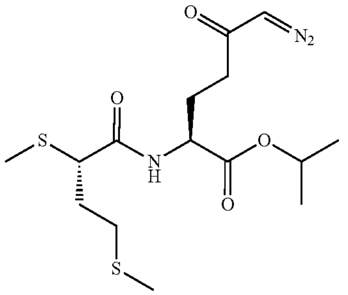 | isopropyl (S)-2-((S)-2,4-bis(methylthio) butanamido)-6-diazo-5-oxohexanoate | 376 |
| 549 | 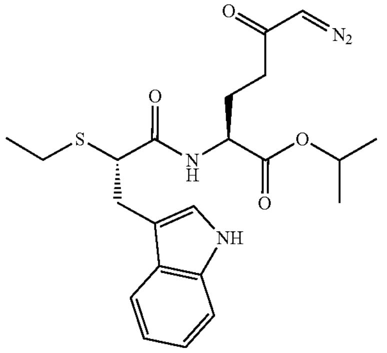 | isopropyl (S)-6-diazo-2-((S)-2-(ethylthio)-3-(1H-indol-3-yl)propanamido)-5-oxohexanoate | 445 |

-continued

| Compound | Structure | IUPAC Name | $^{1}$HNMR & MS: $(M + H)^{+}$ |
|---|---|---|---|
| 550 | 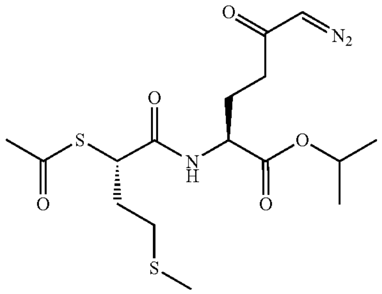 | isopropyl (S)-2-((S)-2-(acetylthio)-4-(methylthio)butanamido)-6-diazo-5-oxohexanoate | 404 |
| 551 | 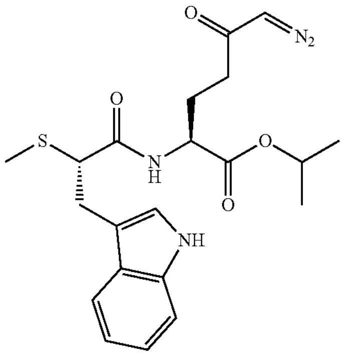 | isopropyl (S)-2-((S)-3-(1H-indol-3-yl)-2-(methylthio)propanamido)-6-diazo-5-oxohexanoate | 431 |
| 552 | 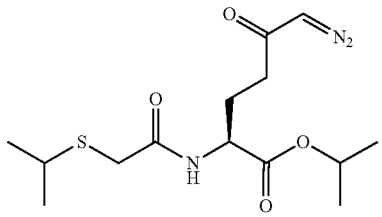 | isopropyl (S)-6-diazo-2-(2-(isopropylthio) acetamido)-5-oxohexanoate | 330 |
| 553 | 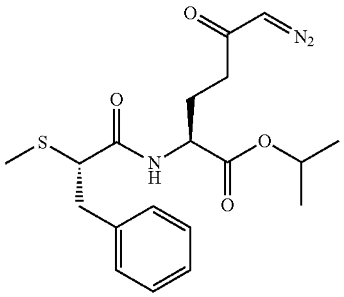 | isopropyl (S)-6-diazo-2-((S)-2-(methylthio)-3-phenylpropanamido)-5-oxohexanoate | 392 |
| 554 | 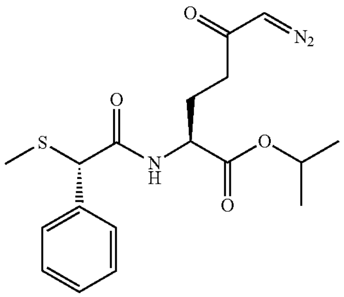 | isopropyl (S)-6-diazo-2-((S)-2-(methylthio)-2-phenylacetamido)-5-oxohexanoate | 378 |

-continued

| Compound | Structure | IUPAC Name | $^1$HNMR & MS: (M + H)$^+$ |
|---|---|---|---|
| 555 | 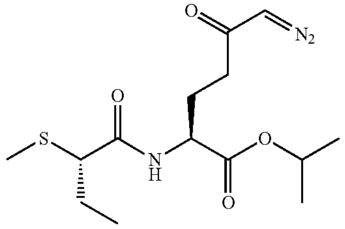 | isopropyl (S)-6-diazo-2-((S)-2-(methylthio) butanamido)-5-oxohexanoate | 330 |
| 556 | 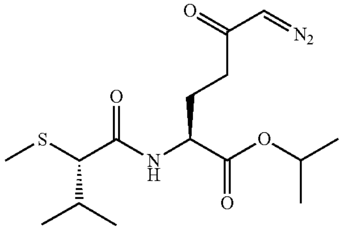 | isopropyl (S)-6-diazo-2-((S)-3-methyl-2-(methylthio) butanamido)-5-oxohexanoate | 344 |
| 557 | 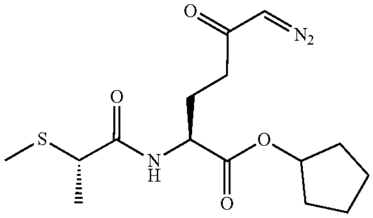 | cyclopentyl (S)-6-diazo-2-((S)-2-(methylthio) propanamido)-5-oxohexanoate | 342 |
| 558 | 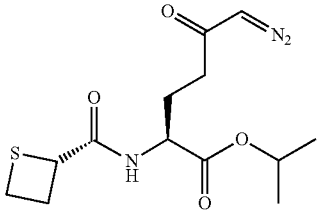 | isopropyl (S)-6-diazo-5-oxo-2-((S)-thietane-2-carboxamido) hexanoate | 314 |
| 559 | 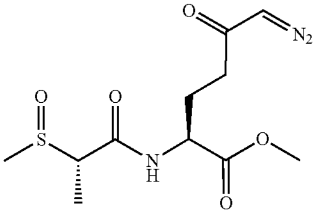 | methyl (2S)-6-diazo-2-((2S)-2-(methylsulfinyl) propanamido)-5-oxohexanoate | 304 |
| 560 | 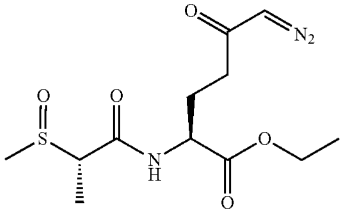 | ethyl (2S)-6-diazo-2-((2S)-2-(methylsulfinyl) propanamido)-5-oxohexanoate | 318 |

-continued

| Compound | Structure | IUPAC Name | $^1$HNMR & MS: $(M + H)^+$ |
|---|---|---|---|
| 561 | 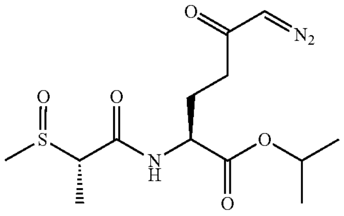 | isopropyl (2S)-6-diazo-2-((2S)-2-(methylsulfinyl)propanamido)-5-oxohexanoate | 332 |
| 562 | 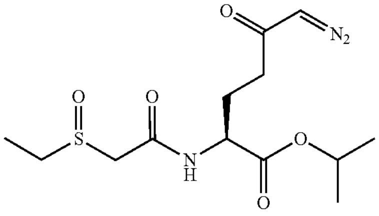 | isopropyl (2S)-6-diazo-2-(2-(ethylsulfinyl)acetamido)-5-oxohexanoate | 332 |
| 563 | 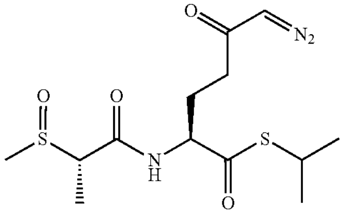 | S-isopropyl (2S)-6-diazo-2-((2S)-2-(methylsulfinyl)propanamido)-5-oxohexanethioate | 348 |
| 564 | 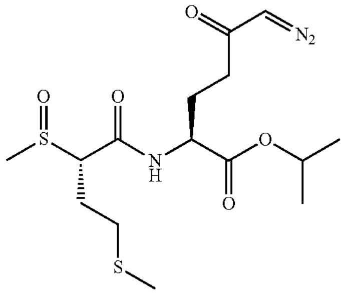 | isopropyl (2S)-6-diazo-2-((2S)-2-(methylsulfinyl)-4-(methylthio)butanamido)-5-oxohexanoate | 392 |
| 565 | 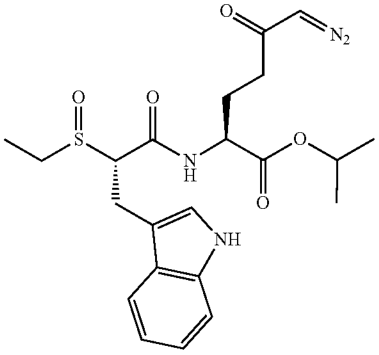 | isopropyl (2S)-6-diazo-2-((2S)-2-(ethylsulfinyl)-3-(1H-indol-3-yl)propanamido)-5-oxohexanoate | 461 |

-continued

| Compound | Structure | IUPAC Name | $^1$HNMR & MS: (M + H)$^+$ |
|---|---|---|---|
| 566 | 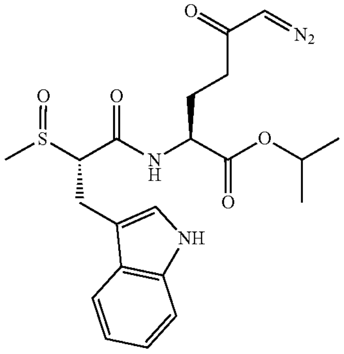 | isopropyl (2S)-2-((2S)-3-(1H-indol-3-yl)-2-(methylsulfinyl) propanamido)-6-diazo-5-oxohexanoate | 447 |
| 567 | 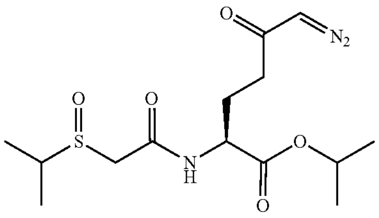 | isopropyl (2S)-6-diazo-2-(2-(isopropylsulfinyl) acetamido)-5-oxohexanoate | 346 |
| 568 | 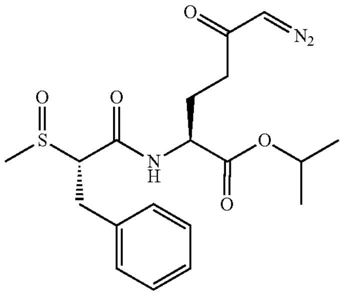 | isopropyl (2S)-6-diazo-2-((2S)-2-(methylsulfinyl)-3-phenylpropanamido)-5-oxohexanoate | 408 |
| 569 | 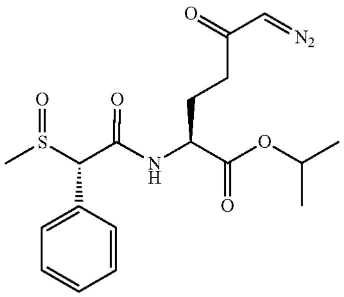 | isopropyl (2S)-6-diazo-2-((2S)-2-(methylsulfinyl)-2-phenylacetamido)-5-oxohexanoate | 394 |
| 570 | 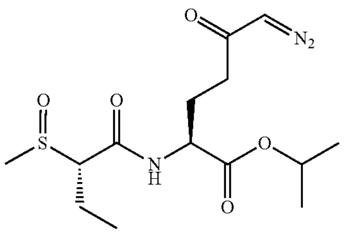 | isopropyl (2S)-6-diazo-2-((2S)-2-(methylsulfinyl) butanamido)-5-oxohexanoate | 346 |

-continued

| Compound | Structure | IUPAC Name | $^{1}$HNMR & MS: (M + H)$^{+}$ |
|---|---|---|---|
| 571 | 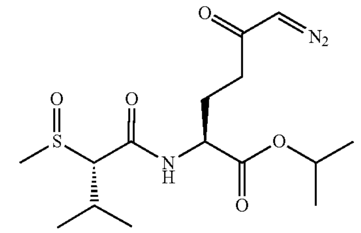 | isopropyl (2S)-6-diazo-2-((2S)-3-methyl-2-(methylsulfinyl) butanamido)-5-oxohexanoate | 360 |
| 572 | 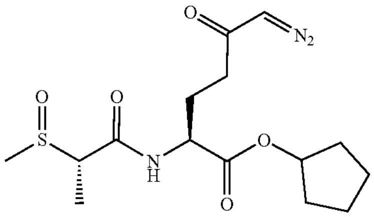 | cyclopentyl (2S)-6-diazo-2-((2S)-2-(methylsulfinyl) propanamido)-5-oxohexanoate | 358 |
| 573 | 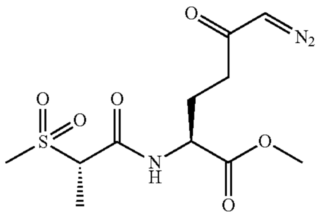 | methyl (S)-6-diazo-2-((S)-2-(methylsulfonyl) propanamido)-5-oxohexanoate | 320 |
| 574 | 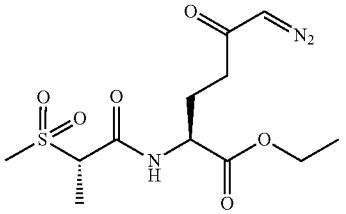 | ethyl (S)-6-diazo-2-((S)-2-(methylsulfonyl) propanamido)-5-oxohexanoate | 334 |
| 575 | 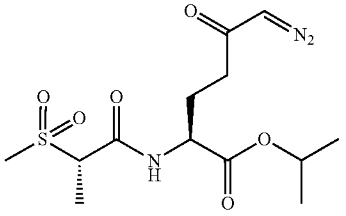 | isopropyl (S)-6-diazo-2-((S)-2-(methylsulfonyl) propanamido)-5-oxohexanoate | 348 |
| 576 | 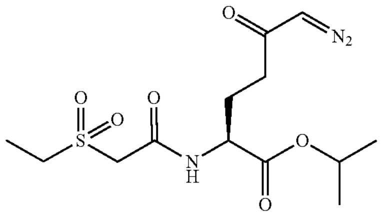 | isopropyl (S)-6-diazo-2-(2-(ethylsulfonyl) acetamido)-5-oxohexanoate | 348 |
| 577 | 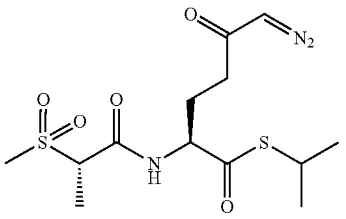 | S-isopropyl (S)-6-diazo-2-((S)-2-(methylsulfonyl) propanamido)-5-oxohexanethioate | 364 |

-continued

| Compound | Structure | IUPAC Name | $^1$HNMR & MS: (M + H)$^+$ |
|---|---|---|---|
| 578 | 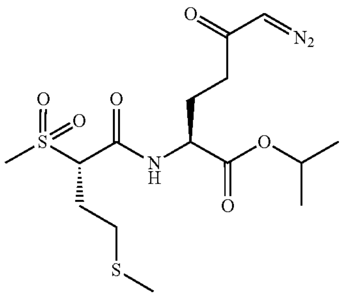 | isopropyl (S)-6-diazo-2-((S)-2-(methylsulfonyl)-4-(methylthio) butanamido)-5-oxohexanoate | 408 |
| 579 | 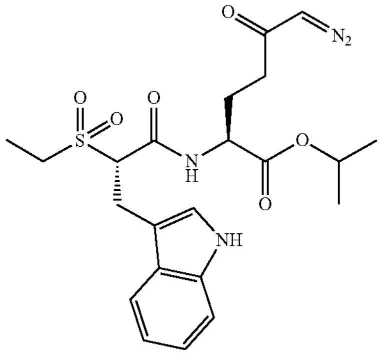 | isopropyl (S)-6-diazo-2-((S)-2-(ethylsulfonyl)-3-(1H-indol-3-yl)propanamido)-5-oxohexanoate | 477 |
| 580 | 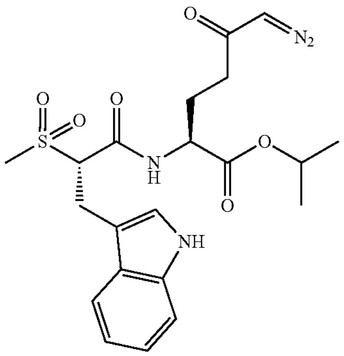 | isopropyl (S)-2-((S)-3-(1H-indol-3-yl)-2-(methylsulfonyl) propanamido)-6-diazo-5-oxohexanoate | 463 |
| 581 | 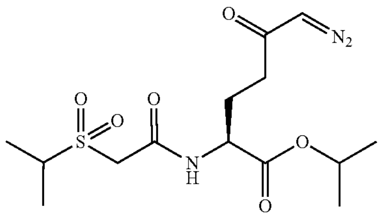 | isopropyl (S)-6-diazo-2-(2-(isopropylsulfonyl) acetamido)-5-oxohexanoate | 362 |
| 582 | 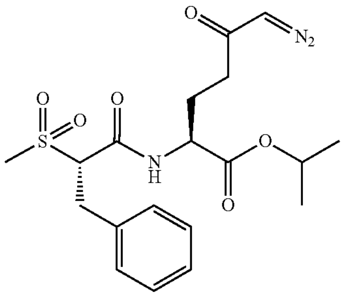 | isopropyl (S)-6-diazo-2-((S)-2-(methylsulfonyl)-3-phenylpropanamido)-5-oxohexanoate | 424 |

-continued

| Compound | Structure | IUPAC Name | $^1$HNMR & MS: (M + H)$^+$ |
|---|---|---|---|
| 583 | 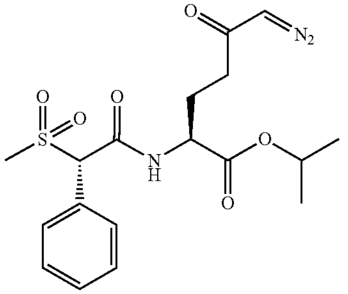 | isopropyl (S)-6-diazo-2-((S)-2-(methylsulfonyl)-2-phenylacetamido)-5-oxohexanoate | 410 |
| 584 | 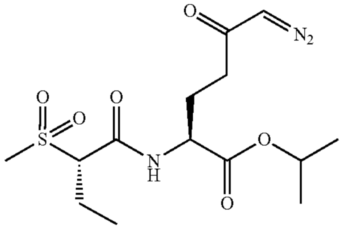 | isopropyl (S)-6-diazo-2-((S)-2-(methylsulfonyl)butanamido)-5-oxohexanoate | 362 |
| 585 | 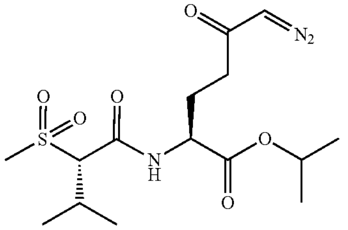 | isopropyl (S)-6-diazo-2-((S)-3-methyl-2-(methylsulfonyl)butanamido)-5-oxohexanoate | 376 |
| 586 | 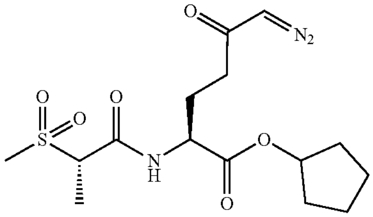 | cyclopentyl (S)-6-diazo-2-((S)-2-(methylsulfonyl)propanamido)-5-oxohexanoate | 374 |

Synthesis of Control Compounds

Compound 60 of WO2017023774 (named "reference compound A") was obtained according to the synthesis route and operation steps of compound 60 in Page 124 of WO2017023774.

Compound 25 of WO2017023774 (named "reference compound 1") was obtained according to the synthesis route and operation steps of compound 25 in Page 100-101 of WO2017023774.

Compound 9 of WO2017023774 (named "reference compound 2") was obtained according to the synthesis route and operation steps of compound 9 in Page 87-88 of WO2017023774.

Compound 47 of WO2017023774 (named "reference compound 3") was obtained according to the synthesis route and operation steps of compound 47 in Page 115-116 of WO2017023774.

Example 7 Plasma Stability of Different Species

Reference compound A, reference compound 1, reference compound 2, compound 2, compound 3, compound 81, compound 443, compound 459 were provided for assay of plasma stability of compounds in different species, and they were shown as below:

Reference Compound A

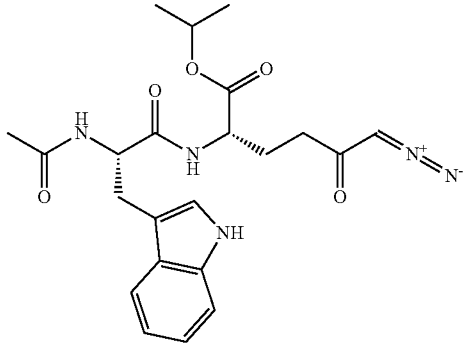

-continued

Reference Compound 1

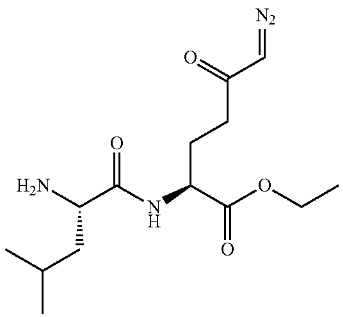

Reference Compound 2

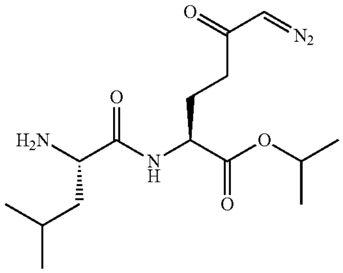

Compound 2

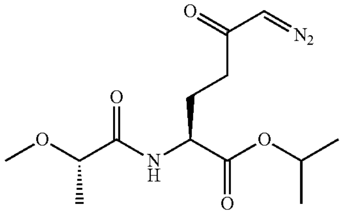

Compound 3

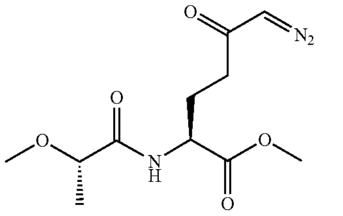

Compound 81

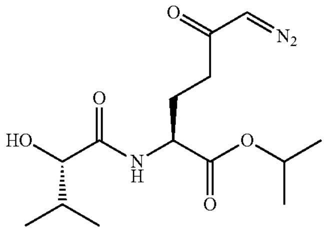

Compound 443

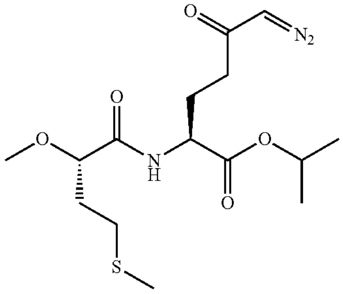

-continued

Compound 459

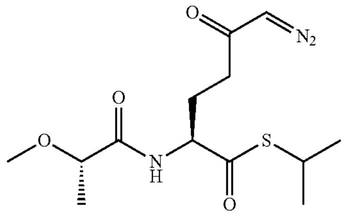

For metabolic stability, plasma from dog, monkey, swine and human were used. For stability, prodrugs (1 μM) were spiked in respective solutions and incubated in an orbital shaker at 37° C. 50 μL aliquots of the mixture in duplicate were removed, and the reaction quenched by addition of four times the volume of ice cold acetonitrile spiked with the internal standard (Dexamethasone 100 ng/mL). The samples were vortexed for 30 s and centrifuged at 15000 g for 5 min. 100 μL of the supernatant was diluted with 100 μL of water and transferred to the 0.6 mL plastic tubes on 96-well plate. Prodrug disappearance was monitored over time using a liquid chromatography and tandem mass spectrometry (LC-MS/MS).

For LC-MS/MS, prodrugs were analyzed on a ExionLC AD HPLC system coupled to REF Triple Quad 5500+ mass spectrometer with an ESI interface on an Phenomenex Kinetex 5 m C18 100A (2.1*50) mm UPLC column. The autosampler was temperature controlled and was operated at 4° C. The mobile phase used for the chromatographic separation was composed of acetonitrile/water containing 0.10% formic acid and will run at a flow rate of 0.6 mL/min for 3.5 min using gradient elution. The column effluent was monitored using TSQ Vantage triple-quadrupole mass-spectrometric detector, equipped with an electrospray probe set in the positive ionization mode. Samples were introduced into the ionization source through a heated nebulized probe (400° C.). Disappearance of prodrugs will be measured from ratio of peak areas of analyte to IS.

For quantification of compound remaining, disappearance of prodrugs was measured from ratio of peak areas of analyte to IS.

FIG. 1 shows the plasma stability of compounds after incubation for 4 hours in the presence of dog, monkey, swine and human plasma. The data show that the Reference compound A, compound 2, compound 3, compound 81, compound 443, compound 459 was substantially intact in the presence of the dog, monkey, swine and human plasma for 4 hours, while few of reference compound 1 and reference compound 2 remained in such conditions.

Example 8 Stability of Liver Microsomes of Different Species

Reference compound A, reference compound 1, reference compound 2, and compound 2, compound 3, compound 81, compound 443, compound 459 were provided for assay of stability of liver microsomes in different species.

For metabolic stability, microsomes from human, monkey, dog, rat and mouse were used. For stability, prodrugs (1 μM) were spiked in each microsomes matrix and incubated in an orbital shaker at 37° C. Aliquots of 50 μL were taken from the reaction solution at 0, 15, 30, 45 and 60 min. The reaction was stopped by the addition of 4 volumes of cold acetonitrile with IS (100 nM alprazolam, 200 nM labetalol, 200 nM caffeine and 2 μM ketoprofen). Samples were centrifuged at 3, 220 g for 40 minutes. Aliquot of 100 μL of the supernatant was mixed with 100 μL of ultra-pure $H_2O$ and then used for LC-MS/MS analysis.

For LC-MS/MS, prodrugs were analyzed on an API 4000 instrument from AB Inc (Canada) with an ESI interface coupled to Shimadzu LC system on an Waters XSelect HSS T3 C18, 2.5 m, 2.1×30 mm column. The mobile phase used for the chromatographic separation was composed of Phase A: water (0.1% formic acid); Phase B: acetonitrile (0.1% formic acid) and will run at a flow rate of 1.0 mL/min for 1.0 min using gradient elution. Samples was introduced into the ionization source through a heated nebulized probe (500° C.). Disappearance of prodrugs will be measured from ratio of peak areas of analyte to IS.

For data analysis, peak areas were determined from extracted ion chromatograms. The slope value, k, was determined by linear regression of the natural logarithm of the remaining percentage of the parent drug vs. incubation time curve. The in vitro half-life (in vitro $t_{1/2}$) was determined from the slope value:

$$\text{in vitro } t_{1/2} = -(0.693/k)$$

Conversion of the in vitro $t_{1/2}$ (min) into the in vitro intrinsic clearance (in vitro $CL_{int}$, in μL/min/mg protein) was done using the following equation (mean of duplicate determinations):

$$\text{in vitro } CL_{int} = \frac{0.693}{t_{1/2}} \times \frac{\text{volume of incubation } (\mu L)}{\text{amount of proteins (mg)}}$$

Table 1 shows the in vitro intrinsic clearance of compounds after incubation for 60 minutes in the presence of human, monkey, dog, rat and mouse liver microsomes.

TABLE 1

In vitro Clint (μL/min/mg protein) of Test Compounds in Different Species of Liver Microsomes

| Compounds | Human | Monkey | Dog | Rat | Mouse |
|---|---|---|---|---|---|
| Reference Compound 1 | 95.34 | 167.25 | 63.64 | 123.55 | 114.88 |
| Reference Compound 2 | 110.42 | 280.56 | 50.25 | 437.21 | 125.68 |
| Reference Compound A | 118.61 | 393.20 | 60.41 | 95.16 | 152.92 |
| Compound 2 | 43.44 | 31.78 | 12.70 | 62.43 | 67.14 |
| Compound 3 | 124.33 | 46.39 | 10.90 | 49.47 | 71.15 |
| Compound 81 | 16.82 | 25.97 | 5.49 | 268.83 | 60.81 |
| Compound 443 | 73.52 | 179.92 | 81.89 | 238.84 | 407.55 |
| Compound 459 | 18.88 | 130.50 | 9.57 | 114.96 | 71.74 |

Example 9 Examination on the Anti-Tumor Efficacy in MC38 Syngeneics in C57BL/6 Mouse Reference compound A, compound 2, compound 3, compound 81, compound 443, compound 459 were provided for the anti-tumor Efficacy in MC38 Syngeneics in C57BL/6 mouse.

Animal species: *Mus musculus*; Strain: C57BL/6; Age: 6-8 weeks; Sex: female.

The MC38 tumor cells were maintained in vitro in DMEM medium supplemented with 10% FBS at 37° C., 5% $CO_2$. The cells growing in an exponential growth phase were harvested and counted for tumor inoculation. The culture MC38 were harvested, re-suspended in PBS containing 50% Matrigel at a density of $1\times10^7$ cells/mL. Each mouse was inoculated subcutaneously in the right flank region with $1\times10^6$ cells in 0.1 mL of PBS containing 50% Matrigel for tumor development.

The treatments were started when the mean tumor size reached 79-118 $mm^3$ (average tumor size 96 $mm^3$). Each group contained 8 tumor bearing mice. Group 1 was treated with Vehicle (10% DMSO+90% Saline), S.C., QD. Group 2 was given treatments with reference compound A at 2 μmol/kg, S.C., QD. Group 3 was given treatments with compound 2 at 2 μmol/kg, S.C., QD. The administration of test articles in each study group was shown in the following Table 2.

In vivo efficacy was examined according to absolute tumor growth inhibition (TGI) and the safety was evaluated according to weight change and survival in mice.

TABLE 2

| Group | Compound | Dose (μmol/kg) | Dosing Route | Schedule |
|---|---|---|---|---|
| 1 | Vehicle | 2 | S.C. | QD × 16 |
| 2 | Reference compound A | 2 | S.C. | QD × 26 |
| 3 | Compound 2 | 2 | S.C. | QD × 26 |

Body Weight

Figure 2:
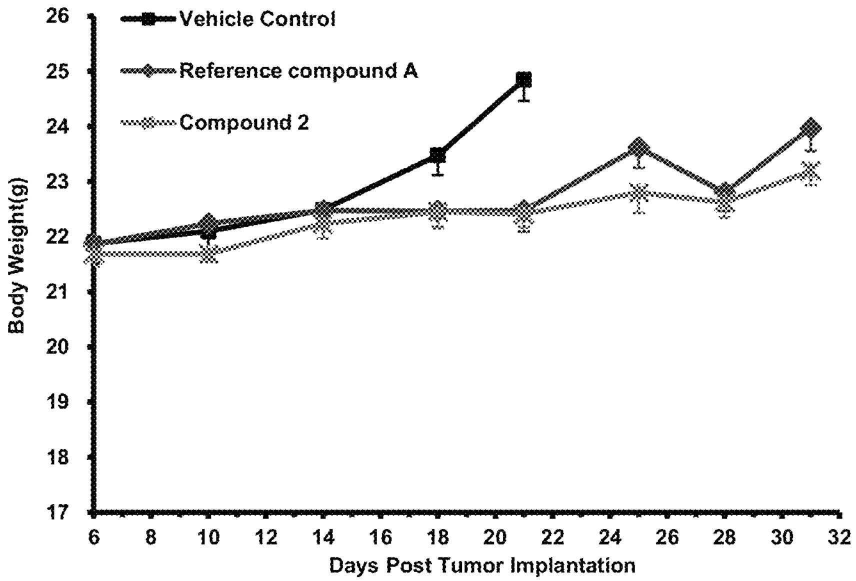
FIG. 2 shows the body weight changes following administration of Reference compound A and Compound 2 in C57BL/6 mice bearing MC38 tumors.

The results of the body weight changes in the tumor-bearing mice are shown in Table 3, FIG. 2.

TABLE 3

The body weight changes (%) of the mice in different groups

| | Dose | BW(g) (Mean ± SEM) | | BW Change |
|---|---|---|---|---|
| Compound | (μmol/kg) | Beginning (D6) | End (D21) | (%) |
| Vehicle | 2 | 21.9 ± 0.4 | 24.9 ± 0.4 | +13.6 |
| Reference Compound A | 2 | 21.9 ± 0.3 | 22.5 ± 0.4 | +2.8 |
| Compound 2 | 2 | 21.7 ± 0.2 | 22.4 ± 0.2 | +3.3 |

Tumor Volumes

Figure 3:
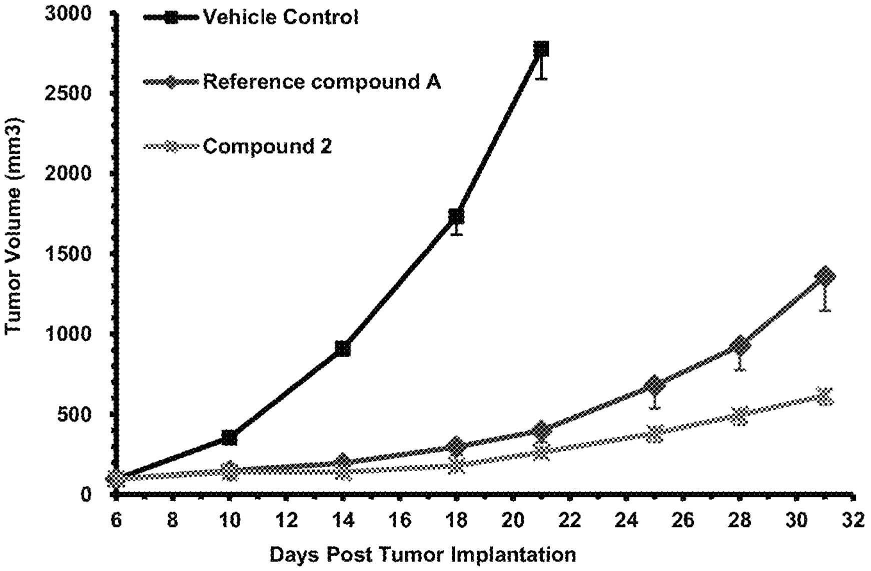
FIG. 3 shows the anti-tumor efficacy of Reference compound A and Compound 2 in C57BL/6 mice bearing MC38 tumors.

The results of tumor sizes in different groups at different time points post tumor inoculation are shown in Table 4 and FIG. 3. The tumor growth inhibition is summarized in Table 5. The result showed that the other treatment groups showed significant anti-tumor effect when compared to the vehicle group. Statistical analysis of difference in tumor volume among the groups was performed using one-way ANOVA followed by individual comparisons using Games-Howell post-hoc test (equal variance not assumed). All data was analyzed using SPSS 22.0 software.

TABLE 4

Mean tumor volume in the different treatment groups

| Compound | Dose (μmol/kg) | TV ($mm^3$) (Mean ± SEM) D6 | D10 | D14 | D18 | D21 | D25 | D28 | D31 |
|---|---|---|---|---|---|---|---|---|---|
| Vehicle | 2 | 96 ± 4 | 354 ± 17 | 909 ± 42 | 1732 ± 114 | 2778 ± 188 | | | |
| Reference compound A | 2 | 96 ± 4 | 148 ± 6 | 196 ± 25 | 297 ± 48 | 399 ± 74 | 680 ± 143 | 928 ± 153 | 1358 ± 213 |
| Compound 2 | 2 | 96 ± 4 | 141 ± 9 | 140 ± 10 | 180 ± 13 | 263 ± 32 | 381 ± 55 | 496 ± 62 | 617 ± 56 |

TABLE 5

Anti-tumor activity of test compounds in MC38 syngeneic model

| Compound | Dose (μmol/kg) | TV ($mm^3$) at D21 (Mean ± SEM) | T/C (%) | TGI (%) | Pvalue (vs. Vehicle) |
|---|---|---|---|---|---|
| Vehicle | 2 | 2778 ± 188 | — | — | — |
| Reference Compound A | 2 | 399 ± 74 | 14.4 | 85.6 | 0.000 |
| Compound 2 | 2 | 263 ± 32 | 9.5 | 90.5 | 0.000 |

Example 10 Examination on the Anti-Tumor Efficacy in MC38 Model in CES1c −/− Mouse Reference compound A and compound 2 obtained from example 2 were provided for the anti-tumor Efficacy in MC38 model in CES1c −/− mouse.

Animal species: *Mus musculus*; Strain: C57BL/6-Ces1c$^{emISmoc}$; Age: 6-8 weeks; Sex: female. (Shanghai Model Organisms). The MC38 tumor cells were maintained in vitro in DMEM medium supplemented with 10% FBS at 37° C., 5% $CO_2$. The cells growing in an exponential growth phase were harvested and counted for tumor inoculation. The culture MC38 were harvested, re-suspended in PBS containing 50% Matrigel at a density of $1\times10^7$ cells/mL. Each mouse was inoculated subcutaneously in the right flank region with $1\times10^6$ in 0.1 mL of PBS containing 50% Matrigel for tumor development.

The treatments were started when the mean tumor size reached 52-132 $mm^3$ (average tumor size 95 $mm^3$). Each group contained 5 tumor bearing mice. Group 1 was treated with Vehicle (10% DMSO+90% Saline), S.C., QD(Subcutaneous injection, quaque die). Group 2 was given treatments with reference compound A at 2 μmol/kg, S.C., QD. Group 3 was given treatments with compound 2 at 2 μmol/kg, S.C., QD. The administration of test articles in each study group was shown in the following Table 6.

In vivo efficacy was examined according to absolute tumor growth inhibition (TGI) and the safety was evaluated according to weight change and survival in mice.

TABLE 6

| Group | Compound | Dose (μmol/kg) | Dosing Route | Schedule |
|---|---|---|---|---|
| 1 | Vehicle | 2 | S.C. | QD × 21 |
| 2 | Reference compound A | 2 | S.C. | QD × 21 |
| 3 | Compound 2 | 2 | S.C. | QD × 21 |

Body Weight

Figure 4:
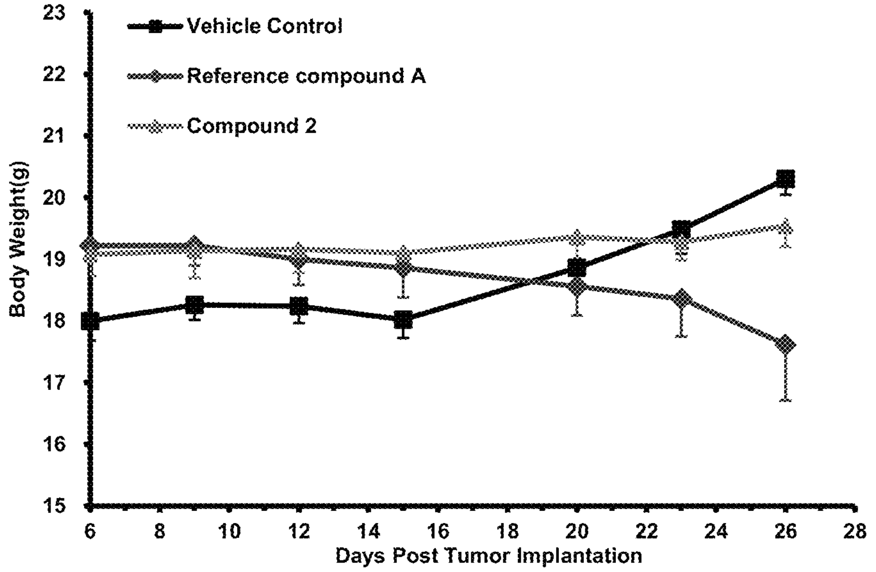
FIG. 4 shows the body weight changes following administration of Reference compound A and Compound 2 in CES1−/− mice bearing MC38 tumors.

Group treated with reference compound A showed some body weight loss, but the group treated with vehicle and the group treated with compound 2 were well-tolerated by the tumor-bearing mice. The results of the body weight changes in the tumor-bearing mice are shown in Table 7, FIG. 4.

TABLE 7

The body weight changes (%) of the mice in different groups

| Compound | Dose (μmol/kg) | BW(g) (Mean ± SEM) Beginning (D6) | End (D26) | BW Change (%) |
|---|---|---|---|---|
| Vehicle | 2 | 18.0 ± 0.3 | 20.3 ± 0.3 | +12.8 |
| Reference Compound A | 2 | 19.2 ± 0.2 | 17.6 ± 0.9 | −8.3 |
| Compound 2 | 2 | 19.1 ± 0.3 | 19.5 ± 0.3 | +2.4 |

Tumor Volumes

Figure 5:
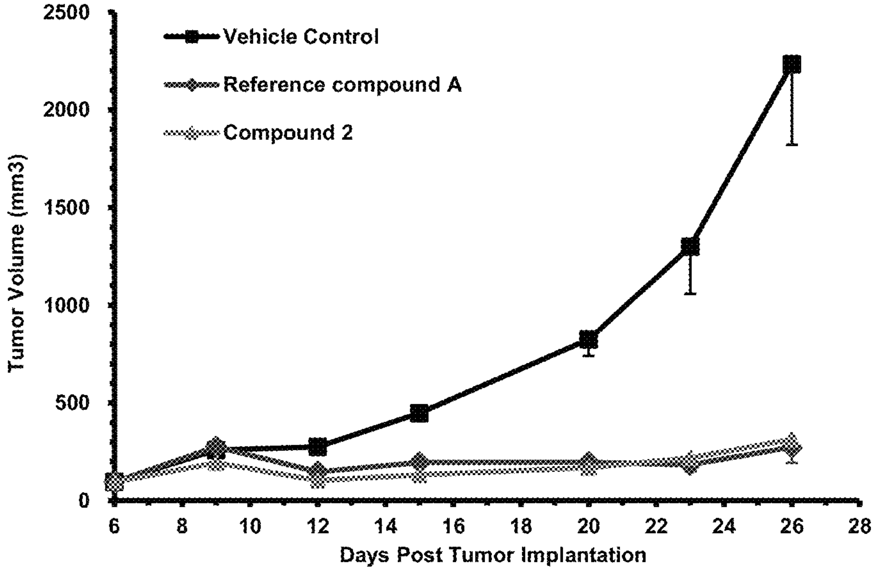
FIG. 5 shows the anti-tumor efficacy of Reference compound A and Compound 2 in CES1−/− mice bearing MC38 tumors.

The results of tumor sizes in different groups at different time points post tumor inoculation are shown in Table 8 and FIG. 5. The tumor growth inhibition is summarized in Table 9. The result showed that all treatment groups showed significant anti-tumor effect when compared to the vehicle group. Statistical analysis of difference in tumor volume among the groups was performed using one-way ANOVA followed by individual comparisons using Games-Howell post-hoc test (equal variance not assumed). All data was analyzed using SPSS 22.0 software.

TABLE 8

Mean tumor volume in the different treatment groups

| Compound | Dose (μmol/kg) | TV ($mm^3$) (Mean ± SEM) D6 | D9 | D12 | D15 | D20 | D23 | D26 |
|---|---|---|---|---|---|---|---|---|
| Vehicle | 2 | 95 ± 13 | 259 ± 13 | 275 ± 22 | 448 ± 29 | 825 ± 85 | 1300 ± 242 | 2234 ± 413 |
| Reference Compound A | 2 | 95 ± 6 | 275 ± 33 | 147 ± 5 | 195 ± 23 | 196 ± 33 | 183 ± 33 | 274 ± 81 |
| Compound 2 | 2 | 95 ± 11 | 193 ± 20 | 103 ± 15 | 131 ± 21 | 169 ± 19 | 219 ± 21 | 313 ± 35 |

TABLE 9

Anti-tumor activity of test compounds in MC38 syngeneic model

| Compound | Dose (μmol/kg) | TV ($mm^3$) at D26 (Mean ± SEM) | T/C (%) | TGI (%) | P value (vs. Vehicle) |
|---|---|---|---|---|---|
| Vehicle | 2 | 2234 ± 413 | — | — | — |
| Reference Compound A | 2 | 274 ± 81 | 12.3 | 87.7 | 0.046 |
| Compound 2 | 2 | 313 ± 35 | 14.0 | 86.0 | 0.052 |

Example 11 Examination on the Anti-Tumor Efficacy in MC38 Model in C57BL/6 Mouse Compound 2, compound 3, compound 81, compound 443 and compound 459 were provided for the anti-tumor Efficacy in MC38 model in C57BL/6 mouse.

Animal species: *Mus musculus*; Strain: C57BL/6; Age: 6-8 weeks; Sex: female. The MC38 tumor cells were maintained in vitro in DMEM medium supplemented with 10% FBS at 37° C., 5% $CO_2$. The cells growing in an exponential growth phase were harvested and counted for tumor inoculation. The culture MC38 were harvested, re-suspended in PBS containing 50% Matrigel at a density of $1\times10^7$ cells/mL. Each mouse was inoculated subcutaneously in the right flank region with $1\times10^6$ cells in 0.1 mL of PBS containing 50% Matrigel for tumor development.

The treatments were started when the mean tumor size reached 82-129 $mm^3$ (average tumor size 102 $mm^3$). Each group contained 6 tumor bearing mice. Group 1 was treated with Vehicle (10% DMSO+90% Saline), S.C., QD. Group 2 was given treatments with compound 2 at 2 μmol/kg, S.C., QD. Group 3 was given treatments with compound 81 at 2 μmol/kg, S.C., QD. Group 4 was given treatments with compound 443 at 2 μmol/kg, S.C., QD. Group 5 was given treatments with compound 459 at 2 μmol/kg, S.C., QD. Group 6 was given treatments with compound 3 at 2 μmol/kg, S.C., QD. The administration of test articles in each study group was shown in the following Table 10.

In vivo efficacy was examined according to absolute tumor growth inhibition (TGI) and the safety was evaluated according to weight change and survival in mice.

TABLE 10

| Group | Compound | Dose (μmol/kg) | Dosing Route | Schedule |
|---|---|---|---|---|
| 1 | Vehicle | 2 | S.C. | QD × 15 |
| 2 | Compound 2 | 2 | S.C. | QD × 15 |
| 3 | Compound 81 | 2 | S.C. | QD × 15 |
| 4 | Compound 443 | 2 | S.C. | QD × 15 |

TABLE 10-continued

| Group | Compound | Dose (μmol/kg) | Dosing Route | Schedule |
|---|---|---|---|---|
| 5 | Compound 459 | 2 | S.C. | QD × 15 |
| 6 | Compound 3 | 2 | S.C. | QD × 15 |

Body Weight

Figure 6:
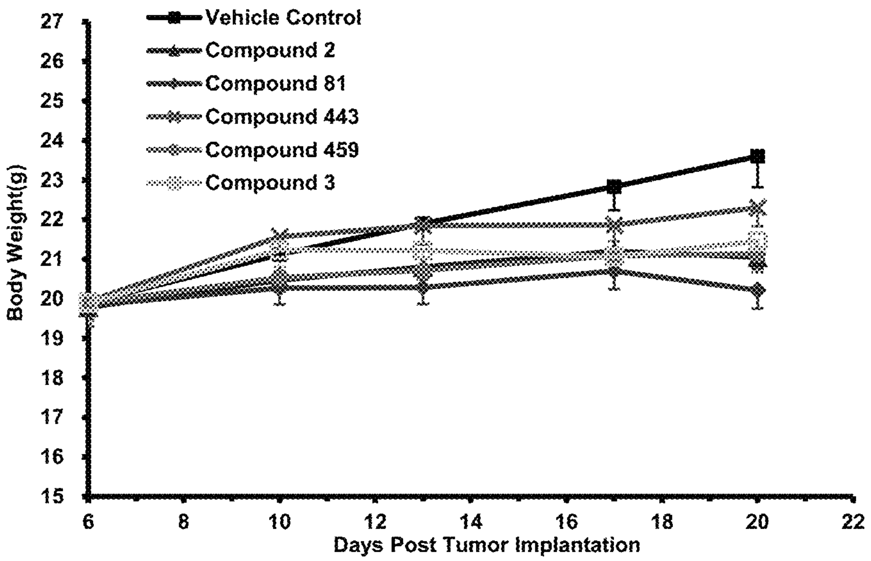
FIG. 6 shows the body weight changes following administration of Compound 2, compound 3, compound 81, compound 443 and compound 459 in C57BL/6 mice bearing MC38 tumors.

The results of the body weight changes in the tumor-bearing mice are shown in Table 11, FIG. 6.

TABLE 11

The body weight changes (%) of the mice in different groups

| Compound | Dose (μmol/kg) | BW(g) (Mean ± SEM) Beginning (D6) | End (D20) | BW Change (%) |
|---|---|---|---|---|
| Vehicle | 2 | 19.9 ± 0.5 | 23.6 ± 0.8 | +18.6 |
| Compound 2 | 2 | 19.8 ± 0.2 | 21.1 ± 0.3 | +6.4 |
| Compound 81 | 2 | 19.8 ± 0.3 | 20.2 ± 0.5 | +1.9 |
| Compound 443 | 2 | 19.9 ± 0.6 | 22.3 ± 0.5 | +11.9 |
| Compound 459 | 2 | 19.9 ± 0.3 | 21.1 ± 0.5 | +6.3 |
| Compound 3 | 2 | 19.9 ± 0.5 | 21.5 ± 0.4 | +7.8 |

Tumor Volumes

Figure 7:
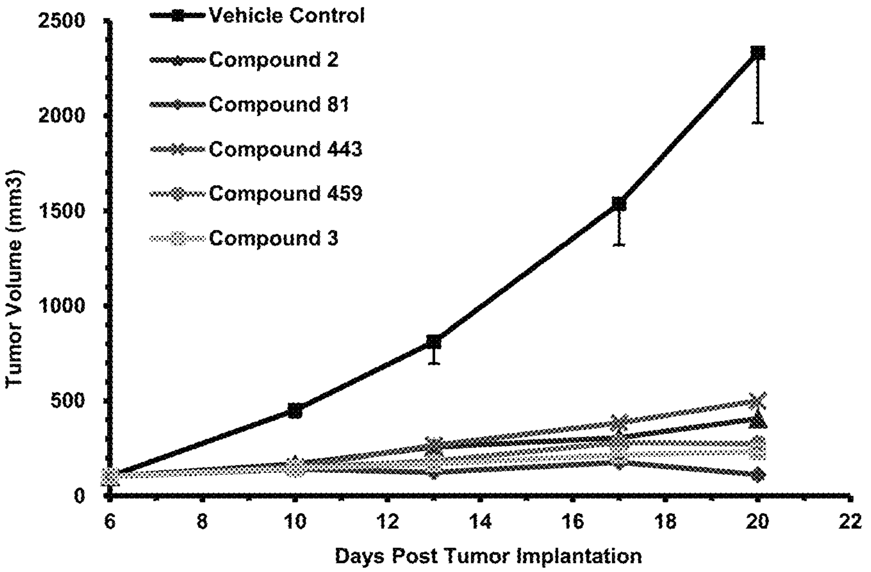
FIG. 7 shows the anti-tumor efficacy of Compound 2, compound 3, compound 81, compound 443 and compound 459 in C57BL/6 mice bearing MC38 tumors.

The results of tumor sizes in different groups at different time points post tumor inoculation are shown in Table 12 and FIG. 7. The tumor growth inhibition is summarized in Table 13. The result showed that the other treatment groups showed significant anti-tumor effect when compared to the vehicle group. Statistical analysis of difference in tumor volume among the groups was performed using one-way ANOVA followed by individual comparisons using Games-Howell post-hoc test (equal variance not assumed). All data was analyzed using SPSS 22.0 software.

TABLE 12

Mean tumor volume in the different treatment groups

| Compound | Dose (μmol/kg) | TV ($mm^3$) (Mean ± SEM) D6 | D10 | D13 | D17 | D20 |
|---|---|---|---|---|---|---|
| Vehicle | 2 | 102 ± 5 | 451 ± 37 | 810 ± 114 | 1537 ± 216 | 2331 ± 369 |
| Compound 2 | 2 | 102 ± 7 | 167 ± 17 | 257 ± 51 | 306 ± 43 | 407 ± 33 |
| Compound 81 | 2 | 102 ± 6 | 141 ± 9 | 124 ± 10 | 176 ± 13 | 112 ± 22 |
| Compound 443 | 2 | 102 ± 6 | 152 ± 25 | 267 ± 65 | 384 ± 95 | 500 ± 119 |
| Compound 459 | 2 | 102 ± 5 | 148 ± 22 | 183 ± 30 | 281 ± 65 | 275 ± 59 |
| Compound 3 | 2 | 102 ± 6 | 145 ± 16 | 169 ± 9 | 215 ± 27 | 233 ± 31 |

TABLE 13

Anti-tumor activity of test compounds in MC38 syngeneic model

| Compound | Dose (μmol/kg) | TV ($mm^3$) at D21 (Mean ± SEM) | T/C (%) | TGI (%) | P value (vs. Vehicle) |
|---|---|---|---|---|---|
| Vehicle | 2 | 2331 ± 369 | — | — | — |
| Compound 2 | 2 | 407 ± 33 | 17.5 | 82.5 | 0.022 |
| Compound 81 | 2 | 112 ± 22 | 4.8 | 95.2 | 0.012 |
| Compound 443 | 2 | 500 ± 119 | 21.5 | 78.5 | 0.023 |
| Compound 459 | 2 | 275 ± 59 | 11.8 | 88.2 | 0.016 |
| Compound 3 | 2 | 233 ± 31 | 10.0 | 90.0 | 0.015 |

What is claimed is:

1. A compound or a pharmaceutically acceptable salt thereof, a stereoisomer thereof, a tautomer thereof, and an isotopic substitution thereof, wherein the compound is selected from:

| | |
|---|---|
| 1 | isopropyl (S)-6-diazo-2-((S)-2-methoxypropanamido)-5-oxohexanoate |
| 2 | methyl (S)-6-diazo-2-((S)-2-methoxypropanamido)-5-oxohexanoate |
| 3 | (S)-6-diazo-2-((S)-2-methoxypropanamido)-5-oxohexanoic acid |
| 4 | ethyl (S)-6-diazo-2-((S)-2-methoxypropanamido)-5-oxohexanoate |
| 5 | isopropyl (S)-6-diazo-2-(2-methoxyacetamido)-5-oxohexanoate |
| 6 | isopropyl (S)-6-diazo-2-(2-ethoxyacetamido)-5-oxohexanoate |
| 7 | isopropyl (S)-6-diazo-2-((S)-2-hydroxypropanamido)-5-oxohexanoate |
| 8 | isopropyl (S)-6-diazo-2-((S)-2-hydroxy-4-methylpentanamido)-5-oxohexanoate |
| 9 | isopropyl (S)-6-diazo-2-((S)-2-ethoxypropanamido)-5-oxohexanoate |
| 10 | isopropyl (S)-6-diazo-2-((S)-2-isopropoxypropanamido)-5-oxohexanoate |
| 11 | isopropyl (S)-6-diazo-2-(2-hydroxyacetamido)-5-oxohexanoate |
| 12 | isopropyl (S)-6-diazo-2-((S)-2-hydroxybutanamido)-5-oxohexanoate |
| 13 | isopropyl (S)-6-diazo-2-((S)-2-methoxybutanamido)-5-oxohexanoate |
| 14 | isopropyl (S)-6-diazo-2-((S)-2-ethoxybutanamido)-5-oxohexanoate |
| 15 | isopropyl (S)-6-diazo-2-((S)-2-isopropoxybutanamido)-5-oxohexanoate |
| 16 | isopropyl (S)-6-diazo-2-((S)-2-hydroxy-3-methylbutanamido)-5-oxohexanoate |
| 17 | isopropyl (S)-6-diazo-2-((S)-2-methoxy-3-methylbutanamido)-5-oxohexanoate |
| 18 | isopropyl (S)-6-diazo-2-((S)-2-ethoxy-3-methylbutanamido)-5-oxohexanoate |
| 19 | isopropyl (S)-6-diazo-2-((S)-2-isopropoxy-3-methylbutanamido)-5-oxohexanoate |
| 20 | isopropyl (S)-6-diazo-2-((2S,3R)-2-hydroxy-3-methylpentanamido)-5-oxohexanoate |
| 21 | isopropyl (S)-6-diazo-2-((2S,3R)-2-methoxy-3-methylpentanamido)-5-oxohexanoate |
| 22 | isopropyl (S)-6-diazo-2-((2S,3R)-2-ethoxy-3-methylpentanamido)-5-oxohexanoate |
| 23 | isopropyl (S)-6-diazo-2-((2S,3R)-2-isopropoxy-3-methylpentanamido)-5-oxohexanoate |
| 24 | isopropyl (S)-6-diazo-2-((S)-2-hydroxypentanamido)-5-oxohexanoate |
| 25 | isopropyl (S)-6-diazo-2-((S)-2-methoxypentanamido)-5-oxohexanoate |
| 26 | isopropyl (S)-6-diazo-2-((S)-2-ethoxypentanamido)-5-oxohexanoate |
| 27 | isopropyl (S)-6-diazo-2-((S)-2-isopropoxypentanamido)-5-oxohexanoate |
| 28 | isopropyl (S)-6-diazo-2-((S)-2-methoxy-4-methylpentanamido)-5-oxohexanoate |
| 29 | isopropyl (S)-6-diazo-2-((S)-2-ethoxy-4-methylpentanamido)-5-oxohexanoate |
| 30 | isopropyl (S)-6-diazo-2-((S)-2-isopropoxy-4-methylpentanamido)-5-oxohexanoate |
| 31 | isopropyl (S)-6-diazo-2-((S)-2-hydroxy-3,3-dimethylbutanamido)-5-oxohexanoate |
| 32 | isopropyl (S)-6-diazo-2-((S)-2-methoxy-3,3-dimethylbutanamido)-5-oxohexanoate |
| 33 | isopropyl (S)-6-diazo-2-((S)-2-ethoxy-3,3-dimethylbutanamido)-5-oxohexanoate |
| 34 | isopropyl (S)-6-diazo-2-((S)-2-isopropoxy-3,3-dimethylbutanamido)-5-oxohexanoate |
| 35 | isopropyl (S)-6-diazo-2-((S)-2-hydroxyhexanamido)-5-oxohexanoate |
| 36 | isopropyl (S)-6-diazo-2-((S)-2-methoxyhexanamido)-5-oxohexanoate |
| 37 | isopropyl (S)-6-diazo-2-((S)-2-ethoxyhexanamido)-5-oxohexanoate |
| 38 | isopropyl (S)-6-diazo-2-((S)-2-isopropoxyhexanamido)-5-oxohexanoate |
| 39 | isopropyl (S)-6-diazo-2-(3-methoxy-2-oxopropanamido)-5-oxohexanoate |
| 40 | isopropyl (S)-6-diazo-2-(3-hydroxy-2-oxopropanamido)-5-oxohexanoate |
| 41 | isopropyl (S)-6-diazo-2-(3-hydroxypropanamido)-5-oxohexanoate |
| 42 | isopropyl (S)-6-diazo-2-((S)-3-hydroxybutanamido)-5-oxohexanoate |
| 43 | isopropyl (S)-6-diazo-2-(3-methoxypropanamido)-5-oxohexanoate |
| 44 | isopropyl (S)-6-diazo-2-((S)-3-methoxybutanamido)-5-oxohexanoate |
| 45 | isopropyl (S)-6-diazo-2-((S)-3-hydroxy-2-methylpropanamido)-5-oxohexanoate |
| 46 | isopropyl (S)-6-diazo-2-((S)-3-methoxy-2-methylpropanamido)-5-oxohexanoate |
| 47 | isopropyl (S)-6-diazo-2-((2S,3R)-3-hydroxy-2-methylbutanamido)-5-oxohexanoate |
| 48 | isopropyl (S)-6-diazo-2-((2S,3R)-3-methoxy-2-methylbutanamido)-5-oxohexanoate |
| 49 | isopropyl (S)-6-diazo-2-((2R,3R)-3-hydroxy-2-methylbutanamido)-5-oxohexanoate |

-continued

| | |
|---|---|
| 50 | isopropyl (S)-6-diazo-2-((2R,3R)-3-methoxy-2-methylbutanamido)-5-oxohexanoate |
| 51 | isopropyl (S)-6-diazo-2-((2R,3S)-3-hydroxy-2-methylbutanamido)-5-oxohexanoate |
| 52 | isopropyl (S)-6-diazo-2-((2R,3S)-3-methoxy-2-methylbutanamido)-5-oxohexanoate |
| 53 | isopropyl (S)-6-diazo-2-((R)-3-hydroxybutanamido)-5-oxohexanoate |
| 54 | isopropyl (S)-6-diazo-2-((2S,3S)-3-hydroxy-2-methylbutanamido)-5-oxohexanoate |
| 55 | isopropyl (S)-6-diazo-2-((2S,3S)-3-methoxy-2-methylbutanamido)-5-oxohexanoate |
| 56 | isopropyl (S)-6-diazo-2-((R)-3-methoxybutanamido)-5-oxohexanoate |
| 57 | isopropyl (S)-6-diazo-2-((R)-3-hydroxy-2-methylpropanamido)-5-oxohexanoate |
| 58 | isopropyl (S)-6-diazo-2-((R)-3-methoxy-2-methylpropanamido)-5-oxohexanoate |
| 59 | tert-butyl (S)-6-diazo-2-((S)-2-methoxypropanamido)-5-oxohexanoate |
| 60 | tert-butyl (S)-6-diazo-2-((R)-2-methoxypropanamido)-5-oxohexanoate |
| 61 | isopropyl (S)-6-diazo-2-((S)-2-methoxy-4-(methylthio)butanamido)-5-oxohexanoate |
| 62 | isopropyl (S)-6-diazo-2-(2-hydroxy-2-methylpropanamido)-5-oxohexanoate |
| 63 | methyl (S)-6-diazo-2-((S)-2-methoxy-4-(methylthio)butanamido)-5-oxohexanoate |
| 64 | methyl (S)-6-diazo-2-((S)-2-hydroxy-3-methylbutanamido)-5-oxohexanoate |
| 65 | methyl (S)-6-diazo-2-(2-isopropoxyacetamido)-5-oxohexanoate |
| 66 | (S)-6-diazo-2-((S)-2-hydroxypropanamido)-5-oxohexanoic acid |
| 67 | isopropyl (S)-6-diazo-2-(2-isopropoxyacetamido)-5-oxohexanoate |
| 68 | methyl (S)-6-diazo-2-(2-methoxyacetamido)-5-oxohexanoate |
| 69 | S-isopropyl (S)-6-diazo-2-((S)-2-methoxypropanamido)-5-oxohexanethioate |
| 70 | (S)-6-diazo-2-((S)-2-methoxy-4-(methylthio)butanamido)-5-oxohexanoic acid |
| 71 | isopropyl (S)-6-diazo-2-((S)-2-(methoxy-d3)propanamido)-5-oxohexanoate |
| 72 | (S)-6-diazo-2-((S)-2-(methoxy-d3)propanamido)-5-oxohexanoic acid |
| 73 | methyl (S)-6-diazo-2-((S)-2-(methoxy-d3)propanamido)-5-oxohexanoate |
| 74 | ethyl (S)-6-diazo-2-((S)-2-(methoxy-d3)propanamido)-5-oxohexanoate |
| 75 | S-isopropyl (S)-6-diazo-2-((S)-2-(methoxy-d3)propanamido)-5-oxohexanethioate |
| 76 | isopropyl (S)-6-diazo-2-((S)-2-(methoxy-d3)-4-(methylthio) butanamido)-5-oxohexanoate |
| 77 | methyl-d3 (S)-6-diazo-2-((S)-2-methoxypropanamido)-5-oxohexanoate |
| 78 | ethyl-2,2,2-d3 (S)-6-diazo-2-((S)-2-methoxypropanamido)-5-oxohexanoate |
| 79 | isopropyl (S)-6-diazo-2-(2-(ethoxy-2,2,2-d3)acetamido)-5-oxohexanoate |
| 80 | isopropyl (S)-6-diazo-2-(2-(ethoxy-d5)acetamido)-5-oxohexanoate |
| 81 | ethyl-d5 (S)-6-diazo-2-((S)-2-methoxypropanamido)-5-oxohexanoate |
| 82 | propan-2-yl-d7 (S)-6-diazo-2-((S)-2-methoxypropanamido)-5-oxohexanoate |
| 83 | propan-2-yl-d7 (S)-6-diazo-2-((S)-2-hydroxypropanamido)-5-oxohexanoate |
| 84 | propan-2-yl-d7 (S)-6-diazo-2-((S)-2-hydroxy-3-methylbutanamido)-5-oxohexanoate |
| 85 | propan-2-yl-d7 (S)-6-diazo-2-(2-ethoxyacetamido)-5-oxohexanoate |
| 86 | S-(propan-2-yl-d7) (S)-6-diazo-2-((S)-2-methoxypropanamido)-5-oxohexanethioate |
| 87 | propan-2-yl-d7 (S)-6-diazo-2-((S)-2-methoxy-4-(methylthio) butanamido)-5-oxohexanoate |
| 88 | methyl-d3 (S)-6-diazo-2-((S)-2-(methoxy-d3)propanamido)-5-oxohexanoate |
| 89 | ethyl-2,2,2-d3 (S)-6-diazo-2-((S)-2-(methoxy-d3)propanamido)-5-oxohexanoate |
| 90 | ethyl-d5 (S)-6-diazo-2-((S)-2-(methoxy-d3)propanamido)-5-oxohexanoate |
| 91 | propan-2-yl-d7 (S)-6-diazo-2-((S)-2-(methoxy-d3)propanamido)-5-oxohexanoate |
| 92 | propan-2-yl-d7 (S)-6-diazo-2-(2-(ethoxy-2,2,2-d3)acetamido)-5-oxohexanoate |
| 93 | S-(propan-2-yl-d7) (S)-6-diazo-2-((S)-2-(methoxy-d3)propanamido)-5-oxohexanethioate |
| 94 | propan-2-yl-d7 (S)-6-diazo-2-((S)-2-(methoxy-d3)-4-(methylthio)butanamido)-5-oxohexanoate |
| 95 | propan-2-yl-d7 (S)-6-diazo-2-(2-(ethoxy-d5)acetamido)-5-oxohexanoate |

-continued

| | |
|---|---|
| 96 | methyl 6-diazo-2-((S)-2-methoxypropanamido)-5-oxohexanoate-2-d |
| 97 | ethyl 6-diazo-2-((S)-2-methoxypropanamido)-5-oxohexanoate-2-d |
| 98 | isopropyl 6-diazo-2-((S)-2-methoxypropanamido)-5-oxohexanoate-2-d |
| 99 | isopropyl 6-diazo-2-(2-ethoxyacetamido)-5-oxohexanoate-2-d |
| 100 | S-isopropyl 6-diazo-2-((S)-2-methoxypropanamido)-5-oxohexanethioate-2-d |
| 101 | isopropyl 6-diazo-2-((S)-2-methoxy-4-(methylthio)butanamido)-5-oxohexanoate-2-d |
| 102 | isopropyl 6-diazo-2-((S)-2-hydroxypropanamido)-5-oxohexanoate-2-d |
| 103 | isopropyl 6-diazo-2-((S)-2-hydroxy-3-methylbutanamido)-5-oxohexanoate-2-d |
| 104 | propan-2-yl-1,1,1,3,3,3-d6 (S)-6-diazo-2-((S)-2-(methoxy-d3)propanamido)-5-oxohexanoate |
| 105 | propan-2-yl-1,1,1,3,3,3-d6 (S)-6-diazo-2-(2-(ethoxy-2,2,2-d3) acetamido)-5-oxohexanoate |
| 106 | S-(propan-2-yl-1,1,1,3,3,3-d6) (S)-6-diazo-2-((S)-2-(methoxy-d3)propanamido)-5-oxohexanethioate |
| 107 | propan-2-yl-1,1,1,3,3,3-d6 (S)-6-diazo-2-((S)-2-(methoxy-d3)-4-(methylthio)butanamido)-5-oxohexanoate |
| 108 | propan-2-yl-1,1,1,3,3,3-d6 (S)-6-diazo-2-(2-(ethoxy-d5)acetamido)-5-oxohexanoate |
| 109 | propan-2-yl-1,1,1,3,3,3-d6 (S)-6-diazo-2-((S)-2-hydroxypropanamido)-5-oxohexanoate |
| 110 | propan-2-yl-1,1,1,3,3,3-d6 (S)-6-diazo-2-((S)-2-hydroxy-3-methylbutanamido)-5-oxohexanoate |
| 111 | propan-2-yl-1,1,1-d3 (2S)-6-diazo-2-((S)-2-(methoxy-d3) propanamido)-5-oxohexanoate |
| 112 | propan-2-yl-1,1,1-d3 (2S)-6-diazo-2-(2-(ethoxy-2,2,2-d3)acetamido)-5-oxohexanoate |
| 113 | S-(propan-2-yl-1,1,1-d3) (2S)-6-diazo-2-((S)-2-(methoxy-d3 )propanamido)-5-oxohexanethioate |
| 114 | propan-2-yl-1, 1,1-d3 (2S)-6-diazo-2-((S)-2-(methoxy-d3)-4-(methylthio)butanamido)-5-oxohexanoate |
| 115 | propan-2-yl-1,1,1-d3 (2S)-6-diazo-2-(2-(ethoxy-d5)acetamido)-5-oxohexanoate |
| 116 | propan-2-yl-1,1,1-d3 (2S)-6-diazo-2-((S)-2-hydroxypropanamido)-5-oxohexanoate |
| 117 | propan-2-yl-1,1,1-d3 (2S)-6-diazo-2-((S)-2-hydroxy-3-methylbutanamido)-5-oxohexanoate |
| 118 | propan-2-yl-1,1,1,3,3,3-d6 (S)-6-diazo-2-((S)-2-methoxypropanamido)-5-oxohexanoate |
| 119 | propan-2-yl-1,1,1,3,3,3-d6 (S)-6-diazo-2-(2-ethoxyacetamido)-5-oxohexanoate |
| 120 | S-(propan-2-yl-1,1,1,3,3,3-d6) (S)-6-diazo-2-((S)-2-methoxypropanamido)-5-oxohexanethioate |
| 121 | propan-2-yl-1,1,1,3,3,3-d6 (S)-6-diazo-2-((S)-2-methoxy-4-(methylthio)butanamido)-5-oxohexanoate |
| 122 | propan-2-yl-1,1,1-d3 (2S)-6-diazo-2-((S)-2-methoxypropanamido)-5-oxohexanoate |
| 123 | propan-2-yl-1,1,1-d3 (2S)-6-diazo-2-(2-ethoxyacetamido)-5-oxohexanoate |
| 124 | S-(propan-2-yl-1,1,1-d3) (2S)-6-diazo-2-((S)-2-methoxypropanamido)-5-oxohexanethioate |
| 125 | propan-2-yl-1,1,1-d3 (2S)-6-diazo-2-((S)-2-methoxy-4-(methylthio)butanamido)-5-oxohexanoate. |

2. A pharmaceutical composition comprising the compound, the pharmaceutically acceptable salt thereof, the stereoisomer thereof, the tautomer thereof, and the isotopic substitution thereof according to claim 1; and a pharmaceutically acceptable carrier, diluent or excipient.

3. The compound or the pharmaceutically acceptable salt thereof, the stereoisomer thereof, the tautomer thereof, and the isotopic substitution thereof according to claim 1, wherein the compound is selected from:

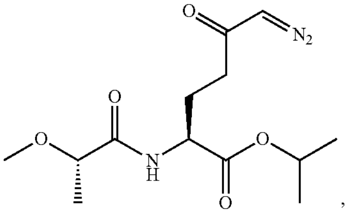

,

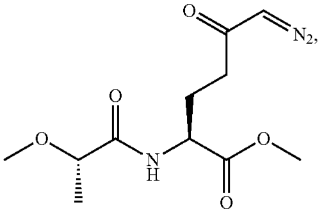

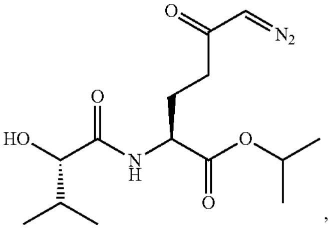

,

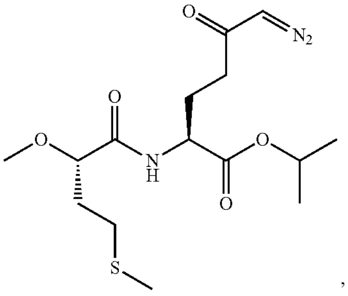

, or

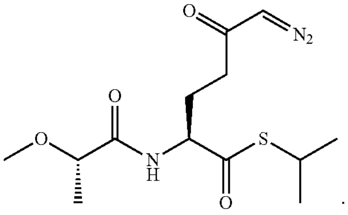

.

4. The compound or the pharmaceutically acceptable salt thereof, the stereoisomer thereof, the tautomer thereof, and the isotopic substitution thereof according to claim 1, wherein the compound is

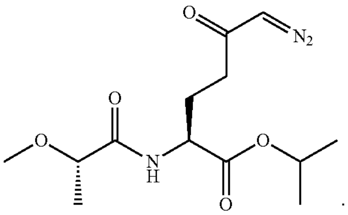

.

* * * * *